(12) United States Patent
Bobkov et al.

(10) Patent No.: US 12,344,678 B2
(45) Date of Patent: Jul. 1, 2025

(54) FcRn/HSA BINDING MOLECULES AND METHODS OF USE

(71) Applicant: argenx BV, Ghent (BE)

(72) Inventors: Vladimir Bobkov, Ghent (BE); Karen Silence, Ghent (BE); Jolien Van Santbergen, Ghent (BE); René Bigirimana, Ghent (BE); Judith Baumeister, Ghent (BE); Johannes de Haard, Ghent (BE); Christophe Blanchetot, Ghent (BE)

(73) Assignee: argenx BV, Ghent (BE)

( * ) Notice: Subject to any disclaimer, the term of this patent is extended or adjusted under 35 U.S.C. 154(b) by 0 days.

(21) Appl. No.: 18/980,920

(22) Filed: Dec. 13, 2024

(65) Prior Publication Data
US 2025/0122310 A1  Apr. 17, 2025

Related U.S. Application Data

(63) Continuation of application No. PCT/EP2023/066180, filed on Jun. 15, 2023.

(60) Provisional application No. 63/352,589, filed on Jun. 15, 2022.

(51) Int. Cl.
C07K 16/42   (2006.01)
C07K 16/18   (2006.01)
A61K 39/00   (2006.01)

(52) U.S. Cl.
CPC .......... C07K 16/4258 (2013.01); C07K 16/18 (2013.01); *A61K 2039/505* (2013.01); *C07K 2317/569* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,326,856 A | 7/1994 | Coughlin et al. | |
| 5,624,821 A | 4/1997 | Winter et al. | |
| 5,648,260 A | 7/1997 | Winter et al. | |
| 5,677,425 A | 10/1997 | Bodmer et al. | |
| 5,869,046 A | 2/1999 | Presta et al. | |
| 5,885,573 A | 3/1999 | Bluestone et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,277,375 B1 | 8/2001 | Ward | |
| 6,528,624 B1 | 3/2003 | Idusogie et al. | |
| 6,737,056 B1 | 5/2004 | Presta | |
| 6,821,505 B2 | 11/2004 | Ward | |
| 6,992,234 B2 | 1/2006 | Roopenian | |
| 7,083,784 B2 | 8/2006 | Dall'Acqua et al. | |
| 7,183,387 B1 | 2/2007 | Presta | |
| 7,670,600 B2 | 3/2010 | Dall'Acqua et al. | |
| 7,704,497 B2 | 4/2010 | Dall'Acqua et al. | |
| 8,012,476 B2 | 9/2011 | Dall'Acqua et al. | |
| 8,021,856 B2 | 9/2011 | Umana et al. | |
| 8,067,232 B2 | 11/2011 | Kanda et al. | |
| 8,101,186 B2 | 1/2012 | Mezo et al. | |
| 8,163,881 B2 | 4/2012 | Ober | |
| 8,195,661 B2 | 6/2012 | Kalavade | |
| 8,216,805 B2 | 7/2012 | Carter et al. | |
| 8,273,351 B2 | 9/2012 | TenHoor et al. | |
| 8,323,962 B2 | 12/2012 | Dall'Acqua et al. | |
| 8,475,792 B2 | 7/2013 | Dall'Acqua et al. | |
| 8,680,237 B2 | 3/2014 | Strome et al. | |
| 8,795,661 B2 | 8/2014 | Dall'Acqua et al. | |
| 8,815,246 B2 | 8/2014 | TenHoor et al. | |
| 8,834,871 B2 | 9/2014 | Ober | |
| 9,260,520 B2 | 2/2016 | TenHoor et al. | |
| 9,573,992 B2 * | 2/2017 | Dombrecht | C07K 16/2863 |
| 10,316,073 B2 | 6/2019 | Ulrichts et al. | |
| 11,505,585 B2 | 11/2022 | Ulrichts et al. | |
| 11,591,388 B2 | 2/2023 | Borgions et al. | |
| 12,202,900 B2 | 1/2025 | de Haard et al. | |
| 12,240,875 B2 | 3/2025 | de Haard et al. | |
| 2004/0002587 A1 | 1/2004 | Watkins et al. | |
| 2004/0010124 A1 | 1/2004 | Johnson et al. | |
| 2004/0047862 A1 | 3/2004 | Lazarus et al. | |

(Continued)

FOREIGN PATENT DOCUMENTS

| | | |
|---|---|---|
| EP | 0227110 A2 | 7/1987 |
| WO | WO1994029351 A2 | 12/1994 |

(Continued)

OTHER PUBLICATIONS

Vincke, Cecile, et al. "General strategy to humanize a camelid single-domain antibody and identification of a universal humanized nanobody scaffold." Journal of Biological Chemistry 284.5 (2009): 3273-3284. (Year: 2009).*

Kipriyanov, Sergey M., and Favrice Le Gall. "Generation and production of engineered antibodies." Molecular biotechnology 26.1 (2004): 39-60. (Year: 2004).*

Ghahroudi, M et al. "Selection and identification of single domain antibody fragments from camel heavy-chain antibodies." FEBS letters vol. 414,3 (1997): 521-6. doi:10.1016/s0014-5793(97)01062-4 (Year: 1997).*

"Vyvgart™ (efgartigimod alfa-fcab) injection, for intravenous Use", Initial U.S. Approval, Dec. 2021, 14 pages.

Alexion Pharmaceuticals Inc., "A Phase 1b/2, Multicenter, Open-Label, Safety, and Dose-Finding Study of SYNT001 in Subjects with Pemphigus (Vulgaris or Foliaceus)", Retrieved from: https://cdn.clinicaltrials.gov/large-docs/04/NCT03075904/SAP_000.pdf, Protocol ID: SYNT001-103, NCT No. NCT03075904, Mar. 25, 2019, 32 pages.

(Continued)

*Primary Examiner* — Zachariah Lucas
*Assistant Examiner* — Lia E Taylor
(74) *Attorney, Agent, or Firm* — Dechert LLP; Andrew T. Wilkins; Sharla F. Flohr

(57) ABSTRACT

Provided herein are binding molecules comprising a human neonatal Fc receptor (FcRn) binding molecule and at least one antigen-binding domain linked to the FcRn binding molecule. Polynucleotides, vectors, host cells, and methods of production are also provided herein. Methods of treating an antibody-mediated disorder with an FcRn/antigen-binding molecule are further provided.

14 Claims, 39 Drawing Sheets

Specification includes a Sequence Listing.

(56) References Cited

U.S. PATENT DOCUMENTS

| | | |
|---|---|---|
| 2004/0265321 A1 | 12/2004 | Johnson et al. |
| 2005/0053598 A1 | 3/2005 | Burke et al. |
| 2006/0210557 A1 | 9/2006 | Luisi et al. |
| 2007/0092507 A1 | 4/2007 | Balthasar et al. |
| 2009/0252729 A1 | 10/2009 | Farrington et al. |
| 2011/0066111 A1 | 3/2011 | Teschner et al. |
| 2011/0081345 A1 | 4/2011 | Moore et al. |
| 2011/0243966 A1 | 10/2011 | Farrington et al. |
| 2013/0142802 A1 | 6/2013 | Chang et al. |
| 2013/0156765 A1 | 6/2013 | Block et al. |
| 2014/0302028 A1 | 10/2014 | Zha |
| 2016/0252497 A1 | 9/2016 | Ling |
| 2016/0264669 A1 | 9/2016 | Ulrichts et al. |
| 2017/0260238 A1 | 9/2017 | Abrahmsen et al. |
| 2019/0194277 A1 | 6/2019 | de Haard et al. |
| 2020/0024344 A1 | 1/2020 | de Haard et al. |
| 2021/0236596 A1 | 8/2021 | Verheesen et al. |
| 2022/0275035 A1 | 9/2022 | Ulrichts et al. |
| 2022/0298241 A1 | 9/2022 | Blumberg et al. |
| 2023/0357382 A1 | 11/2023 | Borgions et al. |
| 2024/0325528 A1 | 10/2024 | Van Bragt et al. |
| 2024/0369467 A1 | 11/2024 | Verheesen et al. |
| 2025/0051453 A1 | 2/2025 | Verheesen et al. |
| 2025/0084171 A1 | 3/2025 | van der Woning et al. |
| 2025/0101111 A1 | 3/2025 | Brinkhaus et al. |

FOREIGN PATENT DOCUMENTS

| | | |
|---|---|---|
| WO | WO1996022024 A1 | 7/1996 |
| WO | WO1997034631 A1 | 9/1997 |
| WO | 1998023289 A1 | 6/1998 |
| WO | WO1999004813 A1 | 2/1999 |
| WO | WO1999058572 A1 | 11/1999 |
| WO | WO2000042072 A2 | 7/2000 |
| WO | WO2001058957 A2 | 8/2001 |
| WO | WO2002043658 A2 | 6/2002 |
| WO | WO2002060919 A2 | 8/2002 |
| WO | WO2004016750 A2 | 2/2004 |
| WO | WO2004029207 A2 | 4/2004 |
| WO | WO2004035752 A2 | 4/2004 |
| WO | WO2004063343 A2 | 7/2004 |
| WO | WO2004063351 A2 | 7/2004 |
| WO | WO2004099249 A2 | 11/2004 |
| WO | WO2005040217 A2 | 5/2005 |
| WO | 2006028936 A2 | 3/2006 |
| WO | 2006122787 A1 | 11/2006 |
| WO | WO2006118772 A2 | 11/2006 |
| WO | WO2006130834 A2 | 12/2006 |
| WO | WO2007098420 A2 | 8/2007 |
| WO | WO2009100105 A2 | 8/2009 |
| WO | WO2009131702 A2 | 10/2009 |
| WO | WO2010014909 A1 | 2/2010 |
| WO | WO2010106180 A2 | 9/2010 |
| WO | WO2010111254 A1 | 9/2010 |
| WO | WO2011044368 A1 | 4/2011 |
| WO | WO2011080209 A2 | 7/2011 |
| WO | WO2012160448 A2 | 11/2012 |
| WO | 2012175400 A1 | 12/2012 |
| WO | WO2012167039 A1 | 12/2012 |
| WO | WO2013063186 A2 | 5/2013 |
| WO | WO2013074598 A1 | 5/2013 |
| WO | WO2013100702 A1 | 7/2013 |
| WO | WO2013166604 A1 | 11/2013 |
| WO | WO2013192504 A1 | 12/2013 |
| WO | WO2014008391 A1 | 1/2014 |
| WO | WO2014019727 A1 | 2/2014 |
| WO | WO2014140366 A1 | 9/2014 |
| WO | WO2014204280 A1 | 12/2014 |
| WO | WO2015071330 A1 | 5/2015 |
| WO | WO2015073721 A1 | 5/2015 |
| WO | WO2015081073 A2 | 6/2015 |
| WO | WO2015100299 A1 | 7/2015 |
| WO | WO2016042083 A1 | 3/2016 |
| WO | WO2016123521 A2 | 8/2016 |
| WO | WO2016142782 A1 | 9/2016 |
| WO | WO2016180765 A1 | 11/2016 |
| WO | WO2016183352 A1 | 11/2016 |
| WO | WO2017012959 A1 | 1/2017 |
| WO | WO2017121330 A1 | 7/2017 |
| WO | WO2017189959 A1 | 11/2017 |
| WO | WO2018023136 A1 | 2/2018 |
| WO | WO2018083122 A1 | 5/2018 |
| WO | 2018187057 A1 | 10/2018 |
| WO | WO2019110823 A1 | 6/2019 |
| WO | WO2019118791 A1 | 6/2019 |
| WO | WO2019234713 A2 | 12/2019 |
| WO | WO2020078905 A1 | 4/2020 |
| WO | WO2020097099 A1 | 5/2020 |
| WO | 2020208177 A1 | 10/2020 |
| WO | WO2020227515 A1 | 11/2020 |
| WO | WO2020236695 A1 | 11/2020 |
| WO | WO2020245420 A1 | 12/2020 |
| WO | WO2021022249 A1 | 2/2021 |
| WO | WO2020245420 A9 | 4/2021 |
| WO | WO2021140202 A1 | 7/2021 |
| WO | WO2021216756 A2 | 10/2021 |
| WO | WO2022098955 A1 | 5/2022 |
| WO | WO2023012515 A2 | 2/2023 |
| WO | WO2023135321 A1 | 7/2023 |
| WO | WO2023156614 A1 | 8/2023 |
| WO | WO2023209036 A1 | 11/2023 |
| WO | WO2023242361 A1 | 12/2023 |
| WO | WO2023242362 A1 | 12/2023 |
| WO | WO2023242371 A1 | 12/2023 |
| WO | WO2023242372 A1 | 12/2023 |
| WO | 2024052358 A1 | 3/2024 |
| WO | WO2024100453 A1 | 5/2024 |
| WO | WO2024100455 A1 | 5/2024 |
| WO | WO2024105445 A2 | 5/2024 |
| WO | WO2024147074 A1 | 7/2024 |
| WO | WO2024150073 A1 | 7/2024 |
| WO | WO2024189430 A1 | 9/2024 |
| WO | 2025017368 A1 | 1/2025 |

OTHER PUBLICATIONS

Briani et al., "Therapeutic Monoclonal Antibody Therapies in Chronic Autoimmune Demyelinating Neuropathies", Neurotherapeutics, 2022, 19(3):874-884.

Brinkhaus et al., "Glycine 236 in the Lower Hinge Region of Human IgG1 Differentiates FcgammaR from Complement Effector Function", The Journal of Immunology, Dec. 15, 2020, 205(12):3456-3467.

Miyamoto et al., "Pemphigus "Is Rituximab effective?"", MB Derma, 2012, 190:91-93 (English Translation and Official Copy).

Nelke et al., "Neonatal Fc Receptor-Targeted Therapies in Neurology", Neurotherapeutics, 2022, 19(3):729-740.

Simpson et al., "The Validated Investigator Global Assessment for Atopic Dermatitis (vIGA-AD): The development and reliability testing of a novel clinical outcome measurement instrument for the severity of atopic dermatitis", Journal of the American Academy of Dermatology, Sep. 2020, 83(3):839-846.

Smith et al., "Mouse model recapitulating human FcGamma receptor structural and functional diversity", PNAS, Apr. 17, 2012, 109(16):6181-6186.

Svaina et al., "Chronic Inflammatory Demyelinating Polyneuropathy (CIDP): Current Therapies and Future Approaches", Current Pharmaceutical Design, 2022, 28(11):854-862.

Syntimmune, Inc., "Syntimmune Announces Positive Preliminary Results from Clinical Proof-of-Concept Trial of SYNT001 in Pemphigus Vulgaris and Foliaceus", Retrieved from: https://www.businesswire.com/news/home/20180517006057/en/Syntimmune-Announces-Positive-Preliminary-Results-Clinical-Proofof-Concept, May 17, 2018, 2 pages.

International Search Report and Written Opinion received for PCT Application No. PCT/IB2024/000374, mailed on Nov. 12, 2024, 16 pages.

"Assignment submission for U.S. Appl. No. 61/920,547 confirming change of legal form of arGEN-X B.V. to arGEN-X N.V. on May 28,

(56) References Cited

OTHER PUBLICATIONS

2014", Document D30 submitted with Notice of Opposition for European Patent No. 3087095 (U.S. Appl. No. 61/920,547), dated May 7, 2020, 4 pages.

"Appeal from the United States District Court for the District of Delaware", *Amgen Inc.* v. *Sanofi*, 2017-1480, Oct. 5, 2017, 24 pages.

"Auxiliary Request 1—Annotated Version" for European Patent No. 3087095 (Application No. 14827372.5), dated Oct. 28, 2020, 5 pages.

"Auxiliary Request 1—Clean Version" for European Patent No. 3087095 (Application No. 14827372.5), dated Oct. 28, 2020, 5 pages.

"Auxiliary Request 2—Annotated Version" for European Patent No. 3087095 (Application No. 14827372.5), dated Oct. 28, 2020, 5 pages.

"Auxiliary Request 2—Clean Version" for European Patent No. 3087095 (Application No. 14827372.5), dated Oct. 28, 2020, 4 pages.

"Declaration of Pieter Spuijbroek", Document D42 submitted with Reply to Notice of Opposition for European Patent No. 3087095 (Application No. 14827372.5), dated Oct. 28, 2020, 5 pages.

"Guidance for Industry Estimating the maximum safe starting dose in initial clinical trials for therapeutics in adult healthy volunteers", FDA, Jul. 2005, 30 pages.

"Main Request—Annotated Version" for European Patent No. 3087095 (Application No. 14827372.5), dated Oct. 28, 2020, 5 pages.

"Main Request—Clean Version" for European Patent No. 3087095 (Application No. 14827372.5), dated Oct. 28, 2020, 5 pages.

"Sequence Alignment of SEQ ID No. 22 from D6 vs SEQ ID Nos. 1, 2, and 3 from opposed patent", Document D32 submitted with Notice of Opposition for European Patent No. 3087095 (Application No. 14827372.5), dated May 7, 2020, 1 page.

"Sequence Alignment of SEQ ID Nos. 1, 2 and 3 from opposed patent vs corresponding portion of Uniprot ID: P01857", Document D24 submitted with Notice of Opposition for European Patent No. 3087095 (Application No. 14827372.5), dated May 7, 2020, 1 page.

"Swiss Webster Mice", Taconic—Models for Life, Aug. 23, 2018, pp. 1-7.

"UniProtKB—P01857 (IGHG1_HUMAN)", Document D43 submitted with Reply to Notice of Opposition for European Patent No. 3087095 (Application No. 14827372.5), dated Oct. 28, 2020, 6 pages.

Abdiche et al., "The neonatal Fc receptor (FcRn) binds independently to both sites of the IgG homodimer with identical affinity", mAbs, 2015, 7(2):331-343.

Akilesh et al., "The MHC class I-like Fc receptor promotes humorally mediated autoimmune disease", The Journal of Clinical Investigation, May 2004, 113(9):1328-1333.

Alegre et al., "A Non-Activating "Humanized" Anti-CD3 Monoclonal Antibody Retains Immunosuppressive Properties In Vivo", Transplantation, Jun. 1994, 57(11):1537-1543.

Alipour-Faz et al., "A comparison between IVIG and plasma exchange as preparations before thymectomy in myasthenia gravis patients", Acta Neurol Belg, 2016, 117(1):245-249.

Allen et al., "Efgartigimod in Chronic Inflammatory Demyelinating Polyneuropathy: Adhere Phase 2 Trial Design", Muscle and Nerve, Oct. 1, 2020, 62(Suppl. 1):abstract, 1 page.

Andersen et al., "Structure-based mutagenesis reveals the albumin-binding site of the neonatal Fc receptor", Nature Communications, 2012, 3(610), pp. 1-9.

Anonymous, "A Randomized, Double-Blinded, Placebo-Controlled Trial of Efgartigimod PH20 SC in Adult Patients With Pemphigus (Vulgaris or Foliaceus)", Jul. 16, 2021, Retrieved from: https://rctportal.niph.go.jp/en/detail?trial_id=jRCT2061210025, 4 pages.

Anonymous, "argenx announces initial results from Phase 1 multiple ascending dose (MAD) study of ARGX-113 in healthy volunteers—Argenx", Jun. 29, 2016, 3 pages.

Anthony et al., "Recapitulation of IVIG Anti-Inflammatory Activity with a Recombinant IgG Fc", Science, Apr. 18, 2008, 320(5874):373-376.

Antohe et al., "Expression of Functionally active FcRn and the Differentiated Bidirectional Transport of IgG in Human Placental Endothelial Cells", Human Immunol., 2001, 62(2):93-105.

Arduin et al., "Highly reduced binding to high and low affinity mouse Fc gamma receptors by L234A/L235A and N297A Fc mutations engineered into mouse IgG2a", Molecular Immunology, 2015, 63(2):456-463.

Argen-X N.V., "arGEN-X advances ARGX-113 into preclinical development for autoimmune disorders", Press Release, arGEN-X, Apr. 24, 2014, 3 pages.

Argen-X N.V., "arGEN-X Announces Positive Preclinical Results for ARGX-113", Press Release. EURONEXT, Aug. 19, 2014, 3 pages.

Argen-X N.V., "Prospectus for Public Offering of arGEN-X N.V.", Jun. 20, 2014, 253 pages.

Argen-X, "An Emerging Antibody Force: Company Presentation", Presentation Slides, Oct. 2013, 15 pages.

Argen-X, "ARGX-113", Retrieved from: http://www.argen-x.com/en-GB/contenl/argx-113/22, 2017, 4 pages.

Argen-X, "ARGX-113: Development Opportunity in Autoimmunity", Presentation Slides, Oct. 2013, 17 pages.

Armour et al., "Recombinant human IgG molecules lacking Fc gamma receptor I binding and monocyte triggering activities", Eur. J. Immunol., 1999, 29(8):2613-2624.

Azevedo, "argenx Doses First Subject in Study Evaluating Subcutaneous ARGX-113 for Autoimmune Diseases", Myasthenia Gravis News, Oct. 31, 2017, 2 pages.

Balighi et al., "Comparing early and late treatments with rituximab in pemphigus vulgaris: which one is better?", Archives of Dermatological Research, 2019, 311(1):63-69.

Ballow, "Mechanisms of Action of Intravenous Immunoglobulin Therapy and Potential Use in Autoimmune Connective Tissue Diseases", Cancer, 1991, 68(6):1430-1436.

Barth et al., "Comparison of IVIg and PLEX in patients with myasthenia gravis", Neurology, Jun. 7, 2011, 76(23):2017-2023.

Basta et al., "High-dose intravenous immunoglobulin exerts its beneficial effect in patients with dermatomyositis by blocking endomysial deposition of activated complement fragments", The Journal of Clinical Investigation, 1994, 94(5):1729-1735.

Bitonti et al., "Pulmonary delivery of an erythropoietin Fc fusion protein in non-human primates through an immunoglobulin transport pathway", PNAS, Jun. 29, 2004, 101(26):9763-9768.

Blanchette et al., "Intensive plasma exchange therapy in ten patients with idiopathic thrombocytopenia purpura", Transfusion, 1984, 24(5):388-394.

Blumberg et al., "Antibodies in the breakdown lane", Nature Biotechnology, Oct. 2005, 23(10):1232-1234.

Blumberg et al., "Blocking FcRn in humans reduces circulating IgG levels and inhibits IgG immune complex-mediated immune responses", Sci. Adv., Dec. 18, 2019, 5(12):eaax9586, 12 pages.

Brinkhaus et al., "The Fab region of IgG impairs the internalization pathway of FcRn upon Fc management", Nature Communications, 2022, 13(1):6073, pp. 1-14.

Broome et al., "Abstract PB0830: Efficacy and Safety of Efgartigimod PH20 Subcutaneous in Adult Patients with Primary Immune Thrombocytopenia: Advance SC, a Global Phase 3 Clinical Trial in Progress", Res Pract Thromb Haemost., 2021, 5(Suppl. 2), 2 pages.

Broome et al., "Efficacy and safety of the neonatal Fc receptor inhibitor efgartigimod in adults with primary immune thrombocytopenia (Advance IV): a multicentre, randomised, placebo-controlled, phase 3 trial", Lancet, Sep. 28, 2023, 402(10413):1648-1659.

Bruhns et al., "Colony-Stimulating Factor-1-Dependent Macrophages are Responsible for IVIG Protection in Antibody-Induced Autoimmune Disease", Immunity, Apr. 2003, 18(4):573-581.

Brych et al., "Characterization of Antibody Aggregation: Role of Buried, Unpaired Cysteines in Particle Formation", Journal of Pharmaceutical Sciences, Feb. 2010, 99(2):764-781.

Burmeister et al., "Crystal structure at 2.2 Å resolution of the MHC-related neonatal Fc receptor", Nature, Nov. 24, 1994, 372(6504):336-343.

(56) References Cited

OTHER PUBLICATIONS

Burns, "History of outcome measures for myasthenia gravis", Muscle & Nerve, Jul. 2010, 42(1):5-13.
Burns, "Of Mice and Children: Lessons From a Kawasaki Mouse Model", Circulation, 2012, 125:1480-1481.
Bussel et al., "A randomized, double-blind study of romiplostim to determine its safety and efficacy in children with immune thrombocytopenia", Blood, Jul. 7, 2011, 118(1):28-36.
Bussel et al., "Eltrombopag for the Treatment of Chronic Idiopathic Thrombocytopeni Purpura", The New England Journal of Medicine, Nov. 29, 2007, 357(22):2237-2247.
Bussel et al., "Long-Term use of the Thrombopoietin-Mimetic Romiplostim in Children With Severe Chronic Immune Thrombocytopenia (ITP): Romiplostim in Pediatric ITP", Pediatric Blood Cancer, 2015, 62(2):208-213.
Bystryn et al., "IVIg selectively and rapidly decreases circulating pathogenic autoantibodies in pemphigus vulgaris", Autoimmunity, Nov. 2006, 39(7):601-607.
Carter, "Potent antibody therapeutics by design", Nature Reviews, Immunology, May 2006, 6(5):343-357.
Challa et al., "Autoantibody depletion ameliorates disease in murine experimental autoimmune encephalomyelitis", mAbs, Sep./Oct. 2013, 5(5):655-659.
Challa et al., "Neonatal Fc receptor expression in macrophages is indispensable for IgG homeostasis", MABS., 2019, 11(5):848-860.
Chaudhury et al., "The Major Histocompatibility Complex-related Fc Receptor for IgG (FcRn) Binds Albumin and Prolongs Its Lifespan", The Journal of Experimental Medicine, Feb. 3, 2003, 197(3):315-322.
Cipriani et al., "MET as a target for treatment of chest tumours", Lung Cancer, Feb. 2009, 63(2):169-179.
Clarkson et al., "Treatment of Refractory Immune Thrombocytopeniaurpura with an Anti-Fc gamma-Receptor Antibody", The New England Journal of Medicine, May 8, 1986, 314(9):1236-1239.
ClinicalTrials.gov, "A Study of Nipocalimab in Adults With Primary Sjogren's Syndrome (pSS)", ClinicalTrials.gov Identifier: NCT04968912, Jul. 20, 2021, 9 pages.
ClinicalTrials.gov, "A Study to Assess Effectiveness and Safety of Efgartigimod in Chinese Patients With Lupus Nephritis (ZL-1103-013)", ClinicalTrials.gov Identifier: NCT05810948, Oct. 2, 2023, 17 pages.
ClinicalTrials.gov, "A Study to Assess the Long-term Safety and Efficacy of a Subcutaneous Formulation of Efgartigimod PH20 SC in Adults With Pemphigus (Vulgaris or Foliaceus) (Address+)", ClinicalTrials.gov Identifier: NCT04598477, Oct. 22, 2020, 10 pages.
ClinicalTrials.gov, "A Study to Evaluate the Safety, Efficacy, and Pharmacokinetics of ARGX-113 in Patients with ITP", ClinicalTrials.gov Identifier: NCT03102593, Apr. 6, 2017, 7 pages.
ClinicalTrials.gov, "A Study to Evaluate the Safety, PD, PK and Efficacy of ARGX-113 in Patients with Pemphigus", ClinicalTrials.gov Identifier: NCT03334058, Nov. 7, 2017, 8 pages.
ClinicalTrials.gov, "Efficacy and Safety Study of Efgartigimod in Adults With Post-COVID-19 POTS (POTS)", ClinicalTrials.gov Identifier: NCT05633407, Nov. 29, 2022, 13 pages.
ClinicalTrials.gov, "Evaluating the Long-Term Safety and Tolerability of Efgartigimod PH20 SC Administered Subcutaneously in Patients With Generalized Myasthenia Gravis (Adaptsc+)", ClinicalTrials.gov Identifier: NCT04818671, Mar. 26, 2021, 7 pages.
ClinicalTrials.gov, "History of Changes for Study: NCT05267600—A Phase 2/3 Study of Efgartigimod PH20 SC in Adult Participants With Bullous Pemphigoid (Ballad)", Apr. 14, 2022, 7 pages.
ClinicalTrials.gov, "History of Changes for Study: NCT05810961—A Study to Assess Effectiveness and Safety of Efgartigimod in Chinese Patients With Primary Membranous Nephropathy (ZL-1103-014)", Oct. 2, 2023, 11 pages.
Coetzee et al., "The Effect of Monoclonal Anti-human-platelet Antibodies on Platelet Kinetics in a Baboon Model: IgG Subclass Dependency", Thromb Haemost, 2000, 83(1):148-156.
Crow et al., "The Mechanisms of Action of Intravenous Immunoglobulin and Polyclonal Anti-D Immunoglobulin in the Amelioration of Immune Thrombocytopeni Purpura: What Do We Really Know?", Transfusion Medicine Reviews, Apr. 2008, 22(2):103-116.
Crow et al., "The neonatal Fc receptor (FcRn) is not required for IVIg or anti-CD44 monoclonal antibody-mediated amelioration of murine immune thrombocytopenia", Blood, Dec. 8, 2011, 118(24):6403-6406.
Dalakas et al., "A controlled trial of high-dose intravenous immune globulin infusions as treatment for dermatomyositis", N Engl J Med., Dec. 30, 1993, 329(27):1993-2000.
Dalakas et al., "High-dose intravenous immune globulin for stiff-person syndrome", The New England Journal of Medicine, Dec. 27, 2001, 345(26):1870-1876.
Dalakas, "Update on Intravenous Immunoglobulin in Neurology: Modulating Neuro-autoimmunity, Evolving Factors on Efficacy and Dosing and Challenges on Stopping Chronic IVIg Therapy", Neurotherapeutics, 2021, 18(4):2397-2418.
Dall'Acqua et al., "Increasing the Affinity of a Human IgG1 for the Neonatal Fc Receptor: Biological Consequences", The Journal of Immunology, 2002, 169:5171-5180.
Dall'Acqua et al., "Properties of Human IgG1s Engineered for Enhanced Binding to the Neonatal Fc receptor (FcRn)", Journal of Biological Chemistry, Aug. 18, 2006, 281(33):23514-23524.
Darabi et al., "Current usage of intravenous immune globulin and the rationale behind it: the Massachusetts General Hospital data and a review of the literature", Transfusion, May 2006, 46(5):741-753.
Daugherty et al., "Formulation and delivery issues for monoclonal antibody therapeutics", Advanced Drug Delivery Reviews, 2006, 58(5-6):686-706.
De Haard et al., "Advancing ARGX-113 and ARGX-110 to Clinical Proof of Concept", Dec. 4, 2016, pp. 1-57.
Debré et al., "Infusion of Fc gamma fragments for treatment of children with acute immune thrombocytopenia purpura", The Lancet, Oct. 16, 1993, 342(8877):945-949.
Deisenhofer, "Crystallographic Refinement and Atomic Models of a Human Fc Fragment and Its Complex with Fragment B of Protein A from *Staphylococcus aureus* at 2.9- and 2.8-Å Resolution", Biochemistry, Apr. 28, 1981, 20(9):2361-2370.
Deng et al., "Pharmacokinetic/Pharmacodynamic Modeling of IVIG Effects in a Murine Model of Immune Thrombocytopenia", Journal of Pharmaceutical Sciences, Jun. 2007, 96(6):1625-1637.
Dick Jr., et al., "C-Terminal Lysine Variants in Fully Human Monoclonal Antibodies: Investigation of Test Methods and Possible Causes", Biotechnology and Bioengineering, Aug. 15, 2008, 100(6):1132-1143.
Dickinson et al., "Bidirectional FcRn-dependent IgG transport in a polarized human intestinal epithelial cell line", The Journal of Clinical Investigation, Oct. 1999, 104(7):903-911.
Dimitrov, "Engineered CH2 domains (nanoantibodies)", mAbs, Jan./Feb. 2009, 1(1):26-28.
Duncan et al., "Localization of the binding site for the human high-affinity Fc receptor on IgG", Nature, Apr. 7, 1988, 332(6164):563-564.
Dylewski et al., "Exploiting the neonatal crystallizable fragment receptor to treat kidney disease", Kidney International, 2024, 105(1):54-64.
Eddleston et al., "Blockade of the Neonatal Fc Receptor (FcRn) Represents an Effective Mechanism for the Removal of Pathogenic Autoantibodies in Primary Immune Thrombocytopenia", Blood, Dec. 7, 2017, 130(Suppl. 1):230, 3 pages.
Edelman et al., "The covalent structure of an entire gamma G immunoglobulin molecule", Proc. N. A. S., Mar. 21, 1969, 63(1):78-85.
El-Salem et al., "Treatment of MuSK-Associated Myasthenia Gravis", Curr Treat Options Neurol, Feb. 8, 2014, 16(4):283, 17 pages.
Evoli et al., "Diagnosis and therapy of myasthenia gravis with antibodies to muscle-specific kinase", Autoimmunity Reviews, 2013, 12(9):931-935.
Eymard, "Antibodies in myasthenia gravis", Rev. Neurol., 2009, 165(2):137-143.

(56) References Cited

OTHER PUBLICATIONS

Federico et al., "Multifocal motor neuropathy improved by IVIg: Randomized, double-blind, placebo-controlled study", Neurology, 2000, 55(9):1256-1262.
Firan et al., "The MHC class I-related receptor, FcRn, plays an essential role in the maternofetal transfer of gamma-globulin in humans", International Immunology, 2001, 13(8):993-1002.
Flaherty et al., "Nonclinical Evaluation of GMA161—An Antihuman CD16 (Fc gamma RIII) Monoclonal Antibody for Treatment of Autoimmune Disorders in CD16 Transgenic Mice", Toxicological Sciences, 2012, 125(1):299-309.
Furusho et al., "High-dose intravenous gammaglobulin for Kawasaki disease", Lancet, Nov. 10, 1984, 2:1055-1058.
Gan et al., "Analyses of the recycling receptor, FcRn, in live cells reveal novel pathways for lysosomal delivery", Traffic, May 2009, 10(5):600-614.
Garcia et al., "Kinetics and thermodynamics of T cell receptor-autoantigen interactions in murine experimental autoimmune encephalomyelitis", PNAS, Jun. 5, 2001, 98(12):6818-6823.
Genbank Accession No. NM_000569, "*Homo sapiens* Fc fragment of IgG receptor IIIa (FCGR3A), transcript variant 1, mRNA", National Center for Biotechnology Information, Retrieved from: http://www.ncbi.nlm.nih.gov/nuccore/NM_000569, Jul. 2, 2016, 4 pages.
Ghanima et al., "Pharmacokinetic / Pharmacodynamic (PK/PD) Simulations Guide Selection of the Dose for Administration of Efgartigimod Subcutaneously in a Phase 3 Clinical Trial in Patients with Primary Immune Thrombocytopenia", Blood, Nov. 5, 2021, 138(Supplement 1):3165-3167.
Ghetie et al., "Abnormally short serum half-lives of IgG in beta 2-microglobulin-deficient mice", Eur. J. Immunol., 1996, 26(3):690-696.
Ghetie et al., "FcRn: the MHC class I-related receptor that is more than an IgG transporter", Immunology Today, 1997, 18(12):592-598.
Ghetie et al., "Increasing the serum persistence of an IgG fragment by random mutagenesis", Nature Biotechnology, Jul. 1997, 15(7):637-640.
Ghetie et al., "Multiple Roles for the Major Histocompatibility Complex class I-Related Receptor FcRn", Annu. Rev. Immunol., 2000, 18(1):739-766.
Ghetie et al., "Transcytosis and catabolism of antibody", Immunologic Research, 2002, 25(2):97-113.
Gilhus et al., "Myasthenia Gravis: A Review of Available Treatment Approaches", Autoimmune Diseases, 2011, Article ID 847393, 7 pages.
Goebeler et al., "Treatment of pemphigus vulgaris and foliaceus with efgartigimod, a neonatal Fc receptor inhibitor: a phase II multicentre, open-label feasibility trial", British Journal of Dermatology, 2022, 186(3):429-439.
Goh et al., "Impact of host cell line choice on glycan profile", Critical Reviews in Biotechnology, 2018, 38(6):851-867.
Gomez-Guerrero et al., "Administration of IgG Fc Fragments Prevents Glomerular Injury in Experimental Immune Complex Nephritis", The Journal of Immunology, 2000, 164(4):2092-2101.
Grau, "IgG core a-fucosylation and its impact on Fc gamma RIIIa binding", Pharma Research and Early Development, Sep. 21, 2011, pp. 1-20.
Grevys et al., "Fc Engineering of Human IgG1 for Altered Binding to the Neonatal Fc Receptor Affects Fc Effector Functions", The Journal of Immunology, 2015, 194(11):5497-5508.
Guptill et al., "Effect of FcRn antagonism on protective antibodies and to vaccines in IgG-mediated autoimmune diseases pemphigus and generalised myasthenia gravis", Autoimmunity, 2022, 55(8):620-631.
Guptill et al., "Effect of therapeutic plasma exchange on immunoglobulins in myasthenia gravis", Autoimmunity, Aug. 11, 2016, 49(7):472-479.

Ha et al., "Immunoglobulin Fc Heterodimer Platform Technology: From Design to Applications in Therapeutic Antibodies and Proteins", Frontiers in Immunology, Oct. 6, 2016, 7(394), pp. 1-16.
Haller, "Converting Intravenous Dosing to Subcutaneous Dosing with Recombinant human Hyaluronidase", Pharmaceutical Technology, Advanstar Communications Inc., Oct. 2, 2007, 31(10), pp. 1-5.
Hansen et al., "Intravenous Immunoglobulin Mediates an Increase in Anti-Platelet Antibody Clearance via the FcRn Receptor", Thromb Haemost., 2002, 88:898-899.
Hanson, "The role of the Immunoglobulin G1 Fc N-glycan in Fc gamma RIIIa affinity", Graduate Thesis and Dissertations, Paper 14135, 2014, 69 pages.
Heo, "Efgartigimod: First Approval", Drugs, Feb. 18, 2022, 82(3):341-348
Hettmann et al., "Development of the clinical candidate PBD-C06, a humanized pGlu3-ABeta-specific antibody against Alzheimer's disease with reduced complement activation", Scientific Reports, 2020, 10(3294), pp. 1-13.
Hinton et al., "Engineered human IgG Antibodies with Longer Serum Half-Lives in Primates", The Journal of Biological Chemistry, Feb. 20, 2004, 279(8):6213-6216.
Hoffman, "Subcutaneous Efgartigimod Shows Noninferiority to IV Formulation in Generalized Myasthenia Gravis", NeurologyLive, Retrieved from: https://web.archive.org/web/20220326043901/https://www.neurologylive.com/view/subcutaneous-efgartigimod-noninferior-iv-formulation-vygart-generalized-myasthenia-gravis, Mar. 23, 2022, 3 pages.
Howard et al., "A double-blind placebo-controlled study to evaluate safety and efficacy of FcRn antagonist ARGX-113 (efgartigimod) in generalized myasthenia gravis", 70th Annual Meeting of the American Academy of Neurology, AAN, 2018, 1 page.
Howard et al., "Randomized phase 2 study of FcRn antagonist efgartigimod in generalized myasthenia gravis", Neurology, Jun. 4, 2019, 92(23), pp. 1-8.
Howard Jr. et al., "A Randomized, Double-Blind, Placebo-Controlled Phase II Study of Eculizumab in Patients with Refractory Generalized Myasthenia Gravis", Muscle & Nerve, Jul. 2013, 48(1):76-84.
Howard Jr. et al., "Poster 133: Response to Coronavirus 2019 Vaccination in Patients Receiving Efgartigimod", Aanem, Sep. 21-24, 2022, 1 page.
Howard Jr. et al., "Safety, efficacy, and tolerability of efgartigimod in patients with generalised myasthenia gravis (Adapt): a multicentre, randomised, placebo-controlled, phase 3 trial", Lancet Neurology, Jul. 2021, 20(7):526-536.
Huang et al., "The central residues of a T cell receptor sequence motif are key determinants of autoantigen recognition in murine experimental autoimmune encephalomyelitis", Eur. J. Immunol., 2005, 35(1):299-304.
Hubbard et al., "Poster—97: Design of a Phase 2, Multicenter, Randomized, Placebo-Controlled, Double-blind Study to Assess the Efficacy and Safety of Nipocalimab, an FcRn Antagonist, in Adults with Primary Sjogrens Syndrome", Clinical and Experimental Rheumatology, 2022, 40:2477-2579.
Hutchins et al., "Improved biodistribution, tumor targeting, and reduced immunogenicity in mice with a gamma4 variant of Campath-1 H", Proc. Natl. Acad. Sci., Dec. 1995, 92:11980-11984.
Idusogie et al., "Engineered Antibodies with Increased Activity to Recruit Complement", The Journal of Immunology, 2001, 166(4):2571-2575.
Idusogie et al., "Mapping of the C1q binding site on rituxan, a chimeric antibody with a human IgG1 Fc", The Journal of Immunology, 2000, 164(8):4178-4184.
Imbach et al., "High-dose intravenous gammaglobulin for idiopathic thrombocytopeni purpura in childhood", The Lancet, Jun. 6, 1981, 317(8232):1228-1231.
Imbach et al., "Intravenous immunoglobulin versus oral corticosteroids in acute immune thrombocytopenia purpura in childhood", The Lancet, Aug. 31, 1985, 326(8453):464-468.
Imbach et al., "Intravenous immunoglobulins induce potentially synergistic immunomodulations in autoimmune disorders", Vox Sanguinis, 2009, pp. 1-10.

(56) References Cited

OTHER PUBLICATIONS

Imbach, "Treatment of immune thrombocytopenia with intravenous immunoglobulin and insights for other diseases: A historical review", Swiss Medical Weekly, May 31, 2012, pp. 1-10.
Ishii-Watabe et al., "Molecular Design of Therapeutics Monoclonal Antibodies", Journal of Pharmaceutical Science and Technology, Japan, 2014, 74(1):4-11 (English Abstract Submitted).
Israel et al., "Increased clearance of IgG in mice that lack Beta 2-microglobulin: possible protective role of FcRn", Immunology, 1996, 89(4):573-578.
Jacob et al., "Presence and Pathogenic Relevance of Antibodies to Clustered Acetylcholine Receptor in Ocular and Generalized Myasthenia Gravis", Arch Neurol., Aug. 2012, 69(8):994-1001.
Jain et al., "Fully recombinant IgG2a Fc multimers (stradomers) effectively treat collagen-induced arthritis and prevent idiopathic thrombocytopenia purpura in mice", Arthritis Research & Therapy, 2012, 14:R192, pp. 1-12.
Janeway et al., "The interaction of the antibody molecule with specific antigen", Immunobiology: The Immune System in Health and Disease. 5th edition., 2001, 5 pages.
Jaretzki III et al., "Myasthenia Gravis: Recommendations for Clinical Research Standards", Ann Thorac Surg., 2000, 70(1):327-334.
Jaretzki III et al., "Myasthenia gravis: recommendations for clinical research standards", Neurology, 2000, 55(1):16-23.
Jefferis et al., "Human immunoglobulin allotypes: Possible implications for immunogenicity", MAbs, Jul./Aug. 2009, 1(4):332-338.
Jefferis et al., "Interaction sites on human IgG-Fc for Fc gamma R: current models", Immunology Letters, 2002, 82:57-65.
Jefferis et al., "Modulation of Fc gamma R and human complement activation by IgG3-core oligosaccharide interactions", Immunology Letters, 1996, 54(2-3):101-104.
Jefferis et al., "Recognition sites on human IgG for Fc gamma receptors: the role of glycosylation", Immunology Letters, 1995, 44(2-3):111-117.
Joshi et al., "An Update on Disease Modifying Antirheumatic Drugs", Inflammation & Allergy—Drug Targets, 2014, 13(4):249-261.
Julien et al., "Abstract No. L10—Efgartigimod Prevents Necrosis and Allows for Muscle Fiber Regeneration in a Humanized Mouse Model of Immune-mediated Necrotizing Myopathy (IMNM)", Meeting—ACR Convergence, Oct. 18, 2022, pp. 1-4.
Junghans et al., "The protection receptor for IgG catabolismis the beta2-microglobulin-containing neonatal intestinal transport receptor", Proc. Natl. Acad. Sci., May 1996, 93(11):5512-5516.
Junghans, "Finally! The Brambell receptor (FcRB): Mediator of Transmission of Immunity and Protection from Catabolismfor IgG", Immunologic Research, 1997, 16(1):29-57.
Kabat et al., "Sequences of Proteins of Immunological Interest", 5th Edition, U.S. Department of Health and Human Services, 1991, (Title Page and Table of Contents), 11 pages.
Kabat et al., "Unusual Distributions of Amino Acids in Complementarity-determining (Hypervariable) Segments of Heavy and Light Chains of Immunoglobulins and Their Possible Roles in Specificity of Antibody-combining Sites", The Journal of Biological Chemistry, Oct. 10, 1977, 252(19):6609-6616.
Kanda et al., "Comparison of biological activity among nonfucosylated therapeutic IgG1 antibodies with three different N-linked Fc oligosaccharides: the high-mannose, hybrid, and complex types", Glycobiology, Sep. 29, 2006, 17(1):104-118.
Kaneko et al., "Anti-Inflammatory Activity of Immunoglobulin G Resulting from Fc Sialylation", Science, Aug. 4, 2006, 313(5787):670-673.
Kang et al., "Rapid Formulation Development for Monoclonal Antibodies", BioProcess International, Retrieved from: https://bioprocessintl.com/manufacturing/formulation/rapid-formulation-development-for-monoclonal-antibodies/, Apr. 12, 2016, 7 pages.
Kasperkiewicz et al., "Pemphigus", Nature Reviews Disease Primers, 2017, 3(Article No. 17026), pp. 1-40.

Kasprick et al., "Treatment with anti-neonatal Fc receptor (FcRn) antibody ameliorates experimental epidermolysis bullosa acquisita in mice", Br J Pharmacol., 2020, 177(10):2381-2392.
Khan et al., "Clinical Practice Updates in the Management of Immune Thrombocytopenia", P&T, Dec. 2017, 42(12):756-763.
Kiessling et al., "The FcRn inhibitor rozanolixizumab reduces human serum IgG concentration: A randomized phase 1 study", Sci. Transl. Med., Nov. 1, 2017, 9(414), pp. 1-12.
Kiessling et al., "Safety, Pharmacokinetics and Pharmacodynamics of the FCRN Inhibitor UCB7665: A Phase I Study", Journal of the Peripheral Nervous System, 2017, 22(3):226-414, 1 page.
Kim et al., "Localization of the site of the murine IgG1 molecule that is involved in binding to the murine intestinal Fc receptor", Eur. J. Immunol., 1994, 24(10):2429-2434.
Kim et al., "Mapping the site on human IgG for binding of the MHC class I-related receptor, FcRn", Eur. J. Immunol., 1999, 29:2819-2825.
Knoebl et al., "Pb2305-Efgartigimod: Clinical Development of a Novel FcRn Antagonist in the Treatment of Autoimmune Diseases", Hemasphere, 2022, 6:2175-2176.
Kobayashi et al., "FcRn-mediated transcytosis of immunoglobulin G in human renal proximal tubular epithelial cells", Am J Physiol Renal Physiol., 2002, 282:F358-F365.
Law et al., "High-Dose Intravenous Immune Globulin and The Response to Splenectomy in Patients with Idiopathic Thrombocytopeniaurpura", The New England Journal of Medicine, May 22, 1997, 336(21):1494-1498.
Li et al., "Complete FcRn dependence for intravenous Ig therapy in autoimmune skin blistering diseases", The Journal of Clinical Investigation, Dec. 2005, 115(12):3440-3450.
Li et al., "Myasthenia gravis: Newer therapies offer sustained improvement", Cleveland Clinic Journal of Medicine, Nov. 2013, 80(11):711-721.
Liu et al., "Amelioration of Experimental Autoimmune Myasthenia Gravis in Rats by Neonatal FcR Blockade", The Journal of Immunology, 2007, 178(8):5390-5398.
Liu et al., "Comparing the Autoantibody Levels and Clinical Efficacy of Double Filtration Plasmapheresis, Immunoadsorption, and Intravenous Immunoglobulin for the Treatment of Late-onset Myasthenia Gravis", Therapeutic Apheresis and Dialysis, 2010, 14(2):153-160.
Lobner et al., "Engineered IgG1-Fc—one fragment to bind them all", Immunological Reviews, 2016, 270(1):113-131.
Low et al., "Inhibitors of the FcRn:IgG Protein-Protein Interaction", The AAPS Journal, Sep. 2009, 11(3):432-434.
Lund et al., "Human Fc gamma RI and Fc gamma RII interact with distinct but overlapping sites on human IgG", J Immunol., Oct. 15, 1991, 147(8):2657-2662.
Lund et al., "Multiple binding sites on the CH2 Domain of IgG for Mouse Fc Gamma RII", Molecular Immunology, 1992, 29(1):53-59.
Lund et al., "Multiple interactions of IgG with its core oligosaccharide can modulate recognition by complement and human Fc gamma receptor I and influence the synthesis of its oligosaccharide chains", The Journal of Immunology, 1996, 157(11):4963-4969.
Lund et al., "Oligosaccharide-protein interactions in IgG can modulate recognition by Fc gamma receptors", The FASEB Journal, Aug. 2016, 9(1):115-119.
Lutterbach et al., "Lung Cancer Cell Lines Harboring MET Gene Amplification are Dependent on Met for Growth and Survival", Cancer Research, Mar. 1, 2007, 67(5):2081-2088.
MacCallum et al., "Antibody-antigen Interactions: Contact Analysis and Binding Site Topography", J. Mol. Biol., 1996, 262(5):732-745.
Maho-Vaillant et al., "FcRn Antagonism Leads to a Decrease of Desmoglein-Specific B Cells: Secondary Analysis of a Phase 2 Study of Efgartigimod in Pemphigus Vulgaris and Pemphigus Foliaceus", Frontiers in Immunology, May 2022, 13(Article 863095), pp. 1-14.
Martin et al., "Crystal Structure at 2.8 A of an FcRn/Heterodimeric Fc Complex: Mechanism of pH-Dependent Binding", Molecular Cell, Apr. 2001, 7(4):867-877.
Massachusetts General Hospital, "Supremol's Sm101 Shows a Sustained Clinical Activity and a Favorable Safety Profile in Pri-

(56) References Cited

OTHER PUBLICATIONS mary Immune Thrombocytopenia (ITP) Patients", Press Release. Evaluate Ltd., Dec. 10, 2012, 1 page.
McCarthy et al., "Bidirectional transcytosis of IgG by the rat neonatal Fc receptor expressed in a rat kidney cell line: a system to study protein transport across epithelia", Journal of Cell Science, 2000, 113(Pt 7):1277-1285.
Medesan et al., "Comparative studies of rat IgG to further delineate the Fc:FcRn interaction site", European Journal of Immunology, 1998, 28(7):2092-2100.
Medesan et al., "Delineation of the Amino Acid Residues Involved in Transcytosis and Catabolism of Mouse IgG1", The Journal of Immunology, 1997, 158(5):2211-2217.
Mendell et al., "Randomized controlled trial of IVIg in untreated chronic inflammatory demyelinating polyradiculoneuropathy", Neurology, Feb. 2001, 56(4):445-449.
Meriggioli et al., "Autoimmune myasthenia gravis: emerging clinical and biological heterogeneity", Lancet Neurol., May 2009, 8(5):475-490.
Mezo et al., "Reduction of IgG in nonhuman primates by a peptide antagonist of the neonatal Fc receptor FcRn", PNAS, Feb. 19, 2008, 105(7):2337-2342.
Mi et al., "Targeting the neonatal Fc receptor for antigen delivery using engineered Fc fragments", The Journal of Immunology, Dec. 1, 2008, 181(11):7550-7561.
Miyagawa, "Idiopathic Thrombocytopenia Purpura", Mebio., 2017, 34(6):102-107.
Mohamed et al., "Massive intravascular haemolysis after high dose intravenous immunoglobulin therapy", British Journal of Haematology, Jan. 7, 2013, 160(5):570, 1 page.
Monnet et al., "Combined glyco- and protein-Fc engineering simultaneously enhance cytotoxicity and half-life of a therapeutic antibody", mAbs, Mar./Apr. 2014, 6(2):422-436.
Montoyo et al., "Conditional deletion of the MHC class I-related receptor FcRn reveals the sites of IgG homeostasis in mice", PNAS, Feb. 24, 2009, 106(8):2788-2793.
Morea et al., "Antibody Modeling: Implications for Engineering and Design", Methods, 2000, 20(3):267-279.
Newburger et al., "Diagnosis, Treatment, and Long-Term Management of Kawasaki Disease: A Statement for Health Professionals From the Committee on Rheumatic Fever, Endocarditis, and Kawasaki Disease, Council on Cardiovascular Disease in the Young, American Heart Association", Pediatrics, Dec. 2004, 114(6):1708-1733.
Newland et al., "High-Dose Intravenous IgG in Adults with Autoimmune Thrombocytopenia", The Lancet, Jan. 15, 1983, 321(8316):84-87.
Newland et al., "Phase 2 study of efgartigimod, a novel FcRn antagonist, in adult patients with primary immune thrombocytopenia", Am J Hematol., 2020, 95(2):178-187.
Nieswandt et al., "Acute Systemic Reaction and Lung Alterations Induced by an Antiplatelet Integrin gpIIb/IIIa Antibody in Mice", Blood, Jul. 15, 1999, 94(2):684-693.
Niknami et al., "Beneficial effect of a multimerized immunoglobulin Fc in an animal model of inflammatory neuropathy (experimental autoimmune neuritis)", Journal of the Peripheral Nervous System, 2013, 18(2):141-152.
Ober et al., "Exocytosis of IgG as mediated by the receptor, FcRn: An analysis at the single-molecule level", PNAS, Jul. 27, 2004, 101(30):11076-11081.
Ober et al., "Visualizing the Site and Dynamics of IgG Salvage by the MHC class I-Related Receptor, FcRn", The Journal of Immunology, 2004, 172:2021-2029.
Olaru et al., "Neonatal Fc Receptor Promotes Immune Complex-Mediated Glomerular Disease", J Am Soc Nephrol, 2014, 25(5):918-925.
Oshima et al., "Characterization of murine CD70 by molecular cloning and mAb", International Immunology, 1998, 10(4):517-526.
Patel et al., "FcRn blockade by Fc engineering ameliorates arthritis in a murine model", J Immunol., Jul. 15, 2011, 187(2):1015-1022.
Patel et al., "Neonatal Fc receptor blockade by Fc engineering ameliorates arthritis in a murine model", The Journal of Immunology, 2011, 187(2):1015-1022.
Patel et al., "Neonatal Fc receptor in human immunity: Function and role in therapeutic intervention", J Allergy Clin Immunol., Sep. 2020, 146(3):467-478.
Peene et al., "AB0520: Treatment of Primary Sjogren's Syndrome by Inhibiting FcRn: A Phase 2 Randomized, Placebo Controlled, Double-Blind, Proof of Concept Study with Efgartigimod", Scientific Abstracts, May 30, 2023, 1455-1456.
Peter et al., "Targeting FcRn for immunomodulation: Benefits, risks, and practical considerations", J. Allergy Clin. Immunol., Sep. 2020, 146(3):479-491.
Pevzner et al., "Anti-LRP4 autoantibodies in AChR-and MuSK-antibody-negative myasthenia gravis", J. Neurol., 2012, 259(3):427-435.
Polanco et al., "Spontaneous Remission of Nephrotic Syndrome in Idiopathic Membranous Nephropathy", J Am Soc Nephrol., 2010, 21(4):697-704.
Popov et al., "The Stoichiometry and Affinity of the Interaction of Murine Fc Fragments with the MHC Class I-Related receptor, FcRn", Molecular Immunology, 1996, 33(6):521-530.
Prabhat et al., "Elucidation of intracellular recycling pathways leading to exocytosis of the Fc receptor, FcRn, by using multifocal plane microscopy", PNAS, Apr. 3, 2007, 104(14):5889-5894.
Press Release "argenx Announces Approval of Vyvgart (efgartigimod alfa) in Japan for Adults with Primary Immune Thrombocytopenia", Mar. 26, 2024, 4 pages.
Press Release "argenx Reports Topline Results from Address Study of Efgartigimod SC in Pemphigus", Dec. 20, 2023, 5 pages.
Press Release "argenx Reports Topline Results from Advance-SC Study of Vyvgart Hytrulo in Primary Immune Thrombocytopenia", Nov. 28, 2023, 4 pages.
Press Release, "argenx Advances Clinical Development of Efgartigimod in Primary Sjogren's Disease", Mar. 27, 2024, 3 pages.
Press Release, "argenx Advances Clinical Development of Efgartigimod SC in Idiopathic Inflammatory Myopathies", Nov. 20, 2024, 3 pages.
Press Release, "argenx and Zai Lab Announce Approval of Efgartigimod Alfa Injection (Subcutaneous Injection) for Generalized Myasthenia Gravis in China", Jul. 16, 2024, 4 pages.
Press Release, "argenx and Zai Lab Announce Approval of Vyvgart Hytrulo for Chronic Inflammatory Demyelinating Polyneuropathy in China", Nov. 11, 2024, 4 pages.
Press Release, "argenx Announces Approval of Vyvdura (efgartigimod alfa and hyaluronidase-qvfc) in Japan for Adults with Chronic Inflammatory Demyelinating Polyneuropathy", Dec. 27, 2024, 4 pages.
Press Release, "argenx Announces FDA Approval of Vyvgart Hytrulo for Chronic Inflammatory Demyelinating Polyneuropathy", Jun. 21, 2024, 5 pages.
Press Release, "argenx Announces Publication in The Lancet Neurology of Pivotal Adhere Study Data in Chronic Inflammatory Demyelinating Polyneuropathy", Sep. 19, 2024, 5 pages.
Press Release, "argenx Data Highlight Evidence that Vyvgart and Vyvgart Hytrulo Drive Transformative Outcomes for Patients with Debilitating Autoimmune Disease", Apr. 16, 2024, 6 pages.
Press Release, "argenx Highlights 2025 Strategic Priorities", Jan. 13, 2025, 7 pages.
Press Release, "argenx Highlights Breadth of Autoimmune Pipeline with New Multifocal Motor Neuropathy Data at 2024 Peripheral Nerve Society Annual Meeting", Jun. 25, 2024, 5 pages.
Press Release, "argenx Highlights Data Showing Patient Impact Across Multiple Immunology Programs at 2024 American Association of Neuromuscular & Electrodiagnostic Medicine Annual Meeting and Myasthenia Gravis Foundation of America Scientific Sessions", Oct. 15, 2024, 9 pages.
Press Release, "argenx Reports First Quarter 2024 Financial Results and Provides Business Update", May 9, 2024, 7 pages.

(56) References Cited

OTHER PUBLICATIONS

Press Release, "argenx Reports Half Year 2024 Financial Results and Provides Second Quarter Business Update", Jul. 25, 2024, 7 pages.
Press Release, "argenx Reports Third Quarter 2024 Financial Results and Provides Business Update", Oct. 31, 2024, 8 pages.
Press Release, "argenx to unveil its 'Vision 2030: Taking Breakthrough Science to 50,000 Patients' during its Upcoming R&D Day on Jul. 16, 2024", Jun. 17, 2024, 4 pages.
Presta et al., "Engineering therapeutic antibodies for improved function", Biochemical Society Transactions, 2002, 30(4):487-490.
Putnam et al., "Proteins In Multiple Myeloma: VIII. Biosynthesis of Abnormal Proteins", J. Biol. Chem., 1958, 231(2):671-684.
Pyzik et al., "The Neonatal Fc Receptor (FcRn): A Misnomer?", Frontiers in Immunology, Jul. 10, 2019, 10(Article 1540), pp. 1-24.
Raghavan et al., "Analysis of the pH Dependence of the Neonatal Fc Receptor/Immunoglobulin G Interaction Using Antibody and Receptor Variants", Biochemistry, 1995, 34(45):14649-14657.
Reddy et al., "Elimination of Fc Receptor-Dependent Effector Functions of a Modified IgG4 Monoclonal Antibody to Human CD4", The Journal of Immunology, 2000, 164(4):1925-1933.
Robak et al., "Efficacy and safety of a new intravenous immunoglobulin 10% formulation (octagam 10%) in patients with immune thrombocytopenia", Hematology, 2010, 15(5):351-359.
Robak et al., "Phase II, Multiple-Dose Study of Anti-FcRn Antibody, Rozanolixizumab (UCB7665), in Patients with Primary Immune Thrombocytopenia: Interim Analysis", Blood, Dec. 7, 2017, 130(Suppl. 1):15, 8 pages.
Robak et al., "Single-Agent Ibrutinib Vs Chemoimmunotherapy Regimens for Treatment-Naive Patients with Chronic Lymphocytic Leukemia (CLL): A Cross-Trial Comparison", Blood, Dec. 7, 2017, 130(Suppl. 1):1750, 6 pages.
Rojas-Rivera et al., "Recent Clinical Trials Insights into the Treatment of Primary Membranous Nephropathy", Drugs, 2022, 82(2):109-132.
Roopenian et al., "FcRn: the neonatal Fc receptor comes of age", Nature Reviews, Immunology, Sep. 2007, 7(9):715-725.
Roopenian et al., "The MHC class I-like IgG Receptor Controls Perinatal IgG Transport, IgG Homeostasis, and Fate of IgG-Fc-Coupled Drugs", The Journal of Immunology, May 2003, 170(7):3528-3533.
Rosenwasser et al., "Anti-CD23", Clinical Reviews in Allergy and Immunology, 2005, 29(1):61-72.
Roux et al., "Comparisons of the Ability of Human IgG3 Hinge Mutants, IgM, IgE, and IgA2, to Form Small Immune Complexes: A Role for Flexibility and Geometry", The Journal of Immunology, 1998, 161(8):4083-4090.
Rudikoff et al., "Single amino acid substitution altering antigen-binding specificity", Proc. Natl. Acad. Sci., Mar. 1982, 79(6):1979-1983.
Samuelsson et al., "Anti-inflammatory Activity of IVIG Mediated Through the Inhibitory Fc Receptor", Science, Jan. 19, 2001, 291(5503):484-486.
Schwab et al., "Intravenous immunoglobulin therapy: how does IgG modulate the immune system?", Nature Reviews, Immunology, Mar. 2013, 13(3):176-189.
Seidling et al., "Analysis of High-dose Intravenous Immunoglobulin Therapy in 16 Patients with Refractory Autoimmune Blistering Skin Disease: High Efficacy and No Serious Adverse Events", Acta Derm Venereol., 2013, 93(3):346-349.
Semple, "Animal models of immune thrombocytopenia (ITP)", Annals of Hematology, 2010, 89(Suppl 1):S37-S44.
Sesarman et al., "The neonatal Fc receptor as therapeutic target in IgG-mediated autoimmune diseases", Cell. Mol. Life Sci., 2010, 67(15):2533-2550.
Sewell, "First National Immunoglobulin Database Report (2008-2009)", Department of Health, Jan. 2010, 82 pages.
Shang et al., "Modular protein expression by RNA trans-splicing enables flexible expression of antibody formats in mammalian cells from a dual-host phage display vector", Protein Engineering, Design & Selection, 2015, 28(10):437-444.
Shelton, "Acquired myasthenia gravis: what we have learned from experimental and spontaneous animal models", Veterinary Immunology and Immunopathology, 1999, 69(2-4):239-249.
Shields et al., "High resolution mapping of the binding site on human IgG1 for Fc gamma RI, Fc gamma RII, Fc gamma RIII, and FcRn and design of IgG1 variants with improved binding to the Fc gamma R", The Journal of Biological Chemistry, Mar. 2, 2001, 276(9):6591-6604.
Silvestri et al., "Treatment-Refractory Myasthenia Gravis", Journal of Clinical Neuromuscular Disease, Jun. 2014, 15(4):167-178.
Sockolosky et al., "The neonatal Fc receptor, FcRn, as a target for drug delivery and therapy", Advanced Drug Delivery Reviews, 2015, 91:109-124.
Soliven, "Autoimmune neuropathies: insights from animal models", Journal of the Peripheral Nervous System, 2012, 17(Supplement):28-33.
Sordé et al., "Massive immune response against IVIg interferes with response against other antigens in mice: A new mode of action?", PLoS One, Oct. 12, 2017, 12(10):e0186046, pp. 1-15.
Spiekermann et al., "Receptor-mediated Immunoglobulin G Transport Across Mucosal Barriers in Adult Life: Functional Expression of FcRn in the Mammalian Lung", J. Exp. Med., Aug. 5, 2002, 196(3):303-310.
Stamos et al., "Crystal structure of the HGF Beta-chain in complex with the Sema domain of the Met receptor", EMBO Journal, 2004, 23(12):2325-2335.
Swiercz et al., "Use of Fc-Engineered Antibodies as Clearing Agents to Increase Contrast During PET", The Journal of Nuclear Medicine, Jul. 2014, 55(7):1204-1207.
Tavakolpour, "Current and future treatment options for pemphigus: Is it time to move towards more effective treatments?", International Immunopharmacology, 2017, 53:133-142.
Tramontano et al., "Framework Residue 71 is a Major Determinant of the Position and Conformation of the Second Hypervariable Region in the VH Domains of Immunoglobulins", J. Mol. Biol., 1990, 215(1):175-182.
Ulrichts et al., "ARGX-113, a Novel Fc-Based Approach for Antibody-Induced Pathologies Such as Primary Immune Thrombocytopenia", Blood, Dec. 2, 2016, 128(22):4919, 6 pages.
Ulrichts et al., "ARGX-113: Towards a Safe and Selective Elimination of Pathogenic Autoantibodies", 13th International Conference on Myasthenia Gravis and Related Disorders, New York, Poster Presentation, May 15-17, 2017, 1 page.
Ulrichts et al., "Neonatal Fc receptor antagonist efgartigimod safely and sustainably reduces IgGs in humans", The Journal of Clinical Investigation, 2018, 128(10):4372-4386.
Ulrichts et al., "Supplementary Data Neonatal Fc receptor antagonist efgartigimod safely and sustainably reduces IgGs in humans", J. Clin. Invest., Supplementary Data, 2018, 128(10):4372-4386, pp. 1-15.
Vaccaro et al., "Divergent activities of an engineered antibody in murine and human systems have implications for therapeutic antibodies", PNAS, Dec. 5, 2006, 103(49):18709-18714.
Vaccaro et al., "Engineering the Fc region of immunoglobulin G to modulate in vivo antibody levels", Nature Biotechnology, Oct. 2005, 23(10):1283-1288.
Van Der Meché et al., "A randomized trial comparing intravenous immune globulin and plasma exchange in Guillain-Barré syndrome", New England Journal of Medicine, Apr. 23, 1992, 326(17):1123-1129.
Van Der Woning, "R&D Day: Fifth Efgartigimod Indication: Myositis", Argenx, Jul. 20, 2021, pp. 23-37.
Van Faassen et al., "Serum albumin-binding VHHs with variable pH sensitivities enable tailored half-life extension of biologics", The FASEB Journal, 2020, 34(6):8155-8171.
Verschuuren et al., "A double-blind placebocontrolled study to evaluate safety and efficacy of fcrn antagonist ARGX-113 in generalized MG", Journal of Neuromuscular Diseases, 2018, 5(Supplement 1):S327-S328.
Vitetta et al., "Considering Therapeutic Antibodies", Science, Jul. 21, 2006, 313(2):308-309.

(56) References Cited

OTHER PUBLICATIONS

Wang et al., "Antibody Structure, Instability, and Formulation", Journal of Pharmaceutical Sciences, Jan. 2007, 96(1):1-26.
Wang, "Protein aggregation and its inhibition on biopharmaceutics", International Journal of Pharmaceutics, 2005, 289(1-2):1-30.
Wani et al., "Familial hypercatabolic hypoproteinemia caused by deficiency of the neonatal Fc receptor, FcRn, due to a mutant Beta2-microglobulin gene", PNAS, Mar. 28, 2006, 103(13):5084-5989.
Ward et al., "Multitasking by Exploitation of Intracellular Transport Functions: The Many Faces of FcRn", Chapter 4, Advances in Immunology, 2009, 103:77-115.
Warne, "Development of high concentration protein biopharmaceuticals: The use of platform approaches in formulation development", European Journal of Pharmaceutics and Biopharmaceutics, 2011, 78(2):208-212.
Weiner et al., "Tunable antibodies", Nature Biotechnology, May 2005, 23(5):556-557.
Wittlin et al., "Pharmacokinetic/Pharmacodynamic Simulations Guide Selection of the Dose for Administration of Efgartigimod Subcutaneously in a Phase 3 Clinical Trial in Patients with Primary Immune Thrombocytopenia", British Journal of Haematology, Abstract of the 62nd Annual Scientific Meeting of The British Society for Haematology, Apr. 1, 2022, 197(Suppl. 1):44.
Woods Jr. et al., "Autoantibodies Against Platelet Glycoprotein Ib in Patients With Chronic Immune Thrombocytopenia Purpura", Blood, Jul. 1984, 64(1):156-160.
Xu et al., "In Vitro Characterization of Five Humanized OKT3 Effector Function Variant Antibodies", Cellular Immunology, 2000, 200(1):16-26.
Yamane-Ohnuki et al., "Establishment of FUTB Knockout Chinese Hamster Ovary Cells: An Ideal Host Cell Line for Producing Completely Defucosylated Antibodies With Enhanced Antibody-Dependent Cellular Cytotoxicity", Biotechnology and Bioengineering, Sep. 5, 2004, 87(5):614-622.
Yang et al., "Non-radioactive serological diagnosis of myasthenia gravis and clinical features of patients from Tianjin, China", Journal of Neurological Sciences, 2011, 301(1-2):71-76.
Ying et al., "Engineered Soluble Monomeric IgG1 CH3 Domain", Journal of Biological Chemistry, Aug. 30, 2013, 288(35):25154-25164.
Ying et al., "Soluble Monomeric IgG1 Fc", The Journal of Biological Chemistry, Jun. 1, 2012, 287(23):19399-19408.
Yoshida et al., "Human Neonatal Fc Receptor Mediates Transport of IgG into Luminal Secretions for Delivery of Antigens to Mucosal Dendritic Cells", Immunity, Jun. 2004, 20(6):769-783.
Zhang et al., "Autoantibodies to Lipoprotein-Related Protein in Patients with Double-Seronegative Myasthenia Gravis", Arch Neurol., 2012, 69(4):445-451.
Zhou et al., "Conferring the Binding Properties of the Mouse MHC class I-related Receptor, FcRn, onto the Human Ortholog by Sequential Rounds of Site-directed Mutagenesis", J. Mol. Biol., 2005, 345(5):1071-1081.
Zhou et al., "Generation of Mutated Variants of the Human Form of the MHC Class I-related Receptor, FcRn, with Increased Affinity for Mouse Immunoglobulin G" J. Mol. Biol., 2003, 332(4):901-913.
Zinman et al., "IV immunoglobulin in patients with myasthenia gravis: A randomized controlled trial", Neurology, Mar. 13, 2007, 68(11):837-841.
"Corrected Filing Receipt for U.S. Appl. No. 61/920,547 dated Apr. 16, 2015", Document D27 submitted with Notice of Opposition for European Patent No. 3087095 (U.S. Appl. No. 61/920,547), dated May 7, 2020, 3 pages.
"Corrected Filing Receipt for U.S. Appl. No. 61/920,547 dated Apr. 18, 2014", Document D26 submitted with to Notice of Opposition for European Patent No. 3087095 (U.S. Appl. No. 61/920,547), dated May 7, 2020, 3 pages.
"Cover Letter to the European Patent Office" for European Patent No. 3087095 (Application No. 14827372.5), dated Oct. 28, 2020, 1 page.
"Filing Receipt for U.S. Appl. No. 61/920,547 dated Jan. 21, 2014", Document D25 submitted with Notice of Opposition for European Patent No. 3087095 (U.S. Appl. No. 61/920,547), dated May 7, 2020, 3 pages.
"Inventor Assignment of U.S. Appl. No. 61/920,547 to arGEN-X B.V. executed Oct. 31, 2014 and Nov. 4, 2014", Document D29 submitted with Notice of Opposition for European Patent No. 3087095 (U.S. Appl. No. 61/920,547), dated May 7, 2020, 10 pages.
"Inventor Assignment of U.S. Appl. No. 61/920,547 to The Board of Regents of the University of Texas System executed Dec. 23, 2014", Document D28 submitted with Notice of Opposition for European Patent No. 3087095 (U.S. Appl. No. 61/920,547), dated May 7, 2020, 4 pages.
"Notice of Opposition" to European Patent No. 3087095 (Application No. 14827372.5), dated May 7, 2020, 47 pages.
"Online Filing Acknowledgement for Notice of Opposition" for European Patent No. 3087095 (Application No. 14827372.5), dated May 7, 2020, 3 pages.
"Online Filing Acknowledgement for Reply to Notice of Opposition" for European Patent No. 3087095 (Application No. 14827372.5), dated Oct. 28, 2020, 2 pages.
"PCT Request for as filed for PCT/US2014/072087 on Dec. 23, 2014", Document D34 submitted with Notice of Opposition for European Patent No. 3087095 (Application No. 14827372.5), dated May 7, 2020, 6 pages.
"Proof of Employment for Inventor/Applicant Sally Ward", Document D40 submitted with Reply to Notice of Opposition for European Patent No. 3087095 (Application No. 14827372.5), dated Oct. 28, 2020, 1 page.
"Reply to Notice of Opposition" for European Patent No. 3087095 (Application No. 14827372.5), dated Oct. 28, 2020, 35 pages.
"Rule 90101 of the Rules and Regulations of the Board of Regents of the University of Texas System governing intellectual property" dated Feb. 27, 2012, Document D41 submitted with Reply to Notice of Opposition for European Patent No. 3087095 (Application No. 14827372.5), on Oct. 28, 2020, 21 pages.
International Preliminary Report on Patentability received for PCT Patent Application No. PCT/EP2013/068399, mailed on Mar. 10, 2015, 10 pages.
International Preliminary Report on Patentability received for PCT Patent Application No. PCT/EP2018/084034, mailed on Jun. 18, 2020, 11 pages.
International Preliminary Report on Patentability received for PCT Patent Application No. PCT/EP2020/065716, mailed on Dec. 16, 2021, 8 pages.
International Preliminary Report on Patentability received for PCT Patent Application No. PCT/IB2016/000398, mailed on Sep. 21, 2017, 11 pages.
International Preliminary Report on Patentability received for PCT Patent Application No. PCT/IB2019/054786, mailed on Dec. 17, 2020, 15 pages.
International Preliminary Report on Patentability received for PCT Patent Application No. PCT/US2006/021456, mailed on Dec. 6, 2007, 8 pages.
International Preliminary Report on Patentability received for PCT Patent Application No. PCT/US2014/072087, mailed on Jul. 7, 2016, 8 pages.
International Search Report and Written Opinion received for PCT Patent Application No. PCT/EP2013/068399, mailed on Apr. 9, 2014, 16 pages.
International Search Report and Written Opinion received for PCT Patent Application No. PCT/EP2017/077966, mailed Jan. 29, 2018, 12 pages.
International Search Report and Written Opinion received for PCT Patent Application No. PCT/EP2018/084034, mailed Feb. 18, 2019, 15 pages.
International Search Report and Written Opinion received for PCT Patent Application No. PCT/EP2020/065716, mailed Sep. 14, 2020, 10 pages.
International Search Report and Written Opinion received for PCT Patent Application No. PCT/EP2021/050275, mailed Apr. 8, 2021, 13 pages.

(56) References Cited

OTHER PUBLICATIONS

International Search Report and Written Opinion received for PCT Patent Application No. PCT/EP2023/050980, mailed on Apr. 12, 2023, 13 pages.
International Search Report and Written Opinion received for PCT Patent Application No. PCT/EP2023/054065, mailed on May 3, 2023, 14 pages.
International Search Report and Written Opinion received for PCT Patent Application No. PCT/EP2023/061012, mailed on Aug. 3, 2023, 15 pages.
International Search Report and Written Opinion received for PCT Patent Application No. PCT/EP2023/066162, mailed on Aug. 25, 2023, 18 pages.
International Search Report and Written Opinion received for PCT Patent Application No. PCT/EP2023/066163, mailed on Sep. 27, 2023, 22 pages.
International Search Report and Written Opinion received for PCT Patent Application No. PCT/EP2023/066180, mailed on Nov. 17, 2023, 19 pages.
International Search Report and Written Opinion received for PCT Patent Application No. PCT/IB2016/000398, mailed on Aug. 22, 2016, 16 pages.
International Search Report and Written Opinion received for PCT Patent Application No. PCT/IB2019/054786, mailed on Dec. 18, 2019, 27 pages.
International Search Report and Written Opinion received for PCT Patent Application No. PCT/IB2022/000443, mailed on Mar. 6, 2023, 29 pages.
International Search Report and Written Opinion received for PCT Patent Application No. PCT/IB2023/000679, mailed on Apr. 3, 2024, 17 pages.
International Search Report and Written Opinion received for PCT Patent Application No. PCT/IB2023/000688, mailed on Apr. 29, 2024, 16 pages.
International Search Report and Written Opinion received for PCT Patent Application No. PCT/IB2023/000696, mailed on Jun. 4, 2024, 21 pages.
International Search Report and Written Opinion received for PCT Patent Application No. PCT/IB2024/000018, mailed on May 24, 2024, 16 pages.
International Search Report and Written Opinion received for PCT Patent Application No. PCT/IB2024/000041, mailed on Jun. 3, 2024, 14 pages.
International Search Report and Written Opinion received for PCT Patent Application No. PCT/IB2024/000120, dated Jul. 15, 2024, 14 pages.
International Search Report and Written Opinion received for PCT Patent Application No. PCT/US2006/021456, mailed on Nov. 17, 2006, 8 pages.
International Search Report and Written Opinion received for PCT Patent Application No. PCT/US2014/072087, mailed on May 12, 2015, 14 pages.
Invitation to Pay Additional Fees received for PCT Patent Application No. PCT/EP2023/066180, mailed Sep. 27, 2023, 13 pages.
Invitation to Pay Additional Fees received for PCT Patent Application No. PCT/IB2023/000696, mailed on Apr. 12, 2024, 15 pages.

* cited by examiner

```
                              SEQUENCE LISTING

Sequence total quantity: 182
SEQ ID NO: 1             moltype = AA  length = 221
FEATURE                  Location/Qualifiers
source                   1..221
                         mol_type = protein
                         organism = synthetic construct
SEQUENCE: 1
CPPCPAPELL GGPSVFLFPP KPKDTLYITR EPEVTCVVVD VSHEDPEVKF NWYVDGVEVH   60
NAKTKPREEQ YNSTYRVVSV LTVLHQDWLN GKEYKCKVSN KALPAPIEKT ISKAKGQPRE  120
PQVYTLPPSR DELTKNQVSL TCLVKGFYPS DIAVEWESNG QPENNYKTTP PVLDSDGSFF  180
LYSKLTVDKS RWQQGNVFSC SVMHEALKFH YTQKSLSLSP G                     221

SEQ ID NO: 2             moltype = AA  length = 227
FEATURE                  Location/Qualifiers
source                   1..227
                         mol_type = protein
                         organism = synthetic construct
SEQUENCE: 2
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALKFHYTQKS LSLSPGK                227

SEQ ID NO: 3             moltype = AA  length = 226
FEATURE                  Location/Qualifiers
source                   1..226
                         mol_type = protein
                         organism = synthetic construct
SEQUENCE: 3
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALKFHYTQKS LSLSPG                 226

SEQ ID NO: 4             moltype = AA  length = 221
FEATURE                  Location/Qualifiers
source                   1..221
                         mol_type = protein
                         organism = synthetic construct
SEQUENCE: 4
CPPCPAPELL GGPSVFLFPP KPKDTLYITR EPEVTCVVVD VSHEDPEVKF NWYVDGVEVH   60
NAKTKPREEQ YNSTYRVVSV LTVLHQDWLN GKEYKCKVSN KALPAPIEKT ISKAKGQPRE  120
PQVYTLPPSR DELTKNQVSL WCLVKGFYPS DIAVEWESNG QPENNYKTTP PVLDSDGSFF  180
LYSKLTVDKS RWQQGNVFSC SVMHEALKFH YTQKSLSLSP G                     221

SEQ ID NO: 5             moltype = AA  length = 226
FEATURE                  Location/Qualifiers
source                   1..226
                         mol_type = protein
                         organism = synthetic construct
SEQUENCE: 5
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLWCLVK GFYPSDIAVE WESNGQPENN YKTTPPVLDS  180
```

```
DGSFFLYSKL TVDKSRWQQG NVFSCSVMHE ALKFHYTQKS LSLSPG              226

SEQ ID NO: 6               moltype = AA  length = 227
FEATURE                    Location/Qualifiers
source                     1..227
                           mol_type = protein
                           organism = synthetic construct
SEQUENCE: 6
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLWCLVK GFYPSDIAVE WESNGQPENN YKTTPPVLDS  180
DGSFFLYSKL TVDKSRWQQG NVFSCSVMHE ALKFHYTQKS LSLSPGK             227

SEQ ID NO: 7               moltype = AA  length = 221
FEATURE                    Location/Qualifiers
source                     1..221
                           mol_type = protein
                           organism = synthetic construct
SEQUENCE: 7
CPPCPAPELL GGPSVFLFPP KPKDTLYITR EPEVTCVVVD VSHEDPEVKF NWYVDGVEVH   60
NAKTKPREEQ YNSTYRVVSV LTVLHQDWLN GKEYKCKVSN KALPAPIEKT ISKAKGQPRE  120
PQVYTLPPSR DELTKNQVSL SCAVKGFYPS DIAVEWESNG QPENNYKTTP PVLDSDGSFF  180
LVSKLTVDKS RWQQGNVFSC SVMHEALKFH YTQKSLSLSP G                  221

SEQ ID NO: 8               moltype = AA  length = 226
FEATURE                    Location/Qualifiers
source                     1..226
                           mol_type = protein
                           organism = synthetic construct
SEQUENCE: 8
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLSCAVK GFYPSDIAVE WESNGQPENN YKTTPPVLDS  180
DGSFFLVSKL TVDKSRWQQG NVFSCSVMHE ALKFHYTQKS LSLSPG              226

SEQ ID NO: 9               moltype = AA  length = 227
FEATURE                    Location/Qualifiers
source                     1..227
                           mol_type = protein
                           organism = synthetic construct
SEQUENCE: 9
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLSCAVK GFYPSDIAVE WESNGQPENN YKTTPPVLDS  180
DGSFFLVSKL TVDKSRWQQG NVFSCSVMHE ALKFHYTQKS LSLSPGK             227

SEQ ID NO: 10              moltype = AA  length = 5
FEATURE                    Location/Qualifiers
source                     1..5
                           mol_type = protein
                           organism = synthetic construct
SEQUENCE: 10
SFGMS                                                            5

SEQ ID NO: 11              moltype = AA  length = 17
FEATURE                    Location/Qualifiers
source                     1..17
                           mol_type = protein
                           organism = synthetic construct
SEQUENCE: 11
SISGSGSDTL YADSVKG                                              17

SEQ ID NO: 12              moltype = AA  length = 6
FEATURE                    Location/Qualifiers
source                     1..6
                           mol_type = protein
                           organism = synthetic construct
SEQUENCE: 12
GGSLSR                                                           6

SEQ ID NO: 13              moltype = AA  length = 5
FEATURE                    Location/Qualifiers
source                     1..5
                           mol_type = protein
                           organism = synthetic construct
SEQUENCE: 13
AFGMS                                                            5

SEQ ID NO: 14              moltype = AA  length = 5
```

```
FEATURE                Location/Qualifiers
source                 1..5
                       mol_type = protein
                       organism = synthetic construct
SEQUENCE: 14
SAGMS                                                                          5

SEQ ID NO: 15          moltype = AA  length = 5
FEATURE                Location/Qualifiers
source                 1..5
                       mol_type = protein
                       organism = synthetic construct
SEQUENCE: 15
SFAMS                                                                          5

SEQ ID NO: 16          moltype = AA  length = 5
FEATURE                Location/Qualifiers
source                 1..5
                       mol_type = protein
                       organism = synthetic construct
SEQUENCE: 16
SFGAS                                                                          5

SEQ ID NO: 17          moltype = AA  length = 5
FEATURE                Location/Qualifiers
source                 1..5
                       mol_type = protein
                       organism = synthetic construct
SEQUENCE: 17
SFGMA                                                                          5

SEQ ID NO: 18          moltype = AA  length = 17
FEATURE                Location/Qualifiers
source                 1..17
                       mol_type = protein
                       organism = synthetic construct
SEQUENCE: 18
AISGSGSDTL YADSVKG                                                            17

SEQ ID NO: 19          moltype = AA  length = 17
FEATURE                Location/Qualifiers
source                 1..17
                       mol_type = protein
                       organism = synthetic construct
SEQUENCE: 19
SASGSGSDTL YADSVKG                                                            17

SEQ ID NO: 20          moltype = AA  length = 17
FEATURE                Location/Qualifiers
source                 1..17
                       mol_type = protein
                       organism = synthetic construct
SEQUENCE: 20
SIAGSGSDTL YADSVKG                                                            17

SEQ ID NO: 21          moltype = AA  length = 17
FEATURE                Location/Qualifiers
source                 1..17
                       mol_type = protein
                       organism = synthetic construct
SEQUENCE: 21
SISASGSDTL YADSVKG                                                            17

SEQ ID NO: 22          moltype = AA  length = 17
FEATURE                Location/Qualifiers
source                 1..17
                       mol_type = protein
                       organism = synthetic construct
SEQUENCE: 22
SISGAGSDTL YADSVKG                                                            17

SEQ ID NO: 23          moltype = AA  length = 17
FEATURE                Location/Qualifiers
source                 1..17
                       mol_type = protein
                       organism = synthetic construct
SEQUENCE: 23
SISGSASDTL YADSVKG                                                            17
```

```
SEQ ID NO: 24            moltype = AA   length = 17
FEATURE                  Location/Qualifiers
source                   1..17
                         mol_type = protein
                         organism = synthetic construct
SEQUENCE: 24
SISGSGADTL YADSVKG                                                           17

SEQ ID NO: 25            moltype = AA   length = 17
FEATURE                  Location/Qualifiers
source                   1..17
                         mol_type = protein
                         organism = synthetic construct
SEQUENCE: 25
SISGSGSATL YADSVKG                                                           17

SEQ ID NO: 26            moltype = AA   length = 17
FEATURE                  Location/Qualifiers
source                   1..17
                         mol_type = protein
                         organism = synthetic construct
SEQUENCE: 26
SISGSGSDAL YADSVKG                                                           17

SEQ ID NO: 27            moltype = AA   length = 17
FEATURE                  Location/Qualifiers
source                   1..17
                         mol_type = protein
                         organism = synthetic construct
SEQUENCE: 27
SISGSGSDTA YADSVKG                                                           17

SEQ ID NO: 28            moltype = AA   length = 17
FEATURE                  Location/Qualifiers
source                   1..17
                         mol_type = protein
                         organism = synthetic construct
SEQUENCE: 28
SISGSGSDTL AADSVKG                                                           17

SEQ ID NO: 29            moltype = AA   length = 17
FEATURE                  Location/Qualifiers
source                   1..17
                         mol_type = protein
                         organism = synthetic construct
SEQUENCE: 29
SISGSGSDTL YAASVKG                                                           17

SEQ ID NO: 30            moltype = AA   length = 17
FEATURE                  Location/Qualifiers
source                   1..17
                         mol_type = protein
                         organism = synthetic construct
SEQUENCE: 30
SISGSGSDTL YADAVKG                                                           17

SEQ ID NO: 31            moltype = AA   length = 17
FEATURE                  Location/Qualifiers
source                   1..17
                         mol_type = protein
                         organism = synthetic construct
SEQUENCE: 31
SISGSGSDTL YADSAKG                                                           17

SEQ ID NO: 32            moltype = AA   length = 17
FEATURE                  Location/Qualifiers
source                   1..17
                         mol_type = protein
                         organism = synthetic construct
SEQUENCE: 32
SISGSGSDTL YADSVAG                                                           17

SEQ ID NO: 33            moltype = AA   length = 17
FEATURE                  Location/Qualifiers
source                   1..17
                         mol_type = protein
                         organism = synthetic construct
SEQUENCE: 33
SISGSGSDTL YADSVKA                                                           17
```

```
SEQ ID NO: 34              moltype = AA  length = 6
FEATURE                    Location/Qualifiers
source                     1..6
                           mol_type = protein
                           organism = synthetic construct
SEQUENCE: 34
AGSLSR                                                                     6

SEQ ID NO: 35              moltype = AA  length = 6
FEATURE                    Location/Qualifiers
source                     1..6
                           mol_type = protein
                           organism = synthetic construct
SEQUENCE: 35
GASLSR                                                                     6

SEQ ID NO: 36              moltype = AA  length = 6
FEATURE                    Location/Qualifiers
source                     1..6
                           mol_type = protein
                           organism = synthetic construct
SEQUENCE: 36
GGALSR                                                                     6

SEQ ID NO: 37              moltype = AA  length = 6
FEATURE                    Location/Qualifiers
source                     1..6
                           mol_type = protein
                           organism = synthetic construct
SEQUENCE: 37
GGSASR                                                                     6

SEQ ID NO: 38              moltype = AA  length = 6
FEATURE                    Location/Qualifiers
source                     1..6
                           mol_type = protein
                           organism = synthetic construct
SEQUENCE: 38
GGSLAR                                                                     6

SEQ ID NO: 39              moltype = AA  length = 6
FEATURE                    Location/Qualifiers
source                     1..6
                           mol_type = protein
                           organism = synthetic construct
SEQUENCE: 39
GGSLSA                                                                     6

SEQ ID NO: 40              moltype = AA  length = 6
FEATURE                    Location/Qualifiers
source                     1..6
                           mol_type = protein
                           organism = synthetic construct
SEQUENCE: 40
GGTLSR                                                                     6

SEQ ID NO: 41              moltype = AA  length = 17
FEATURE                    Location/Qualifiers
source                     1..17
                           mol_type = protein
                           organism = synthetic construct
SEQUENCE: 41
SIAASGSDTL YADSVKG                                                        17

SEQ ID NO: 42              moltype = AA  length = 115
FEATURE                    Location/Qualifiers
source                     1..115
                           mol_type = protein
                           organism = synthetic construct
SEQUENCE: 42
EVQLLESGGG LVQPGGSLRL SCAASGFTFR SFGMSWVRQA PGKGPEWVSS ISGSGSDTLY          60
ADSVKGRFTI SRDNSKNTLY LQMNSLRPED TAVYYCTIGG SLSRSSQGTL VTVSS              115

SEQ ID NO: 43              moltype = AA  length = 115
FEATURE                    Location/Qualifiers
source                     1..115
                           mol_type = protein
                           organism = synthetic construct
```

-continued

```
SEQUENCE: 43
EVQLLESGGG LVQPGGSLRL SCAASGFTFR AFGMSWVRQA PGKGPEWVSS ISGSGSDTLY    60
ADSVKGRFTI SRDNSKNTLY LQMNSLRPED TAVYYCTIGG SLSRSSQGTL VTVSS        115

SEQ ID NO: 44           moltype = AA   length = 115
FEATURE                 Location/Qualifiers
source                  1..115
                        mol_type = protein
                        organism = synthetic construct
SEQUENCE: 44
EVQLLESGGG LVQPGGSLRL SCAASGFTFR SAGMSWVRQA PGKGPEWVSS ISGSGSDTLY    60
ADSVKGRFTI SRDNSKNTLY LQMNSLRPED TAVYYCTIGG SLSRSSQGTL VTVSS        115

SEQ ID NO: 45           moltype = AA   length = 115
FEATURE                 Location/Qualifiers
source                  1..115
                        mol_type = protein
                        organism = synthetic construct
SEQUENCE: 45
EVQLLESGGG LVQPGGSLRL SCAASGFTFR SFAMSWVRQA PGKGPEWVSS ISGSGSDTLY    60
ADSVKGRFTI SRDNSKNTLY LQMNSLRPED TAVYYCTIGG SLSRSSQGTL VTVSS        115

SEQ ID NO: 46           moltype = AA   length = 115
FEATURE                 Location/Qualifiers
source                  1..115
                        mol_type = protein
                        organism = synthetic construct
SEQUENCE: 46
EVQLLESGGG LVQPGGSLRL SCAASGFTFR SFGASWVRQA PGKGPEWVSS ISGSGSDTLY    60
ADSVKGRFTI SRDNSKNTLY LQMNSLRPED TAVYYCTIGG SLSRSSQGTL VTVSS        115

SEQ ID NO: 47           moltype = AA   length = 115
FEATURE                 Location/Qualifiers
source                  1..115
                        mol_type = protein
                        organism = synthetic construct
SEQUENCE: 47
EVQLLESGGG LVQPGGSLRL SCAASGFTFR SFGMAWVRQA PGKGPEWVSS ISGSGSDTLY    60
ADSVKGRFTI SRDNSKNTLY LQMNSLRPED TAVYYCTIGG SLSRSSQGTL VTVSS        115

SEQ ID NO: 48           moltype = AA   length = 115
FEATURE                 Location/Qualifiers
source                  1..115
                        mol_type = protein
                        organism = synthetic construct
SEQUENCE: 48
EVQLLESGGG LVQPGGSLRL SCAASGFTFR SFGMSWVRQA PGKGPEWVSA ISGSGSDTLY    60
ADSVKGRFTI SRDNSKNTLY LQMNSLRPED TAVYYCTIGG SLSRSSQGTL VTVSS        115

SEQ ID NO: 49           moltype = AA   length = 115
FEATURE                 Location/Qualifiers
source                  1..115
                        mol_type = protein
                        organism = synthetic construct
SEQUENCE: 49
EVQLLESGGG LVQPGGSLRL SCAASGFTFR SFGMSWVRQA PGKGPEWVSS ASGSGSDTLY    60
ADSVKGRFTI SRDNSKNTLY LQMNSLRPED TAVYYCTIGG SLSRSSQGTL VTVSS        115

SEQ ID NO: 50           moltype = AA   length = 115
FEATURE                 Location/Qualifiers
source                  1..115
                        mol_type = protein
                        organism = synthetic construct
SEQUENCE: 50
EVQLLESGGG LVQPGGSLRL SCAASGFTFR SFGMSWVRQA PGKGPEWVSS IAGSGSDTLY    60
ADSVKGRFTI SRDNSKNTLY LQMNSLRPED TAVYYCTIGG SLSRSSQGTL VTVSS        115

SEQ ID NO: 51           moltype = AA   length = 115
FEATURE                 Location/Qualifiers
source                  1..115
                        mol_type = protein
                        organism = synthetic construct
SEQUENCE: 51
EVQLLESGGG LVQPGGSLRL SCAASGFTFR SFGMSWVRQA PGKGPEWVSS ISASGSDTLY    60
ADSVKGRFTI SRDNSKNTLY LQMNSLRPED TAVYYCTIGG SLSRSSQGTL VTVSS        115

SEQ ID NO: 52           moltype = AA   length = 115
FEATURE                 Location/Qualifiers
source                  1..115
```

```
                              mol_type = protein
                              organism = synthetic construct
SEQUENCE: 52
EVQLLESGGG LVQPGGSLRL SCAASGFTFR SFGMSWVRQA PGKGPEWVSS ISGAGSDTLY     60
ADSVKGRFTI SRDNSKNTLY LQMNSLRPED TAVYYCTIGG SLSRSSQGTL VTVSS          115

SEQ ID NO: 53                 moltype = AA   length = 115
FEATURE                       Location/Qualifiers
source                        1..115
                              mol_type = protein
                              organism = synthetic construct
SEQUENCE: 53
EVQLLESGGG LVQPGGSLRL SCAASGFTFR SFGMSWVRQA PGKGPEWVSS ISGSASDTLY     60
ADSVKGRFTI SRDNSKNTLY LQMNSLRPED TAVYYCTIGG SLSRSSQGTL VTVSS          115

SEQ ID NO: 54                 moltype = AA   length = 115
FEATURE                       Location/Qualifiers
source                        1..115
                              mol_type = protein
                              organism = synthetic construct
SEQUENCE: 54
EVQLLESGGG LVQPGGSLRL SCAASGFTFR SFGMSWVRQA PGKGPEWVSS ISGSGADTLY     60
ADSVKGRFTI SRDNSKNTLY LQMNSLRPED TAVYYCTIGG SLSRSSQGTL VTVSS          115

SEQ ID NO: 55                 moltype = AA   length = 115
FEATURE                       Location/Qualifiers
source                        1..115
                              mol_type = protein
                              organism = synthetic construct
SEQUENCE: 55
EVQLLESGGG LVQPGGSLRL SCAASGFTFR SFGMSWVRQA PGKGPEWVSS ISGSGSATLY     60
ADSVKGRFTI SRDNSKNTLY LQMNSLRPED TAVYYCTIGG SLSRSSQGTL VTVSS          115

SEQ ID NO: 56                 moltype = AA   length = 115
FEATURE                       Location/Qualifiers
source                        1..115
                              mol_type = protein
                              organism = synthetic construct
SEQUENCE: 56
EVQLLESGGG LVQPGGSLRL SCAASGFTFR SFGMSWVRQA PGKGPEWVSS ISGSGSDALY     60
ADSVKGRFTI SRDNSKNTLY LQMNSLRPED TAVYYCTIGG SLSRSSQGTL VTVSS          115

SEQ ID NO: 57                 moltype = AA   length = 115
FEATURE                       Location/Qualifiers
source                        1..115
                              mol_type = protein
                              organism = synthetic construct
SEQUENCE: 57
EVQLLESGGG LVQPGGSLRL SCAASGFTFR SFGMSWVRQA PGKGPEWVSS ISGSGSDTAY     60
ADSVKGRFTI SRDNSKNTLY LQMNSLRPED TAVYYCTIGG SLSRSSQGTL VTVSS          115

SEQ ID NO: 58                 moltype = AA   length = 115
FEATURE                       Location/Qualifiers
source                        1..115
                              mol_type = protein
                              organism = synthetic construct
SEQUENCE: 58
EVQLLESGGG LVQPGGSLRL SCAASGFTFR SFGMSWVRQA PGKGPEWVSS ISGSGSDTLA     60
ADSVKGRFTI SRDNSKNTLY LQMNSLRPED TAVYYCTIGG SLSRSSQGTL VTVSS          115

SEQ ID NO: 59                 moltype = AA   length = 115
FEATURE                       Location/Qualifiers
source                        1..115
                              mol_type = protein
                              organism = synthetic construct
SEQUENCE: 59
EVQLLESGGG LVQPGGSLRL SCAASGFTFR SFGMSWVRQA PGKGPEWVSS ISGSGSDTLY     60
AASVKGRFTI SRDNSKNTLY LQMNSLRPED TAVYYCTIGG SLSRSSQGTL VTVSS          115

SEQ ID NO: 60                 moltype = AA   length = 115
FEATURE                       Location/Qualifiers
source                        1..115
                              mol_type = protein
                              organism = synthetic construct
SEQUENCE: 60
EVQLLESGGG LVQPGGSLRL SCAASGFTFR SFGMSWVRQA PGKGPEWVSS ISGSGSDTLY     60
ADAVKGRFTI SRDNSKNTLY LQMNSLRPED TAVYYCTIGG SLSRSSQGTL VTVSS          115

SEQ ID NO: 61                 moltype = AA   length = 115
```

| FEATURE | Location/Qualifiers |
|---|---|
| source | 1..115 |
| | mol_type = protein |
| | organism = synthetic construct |

SEQUENCE: 61
EVQLLESGGG LVQPGGSLRL SCAASGFTFR SFGMSWVRQA PGKGPEWVSS ISGSGSDTLY 60
ADSAKGRFTI SRDNSKNTLY LQMNSLRPED TAVYYCTIGG SLSRSSQGTL VTVSS 115

| SEQ ID NO: 62 | moltype = AA  length = 115 |
|---|---|
| FEATURE | Location/Qualifiers |
| source | 1..115 |
| | mol_type = protein |
| | organism = synthetic construct |

SEQUENCE: 62
EVQLLESGGG LVQPGGSLRL SCAASGFTFR SFGMSWVRQA PGKGPEWVSS ISGSGSDTLY 60
ADSVAGRFTI SRDNSKNTLY LQMNSLRPED TAVYYCTIGG SLSRSSQGTL VTVSS 115

| SEQ ID NO: 63 | moltype = AA  length = 115 |
|---|---|
| FEATURE | Location/Qualifiers |
| source | 1..115 |
| | mol_type = protein |
| | organism = synthetic construct |

SEQUENCE: 63
EVQLLESGGG LVQPGGSLRL SCAASGFTFR SFGMSWVRQA PGKGPEWVSS ISGSGSDTLY 60
ADSVKARFTI SRDNSKNTLY LQMNSLRPED TAVYYCTIGG SLSRSSQGTL VTVSS 115

| SEQ ID NO: 64 | moltype = AA  length = 115 |
|---|---|
| FEATURE | Location/Qualifiers |
| source | 1..115 |
| | mol_type = protein |
| | organism = synthetic construct |

SEQUENCE: 64
EVQLLESGGG LVQPGGSLRL SCAASGFTFR SFGMSWVRQA PGKGPEWVSS ISGSGSDTLY 60
ADSVKGRFTI SRDNSKNTLY LQMNSLRPED TAVYYCTIAG SLSRSSQGTL VTVSS 115

| SEQ ID NO: 65 | moltype = AA  length = 115 |
|---|---|
| FEATURE | Location/Qualifiers |
| source | 1..115 |
| | mol_type = protein |
| | organism = synthetic construct |

SEQUENCE: 65
EVQLLESGGG LVQPGGSLRL SCAASGFTFR SFGMSWVRQA PGKGPEWVSS ISGSGSDTLY 60
ADSVKGRFTI SRDNSKNTLY LQMNSLRPED TAVYYCTIGA SLSRSSQGTL VTVSS 115

| SEQ ID NO: 66 | moltype = AA  length = 115 |
|---|---|
| FEATURE | Location/Qualifiers |
| source | 1..115 |
| | mol_type = protein |
| | organism = synthetic construct |

SEQUENCE: 66
EVQLLESGGG LVQPGGSLRL SCAASGFTFR SFGMSWVRQA PGKGPEWVSS ISGSGSDTLY 60
ADSVKGRFTI SRDNSKNTLY LQMNSLRPED TAVYYCTIGG ALSRSSQGTL VTVSS 115

| SEQ ID NO: 67 | moltype = AA  length = 115 |
|---|---|
| FEATURE | Location/Qualifiers |
| source | 1..115 |
| | mol_type = protein |
| | organism = synthetic construct |

SEQUENCE: 67
EVQLLESGGG LVQPGGSLRL SCAASGFTFR SFGMSWVRQA PGKGPEWVSS ISGSGSDTLY 60
ADSVKGRFTI SRDNSKNTLY LQMNSLRPED TAVYYCTIGG SASRSSQGTL VTVSS 115

| SEQ ID NO: 68 | moltype = AA  length = 115 |
|---|---|
| FEATURE | Location/Qualifiers |
| source | 1..115 |
| | mol_type = protein |
| | organism = synthetic construct |

SEQUENCE: 68
EVQLLESGGG LVQPGGSLRL SCAASGFTFR SFGMSWVRQA PGKGPEWVSS ISGSGSDTLY 60
ADSVKGRFTI SRDNSKNTLY LQMNSLRPED TAVYYCTIGG SLARSSQGTL VTVSS 115

| SEQ ID NO: 69 | moltype = AA  length = 115 |
|---|---|
| FEATURE | Location/Qualifiers |
| source | 1..115 |
| | mol_type = protein |
| | organism = synthetic construct |

SEQUENCE: 69
EVQLLESGGG LVQPGGSLRL SCAASGFTFR SFGMSWVRQA PGKGPEWVSS ISGSGSDTLY 60
ADSVKGRFTI SRDNSKNTLY LQMNSLRPED TAVYYCTIGG SLSASSQGTL VTVSS 115

```
SEQ ID NO: 70            moltype = AA   length = 115
FEATURE                  Location/Qualifiers
source                   1..115
                         mol_type = protein
                         organism = synthetic construct
SEQUENCE: 70
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG TLSRSSQGTL VTVSS        115

SEQ ID NO: 71            moltype = AA   length = 115
FEATURE                  Location/Qualifiers
source                   1..115
                         mol_type = protein
                         organism = synthetic construct
SEQUENCE: 71
EVQLLESGGG LVQPGGSLRL SCAASGFTFR SFAMSWVRQA PGKGPEWVSS ISGSGSDTLY    60
ADSVKGRFTI SRDNSKNTLY LQMNSLRPED TAVYYCTIGG ALSRSSQGTL VTVSS        115

SEQ ID NO: 72            moltype = AA   length = 115
FEATURE                  Location/Qualifiers
source                   1..115
                         mol_type = protein
                         organism = synthetic construct
SEQUENCE: 72
EVQLLESGGG LVQPGGSLRL SCAASGFTFR SFAMSWVRQA PGKGPEWVSS ISASGSDTLY    60
ADSVKGRFTI SRDNSKNTLY LQMNSLRPED TAVYYCTIGG SLSRSSQGTL VTVSS        115

SEQ ID NO: 73            moltype = AA   length = 115
FEATURE                  Location/Qualifiers
source                   1..115
                         mol_type = protein
                         organism = synthetic construct
SEQUENCE: 73
EVQLLESGGG LVQPGGSLRL SCAASGFTFR SFGMSWVRQA PGKGPEWVSS IAASGSDTLY    60
ADSVKGRFTI SRDNSKNTLY LQMNSLRPED TAVYYCTIGG SLSRSSQGTL VTVSS        115

SEQ ID NO: 74            moltype = AA   length = 115
FEATURE                  Location/Qualifiers
source                   1..115
                         mol_type = protein
                         organism = synthetic construct
SEQUENCE: 74
EVQLLESGGG LVQPGGSLRL SCAASGFTFR SFGMSWVRQA PGKGPEWVSS IAGSGSDTLY    60
ADSVKGRFTI SRDNSKNTLY LQMNSLRPED TAVYYCTIGG ALSRSSQGTL VTVSS        115

SEQ ID NO: 75            moltype = AA   length = 5
FEATURE                  Location/Qualifiers
source                   1..5
                         mol_type = protein
                         organism = synthetic construct
SEQUENCE: 75
SNTMG                                                                 5

SEQ ID NO: 76            moltype = AA   length = 17
FEATURE                  Location/Qualifiers
source                   1..17
                         mol_type = protein
                         organism = synthetic construct
SEQUENCE: 76
AITWSGGTTY YADSVKG                                                   17

SEQ ID NO: 77            moltype = AA   length = 19
FEATURE                  Location/Qualifiers
source                   1..19
                         mol_type = protein
                         organism = synthetic construct
SEQUENCE: 77
EGPKWEPWNG IYHPADFGS                                                 19

SEQ ID NO: 78            moltype = AA   length = 19
FEATURE                  Location/Qualifiers
source                   1..19
                         mol_type = protein
                         organism = synthetic construct
SEQUENCE: 78
EGPKWEPWAG IYHPADFGS                                                 19

SEQ ID NO: 79            moltype = AA   length = 19
```

```
FEATURE                 Location/Qualifiers
source                  1..19
                        mol_type = protein
                        organism = synthetic construct
SEQUENCE: 79
EGPKWEPANG IYHPADFGS                                                    19

SEQ ID NO: 80           moltype = AA   length = 19
FEATURE                 Location/Qualifiers
source                  1..19
                        mol_type = protein
                        organism = synthetic construct
SEQUENCE: 80
EGPKWEPWNG IYHPAAFGS                                                    19

SEQ ID NO: 81           moltype = AA   length = 19
FEATURE                 Location/Qualifiers
source                  1..19
                        mol_type = protein
                        organism = synthetic construct
SEQUENCE: 81
EGAKWEPWNG IYHPADFGS                                                    19

SEQ ID NO: 82           moltype = AA   length = 19
FEATURE                 Location/Qualifiers
source                  1..19
                        mol_type = protein
                        organism = synthetic construct
SEQUENCE: 82
EGPKWEPWNG IAHPADFGS                                                    19

SEQ ID NO: 83           moltype = AA   length = 19
FEATURE                 Location/Qualifiers
source                  1..19
                        mol_type = protein
                        organism = synthetic construct
SEQUENCE: 83
EGPKWEPWNG IYHPADAGS                                                    19

SEQ ID NO: 84           moltype = AA   length = 128
FEATURE                 Location/Qualifiers
source                  1..128
                        mol_type = protein
                        organism = synthetic construct
SEQUENCE: 84
ELQVVESGGG LVQAGGSLRL SCAASGRTFR SNTMGWFRQA PGKEREFVAA ITWSGGTTYY        60
ADSVKGRFAI SGDNAKNTVY LQMNSLKPED TAVYYCAAEG PKWEPWNGIY HPADFGSWGQ       120
GTQVTVSS                                                               128

SEQ ID NO: 85           moltype = AA   length = 128
FEATURE                 Location/Qualifiers
source                  1..128
                        mol_type = protein
                        organism = synthetic construct
SEQUENCE: 85
ELQVVESGGG LVQAGGSLRL SCAASGRTFR SNTMGWFRQA PGKEREFVAA ITWSGGTTYY        60
ADSVKGRFAI SGDNAKNTVY LQMNSLKPED TAVYYCAAEG PKWEPWAGIY HPADFGSWGQ       120
GTQVTVSS                                                               128

SEQ ID NO: 86           moltype = AA   length = 128
FEATURE                 Location/Qualifiers
source                  1..128
                        mol_type = protein
                        organism = synthetic construct
SEQUENCE: 86
ELQVVESGGG LVQAGGSLRL SCAASGRTFR SNTMGWFRQA PGKEREFVAA ITWSGGTTYY        60
ADSVKGRFAI SGDNAKNTVY LQMNSLKPED TAVYYCAAEG PKWEPANGIY HPADFGSWGQ       120
GTQVTVSS                                                               128

SEQ ID NO: 87           moltype = AA   length = 128
FEATURE                 Location/Qualifiers
source                  1..128
                        mol_type = protein
                        organism = synthetic construct
SEQUENCE: 87
ELQVVESGGG LVQAGGSLRL SCAASGRTFR SNTMGWFRQA PGKEREFVAA ITWSGGTTYY        60
ADSVKGRFAI SGDNAKNTVY LQMNSLKPED TAVYYCAAEG PKWEPWNGIY HPAAFGSWGQ       120
GTQVTVSS                                                               128
```

```
SEQ ID NO: 88            moltype = AA   length = 128
FEATURE                  Location/Qualifiers
source                   1..128
                         mol_type = protein
                         organism = synthetic construct
SEQUENCE: 88
ELQVVESGGG LVQAGGSLRL SCAASGRTFR SNTMGWFRQA PGKEREFVAA ITWSGGTTYY    60
ADSVKGRFAI SGDNAKNTVY LQMNSLKPED TAVYYCAAEG AKWEPWNGIY HPADFGSWGQ   120
GTQVTVSS                                                            128

SEQ ID NO: 89            moltype = AA   length = 128
FEATURE                  Location/Qualifiers
source                   1..128
                         mol_type = protein
                         organism = synthetic construct
SEQUENCE: 89
ELQVVESGGG LVQAGGSLRL SCAASGRTFR SNTMGWFRQA PGKEREFVAA ITWSGGTTYY    60
ADSVKGRFAI SGDNAKNTVY LQMNSLKPED TAVYYCAAEG PKWEPWNGIA HPADFGSWGQ   120
GTQVTVSS                                                            128

SEQ ID NO: 90            moltype = AA   length = 128
FEATURE                  Location/Qualifiers
source                   1..128
                         mol_type = protein
                         organism = synthetic construct
SEQUENCE: 90
ELQVVESGGG LVQAGGSLRL SCAASGRTFR SNTMGWFRQA PGKEREFVAA ITWSGGTTYY    60
ADSVKGRFAI SGDNAKNTVY LQMNSLKPED TAVYYCAAEG PKWEPWNGIY HPADAGSWGQ   120
GTQVTVSS                                                            128

SEQ ID NO: 91            moltype = AA   length = 5
FEATURE                  Location/Qualifiers
source                   1..5
                         mol_type = protein
                         organism = synthetic construct
SEQUENCE: 91
VTVSS                                                                 5

SEQ ID NO: 92            moltype =      length =
SEQUENCE: 92
000

SEQ ID NO: 93            moltype =      length =
SEQUENCE: 93
000

SEQ ID NO: 94            moltype =      length =
SEQUENCE: 94
000

SEQ ID NO: 95            moltype =      length =
SEQUENCE: 95
000

SEQ ID NO: 96            moltype =      length =
SEQUENCE: 96
000

SEQ ID NO: 97            moltype =      length =
SEQUENCE: 97
000

SEQ ID NO: 98            moltype =      length =
SEQUENCE: 98
000

SEQ ID NO: 99            moltype =      length =
SEQUENCE: 99
000

SEQ ID NO: 100           moltype =      length =
SEQUENCE: 100
000

SEQ ID NO: 101           moltype =      length =
SEQUENCE: 101
000

SEQ ID NO: 102           moltype =      length =
```

```
SEQUENCE: 102
000

SEQ ID NO: 103          moltype =     length =
SEQUENCE: 103
000

SEQ ID NO: 104          moltype =     length =
SEQUENCE: 104
000

SEQ ID NO: 105          moltype =     length =
SEQUENCE: 105
000

SEQ ID NO: 106          moltype =     length =
SEQUENCE: 106
000

SEQ ID NO: 107          moltype =     length =
SEQUENCE: 107
000

SEQ ID NO: 108          moltype =     length =
SEQUENCE: 108
000

SEQ ID NO: 109          moltype =     length =
SEQUENCE: 109
000

SEQ ID NO: 110          moltype =     length =
SEQUENCE: 110
000

SEQ ID NO: 111          moltype = AA   length = 5
FEATURE                 Location/Qualifiers
source                  1..5
                        mol_type = protein
                        organism = synthetic construct
SEQUENCE: 111
SHGMS                                                                    5

SEQ ID NO: 112          moltype = AA   length = 5
FEATURE                 Location/Qualifiers
source                  1..5
                        mol_type = protein
                        organism = synthetic construct
SEQUENCE: 112
SFGHS                                                                    5

SEQ ID NO: 113          moltype = AA   length = 17
FEATURE                 Location/Qualifiers
source                  1..17
                        mol_type = protein
                        organism = synthetic construct
SEQUENCE: 113
SISGSHSDTL YADSVKG                                                      17

SEQ ID NO: 114          moltype = AA   length = 17
FEATURE                 Location/Qualifiers
source                  1..17
                        mol_type = protein
                        organism = synthetic construct
SEQUENCE: 114
SISGSGSDTH YADSVKG                                                      17

SEQ ID NO: 115          moltype = AA   length = 6
FEATURE                 Location/Qualifiers
source                  1..6
                        mol_type = protein
                        organism = synthetic construct
SEQUENCE: 115
HGSLSR                                                                   6

SEQ ID NO: 116          moltype = AA   length = 6
FEATURE                 Location/Qualifiers
source                  1..6
                        mol_type = protein
```

```
                                           organism = synthetic construct
SEQUENCE: 116
GHSLSR                                                                           6

SEQ ID NO: 117             moltype = AA  length = 6
FEATURE                    Location/Qualifiers
source                     1..6
                           mol_type = protein
                           organism = synthetic construct
SEQUENCE: 117
GGSHSR                                                                           6

SEQ ID NO: 118             moltype = AA  length = 5
FEATURE                    Location/Qualifiers
source                     1..5
                           mol_type = protein
                           organism = synthetic construct
SEQUENCE: 118
SFHMS                                                                            5

SEQ ID NO: 119             moltype = AA  length = 6
FEATURE                    Location/Qualifiers
source                     1..6
                           mol_type = protein
                           organism = synthetic construct
SEQUENCE: 119
GGHLSR                                                                           6

SEQ ID NO: 120             moltype = AA  length = 115
FEATURE                    Location/Qualifiers
source                     1..115
                           mol_type = protein
                           organism = synthetic construct
SEQUENCE: 120
EVQLLESGGG LVQPGGSLRL SCAASGFTFR SHGMSWVRQA PGKGPEWVSS ISGSGSDTLY                60
ADSVKGRFTI SRDNSKNTLY LQMNSLRPED TAVYYCTIGG SLSRSSQGTL VTVSS                   115

SEQ ID NO: 121             moltype = AA  length = 115
FEATURE                    Location/Qualifiers
source                     1..115
                           mol_type = protein
                           organism = synthetic construct
SEQUENCE: 121
EVQLLESGGG LVQPGGSLRL SCAASGFTFR SFGHSWVRQA PGKGPEWVSS ISGSGSDTLY                60
ADSVKGRFTI SRDNSKNTLY LQMNSLRPED TAVYYCTIGG SLSRSSQGTL VTVSS                   115

SEQ ID NO: 122             moltype = AA  length = 115
FEATURE                    Location/Qualifiers
source                     1..115
                           mol_type = protein
                           organism = synthetic construct
SEQUENCE: 122
EVQLLESGGG LVQPGGSLRL SCAASGFTFR SFGMSWVRQA PGKGPEWVSS ISGSHSDTLY                60
ADSVKGRFTI SRDNSKNTLY LQMNSLRPED TAVYYCTIGG SLSRSSQGTL VTVSS                   115

SEQ ID NO: 123             moltype = AA  length = 115
FEATURE                    Location/Qualifiers
source                     1..115
                           mol_type = protein
                           organism = synthetic construct
SEQUENCE: 123
EVQLLESGGG LVQPGGSLRL SCAASGFTFR SFGMSWVRQA PGKGPEWVSS ISGSGSDTHY                60
ADSVKGRFTI SRDNSKNTLY LQMNSLRPED TAVYYCTIGG SLSRSSQGTL VTVSS                   115

SEQ ID NO: 124             moltype = AA  length = 115
FEATURE                    Location/Qualifiers
source                     1..115
                           mol_type = protein
                           organism = synthetic construct
SEQUENCE: 124
EVQLLESGGG LVQPGGSLRL SCAASGFTFR SFGMSWVRQA PGKGPEWVSS ISGSGSDTLY                60
ADSVKGRFTI SRDNSKNTLY LQMNSLRPED TAVYYCTIHG SLSRSSQGTL VTVSS                   115

SEQ ID NO: 125             moltype = AA  length = 115
FEATURE                    Location/Qualifiers
source                     1..115
                           mol_type = protein
                           organism = synthetic construct
SEQUENCE: 125
```

```
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGH SLSRSSQGTL VTVSS        115

SEQ ID NO: 126          moltype = AA  length = 115
FEATURE                 Location/Qualifiers
source                  1..115
                        mol_type = protein
                        organism = synthetic construct
SEQUENCE: 126
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SHSRSSQGTL VTVSS        115

SEQ ID NO: 127          moltype = AA  length = 115
FEATURE                 Location/Qualifiers
source                  1..115
                        mol_type = protein
                        organism = synthetic construct
SEQUENCE: 127
EVQLLESGGG LVQPGGSLRL SCAASGFTFR SFHMSWVRQA PGKGPEWVSS ISGSGSDTLY    60
ADSVKGRFTI SRDNSKNTLY LQMNSLRPED TAVYYCTIGG HLSRSSQGTL VTVSS        115

SEQ ID NO: 128          moltype = AA  length = 216
FEATURE                 Location/Qualifiers
source                  1..216
                        mol_type = protein
                        organism = synthetic construct
SEQUENCE: 128
QSALTQPASV SGSPGQSITI SCTGTGSDVG SYNLVSWYQQ HPGKAPKLMI YGDSERPSGV    60
SNRFSGSKSG NTASLTISGL QAEDEADYYC SSYAGSGIYV FGTGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHKSYSCQVT HEGSTVEKTV APTECS                             216

SEQ ID NO: 129          moltype = AA  length = 445
FEATURE                 Location/Qualifiers
source                  1..445
                        mol_type = protein
                        organism = synthetic construct
SEQUENCE: 129
EVQLLESGGG LVQPGGSLRL SCAASGFTFS TYAMGWVRQA PGKGLEWVSS IGASGSQTRY    60
ADSVKGRFTI SRDNSKNTLY LQMNSLRAED TAVYYCARLA IGDSYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYASTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 130          moltype = AA  length = 219
FEATURE                 Location/Qualifiers
source                  1..219
                        mol_type = protein
                        organism = synthetic construct
SEQUENCE: 130
DIQMTQSPSS LSASVGDRVT ITCKSSQSLV GASGKTYLYW LFQKPGKAPK RLIYLVSTLD    60
SGIPSRFSGS GSGTEFTLTI SSLQPEDFAT YYCLQGFHTP HTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 131          moltype = AA  length = 444
FEATURE                 Location/Qualifiers
source                  1..444
                        mol_type = protein
                        organism = synthetic construct
SEQUENCE: 131
EVPLVESGGG LVQPGGSLRL SCAVSGFTFS NYGMVWVRQA PGKGLEWVAY IDSDGDNTYY    60
RDSVKGRFTI SRDNAKSSLY LQMNSLRAED TAVYYCTTGI VRPFLYWGQG TLVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLGK                                          444

SEQ ID NO: 132          moltype = AA  length = 214
FEATURE                 Location/Qualifiers
source                  1..214
                        mol_type = protein
                        organism = synthetic construct
SEQUENCE: 132
```

```
DIQMTQSPSS LSASVGDRVT ITCKASDHIN NWLAWYQQKP GQAPRLLISG ATSLETGVPS    60
RFSGSGTGKD YTLTISSLQP EDFATYYCQQ YWSTPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 133           moltype = AA  length = 444
FEATURE                  Location/Qualifiers
source                   1..444
                         mol_type = protein
                         organism = synthetic construct
SEQUENCE: 133
QVQLVQSGAE LKKPGASVKL SCKASGYTFT SYGISWVKQA TGQGLEWIGE IYPRSGNTYY    60
NEKFKGRATL TADKSTSTAY MELRSLRSED SAVYFCARST TVRPPGIWGT GTTVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 134           moltype = AA  length = 214
FEATURE                  Location/Qualifiers
source                   1..214
                         mol_type = protein
                         organism = synthetic construct
SEQUENCE: 134
SYVLTQSPSV SVAPGQTARI TCGGNNIGSK SVHWYQQKPG QAPVLVVYDD SDRPSGIPER    60
FSASNSGNTA TLTISRVEAG DEADYYCQVW DSSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                              214

SEQ ID NO: 135           moltype = AA  length = 450
FEATURE                  Location/Qualifiers
source                   1..450
                         mol_type = protein
                         organism = synthetic construct
SEQUENCE: 135
QLLLQESGPG LVKPSETLSL TCTVSGGSLS SSFSYWVWIR QPPGKGLEWI GTIYYSGNTY    60
YNPSLKSRLT ISVDTSKNHF SLKLSSVTAA DTAVYYCARR AGILTGYLDS WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 136           moltype = AA  length = 20
FEATURE                  Location/Qualifiers
source                   1..20
                         mol_type = protein
                         organism = synthetic construct
SEQUENCE: 136
GGGGSGGGGS GGGGSGGGGS                                               20

SEQ ID NO: 137           moltype = AA  length = 361
FEATURE                  Location/Qualifiers
source                   1..361
                         mol_type = protein
                         organism = synthetic construct
SEQUENCE: 137
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKHYTQKS LSLSPGGGGG SGGGGSGGGG   240
SGGGGSEVQL LESGGGLVQP GGSLRLSCAA SGFTFRAFGM SWVRQAPGKG PEWVSSISGS   300
GSDTLYADSV KGRFTISRDN SKNTLYLQMN SLRPEDTAVY YCTIGGSLSR SSQGTLVTVS   360
S                                                                  361

SEQ ID NO: 138           moltype = AA  length = 361
FEATURE                  Location/Qualifiers
source                   1..361
                         mol_type = protein
                         organism = synthetic construct
SEQUENCE: 138
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKHYTQKS LSLSPGGGGG SGGGGSGGGG   240
SGGGGSEVQL LESGGGLVQP GGSLRLSCAA SGFTFRSAGM SWVRQAPGKG PEWVSSISGS   300
```

```
GSDTLYADSV KGRFTISRDN SKNTLYLQMN SLRPEDTAVY YCTIGGSLSR SSQGTLVTVS    360
S                                                                   361

SEQ ID NO: 139          moltype = AA  length = 361
FEATURE                 Location/Qualifiers
source                  1..361
                        mol_type = protein
                        organism = synthetic construct
SEQUENCE: 139
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKFHYTQKS LSLSPGGGGG SGGGGSGGGG    240
SGGGGSEVQL LESGGGLVQP GGSLRLSCAA SGFTFRSFAM SWVRQAPGKG PEWVSSISGS    300
GSDTLYADSV KGRFTISRDN SKNTLYLQMN SLRPEDTAVY YCTIGGSLSR SSQGTLVTVS    360
S                                                                   361

SEQ ID NO: 140          moltype = AA  length = 361
FEATURE                 Location/Qualifiers
source                  1..361
                        mol_type = protein
                        organism = synthetic construct
SEQUENCE: 140
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKFHYTQKS LSLSPGGGGG SGGGGSGGGG    240
SGGGGSEVQL LESGGGLVQP GGSLRLSCAA SGFTFRSFGA SWVRQAPGKG PEWVSSISGS    300
GSDTLYADSV KGRFTISRDN SKNTLYLQMN SLRPEDTAVY YCTIGGSLSR SSQGTLVTVS    360
S                                                                   361

SEQ ID NO: 141          moltype = AA  length = 361
FEATURE                 Location/Qualifiers
source                  1..361
                        mol_type = protein
                        organism = synthetic construct
SEQUENCE: 141
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKFHYTQKS LSLSPGGGGG SGGGGSGGGG    240
SGGGGSEVQL LESGGGLVQP GGSLRLSCAA SGFTFRSFGM AWVRQAPGKG PEWVSSISGS    300
GSDTLYADSV KGRFTISRDN SKNTLYLQMN SLRPEDTAVY YCTIGGSLSR SSQGTLVTVS    360
S                                                                   361

SEQ ID NO: 142          moltype = AA  length = 361
FEATURE                 Location/Qualifiers
source                  1..361
                        mol_type = protein
                        organism = synthetic construct
SEQUENCE: 142
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKFHYTQKS LSLSPGGGGG SGGGGSGGGG    240
SGGGGSEVQL LESGGGLVQP GGSLRLSCAA SGFTFRSFGM SWVRQAPGKG PEWVSAISGS    300
GSDTLYADSV KGRFTISRDN SKNTLYLQMN SLRPEDTAVY YCTIGGSLSR SSQGTLVTVS    360
S                                                                   361

SEQ ID NO: 143          moltype = AA  length = 361
FEATURE                 Location/Qualifiers
source                  1..361
                        mol_type = protein
                        organism = synthetic construct
SEQUENCE: 143
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKFHYTQKS LSLSPGGGGG SGGGGSGGGG    240
SGGGGSEVQL LESGGGLVQP GGSLRLSCAA SGFTFRSFGM SWVRQAPGKG PEWVSSASGS    300
GSDTLYADSV KGRFTISRDN SKNTLYLQMN SLRPEDTAVY YCTIGGSLSR SSQGTLVTVS    360
S                                                                   361

SEQ ID NO: 144          moltype = AA  length = 361
FEATURE                 Location/Qualifiers
source                  1..361
                        mol_type = protein
                        organism = synthetic construct
SEQUENCE: 144
```

```
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSIAGS   300
GSDTLYADSV KGRFTISRDN SKNTLYLQMN SLRPEDTAVY YCTIGGSLSR SSQGTLVTVS   360
S                                                                  361

SEQ ID NO: 145          moltype = AA   length = 361
FEATURE                 Location/Qualifiers
source                  1..361
                        mol_type = protein
                        organism = synthetic construct
SEQUENCE: 145
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISAS   300
GSDTLYADSV KGRFTISRDN SKNTLYLQMN SLRPEDTAVY YCTIGGSLSR SSQGTLVTVS   360
S                                                                  361

SEQ ID NO: 146          moltype = AA   length = 361
FEATURE                 Location/Qualifiers
source                  1..361
                        mol_type = protein
                        organism = synthetic construct
SEQUENCE: 146
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGA   300
GSDTLYADSV KGRFTISRDN SKNTLYLQMN SLRPEDTAVY YCTIGGSLSR SSQGTLVTVS   360
S                                                                  361

SEQ ID NO: 147          moltype = AA   length = 361
FEATURE                 Location/Qualifiers
source                  1..361
                        mol_type = protein
                        organism = synthetic construct
SEQUENCE: 147
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
ASDTLYADSV KGRFTISRDN SKNTLYLQMN SLRPEDTAVY YCTIGGSLSR SSQGTLVTVS   360
S                                                                  361

SEQ ID NO: 148          moltype = AA   length = 361
FEATURE                 Location/Qualifiers
source                  1..361
                        mol_type = protein
                        organism = synthetic construct
SEQUENCE: 148
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GADTLYADSV KGRFTISRDN SKNTLYLQMN SLRPEDTAVY YCTIGGSLSR SSQGTLVTVS   360
S                                                                  361

SEQ ID NO: 149          moltype = AA   length = 361
FEATURE                 Location/Qualifiers
source                  1..361
                        mol_type = protein
                        organism = synthetic construct
SEQUENCE: 149
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSATLYADSV KGRFTISRDN SKNTLYLQMN SLRPEDTAVY YCTIGGSLSR SSQGTLVTVS   360
S                                                                  361

SEQ ID NO: 150          moltype = AA   length = 361
```

```
FEATURE                 Location/Qualifiers
source                  1..361
                        mol_type = protein
                        organism = synthetic construct
SEQUENCE: 150
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDALYADSV KGRFTISRDN SKNTLYLQMN SLRPEDTAVY YCTIGGSLSR SSQGTLVTVS   360
S                                                                  361

SEQ ID NO: 151          moltype = AA   length = 361
FEATURE                 Location/Qualifiers
source                  1..361
                        mol_type = protein
                        organism = synthetic construct
SEQUENCE: 151
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTAYADSV KGRFTISRDN SKNTLYLQMN SLRPEDTAVY YCTIGGSLSR SSQGTLVTVS   360
S                                                                  361

SEQ ID NO: 152          moltype = AA   length = 361
FEATURE                 Location/Qualifiers
source                  1..361
                        mol_type = protein
                        organism = synthetic construct
SEQUENCE: 152
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLAADSV KGRFTISRDN SKNTLYLQMN SLRPEDTAVY YCTIGGSLSR SSQGTLVTVS   360
S                                                                  361

SEQ ID NO: 153          moltype = AA   length = 361
FEATURE                 Location/Qualifiers
source                  1..361
                        mol_type = protein
                        organism = synthetic construct
SEQUENCE: 153
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYAASV KGRFTISRDN SKNTLYLQMN SLRPEDTAVY YCTIGGSLSR SSQGTLVTVS   360
S                                                                  361

SEQ ID NO: 154          moltype = AA   length = 361
FEATURE                 Location/Qualifiers
source                  1..361
                        mol_type = protein
                        organism = synthetic construct
SEQUENCE: 154
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADAV KGRFTISRDN SKNTLYLQMN SLRPEDTAVY YCTIGGSLSR SSQGTLVTVS   360
S                                                                  361

SEQ ID NO: 155          moltype = AA   length = 361
FEATURE                 Location/Qualifiers
source                  1..361
                        mol_type = protein
                        organism = synthetic construct
SEQUENCE: 155
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
```

```
SGGGGSEVQL LESGGGLVQP GGSLRLSCAA SGFTFRSFGM SWVRQAPGKG PEWVSSISGS    300
GSDTLYADSA KGRFTISRDN SKNTLYLQMN SLRPEDTAVY YCTIGGSLSR SSQGTLVTVS    360
S                                                                    361

SEQ ID NO: 156          moltype = AA  length = 361
FEATURE                 Location/Qualifiers
source                  1..361
                        mol_type = protein
                        organism = synthetic construct
SEQUENCE: 156
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV AGRFTISRDN SKNTLYLQMN SLRPEDTAVY YCTIGGSLSR SSQGTLVTVS   360
S                                                                  361

SEQ ID NO: 157          moltype = AA  length = 361
FEATURE                 Location/Qualifiers
source                  1..361
                        mol_type = protein
                        organism = synthetic construct
SEQUENCE: 157
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV KARFTISRDN SKNTLYLQMN SLRPEDTAVY YCTIGGSLSR SSQGTLVTVS   360
S                                                                  361

SEQ ID NO: 158          moltype = AA  length = 361
FEATURE                 Location/Qualifiers
source                  1..361
                        mol_type = protein
                        organism = synthetic construct
SEQUENCE: 158
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV KGRFTISRDN SKNTLYLQMN SLRPEDTAVY YCTIAGSLSR SSQGTLVTVS   360
S                                                                  361

SEQ ID NO: 159          moltype = AA  length = 361
FEATURE                 Location/Qualifiers
source                  1..361
                        mol_type = protein
                        organism = synthetic construct
SEQUENCE: 159
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV KGRFTISRDN SKNTLYLQMN SLRPEDTAVY YCTIGASLSR SSQGTLVTVS   360
S                                                                  361

SEQ ID NO: 160          moltype = AA  length = 361
FEATURE                 Location/Qualifiers
source                  1..361
                        mol_type = protein
                        organism = synthetic construct
SEQUENCE: 160
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV KGRFTISRDN SKNTLYLQMN SLRPEDTAVY YCTIGGALSR SSQGTLVTVS   360
S                                                                  361

SEQ ID NO: 161          moltype = AA  length = 361
FEATURE                 Location/Qualifiers
source                  1..361
                        mol_type = protein
                        organism = synthetic construct
```

```
SEQUENCE: 161
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKHYTQKS LSLSPGGGGG SGGGGSGGGG    240
SGGGGSEVQL LESGGGLVQP GGSLRLSCAA SGFTFRSFGM SWVRQAPGKG PEWVSSISGS    300
GSDTLYADSV KGRFTISRDN SKNTLYLQMN SLRPEDTAVY YCTIGGSASR SSQGTLVTVS    360
S                                                                    361

SEQ ID NO: 162          moltype = AA  length = 361
FEATURE                 Location/Qualifiers
source                  1..361
                        mol_type = protein
                        organism = synthetic construct
SEQUENCE: 162
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKHYTQKS LSLSPGGGGG SGGGGSGGGG    240
SGGGGSEVQL LESGGGLVQP GGSLRLSCAA SGFTFRSFGM SWVRQAPGKG PEWVSSISGS    300
GSDTLYADSV KGRFTISRDN SKNTLYLQMN SLRPEDTAVY YCTIGGSLAR SSQGTLVTVS    360
S                                                                    361

SEQ ID NO: 163          moltype = AA  length = 361
FEATURE                 Location/Qualifiers
source                  1..361
                        mol_type = protein
                        organism = synthetic construct
SEQUENCE: 163
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKHYTQKS LSLSPGGGGG SGGGGSGGGG    240
SGGGGSEVQL LESGGGLVQP GGSLRLSCAA SGFTFRSFGM SWVRQAPGKG PEWVSSISGS    300
GSDTLYADSV KGRFTISRDN SKNTLYLQMN SLRPEDTAVY YCTIGGSLSA SSQGTLVTVS    360
S                                                                    361

SEQ ID NO: 164          moltype = AA  length = 361
FEATURE                 Location/Qualifiers
source                  1..361
                        mol_type = protein
                        organism = synthetic construct
SEQUENCE: 164
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKHYTQKS LSLSPGGGGG SGGGGSGGGG    240
SGGGGSEVQL LESGGGLVQP GGSLRLSCAA SGFTFRSFGM SWVRQAPGKG PEWVSSISGS    300
GSDTLYADSV KGRFTISRDN SKNTLYLQMN SLRPEDTAVY YCTIGGTLSR SSQGTLVTVS    360
S                                                                    361

SEQ ID NO: 165          moltype = AA  length = 361
FEATURE                 Location/Qualifiers
source                  1..361
                        mol_type = protein
                        organism = synthetic construct
SEQUENCE: 165
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKHYTQKS LSLSPGGGGG SGGGGSGGGG    240
SGGGGSEVQL LESGGGLVQP GGSLRLSCAA SGFTFRSFAM SWVRQAPGKG PEWVSSISGS    300
GSDTLYADSV KGRFTISRDN SKNTLYLQMN SLRPEDTAVY YCTIGGALSR SSQGTLVTVS    360
S                                                                    361

SEQ ID NO: 166          moltype = AA  length = 361
FEATURE                 Location/Qualifiers
source                  1..361
                        mol_type = protein
                        organism = synthetic construct
SEQUENCE: 166
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKHYTQKS LSLSPGGGGG SGGGGSGGGG    240
SGGGGSEVQL LESGGGLVQP GGSLRLSCAA SGFTFRSFAM SWVRQAPGKG PEWVSSISAS    300
GSDTLYADSV KGRFTISRDN SKNTLYLQMN SLRPEDTAVY YCTIGGSLSR SSQGTLVTVS    360
S                                                                    361
```

```
SEQ ID NO: 167           moltype = AA   length = 361
FEATURE                  Location/Qualifiers
source                   1..361
                         mol_type = protein
                         organism = synthetic construct
SEQUENCE: 167
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSIAAS   300
GSDTLYADSV KGRFTISRDN SKNTLYLQMN SLRPEDTAVY YCTIGGSLSR SSQGTLVTVS   360
S                                                                  361

SEQ ID NO: 168           moltype = AA   length = 361
FEATURE                  Location/Qualifiers
source                   1..361
                         mol_type = protein
                         organism = synthetic construct
SEQUENCE: 168
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSIAGS   300
GSDTLYADSV KGRFTISRDN SKNTLYLQMN SLRPEDTAVY YCTIGGALSR SSQGTLVTVS   360
S                                                                  361

SEQ ID NO: 169           moltype = AA   length = 361
FEATURE                  Location/Qualifiers
source                   1..361
                         mol_type = protein
                         organism = synthetic construct
SEQUENCE: 169
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSHGM SWVRQAPGKG PEWVSSIGGS   300
GSDTLYADSV KGRFTISRDN SKNTLYLQMN SLRPEDTAVY YCTIGGSLSR SSQGTLVTVS   360
S                                                                  361

SEQ ID NO: 170           moltype = AA   length = 361
FEATURE                  Location/Qualifiers
source                   1..361
                         mol_type = protein
                         organism = synthetic construct
SEQUENCE: 170
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGH SWVRQAPGKG PEWVSSISGS   300
GSDTLYADSV KGRFTISRDN SKNTLYLQMN SLRPEDTAVY YCTIGGSLSR SSQGTLVTVS   360
S                                                                  361

SEQ ID NO: 171           moltype = AA   length = 361
FEATURE                  Location/Qualifiers
source                   1..361
                         mol_type = protein
                         organism = synthetic construct
SEQUENCE: 171
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
HSDTLYADSV KGRFTISRDN SKNTLYLQMN SLRPEDTAVY YCTIGGSLSR SSQGTLVTVS   360
S                                                                  361

SEQ ID NO: 172           moltype = AA   length = 361
FEATURE                  Location/Qualifiers
source                   1..361
                         mol_type = protein
                         organism = synthetic construct
SEQUENCE: 172
DKTHTCPPCP APELLGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
```

```
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTHYADSV KGRFTISRDN SKNTLYLQMN SLRPEDTAVY YCTIGGSLSR SSQGTLVTVS   360
S                                                                  361

SEQ ID NO: 173          moltype = AA   length = 361
FEATURE                 Location/Qualifiers
source                  1..361
                        mol_type = protein
                        organism = synthetic construct
SEQUENCE: 173
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV KGRFTISRDN SKNTLYLQMN SLRPEDTAVY YCTIHGSLSR SSQGTLVTVS   360
S                                                                  361

SEQ ID NO: 174          moltype = AA   length = 361
FEATURE                 Location/Qualifiers
source                  1..361
                        mol_type = protein
                        organism = synthetic construct
SEQUENCE: 174
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV KGRFTISRDN SKNTLYLQMN SLRPEDTAVY YCTIGHSLSR SSQGTLVTVS   360
S                                                                  361

SEQ ID NO: 175          moltype = AA   length = 361
FEATURE                 Location/Qualifiers
source                  1..361
                        mol_type = protein
                        organism = synthetic construct
SEQUENCE: 175
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFGM SWVRQAPGKG PEWVSSISGS   300
GSDTLYADSV KGRFTISRDN SKNTLYLQMN SLRPEDTAVY YCTIGGSHSR SSQGTLVTVS   360
S                                                                  361

SEQ ID NO: 176          moltype = AA   length = 361
FEATURE                 Location/Qualifiers
source                  1..361
                        mol_type = protein
                        organism = synthetic construct
SEQUENCE: 176
DKTHTCPPCP APELLGGPSV FLFPPKPKDT LYITREPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALKFHYTQKS LSLSPGGGGG SGGGGSGGGG   240
SGGGGSEVQL LESGGGLVQP GGSLRLSCAA SGFTFRSFHM SWVRQAPGKG PEWVSSISGS   300
GSDTLYADSV KGRFTISRDN SKNTLYLQMN SLRPEDTAVY YCTIGGHLSR SSQGTLVTVS   360
S                                                                  361

SEQ ID NO: 177          moltype = AA   length = 341
FEATURE                 Location/Qualifiers
source                  1..341
                        mol_type = protein
                        organism = synthetic construct
SEQUENCE: 177
EVQLLESGGG LVQPGGSLRL SCAASGFTFR SFGMSWVRQA PGKGPEWVSS ISGSGSDTLY   60
ADSVKGRFTI SRDNSKNTLY LQMNSLRPED TAVYYCTIGG SLSRSSQGTL VTVSSDKTHT   120
CPPCPAPELL GGPSVFLFPP KPKDTLYITR EPEVTCVVVD VSHEDPEVKF NWYVDGVEVH   180
NAKTKPREEQ YNSTYRVVSV LTVLHQDWLN GKEYKCKVSN KALPAPIEKT ISKAKGQPRE   240
PQVYTLPPSR DELTKNQVSL TCLVKGFYPS DIAVEWESNG QPENNYKTTP PVLDSDGSFF   300
LYSKLTVDKS RWQQGNVFSC SVMHEALKFH YTQKSLSLSP G                      341

SEQ ID NO: 178          moltype = AA   length = 361
FEATURE                 Location/Qualifiers
source                  1..361
                        mol_type = protein
                        organism = synthetic construct
```

```
SEQUENCE: 178
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALKFHYTQKS LSLSPGGGGG SGGGGSGGGG    240
SGGGGSEVQL LESGGGLVQP GGSLRLSCAA SGFTFRSFGM SWVRQAPGKG PEWVSSISGS    300
GSDTLYADSV KGRFTISRDN SKNTLYLQMN SLRPEDTAVY YCTIGGSLSR SSQGTLVTVS    360
S                                                                    361

SEQ ID NO: 179           moltype = AA  length = 15
FEATURE                  Location/Qualifiers
source                   1..15
                         mol_type = protein
                         organism = synthetic construct
SEQUENCE: 179
EPKSCDKTHT CPPCP                                                      15

SEQ ID NO: 180           moltype = AA  length = 372
FEATURE                  Location/Qualifiers
source                   1..372
                         mol_type = protein
                         organism = synthetic construct
SEQUENCE: 180
DKTHTCPPCP APELLGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLWCLVK GFYPSDIAVE WESNGQPENN YKTTPPVLDS    180
DGSFFLYSKL TVDKSRWQQG NVFSCSVMHE ALKFHYTQKS LSLSPGGGGG SGGGGSGGGG    240
SGGGGSGGGG SGGGGSEVQL LESGGGLVQP GGSLRLSCAA SGFTFRSAGM SWVRQAPGKG    300
PEWVSSISGS GSDTLYADSV KGRFTISRDN SKNTLYLQMN SLRPEDTAVY YCTIGGSLSR    360
SSQGTLVTVS SA                                                        372

SEQ ID NO: 181           moltype = AA  length = 10
FEATURE                  Location/Qualifiers
source                   1..10
                         mol_type = protein
                         organism = synthetic construct
SEQUENCE: 181
GGGGSGGGGS                                                            10

SEQ ID NO: 182           moltype = AA  length = 30
FEATURE                  Location/Qualifiers
source                   1..30
                         mol_type = protein
                         organism = synthetic construct
SEQUENCE: 182
GGGGSGGGGS GGGGSGGGGS GGGGSGGGGS                                      30
```

FcRn/HSA BINDING MOLECULES AND METHODS OF USE

CROSS REFERENCE TO RELATED APPLICATIONS

This application is a Continuation of International Patent Application No. PCT/EP2023/066180, filed Jun. 15, 2023, which claims the benefit of and priority to U.S. Provisional Patent Application No. 63/352,589, filed on Jun. 15, 2022, the contents of each of which are incorporated herein by reference in their entirety.

SUBMISSION OF SEQUENCE LISTING XML

The content of the following submission of Sequence Listing XML is incorporated herein by reference in its entirety: a computer readable form (CRF) of the Sequence Listing (file name: P240449WO03—sequence listing.xml, date created: Jun. 15, 2023, size: 171,156 bytes).

FIELD

The present disclosure relates to human neonatal Fc receptor (FcRn)/HSA-binding molecules and methods of using the same.

BACKGROUND

Immunoglobulin gamma (IgG) antibodies play a key role in the pathology of many disorders, such as autoimmune diseases, inflammatory diseases, and disorders in which the pathology is characterized by over-expression of IgG antibodies.

The half-life of IgG in the serum is prolonged relative to the serum half-life of other plasma proteins due, in part, to the binding of the Fc region of IgG to the Fc receptor, FcRn. FcRn binds to IgG and protects the IgG from transport to degradative lysosomes by recycling it back to the extracellular compartment. This recycling is facilitated by the pH-dependent binding of IgG to FcRn, where the IgG/FcRn interaction is stronger at acidic endosomal pH than at extracellular physiological pH.

When the serum concentration of IgG reaches a level that exceeds available FcRn molecules, unbound IgG is not protected from lysosomal degradation and will consequently have a reduced serum half-life. Thus, inhibition of IgG binding to FcRn reduces the serum half-life of IgG by preventing endosomal recycling of IgG. Agents that antagonize the binding of IgG to FcRn, such as FcRn-binding molecules, are useful for regulating, treating, or preventing antibody-mediated disorders, such as autoimmune diseases or inflammatory diseases.

Efgartigimod is a modified human immunoglobulin (Ig) gamma (IgG) 1-derived Fc of the za allotype that binds with nanomolar affinity to human FcRn. Efgartigimod encompasses the IgG1 Fc-region and has been engineered using ABDEG technology to increase its affinity for FcRn at both physiological and acidic pH. The increased affinity for FcRn of efgartigimod at both acidic and physiological pH results in a blockage of FcRn-mediated recycling of IgGs. Efgartigimod has been approved as a weekly intravenous injection for use in the treatment of generalized myasthenia gravis in the U.S. and Japan and is under development for the treatment of several other antibody-mediated disorders.

FcRn also binds to and recycles serum albumin, a modulator of serum cholesterol levels. Efgartigimod advantageously does not negatively impact serum albumin levels in human subjects. However, it has recently been shown that anti-FcRn antibodies can cause a reduction in serum albumin levels and a concomitant increase in serum cholesterol levels in human subjects, both of which are undesirable.

Accordingly, there is a need in the art for improved agents that antagonize FcRn binding to IgG with a longer half-life, lower dose, less frequent administration, better maintenance of albumin levels, and/or reduction or elimination of FcRn degradation, for use in the treatment of antibody-mediated disorders.

SUMMARY

The instant disclosure is broadly directed to neonatal Fc receptor (FcRn) binding molecules linked to one or more antigen-binding domains which specifically bind to human serum albumin (FcRn/antigen-binding molecules or FcRn/HSA-binding molecules) and methods of use thereof. It has been shown for the first time in this application that, unexpectedly, the inclusion of an HSA binding moiety increases the stability (longevity) and FcRn occupancy of FcRn binding molecules linked to one or more antigen-binding domains which specifically bind to HSA.

In an aspect, provided herein is an FcRn/antigen-binding molecule comprising an FcRn binding molecule and a first antigen-binding domain, wherein the first antigen-binding domain is linked to a C-terminus of the FcRn binding molecule, and wherein the first antigen-binding domain specifically binds to human serum albumin (HSA).

In some embodiments, the first antigen-binding domain binds to HSA at pH 7.4 with lower affinity than the binding affinity of Alb23 (SEQ ID NO: 42) for HSA. In some embodiments, the first antigen-binding domain binds to HSA at pH 5.5 with lower affinity than the binding affinity of Alb23 (SEQ ID NO: 42) for HSA.

In some embodiments, the FcRn/antigen-binding molecule binds to HSA at pH 7.4 with a dissociation constant greater than about 2.4 nM. In some embodiments, the FcRn/antigen-binding molecule binds to HSA at pH 5.5 with a dissociation constant greater than about 2.4 nM.

In some embodiments, the FcRn/antigen-binding molecule binds to FcRn at pH 5.5 and/or at pH 6.0 with a higher affinity than the affinity of efgartigimod for FcRn at pH 5.5 and/or pH 6.0. In some embodiments, the FcRn/antigen-binding molecule binds to FcRn at pH 5.5 and/or at pH 6.0 with a lower affinity than the affinity of efgartigimod for FcRn at pH 5.5 and/or pH 6.0.

In any of the above embodiments, binding affinity may optionally be measured by surface plasmon resonance.

In some embodiments, the FcRn binding molecule is a variant Fc region, wherein the variant Fc region comprises a first Fc domain and a second Fc domain which form a dimer.

In some embodiments, the first Fc domain and/or the second Fc domain comprise amino acids Y, T, E, K, and F at EU positions 252, 254, 256, 433, and 434, respectively. In some embodiments, the first Fc domain and/or the second Fc domain comprise amino acids Y, T, E, K, F, and Y at EU positions 252, 254, 256, 433, 434, and 436, respectively.

In some embodiments, both the first Fc domain and the second Fc domain comprise amino acids Y, T, E, K, and F at EU positions 252, 254, 256, 433, and 434, respectively. In some embodiments, both the first Fc domain and the second Fc domain comprise amino acids Y, T, E, K, F, and Y at EU positions 252, 254, 256, 433, 434, and 436, respectively.

In some embodiments, the first Fc domain and/or the second Fc domain is an IgG Fc domain, such as an IgG1 Fc domain. In some embodiments, the first Fc domain and/or the second Fc domain is a human IgG Fc domain, such as a human IgG1 Fc domain.

In some embodiments, both the first Fc domain and the second Fc domain are IgG Fc domains, such as IgG1 Fc domains. In some embodiments, both the first Fc domain and the second Fc domain are human IgG Fc domains, such as human IgG1 Fc domains.

In some embodiments, the first antigen-binding domain is covalently linked to the first Fc domain or the second Fc domain.

In some embodiments, the N-terminus of the first antigen-binding domain is fused to the C-terminus of the first Fc domain. In some embodiments, the N-terminus of the first antigen-binding domain is fused to the C-terminus of the second Fc domain. In some embodiments, the first antigen-binding domain is fused to the first Fc domain or the second Fc domain via a linker. In some embodiments, the linker is a non-cleavable linker. In some embodiments, the linker is a peptide linker. In some embodiments, the peptide linker is a GS linker, optionally from 8 to 40 amino acids in length, optionally 20 or 30 amino acids in length.

In some embodiments, the first Fc domain and/or the second Fc domain comprise an amino acid sequence independently selected from an amino acid sequence set forth in SEQ ID NO: 1, 2, or 3. In some embodiments, the first Fc domain and/or the second Fc domain comprise the amino acid sequence of SEQ ID NO: 2.

In some embodiments, both the first Fc domain and the second Fc domain comprise an amino acid sequence independently selected from an amino acid sequence set forth in SEQ ID NO: 1, 2, or 3. In some embodiments, both the first Fc domain and the second Fc domain comprise the amino acid sequence of SEQ ID NO: 2.

In some embodiments, the amino acid sequence of each of the first Fc domain and the second Fc domain consists of an amino acid sequence independently selected from an amino acid sequence set forth in SEQ ID NO: 1, 2, or 3. In some embodiments, the amino acid sequence of the first Fc domain or the amino acid sequence of the second Fc domain consists of SEQ ID NO: 2.

In some embodiments, the amino acid sequences of both the first Fc domain and the second Fc domain consist of SEQ ID NO: 2.

In some embodiments, the variant Fc region comprises one or more mutations of amino acid residues forming the interface of the CH3 domain of the Fc domains.

In some embodiments, the amino acid sequence of the first Fc domain further comprises amino acid W at EU position 366.

In some embodiments, the amino acid sequence of the first Fc domain comprises an amino acid sequence selected from an amino acid sequence set forth in SEQ ID NO: 4, 5, or 6. In some embodiments, the amino acid sequence of the first Fc domain comprises the amino acid sequence of SEQ ID NO: 5.

In some embodiments, the amino acid sequence of the first Fc domain consists of an amino acid sequence selected from an amino acid sequence set forth in SEQ ID NO: 4, 5, or 6. In some embodiments, the amino acid sequence of the first Fc domain consists of the amino acid sequence of SEQ ID NO: 5.

In some embodiments, the amino acid sequence of the second Fc domain further comprises amino acids S, A, and V at EU positions 366, 368, and 407, respectively.

In some embodiments, the amino acid sequence of the second Fc domain comprises an amino acid sequence selected from an amino acid sequence set forth in SEQ ID NO: 7, 8, or 9. In some embodiments, the amino acid sequence of the second Fc domain comprises the amino acid sequence of SEQ ID NO: 8.

In some embodiments, the amino acid sequence of the second Fc domain consists of an amino acid sequence selected from an amino acid sequence set forth in SEQ ID NO: 7, 8, or 9. In some embodiments, the amino acid sequence of the second Fc domain consists of the amino acid sequence of SEQ ID NO: 8.

In some embodiments, the first antigen-binding domain is selected from a Fab fragment, an sdAb, an scFv, an antibody mimetic, HSA, or an HSA-binding fragment thereof. In some embodiments, the antibody mimetic is an anticalin or a DARPin. In some embodiments, the sdAb is a VHH fragment.

In some embodiments, the first antigen-binding domain is any antigen-binding domain described herein. In some embodiments, the first antigen-binding domain is a VHH fragment comprising the CDR1, CDR2, and CDR3 amino acid sequences of any of the VHH fragments disclosed herein. In some embodiments, the first antigen-binding domain is a VHH fragment comprising the CDR1, CDR2, and CDR3 amino acid sequences of a VHH fragment comprising an amino acid sequence selected from SEQ ID NOs: 43-74, 84-90, and 120-127.

In some embodiments, the first antigen-binding domain is a VHH fragment comprising an amino acid sequence at least 70%, 75%, 80%, 85%, 90%, 95%, 96%, 97%, 98%, or 99% identical to an amino acid sequence selected from SEQ ID NOs: 43-74, 84-90, and 120-127. In some embodiments, the first antigen-binding domain is a VHH fragment comprising an amino acid sequence at least 70%, 75%, 80%, 85%, 90%, 95%, 96%, 97%, 98%, or 99% identical to an amino acid sequence set forth in SEQ ID NO: 44. In some embodiments, the first antigen-binding domain comprises an amino acid sequence selected from SEQ ID NOs: 43-74, 84-90, and 120-127. In some embodiments, the first antigen-binding domain comprises an amino acid sequence set forth in SEQ ID NO: 44.

In some embodiments, the FcRn/antigen-binding molecule further comprises one or more additional amino acids at the C-terminal end of the first antigen-binding domain, for example, when the first antigen-binding domain is a VHH fragment. In some embodiments, the one or more additional amino acids are selected from the group consisting of: a) A; b) AG; c) GG; d) PP; and e) AA.

In some embodiments, the FcRn/antigen-binding molecule further comprises a second antigen-binding domain.

In some embodiments, the second antigen-binding domain is linked to the first Fc domain or the second Fc domain.

In some embodiments, the second antigen-binding domain is fused to the first Fc domain or the second Fc domain via a linker. In some embodiments, the linker is a non-cleavable linker. In some embodiments, the linker is a peptide linker. In some embodiments, the peptide linker is a GS linker, optionally from 8 to 40 amino acids in length, optionally 20 or 30 amino acids in length.

In some embodiments, the second antigen-binding domain is fused to the first Fc domain or the second Fc domain via an IgG hinge region or portion thereof.

In some embodiments, the first antigen-binding domain is fused to the first Fc domain and the second antigen-binding domain is fused to the second Fc domain. In some embodiments, the second antigen-binding domain is fused to the C-terminus of the second Fc domain. In some embodiments, the second antigen-binding domain is fused to the N-terminus of the second Fc domain.

In some embodiments, the first antigen-binding domain is fused to the second Fc domain and the second antigen-binding domain is fused to the first Fc domain. In some embodiments, the second antigen-binding domain is fused to the C-terminus of the first Fc domain. In some embodiments, the second antigen-binding domain is fused to the N-terminus of the first Fc domain.

In some embodiments, the second antigen-binding domain specifically binds to HSA.

In some embodiments, the second antigen-binding domain is selected from a Fab fragment, an sdAb, an scFv, an antibody mimetic, HSA, or an HSA-binding fragment thereof. In some embodiments, the antibody mimetic is an anticalin or a DARPin. In some embodiments, the sdAb is a VHH fragment.

In some embodiments, the second antigen-binding domain is any antigen-binding domain described herein. In some embodiments, the second antigen-binding domain is a VHH fragment comprising the CDR1, CDR2, and CDR3 amino acid sequences of any of the VHH fragments disclosed herein. In some embodiments, the second antigen-binding domain is a VHH fragment comprising the CDR1, CDR2, and CDR3 amino acid sequences of a VHH fragment comprising an amino acid sequence selected from SEQ ID NOs: 43-74, 84-90, and 120-127.

In some embodiments, the second antigen-binding domain is a VHH fragment comprising an amino acid sequence at least 70%, 75%, 80%, 85%, 90%, 95%, 96%, 97%, 98%, or 99% identical to an amino acid sequence selected from SEQ ID NOs: 43-74, 84-90, and 120-127. In some embodiments, the second antigen-binding domain is a VHH fragment comprising an amino acid sequence at least 70%, 75%, 80%, 85%, 90%, 95%, 96%, 97%, 98%, or 99% identical to an amino acid sequence set forth in SEQ ID NO: 44. In some embodiments, the second antigen-binding domain comprises an amino acid sequence selected from SEQ ID NOs: 43-74, 84-90, and 120-127. In some embodiments, the second antigen-binding domain comprises an amino acid sequence set forth in SEQ ID NO: 44.

In some embodiments, the FcRn/antigen-binding molecule further comprises one or more amino acids at the C-terminal end of the second antigen-binding domain, for example, when the second antigen-binding domain is a VHH fragment. In some embodiments, the one or more amino acids are selected from the group consisting of: a) A; b) AG; c) GG; d) PP; and e) AA.

In some embodiments, the first antigen-binding domain and the second antigen-binding domain are identical.

In some embodiments, the FcRn/antigen-binding molecule comprises an FcRn binding molecule and only one antigen-binding domain linked to the FcRn binding molecule.

In an aspect, provided herein is an FcRn/antigen-binding molecule comprising a first heavy chain, wherein the first heavy chain comprises an amino acid sequence at least 70%, 75%, 80%, 85%, 90%, 95%, 96%, 97%, 98%, or 99% identical to the amino acid sequence of any one of SEQ ID NOs: 137-176, and 180. In some embodiments, the first heavy chain comprises an amino acid sequence at least 70%, 75%, 80%, 85%, 90%, 95%, 96%, 97%, 98%, or 99% identical to the amino acid sequence of SEQ ID NO: 180. In some embodiments, the first heavy chain comprises or consists of an amino acid sequence of any one of SEQ ID NOs: 137-176, and 180. In some embodiments, the first heavy chain comprises or consists of an amino acid sequence of SEQ ID NO: 180. In some embodiments, the first heavy chain further comprises one of more amino acids added at the C-terminus, optionally selected from A, AG, GG, and PP.

In some embodiments, the FcRn/antigen-binding molecule further comprises a second heavy chain, wherein the second heavy chain consists of an amino acid sequence at least 70%, 75%, 80%, 85%, 90%, 95%, 96%, 97%, 98%, or 99% identical to the amino acid sequence of SEQ ID NO: 8. In some embodiments, the second heavy chain consists of the amino acid sequence of SEQ ID NO: 8.

In an aspect, provided herein is an antigen-binding domain comprising CDR1, CDR2, and CDR3 amino acid sequences of a VHH fragment comprising an amino acid sequence selected from SEQ ID NOs: 43-74, 84-90, and 120-127.

In some embodiments, the first and/or second antigen-binding domain comprises an amino acid sequence selected from the group consisting of:
a) an amino acid sequence comprising SEQ ID NO: 13 (CDR1), SEQ ID NO: 11 (CDR2), and SEQ ID NO: 12 (CDR3);
b) an amino acid sequence comprising SEQ ID NO: 14 (CDR1), SEQ ID NO: 11 (CDR2), and SEQ ID NO: 12 (CDR3);
c) an amino acid sequence comprising SEQ ID NO: 15 (CDR1), SEQ ID NO: 11 (CDR2), and SEQ ID NO: 12 (CDR3);
d) an amino acid sequence comprising SEQ ID NO: 16 (CDR1), SEQ ID NO: 11 (CDR2), and SEQ ID NO: 12 (CDR3);
e) an amino acid sequence comprising SEQ ID NO: 17 (CDR1), SEQ ID NO: 11 (CDR2), and SEQ ID NO: 12 (CDR3);
f) an amino acid sequence comprising SEQ ID NO: 10 (CDR1), SEQ ID NO: 18 (CDR2), and SEQ ID NO: 12 (CDR3);
g) an amino acid sequence comprising SEQ ID NO: 10 (CDR1), SEQ ID NO: 19 (CDR2), and SEQ ID NO: 12 (CDR3);
h) an amino acid sequence comprising SEQ ID NO: 10 (CDR1), SEQ ID NO: 20 (CDR2), and SEQ ID NO: 12 (CDR3);
i) an amino acid sequence comprising SEQ ID NO: 10 (CDR1), SEQ ID NO: 21 (CDR2), and SEQ ID NO: 12 (CDR3);
j) an amino acid sequence comprising SEQ ID NO: 10 (CDR1), SEQ ID NO: 22 (CDR2), and SEQ ID NO: 12 (CDR3);
k) an amino acid sequence comprising SEQ ID NO: 10 (CDR1), SEQ ID NO: 23 (CDR2), and SEQ ID NO: 12 (CDR3);
l) an amino acid sequence comprising SEQ ID NO: 10 (CDR1), SEQ ID NO: 24 (CDR2), and SEQ ID NO: 12 (CDR3);
m) an amino acid sequence comprising SEQ ID NO: 10 (CDR1), SEQ ID NO: 25 (CDR2), and SEQ ID NO: 12 (CDR3);
n) an amino acid sequence comprising SEQ ID NO: 10 (CDR1), SEQ ID NO: 26 (CDR2), and SEQ ID NO: 12 (CDR3);
o) an amino acid sequence comprising SEQ ID NO: 10 (CDR1), SEQ ID NO: 27 (CDR2), and SEQ ID NO: 12 (CDR3);

p) an amino acid sequence comprising SEQ ID NO: 10 (CDR1), SEQ ID NO: 28 (CDR2), and SEQ ID NO: 12 (CDR3);
q) an amino acid sequence comprising SEQ ID NO: 10 (CDR1), SEQ ID NO: 29 (CDR2), and SEQ ID NO: 12 (CDR3);
r) an amino acid sequence comprising SEQ ID NO: 10 (CDR1), SEQ ID NO: 30 (CDR2), and SEQ ID NO: 12 (CDR3);
s) an amino acid sequence comprising SEQ ID NO: 10 (CDR1), SEQ ID NO: 31 (CDR2), and SEQ ID NO: 12 (CDR3);
t) an amino acid sequence comprising SEQ ID NO: 10 (CDR1), SEQ ID NO: 32 (CDR2), and SEQ ID NO: 12 (CDR3);
u) an amino acid sequence comprising SEQ ID NO: 10 (CDR1), SEQ ID NO: 33 (CDR2), and SEQ ID NO: 12 (CDR3);
v) an amino acid sequence comprising SEQ ID NO: 10 (CDR1), SEQ ID NO: 11 (CDR2), and SEQ ID NO: 34 (CDR3);
w) an amino acid sequence comprising SEQ ID NO: 10 (CDR1), SEQ ID NO: 11 (CDR2), and SEQ ID NO: 35 (CDR3);
x) an amino acid sequence comprising SEQ ID NO: 10 (CDR1), SEQ ID NO: 11 (CDR2), and SEQ ID NO: 36 (CDR3);
y) an amino acid sequence comprising SEQ ID NO: 10 (CDR1), SEQ ID NO: 11 (CDR2), and SEQ ID NO: 37 (CDR3);
z) an amino acid sequence comprising SEQ ID NO: 10 (CDR1), SEQ ID NO: 11 (CDR2), and SEQ ID NO: 38 (CDR3);
aa) an amino acid sequence comprising SEQ ID NO: 10 (CDR1), SEQ ID NO: 11 (CDR2), and SEQ ID NO: 39 (CDR3);
bb) an amino acid sequence comprising SEQ ID NO: 10 (CDR1), SEQ ID NO: 11 (CDR2), and SEQ ID NO: 40 (CDR3);
cc) an amino acid sequence comprising SEQ ID NO: 15 (CDR1), SEQ ID NO: 11 (CDR2), and SEQ ID NO: 36 (CDR3);
dd) an amino acid sequence comprising SEQ ID NO: 15 (CDR1), SEQ ID NO: 21 (CDR2), and SEQ ID NO: 12 (CDR3);
ee) an amino acid sequence comprising SEQ ID NO: 10 (CDR1), SEQ ID NO: 41 (CDR2), and SEQ ID NO: 12 (CDR3);
ff) an amino acid sequence comprising SEQ ID NO: 10 (CDR1), SEQ ID NO: 20 (CDR2), and SEQ ID NO: 36 (CDR3);
gg) an amino acid sequence comprising SEQ ID NO: 111 (CDR1), SEQ ID NO: 11 (CDR2), and SEQ ID NO: 12 (CDR3);
hh) an amino acid sequence comprising SEQ ID NO: 112 (CDR1), SEQ ID NO: 11 (CDR2), and SEQ ID NO: 12 (CDR3);
ii) an amino acid sequence comprising SEQ ID NO: 10 (CDR1), SEQ ID NO: 113 (CDR2), and SEQ ID NO: 12 (CDR3);
jj) an amino acid sequence comprising SEQ ID NO: 10 (CDR1), SEQ ID NO: 114 (CDR2), and SEQ ID NO: 12 (CDR3);
kk) an amino acid sequence comprising SEQ ID NO: 10 (CDR1), SEQ ID NO: 11 (CDR2), and SEQ ID NO: 115 (CDR3);
ll) an amino acid sequence comprising SEQ ID NO: 10 (CDR1), SEQ ID NO: 11 (CDR2), and SEQ ID NO: 116 (CDR3);
mm) an amino acid sequence comprising SEQ ID NO: 10 (CDR1), SEQ ID NO: 11 (CDR2), and SEQ ID NO: 117 (CDR3);
nn) an amino acid sequence comprising SEQ ID NO: 118 (CDR1), SEQ ID NO: 11 (CDR2), and SEQ ID NO: 119 (CDR3);
oo) an amino acid sequence comprising SEQ ID NO: 75 (CDR1), SEQ ID NO: 76 (CDR2), and SEQ ID NO: 77 (CDR3);
pp) an amino acid sequence comprising SEQ ID NO: 75 (CDR1), SEQ ID NO: 76 (CDR2), and SEQ ID NO: 78 (CDR3);
qq) an amino acid sequence comprising SEQ ID NO: 75 (CDR1), SEQ ID NO: 76 (CDR2), and SEQ ID NO: 79 (CDR3);
rr) an amino acid sequence comprising SEQ ID NO: 75 (CDR1), SEQ ID NO: 76 (CDR2), and SEQ ID NO: 80 (CDR3);
ss) an amino acid sequence comprising SEQ ID NO: 75 (CDR1), SEQ ID NO: 76 (CDR2), and SEQ ID NO: 81 (CDR3);
tt) an amino acid sequence comprising SEQ ID NO: 75 (CDR1), SEQ ID NO: 76 (CDR2), and SEQ ID NO: 82 (CDR3); and
uu) an amino acid sequence comprising SEQ ID NO: 75 (CDR1), SEQ ID NO: 76 (CDR2), and SEQ ID NO: 83 (CDR3).

In some embodiments, the antigen-binding domain comprises an amino acid sequence comprising SEQ ID NO: 14 (CDR1), SEQ ID NO: 11 (CDR2), and SEQ ID NO: 12 (CDR3).

In some embodiments, the first and/or second antigen-binding domain comprises an amino acid sequence at least 70%, 75%, 80%, 85%, 90%, 95%, 96%, 97%, 98%, or 99% identical to an amino acid sequence set forth in SEQ ID NO: 43-74, 84-90, and 120-127. In some embodiments, the antigen-binding domain comprises an amino acid sequence at least 70%, 75%, 80%, 85%, 90%, 95%, 96%, 97%, 98%, or 99% identical to an amino acid sequence set forth in SEQ ID NO: 44. In some embodiments, the first and/or second antigen-binding domain comprises an amino acid sequence selected from an amino acid sequence set forth in SEQ ID NO: 43-74, 84-90, and 120-127. In some embodiments, the first and/or second antigen-binding domain comprises an amino acid sequence set forth in SEQ ID NO: 44.

In some embodiments, the antigen-binding domain is an sdAb. In some embodiments, the sdAb is a VHH fragment. In some embodiments, the antigen-binding domain further comprises one or more additional amino acids at the C-terminal end of the VHH fragment. In some embodiments, the one or more additional amino acids are selected from the group consisting of: a) A; b) AG; c) GG; d) PP; and e) AA.

In some embodiments, the antigen-binding domain specifically binds to HSA. In a particular embodiment, the antigen-binding domain is a VHH fragment which binds to HSA with an affinity which is stronger at neutral pH than at acidic pH. In some embodiments, the antigen-binding domain binds to HSA with lower affinity than the binding affinity of Alb23 (SEQ ID NO: 42) for HSA, optionally as measured by surface plasmon resonance.

Also provided is an isolated polynucleotide or polynucleotides encoding any FcRn/antigen-binding molecule described herein or any antigen-binding domain described herein.

Also provided is an expression vector comprising any isolated polynucleotide or polynucleotides described herein.

Also provided is a host cell comprising any isolated polynucleotide or polynucleotides or any expression vector described herein.

A method for producing an FcRn/antigen-binding molecule or an antigen-binding domain is also provided, the method comprising culturing a host cell as described herein under conditions which permit the expression of the FcRn/antigen-binding molecule or antigen-binding domain.

Also provided is a pharmaceutical composition comprising an FcRn/antigen-binding molecule as described herein or an antigen-binding domain as described herein and at least one pharmaceutically acceptable carrier.

Also provided is an FcRn/antigen-binding molecule as described herein, or an antigen-binding domain as described herein, or a pharmaceutical composition thereof for use as a medicament.

Also provided is a method of reducing serum IgG in a subject comprising administering to a subject in need thereof a therapeutically effective amount of an FcRn/antigen-binding molecule as described herein (e.g., an FcRn/HSA-binding molecule as described herein), or an antigen-binding domain as described herein, or a pharmaceutical composition thereof.

Also provided is a method of treating an antibody-mediated disorder in a subject, wherein the method comprises administering to a subject in need thereof a therapeutically effective amount of an FcRn/antigen-binding molecule as described herein (e.g., an FcRn/HSA-binding molecule as described herein), or an antigen-binding domain as described herein, or a pharmaceutical composition thereof.

In some embodiments, the antibody-mediated disorder is an IgG-mediated disorder. In some embodiments, the antibody-mediated disorder is an autoimmune disease. In some embodiments, the autoimmune disease is selected from the group consisting of: allogenic islet graft rejection, alopecia areata, ankylosing spondylitis, antiphospholipid syndrome, autoimmune Addison's disease, Alzheimer's disease, anti-neutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, immune thrombocytopenia (ITP or idiopathic thrombocytopenic purpura, idiopathic thrombocytopenia purpura, immune mediated thrombocytopenia, or primary immune thrombocytopenia), autoimmune urticaria, Behcet's disease, bullous pemphigoid (BP), cardiomyopathy, Castleman disease, celiac sprue-dermatitis, chronic fatigue immune disfunction syndrome, chronic inflammatory demyelinating polyneuropathy (CIDP), Churg-Strauss syndrome, cicatricial pemphigoid, CREST syndrome, cold agglutinin disease, Crohn's disease, dilated cardiomyopathy, discoid lupus, epidermolysis bullosa acquisita, essential mixed cryoglobulinemia, factor VIII deficiency, fibromyalgia-fibromyositis, glomerulonephritis, Graves' disease, Guillain-Barre syndrome, Goodpasture's syndrome, graft-versus-host disease (GVHD), Hashimoto's thyroiditis, hemophilia A, idiopathic inflammatory myopathies (IIMs), idiopathic membranous neuropathy, idiopathic pulmonary fibrosis, IgA neuropathy, IgM polyneuropathies, immune-mediated necrotizing myopathy (IMNM), juvenile arthritis, Kawasaki disease, lichen planus, lichen sclerosus, lupus erythematosus, lupus nephritis, Meniere's disease, mixed connective tissue disease, mucous membrane pemphigoid, multiple sclerosis, Type 1 diabetes mellitus, multifocal motor neuropathy (MMN), myasthenia gravis (MG), generalized myasthenia gravis (gMG), myositis, paraneoplastic bullous pemphigoid, pemphigoid gestationis, pemphigus vulgaris (PV), pemphigus foliaceus (PF), pernicious anemia, polyarteritis nodosa, polychrondritis, polyglandular syndromes, polymyalgia rheumatica, polymyositis, dermatomyositis (DM), necrotizing autoimmune myopathy (NAM), AntiSynthetase Syndrome (ASyS), primary agammaglobulinemia, primary biliary cirrhosis, psoriasis, psoriatic arthritis, relapsing polychondritis, Raynaud's phenomenon, Reiter's syndrome, rheumatoid arthritis, sarcoidosis, scleroderma, Sjögren's syndrome, solid organ transplant rejection, stiff-person syndrome, systemic lupus erythematosus, Takayasu's arteritis, toxic epidermal necrolysis (TEN), Stevens-Johnson syndrome (SJS), temporal arteritis/giant cell arteritis, thrombotic thrombocytopenia purpura, ulcerative colitis, uveitis, dermatitis herpetiformis vasculitis, anti-neutrophil cytoplasmic antibody-associated vasculitides, vitiligo, and Wegener's granulomatosis.

In some embodiments, the FcRn/antigen-binding molecule or antigen-binding domain is administered to the subject simultaneously or sequentially with an additional therapeutic agent.

Also provided is an FcRn/antigen-binding molecule as described herein or an antigen-binding domain as described herein for use in the treatment of an antibody-mediated disorder.

Also provided is use of an FcRn/antigen-binding molecule as described herein (e.g., an FcRn/HSA-binding molecule as described herein) or an antigen-binding domain as described herein for the manufacture of a medicament for treating an antibody-mediated disorder.

BRIEF DESCRIPTION OF THE DRAWINGS

FIG. 10A shows normalized hIgG1 (% pre-dose) post-injection per group. Change in hIgG1 concentration was plotted over time (days post-injection) as % to pre-dose on day 0, −1 h. The datapoints show the mean±SEM of 4 mice per group per timepoint. Broken line represents the LLOQ of the ELISA read-out. FIG. 10B shows normalized total serum IgG (hIVIg, % pre-dose) post-injection per group. Change in hIVIg concentration was plotted over time (days post-injection) as % to pre-dose on day 0, −1 h. The datapoints show the mean±SEM of 4 mice per group per timepoint.

FIG. 16A) and a one-armed (OA)-Fc-ABDEG molecule with an albumin binding VHH fragment fused at the C-terminus of one Fc domain (OA-Fc-ABDEG-Alb23; FIG. 16B).

FIG. 17A shows HEK FcRn WT GFP+ cells incubated with 2500 nM one-armed or two-armed Fc-ABDEG-Alb23 in the absence of HSA or in the presence of 10,000 nM HSA. FIG. 17B shows HEK FcRn WT GFP+ cells incubated with 12,500 nM one-armed or two-armed Fc-ABDEG-Alb23 in the absence of HSA or in the presence of 50,000 nM HSA. Bars represent mean±SEM of duplicate wells; result of two independent runs.

FIG. 22A shows normalized tracer IgG levels (% pre-dose) post-injection per group. Change in tracer IgG levels was plotted overtime (days post-injection) as % to pre-dose on day 0, −2 hrs. FIG. 22B shows serum PK of TA-Fc-ABDEG-Alb23, TA-Alb23-Fc-ABDEG, and OA-Fc-ABDEG-Alb23 after a single IV injection. Serum concentrations of the test items were plotted as an average per group over time during the course of the study. FIG. 22C shows normalized albumin levels (% pre-dose) post-injection per group. Albumin levels were plotted over time (days post-injection) as % relative to pre-dose (day 0, −2 hrs), averaged per group.

FIG. 25A shows pharmacokinetic profiles of OA-Fc-ABDEG-3Rab (25 mg/kg), OA-Fc-ABDEG-20GS-Alb23-F32A (25 mg/kg), and OA-Fc-ABDEG-20GS-Alb23-F32A (25 mg/kg) after a single IP injection in AlbuMus Rag1KO mice. Serum concentrations of the test items were plotted as an average per group over time during the course of the study. Values below low limit of quantification (LLOQ) are excluded from the graph. FIG. 25B shows normalized levels (% pre-dose) of total preloaded human IgG in Albumus Rag1KO after a single IP administration of OA-Fc-ABDEG-3Rab (25 mg/kg), OA-Fc-ABDEG-20GS-Alb23-F32A (25 mg/kg), and OA-Fc-ABDEG-20GS-Alb23-F32A (25 mg/kg). Change in total IgG concentrations was plotted over time (days post-injection) as % to pre-dose on day 0-2 h.

FIG. 26A shows normalized levels (% pre-dose) of total preloaded human IgG post-injection per dose group. Change in total IgG concentrations in AlbuMus Rag1KO mice after single IP administration of ARGX-113 (efgartigimod; 20 mg/kg), TA-Fc-ABDEG-Alb23 (30 mg/kg), OA-Fc-ABDEG-Alb23 (25 mg/kg), OA-Fc-ABDEG-3Rab (25 mg/kg), OA-Fc-ABDEG-Alb23-F32A (25 mg/kg), and OA-Fc-ABDEG-Alb23-M34A (25 mg/kg) was plotted over time (days post-injection) as % to pre-dose on day 0-2 h. The datapoints show the mean±SEM of 4-5 animals per group. FIG. 26B shows normalized levels (% pre-dose) of the tracer human IgG during first 7 days of the study. Change in the concentration of the tracer IgG in Albumus Rag1KO mice after a single IP injection of ARGX-113 (20 mg/kg), TA-Fc-ABDEG-Alb23 (30 mg/kg), OA-Fc-ABDEG-Alb23 (25 mg/kg), OA-Fc-ABDEG-3Rab (25 mg/kg), OA-Fc-ABDEG-Alb23-F32A (25 mg/kg), and OA-Fc-ABDEG-Alb23-M34A (25 mg/kg) was plotted over time (days post-injection) as % to pre-dose on day 0, −2 h. The datapoints show the mean±SEM of 4-5 mice per group per timepoint. After day 4, concentrations of the tracer IgG reached low level of quantification (LLOQ) in the groups treated with ARGX-113 and all OA-Fc-ABDEG-VHH molecules.

The datapoints show the mean±SD of 4-5 animals per group. Values below low limit of quantification (LLOQ) are excluded from the graph.

Figure 26A:
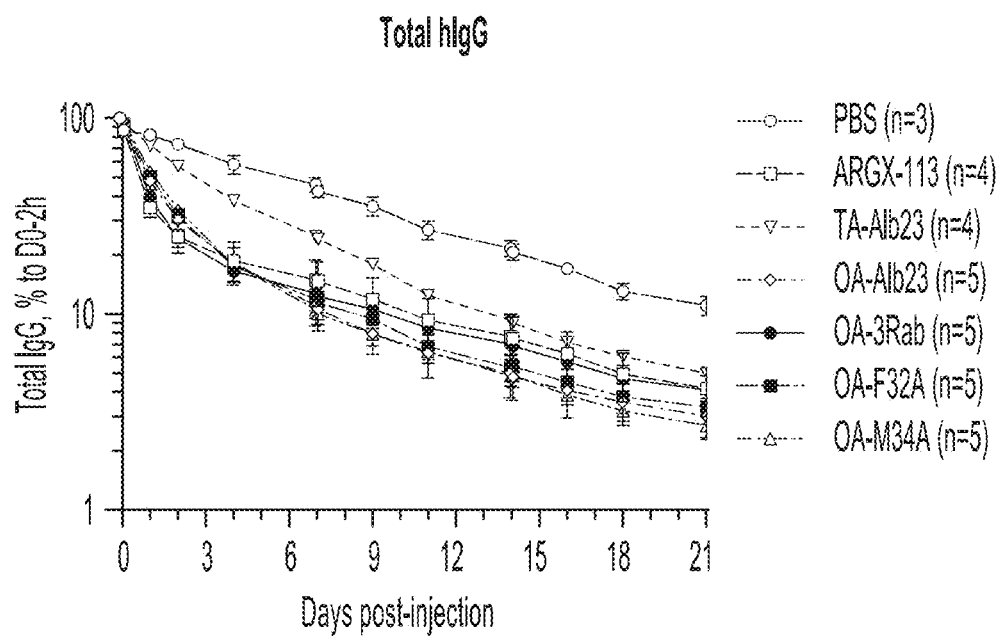
FIGS. 26A-26B show the PD effect of OA-Fc-ABDEG-Alb23 Ala variants in AlbuMus Rag1KO mice.
Figure 26B:
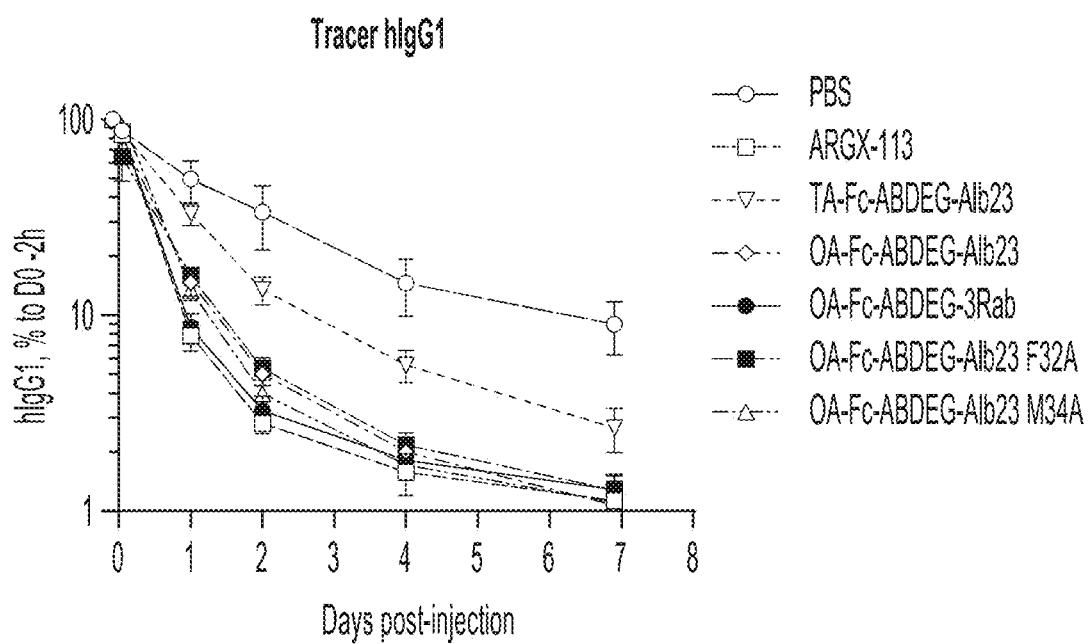
Figure 26C:
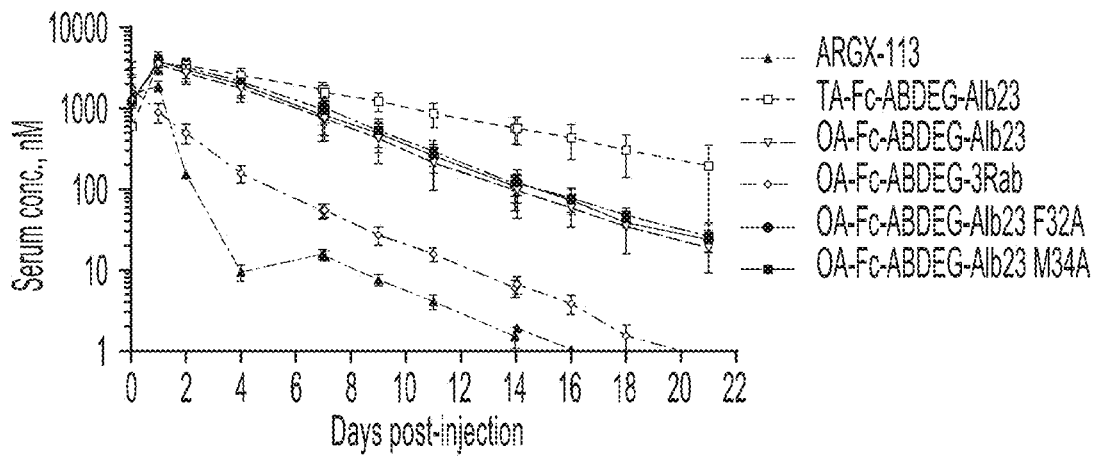
FIG. 26C shows pharmacokinetic profiles in AlbuMus Rag1KO mice after a single IP injection of ARGX-113 (efgartigimod; 20 mg/kg), TA-Fc-ABDEG-Alb23 (30 mg/kg), OA-Fc-ABDEG-Alb23 (25 mg/kg), OA-Fc-ABDEG-3Rab (25 mg/kg), OA-Fc-ABDEG-Alb23-F32A (25 mg/kg), and OA-Fc-ABDEG-Alb23-M34A (25 mg/kg). Serum concentrations of the test items were plotted as an average per group over time during the course of the study.
Figure 26D:
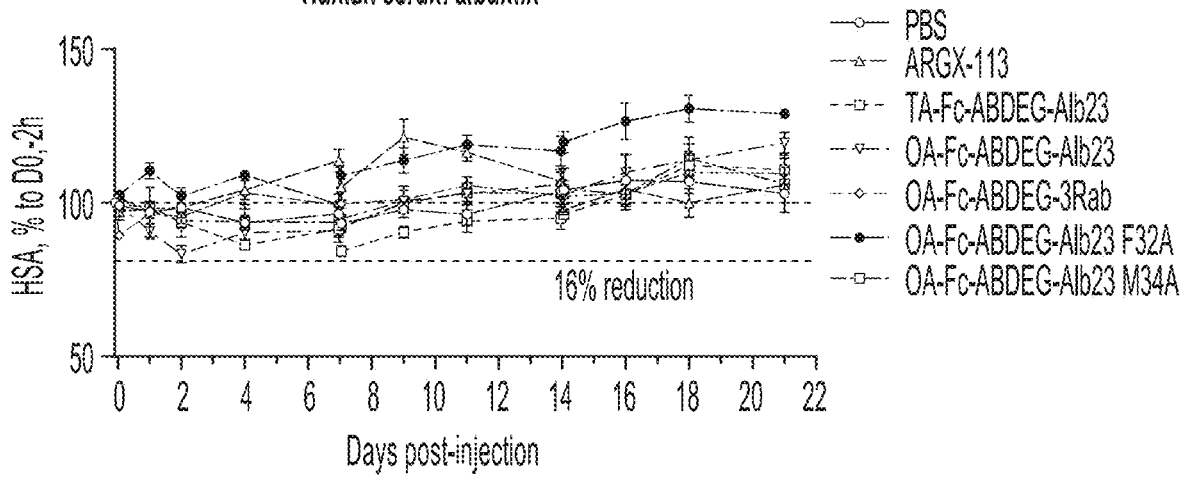

FIG. 26D shows levels of human serum albumin (% to pre-dose) in AlbuMus Rag1KO mice after single IP administration of ARGX-113 (efgartigimod; 20 mg/kg), TA-Fc-ABDEG-Alb23 (30 mg/kg), OA-Fc-ABDEG-Alb23 (25 mg/kg), OA-Fc-ABDEG-3Rab (25 mg/kg), OA-Fc-ABDEG-Alb23-F32A (25 mg/kg), and OA-Fc-ABDEG-Alb23-M34A (25 mg/kg). Albumin levels were plotted over time (days post-injection) as % relative to pre-dose (day 0-2 h) averaged per group. The datapoints show the mean±SEM of 4-5 mice per group, per timepoint.

Figure 27A:
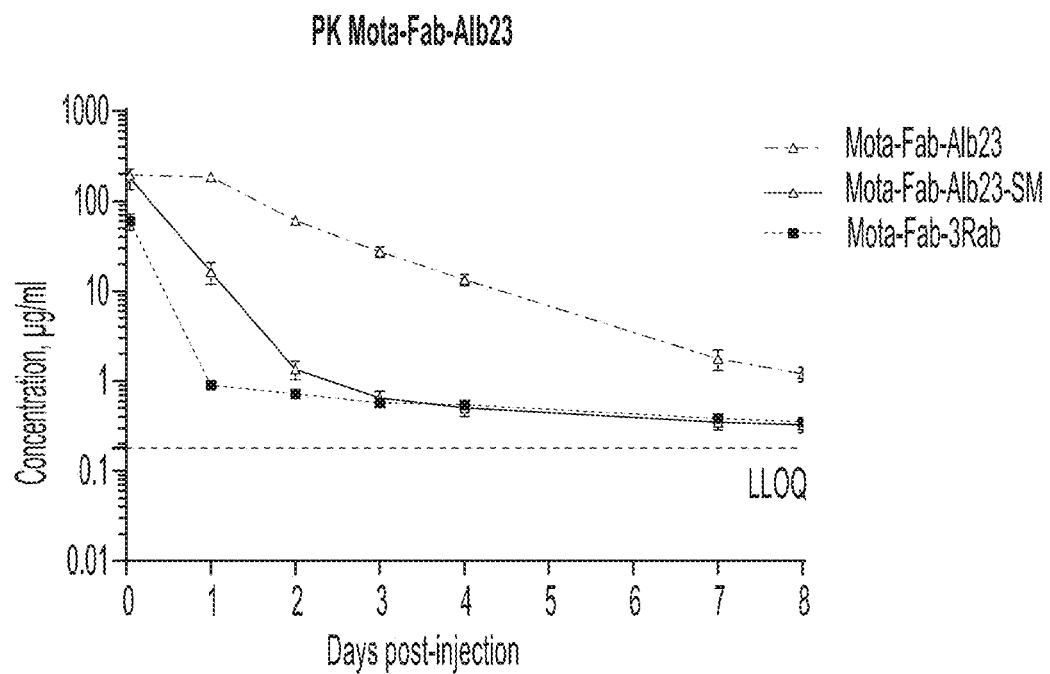
Figure 27B:
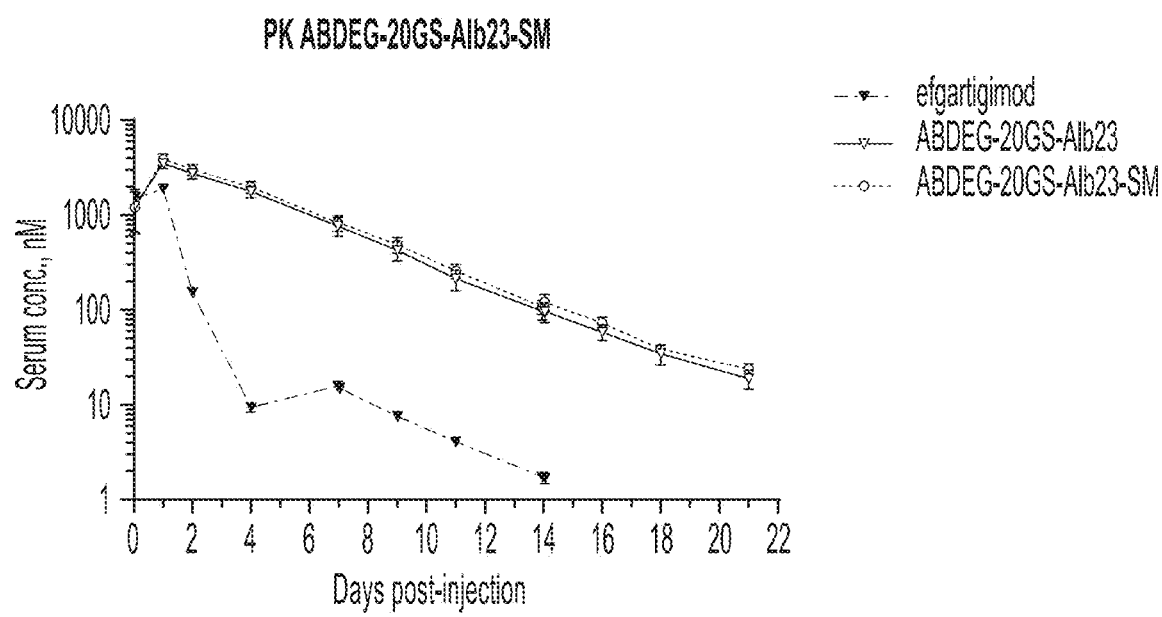

FIGS. 27A-27B show different pharmacokinetic profiles of Mota-Fab constructs (FIG. 27A) and Fc-ABDEG constructs (FIG. 27B) when fused to Alb23-F32A after a single IP injection in AlbuMus Rag1KO mice. Serum concentrations of the test items were plotted as an average per group over time during the course of the study. The datapoints show the mean±SD of 4-5 animals per group. Values below low limit of quantification (LLOQ) are excluded from the graph.

Figure 28A:
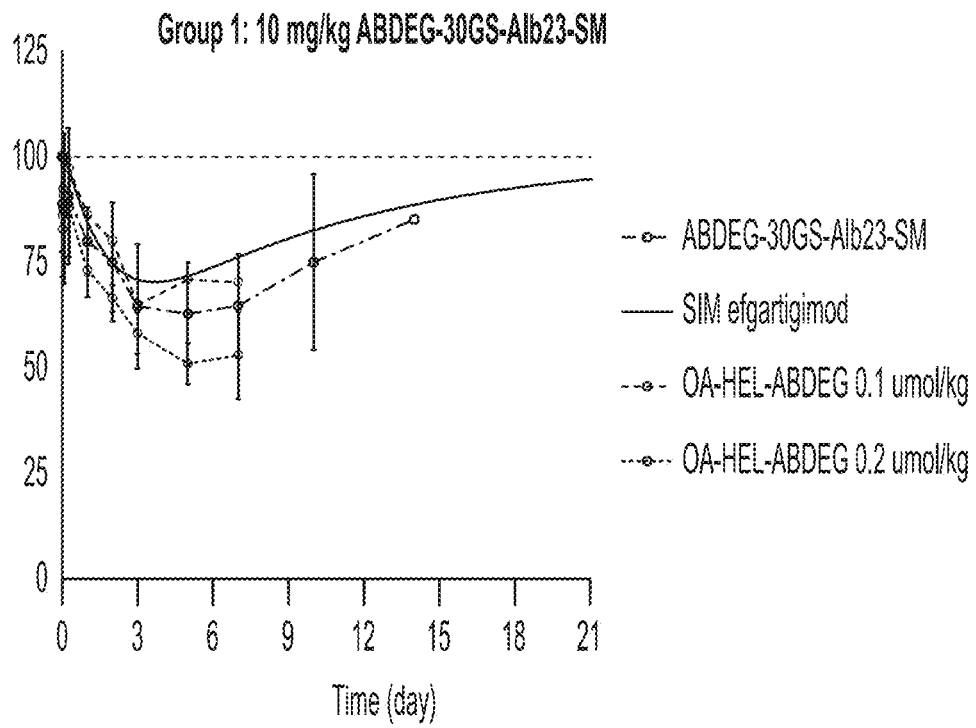
Figure 28B:
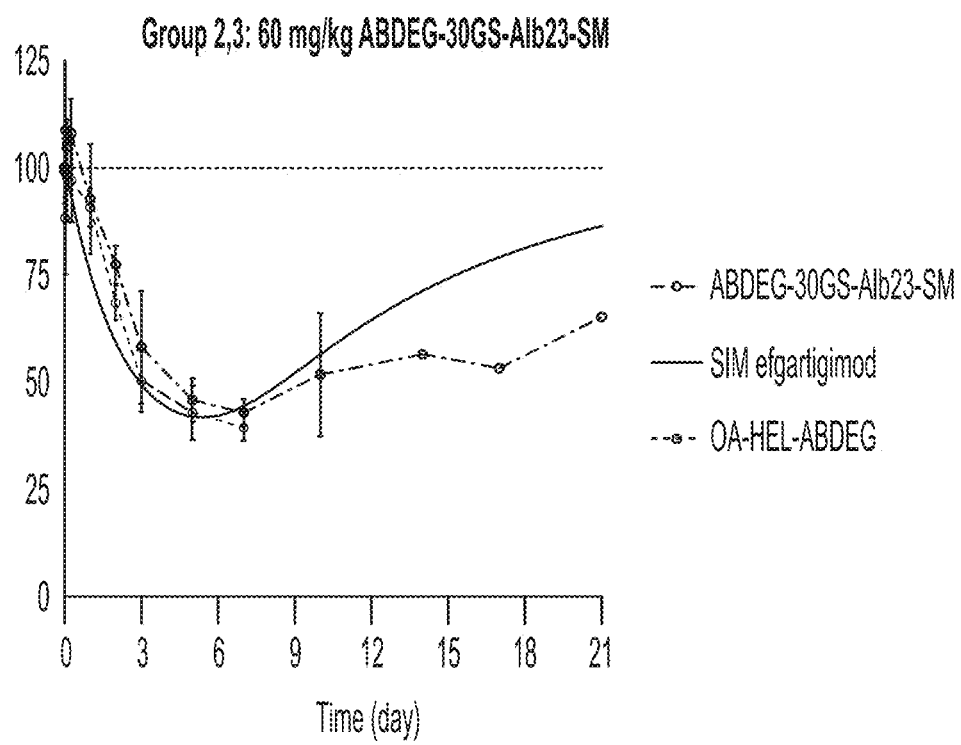

FIGS. 28A-28B show pharmacodynamic (PD) profiles in cynomolgus monkeys treated with one intravenous (IV) dose of an Fc-ABDEG molecule equipped with one anti-HSA VHH with F32A mutation (Alb23-SM) fused at the C-terminus of an Fc domain (ABDEG-30GS-Alb23-SM). % Cynomolgus total serum IgG relative to pre-dose were plotted over time. The datapoints show the mean±SD of 3 individual monkeys (n=3) dosed with 10 mg/kg (FIG. 28A) and 5 individual monkeys (n=5) dosed with 60 mg/kg (FIG. 28B) of OA-Fc-ABDEG-Alb23. Data points with results of only one individual monkey are marked with asterisks. PD profiles in cynomolgus monkeys of equimolar doses of efgartigimod (model simulation) and nearly equimolar doses of OA-HEL-ABDEG (experimental data) plotted for comparison. Time points when presence of ADA was detected and with a steep concentration decline in PK curves are excluded from the graphs.

Figure 29A:
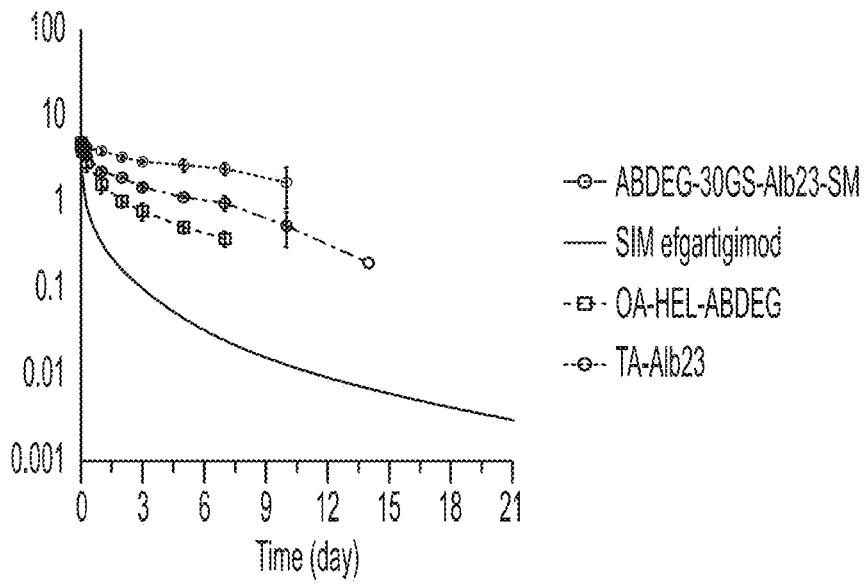
Figure 29B:
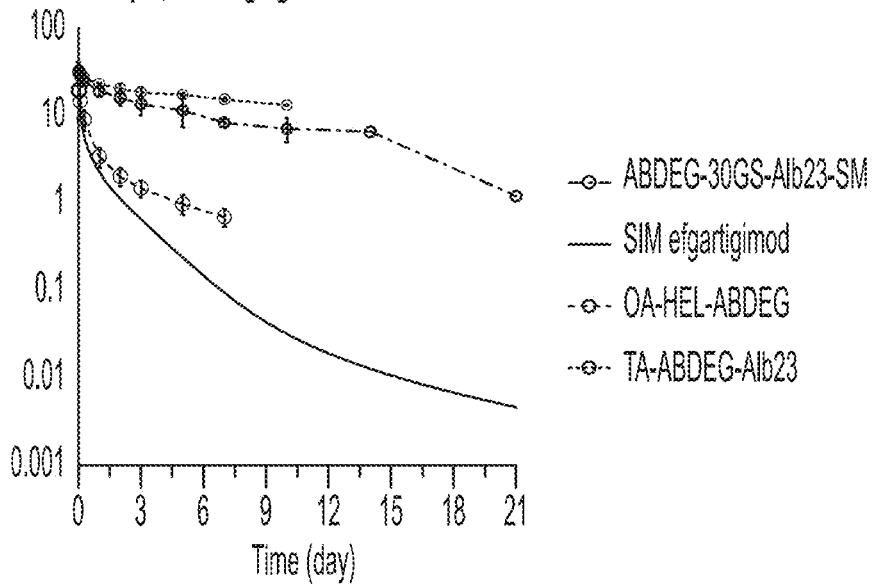

FIGS. 29A-29B show pharmacokinetic profiles in cynomolgus monkeys treated with one intravenous (IV) dose of ABDEG-30GS-Alb23-SM. ABDEG-30GS-Alb23-SM concentration values were plotted over time. The datapoints show the mean±SD of 3 individual monkeys (n=3) dosed with 10 mg/kg (FIG. 29A) and 5 individual monkeys (n=5) dosed with 60 mg/kg (FIG. 29B) of ABDEG-30GS-Alb23-SM. Data points with results of only one individual monkey are marked with asterisks. PK profiles in cynomolgus monkeys of equimolar doses of efgartigimod (model simulation) and nearly equimolar doses of OA-HEL-ABDEG (experimental data) and TA-ABDEG-Alb23 (experimental data) plotted for comparison. Time points when presence of ADA was detected and with a steep concentration decline in PK curves are excluded from the graphs.

Figure 30:
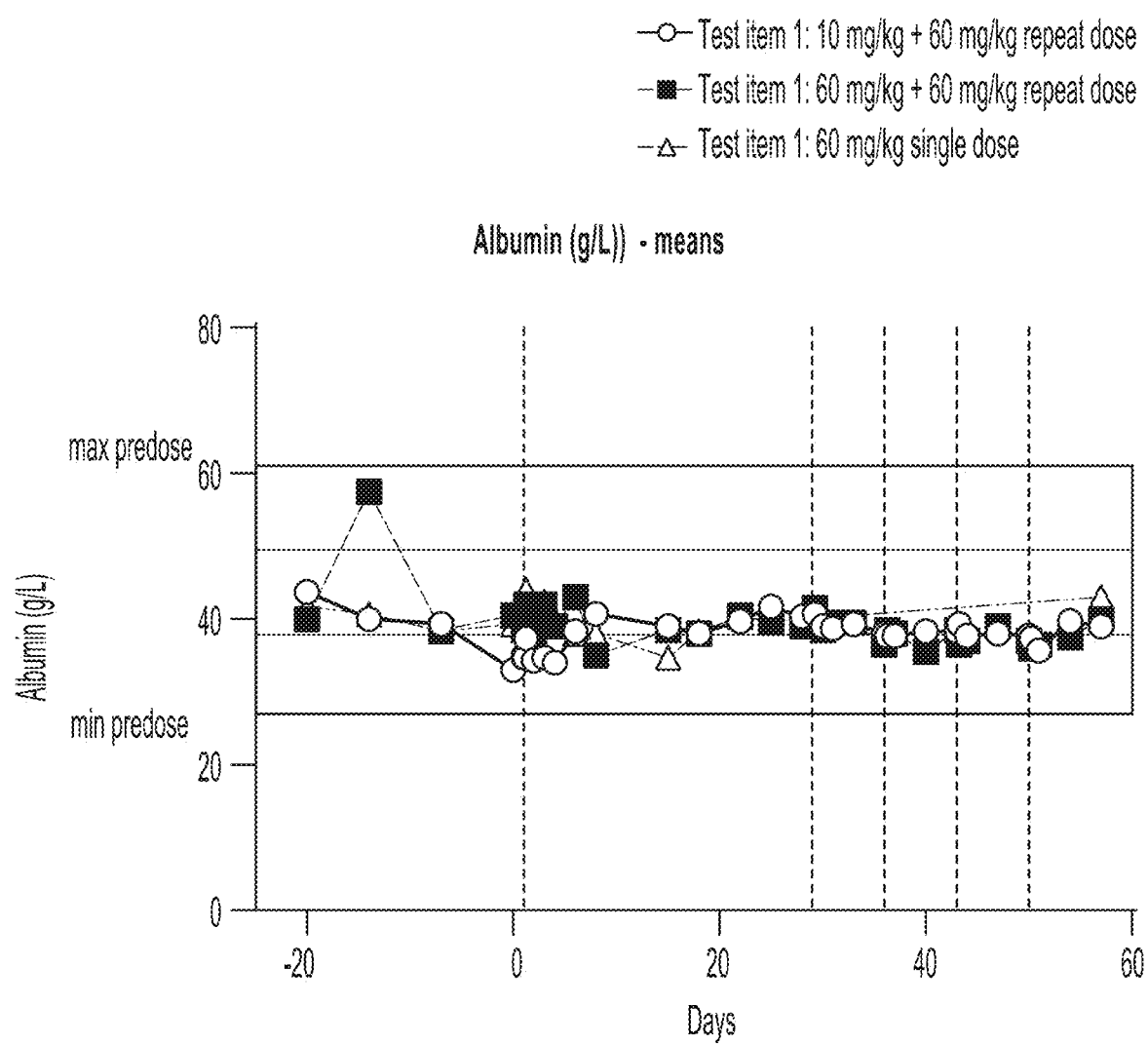

FIG. 30 shows serum albumin levels after injection of ABDEG-30GS-Alb23-SM (analyzed with BCG assay). On day 1, group 1 (n=3) received a 10 mg/kg dose of ABDEG-30GS-Alb23-SM; and group 2 (n=2) and group 3 (n=3) received a 60 mg/kg dose of ABDEG-30GS-Alb23-SM. After 4-week follow-up period, the monkeys in groups 1 and 2 were additionally dosed four times, once every week on day 29, day 36, day 43, and day 50 with 60 mg/kg of ABDEG-30GS-Alb23-SM. Concentrations of albumin were plotted overtime during the course of the study. The dotted lines indicate administration of ABDEG-30GS-Alb23-SM. The data points show the mean±SD of individual monkeys per treatment group. The orange shaded area shows min and max levels of albumin measured at pre-dose in the monkeys used in this study. The grey shaded area shows a normal range of serum albumin in cynomolgus monkeys according to Park et al. (Lab Anim Res. 2016 June; 32(2): 79-86).

Figure 31A:
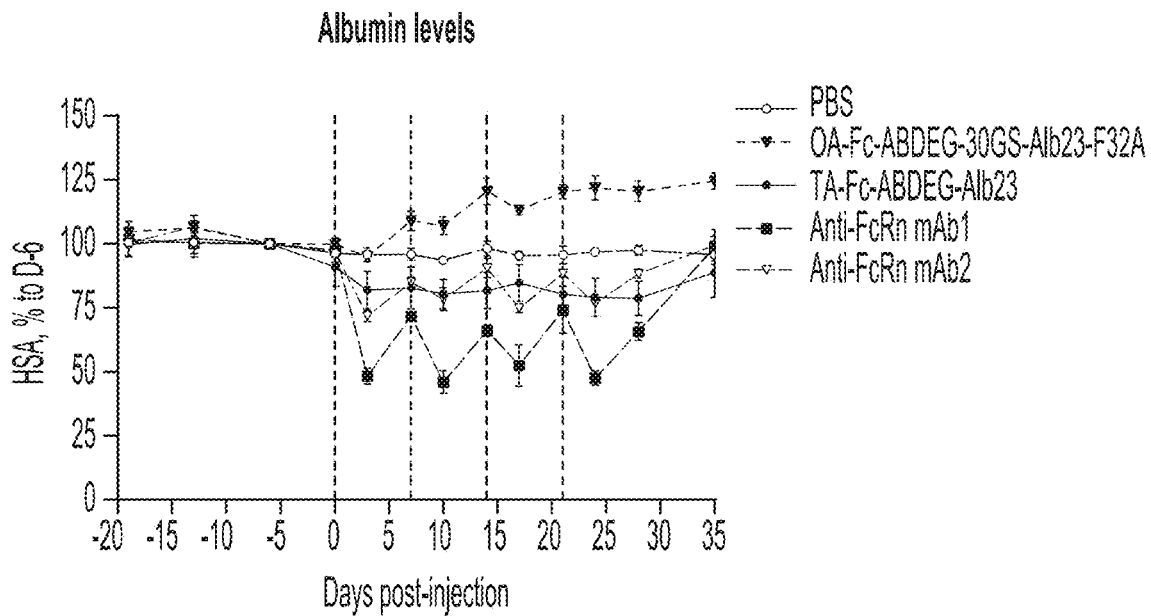

FIG. 31A shows normalized albumin levels (% pre-dose) after 4 IV injections once every week of PBS (placebo), OA-Fc-ABDEG-30GS-Alb23-F32A (45 mg/kg), TA-Fc-ABDEG-Alb23 (50 mg/kg), anti-FcRn mAb1 (100 mg/kg), or anti-FcRn mAb2 (100 mg/kg) in AlbuMus Rag1KO mice. Albumin levels were plotted over time (days post-injection) as % relative to pre-dose (day −6), averaged per group. The datapoints show the mean±SEM of 3-5 mice per group, per timepoint. Dotted lines show injections of test items on day 0, 7, 14, and 21.

Figure 31B:
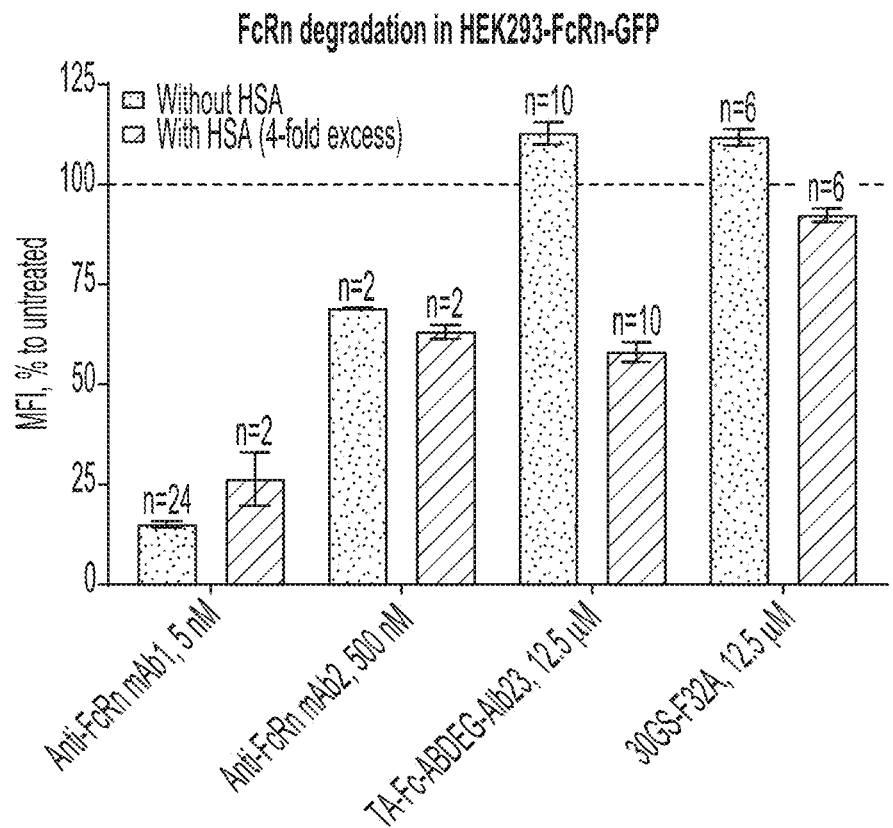

FIG. 31B shows the effect of OA-Fc-ABDEG-30GS-Alb23-F32A (12.5 µM), TA-Fc-ABDEG-Alb23 (12.5 µM), anti-FcRn mAb1 (5 nM), or anti-FcRn mAb2 (500 nM) on FcRn degradation in the presence or absence of human serum albumin (HSA). HEK FcRn WT GFP+ cells were incubated with indicated concentrations of the test molecules in the absence of HSA or in the presence of 50,000 nM HSA. Bars represent mean±SEM of individual experiments (indicated with n) each performed in two technical replicates.

Figure 32:
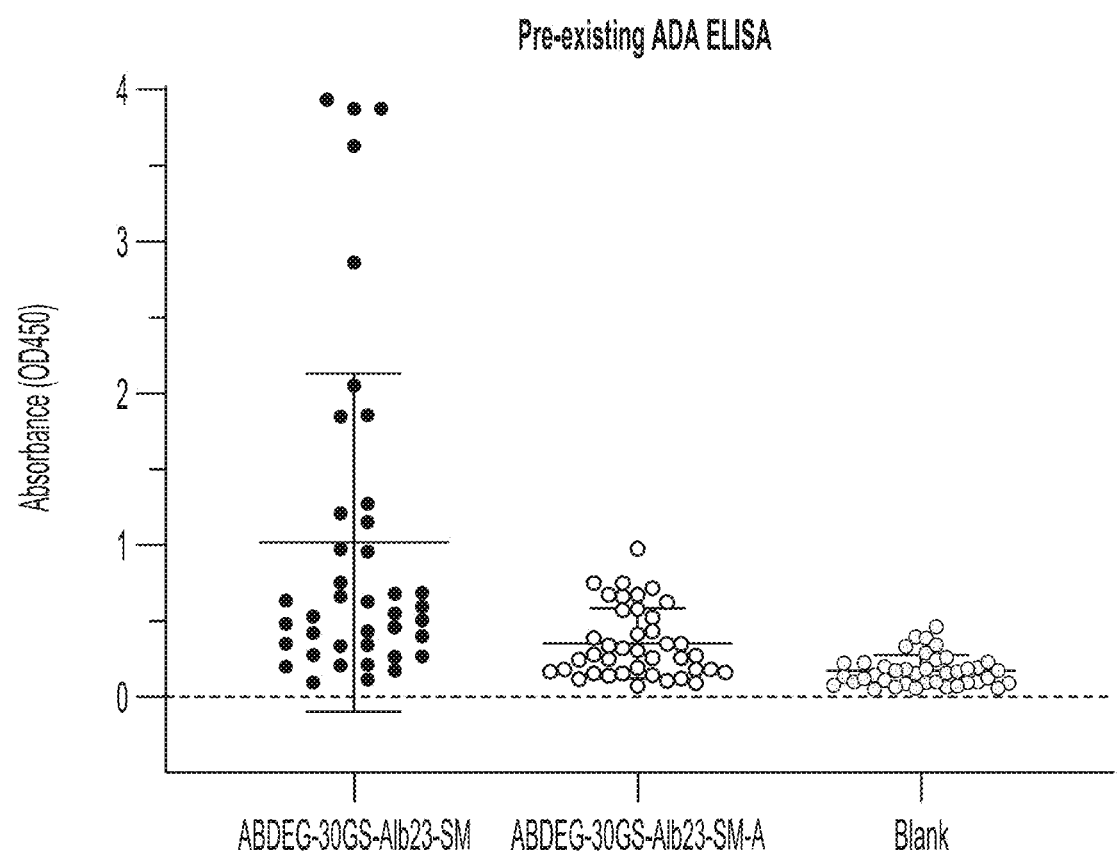

FIG. 32 shows a reduced binding of pre-existing ADA to ABDEG-30GS-Alb23-SM-A. Serum from 40 human individuals positive for pre-existing ADA to ABDEG was used. ABDEG-30GS-Alb23-SM, ABDEG-30GS-Alb23-SM-A, or PBS (blank, no coating) were coated on a 96-well plate, the plate was blocked with 1% PBS-casein, and the serum was applied. Binding of pre-existing ADA to the test articles was detected with HRP-conjugated anti-human Fab IgG. Plotted are absorbance values at $OD_{450}$.

Figure 33A:
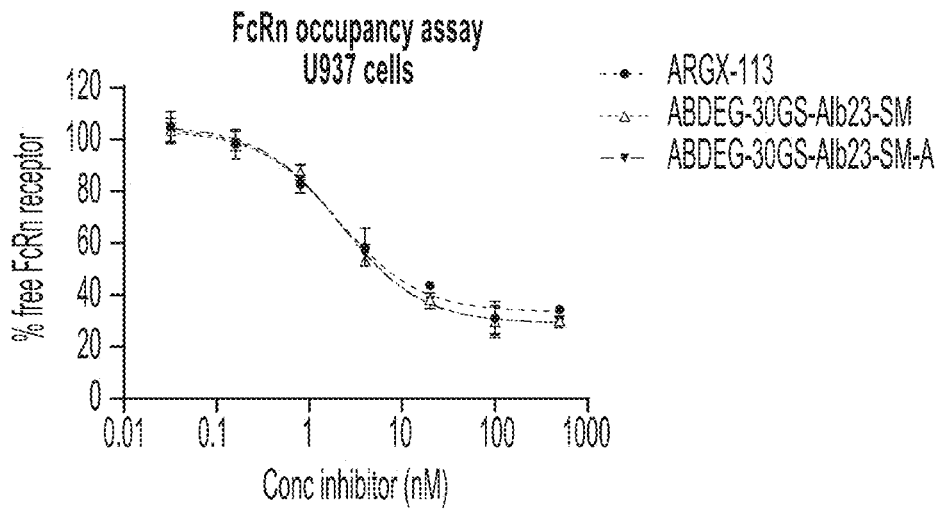

FIG. 33A shows FcRn occupancy by efgartigimod (ARGX-113), ABDEG-30GS-Alb23-SM, and ABDEG-30GS-Alb23-SM-A. U937 cells were incubated with a titration series of the test items in the presence of 2,500 nM HSA. Free FcRn was detected with a fluorescently labelled anti-FcRn Fab fragment recognizing IgG binding site on FcRn. Detected levels of free FcRn were normalized to the FcRn levels in cells treated with the assay buffer (placebo, 100%). Presented are means±SD of 2 independent experiments each performed in technical duplicates.

Figure 33B:
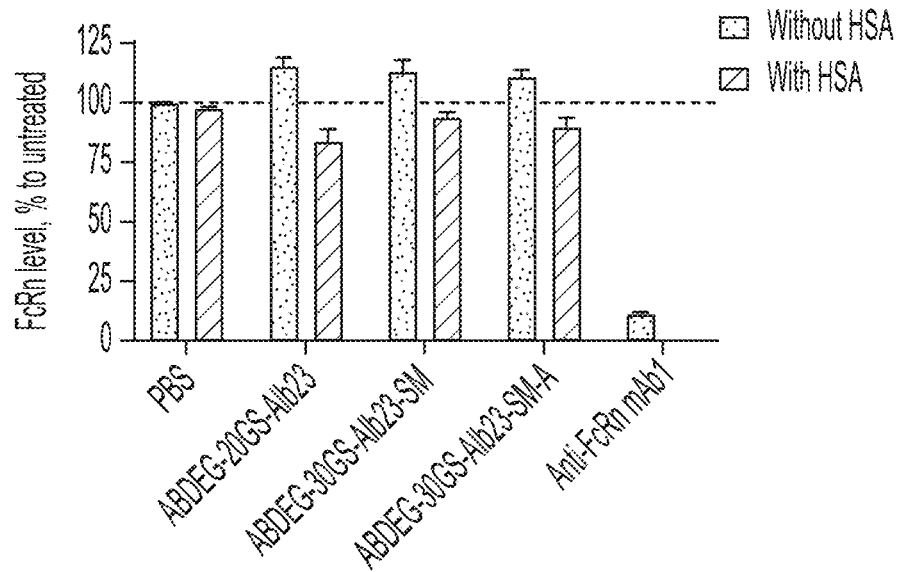

FIG. 33B shows the effect of ABDEG-20GS-Alb23 (12.5 µM), ABDEG-30GS-Alb23-SM (12.5 µM), ABDEG-30GS-Alb23-SM-A (12.5 µM), and anti-FcRn mAb1 (5 nM) on FcRn degradation in the presence or absence of human serum albumin (HSA). HEK FcRn WT GFP+ cells were incubated with indicated concentrations of the test molecules in the absence of HSA or in the presence of 50,000 nM HSA. Bars represent mean±SD of at least three independent experiments each performed in two technical replicates.

Figure 34A:
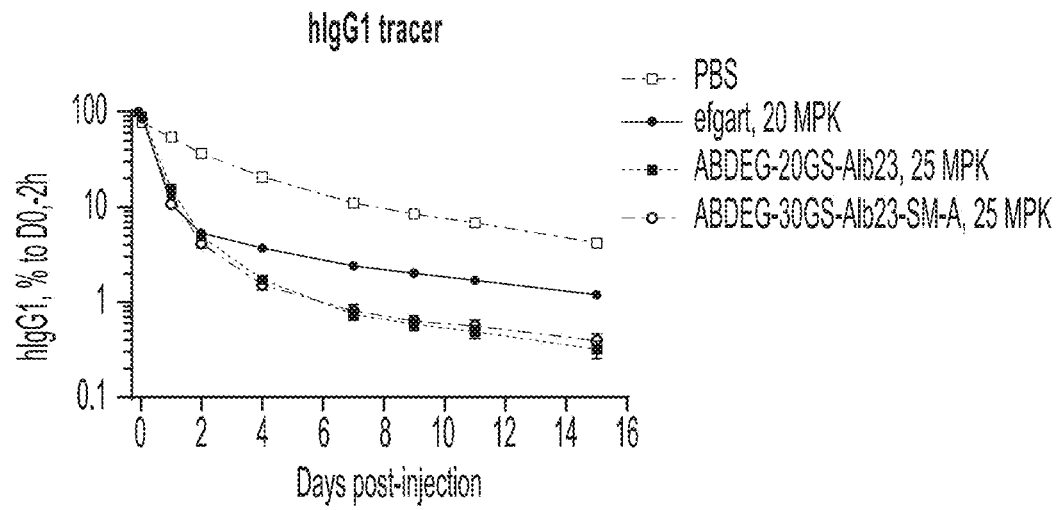

FIG. 34A shows normalized levels (% pre-dose) of tracer human IgG in AlbuMus Rag1KO mice after a single IP injection of PBS (placebo), efgartigimod (20 mg/kg), OA-Fc-ABDEG-30GS-Alb23-F32A (25 mg/kg), and OA-Fc-ABDEG-20GS-Alb23 (25 mg/kg). Change in tracer hIgG concentrations was plotted over time (days post-injection) as % to pre-dose on day 0, −2 h. The data points show the mean±SEM of 5 mice per group per timepoint.

Figure 34B:
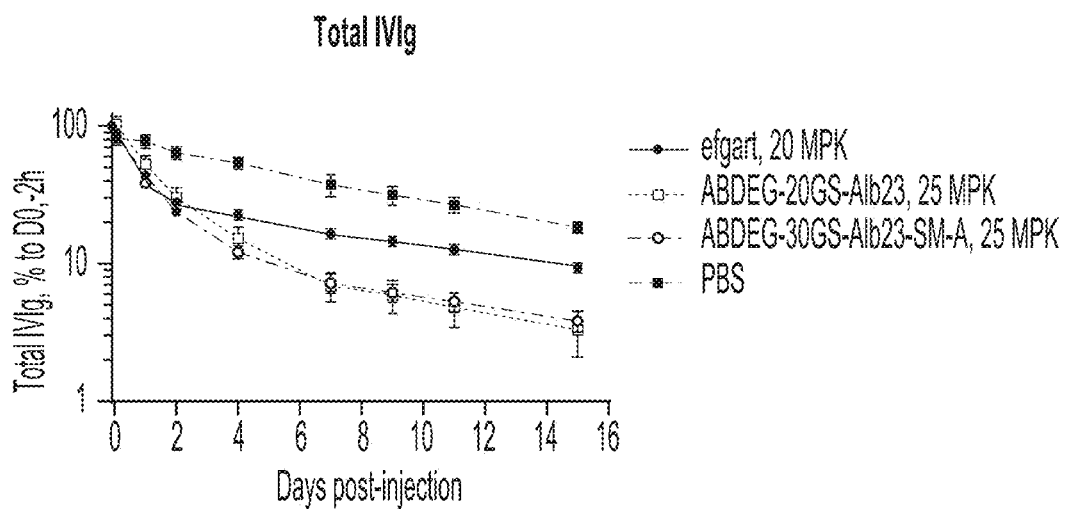

FIG. 34B shows normalized levels (% pre-dose) of total preloaded human IgG in AlbuMus Rag1KO after a single IP administration of PBS (placebo), efgartigimod (20 mg/kg), OA-Fc-ABDEG-30GS-Alb23-F32A (25 mg/kg), and OA-Fc-ABDEG-20GS-Alb23 (25 mg/kg). Change in total IgG concentrations was plotted over time (days post-injection) as % to pre-dose on day 0-2 h. The data points show the mean±SEM of 5 animals per group.

Figure 34C:
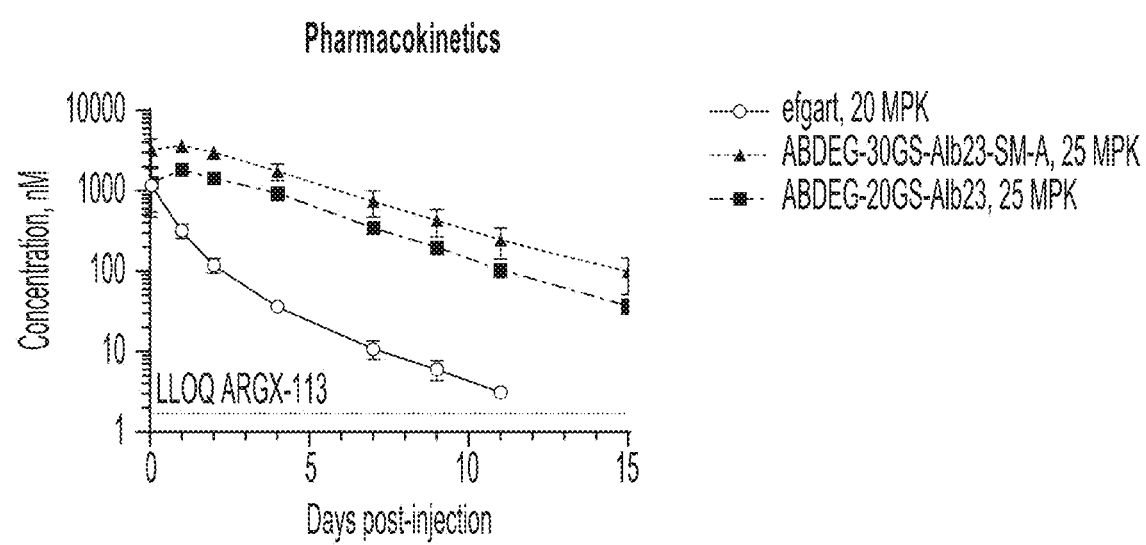

FIG. 34C shows pharmacokinetic profiles of efgartigimod (20 mg/kg), OA-Fc-ABDEG-30GS-Alb23-F32A (25 mg/kg), and OA-Fc-ABDEG-20GS-Alb23 (25 mg/kg) after a single IP injection in AlbuMus Rag1KO mice. Serum concentrations of the test items were plotted as an average per group over time during the course of the study. The data points show the mean±SD of 5 animals per group. Values below low limit of quantification (LLOQ) are excluded from the graph.

DETAILED DESCRIPTION

The present disclosure provides engineered FcRn binding molecules linked to one or more antigen-binding domains (FcRn/antigen-binding molecules). In an aspect, an FcRn/antigen-binding molecule is provided comprising an FcRn binding molecule linked to an anti-HSA antigen-binding domain at the C-terminus, or at the N-terminus, or at a position other than the C-terminus or N-terminus. In some embodiments, the FcRn/antigen-binding molecule comprises an FcRn binding molecule and only one antigen-binding domain. Nucleic acids encoding such FcRn/antigen-binding molecules, vectors, host cells, methods of manufacture, and methods for their use in treating antibody-mediated disorders are also provided herein.

Definitions

As used herein, the term "FcRn" refers to a neonatal Fc receptor. Exemplary FcRn molecules include human FcRn encoded by the FCGRT gene as set forth in RefSeq NM 004107. The amino acid sequence of the corresponding protein is set forth in RefSeq NP_004098.

As used herein, the term "FcRn binding molecule" refers to any agent that specifically binds to FcRn. As used herein, the term "FcRn antagonist" refers to any agent that specifically binds to FcRn and inhibits the binding of immunoglobulin to FcRn (e.g., human FcRn). In an embodiment, the FcRn antagonist comprises an Fc region (e.g., a variant Fc region disclosed herein) that specifically binds to FcRn through the Fc region and inhibits the binding of immunoglobulin to FcRn. In an embodiment, the FcRn antagonist is not a full-length IgG antibody. In an embodiment, the FcRn antagonist comprises an antigen-binding domain that binds a target antigen and a variant Fc region. In an embodiment, the term "FcRn antagonist" refers to an antibody or antigen-binding fragment thereof that specifically binds to FcRn via its antigen binding domain and/or via its Fc region and inhibits the binding of the Fc region of immunoglobulin (e.g., IgG autoantibodies) to FcRn. As used herein, the term "FcRn/antigen-binding molecule" refers to any agent that specifically binds to FcRn and specifically binds to another antigen. In some embodiments, the antigen is IgE, HEL, or HSA. In some embodiments, the antigen is HSA.

As used herein, the term "affinity" or "binding affinity" refers to the strength of the binding interaction between two molecules. As used herein, the term "equilibrium dissociation constant" or "$K_D$" refers to the propensity of bound complex of two molecules to dissociate into two free molecules. Thus, as the binding affinity increases, the $K_D$ decreases.

As used herein, the term "specifically binds" refers to the ability of any molecule to preferentially bind with a given target. For example, a molecule that specifically binds to a given target can bind to other molecules, generally with lower affinity as determined by, e.g., immunoassays, BIAcore™, KinExA 3000 instrument (Sapidyne Instruments, Boise, Id.), or other assays known in the art. In a specific embodiment, molecules that specifically bind to a given target bind to the antigen with a $K_D$ that is at least 2 logs, 2.5 logs, 3 logs, 4 logs or less than the $K_D$ when the molecules bind non-specifically to another target.

As used herein, the term "operably linked" refers to a linkage of polynucleotide sequence elements in a functional relationship. For example, a polynucleotide sequence is operably linked when it is placed into a functional relationship with another polynucleotide sequence. In some embodiments, a transcription regulatory polynucleotide sequence, e.g., a promoter, enhancer, or other expression control element is operably linked to a polynucleotide sequence that encodes a protein if it affects the transcription of the polynucleotide sequence that encodes the protein. Operably linked elements may be contiguous or non-contiguous.

As used herein, the term "linked" refers to a physical linkage (e.g., directly or indirectly linked) between amino acid sequences (e.g., different segments, regions, fragments, or domains). Linked regions, fragments, domains, and segments of the FcRn/antigen-binding molecules of the disclosure may be contiguous or non-contiguous (e.g., linked to one another through a linker). In some embodiments, linkages are covalent. In some embodiments, linkages are non-covalent.

As used herein, the term "covalently linked" refers to the linkage of two molecules or chemical moieties by a covalent bond. In some embodiments, the covalent bond is a peptide bond or a disulfide bond. As used herein, the term "fused" refers to the linkage of two peptides by a peptide bond or a peptide linker. In some embodiments, two proteins are directly and contiguously fused together by a peptide bond. In some embodiments, two proteins are indirectly and non-contiguously fused through a peptide linker. In some embodiments, one protein is fused to a peptide linker by a peptide bond at a first position, and a second protein is fused to a peptide linker by a peptide bond at a second position. As used herein, the term "non-covalently linked" refers to the linkage of two molecules or chemical moieties by a non-covalent interaction or bond. In some embodiments, non-covalent interactions or bonds include hydrogen bonds, electrostatic bonds or interactions, halogen bonds, pi stacking, and van der Waals interactions.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F, (1990) *PNAS* 87: 2264-2268, modified as in Karlin S & Altschul S F, (1993) *PNAS* 90: 5873-5877, each of which is herein incorporated by reference in its entirety. Such an algorithm is incorporated into the NBLAST and XBLAST programs of Altschul S F et al., (1990) *J Mol Biol* 215: 403, which is herein incorporated by reference in its entirety. BLAST nucleotide searches can be performed with the NBLAST nucleotide program parameters set, e.g., at score=100, wordlength=12 to obtain nucleotide sequences homologous to a nucleic acid molecule described herein. BLAST protein searches can be performed with the XBLAST program parameters set, e.g., at score=50, wordlength=3 to obtain amino acid sequences homologous to a protein molecule described herein. To obtain gapped alignments for comparison purposes, Gapped BLAST can be utilized as described in Altschul S F et al., (1997) *Nuc Acids Res* 25: 3389-3402, which is herein incorporated by reference in its entirety. Alternatively, PSI BLAST can be used to perform an iterated search which detects distant relationships between molecules. Id. When utilizing BLAST, Gapped BLAST, and PSI BLAST programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, (1988) *CABIOS* 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the terms "antibody" and "antibodies" include full-length antibodies, antigen-binding fragments of full-length antibodies, and molecules comprising antibody CDRs, VH domains (VH), or VL domains (VL). Examples of antibodies include monoclonal antibodies, recombinantly produced antibodies, monospecific antibodies, multi-specific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single-domain antibodies (sdAb), monovalent antibodies, single chain antibodies or single-chain Fvs (scFv), camelid antibodies, affibody molecules, VHH fragments, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. Antibodies can be of any isotype (e.g., IgG, IgE, IgM, IgD, IgA, or IgY), any subclass (e.g., IgG$_1$, IgG$_2$, IgG$_3$, IgG$_4$, IgA$_1$, or IgA$_2$), or species (e.g., mouse IgG$_{2a}$ or IgG$_{2b}$) of immunoglobulin molecule.

As used herein, the term "antigen-binding domain" (or "antigen binding domain") refers to any polypeptide that specifically binds to an antigen. Examples of antigen-binding domains include polypeptides derived from antibodies, such as Fab fragments, F(ab')$_2$ fragments, disulfide-linked Fvs (sdFv), single-chain Fvs (scFv), CDRs, VH domains (VH), VL domains (VL), single-domain antibodies (sdAb), VHH fragments, camelid antibodies, and antigen-binding fragments of any of the above. The term also encompasses synthetic antigen-binding proteins or antibody mimetic proteins such as, for example, anticalins and DARPins.

In some embodiments, the antigen-binding domain is a VHH fragment. In some embodiments, the VHH fragment has one or more additional amino acids at its C-terminal end. In some embodiments, the one or more additional amino acids are selected from the group consisting of A, AG, GG, and PP.

As used herein, the term "Fc region" refers to the portion of an immunoglobulin formed by the Fc domains of its two heavy chains. The Fc region can be a wild-type Fc region (native Fc region) or a variant Fc region. A native Fc region is homodimeric. The Fc region can be derived from any native immunoglobulin. In some embodiments, the Fc region is formed from an IgA, IgD, IgE, or IgG heavy chain constant region. In some embodiments, the Fc region is formed from an IgG heavy chain constant region. In some embodiments, the IgG heavy chain is an IgG1, IgG2, IgG3, or IgG4 heavy chain constant region. In some embodiments, the Fc region is formed from an IgG1 heavy chain constant region. In some embodiments, the IgG1 heavy chain constant region comprises a G1m1(a), G1m2(x), G1m3(f), or G1m17(z) allotype. See, e.g., Jefferis and Lefranc (2009) *mAbs* 1(4): 332-338, and de Taeye et al., (2020) *Front Immunol.* 11: 740, incorporated herein by reference in their entirety.

As used herein, the term "variant Fc region" refers to a variant of an Fc region with one or more alteration(s) relative to a native Fc region. Alterations can include amino acid substitutions, additions and/or deletions, linkage of additional moieties, and/or alteration of the native glycans. The term encompasses heterodimeric Fc regions where each of the constituent Fc domains is different. The term also encompasses single chain Fc regions where the constituent Fc domains are linked together by a linker moiety.

As used herein, the term "Fc domain" refers to the portion of a single immunoglobulin heavy chain comprising both the CH2 and CH3 domains of the antibody. In some embodiments, the Fc domain comprises at least a portion of a hinge (e.g., upper, middle, and/or lower hinge region) region, a CH2 domain, and a CH3 domain. In some embodiments, the Fc domain does not include the hinge region.

As used herein, the term "hinge region" refers to the portion of a heavy chain molecule that joins the CH1 domain to the CH2 domain. In some embodiments, the hinge region is at most 70 amino acid residues in length. In some embodiments, this hinge region comprises approximately 11-17 amino acid residues and is flexible, thus allowing the two N-terminal antigen binding regions to move independently. In some embodiments, the hinge region is 12 amino acid residues in length. In some embodiments, the hinge region is 15 amino acid residues in length. In some embodiments, the hinge region is 62 amino acid residues in length. Hinge regions can be subdivided into three distinct domains: upper, middle, and lower hinge domains. The FcRn/antigen-binding molecules of the instant disclosure can include all or any portion of a hinge region. In some embodiments, the hinge region is from an IgG1 antibody. In some embodiments, the hinge region comprises the amino acid sequence of EPKSCDKTHTCPPCP (SEQ ID NO: 179).

As used herein, the term "FcRn binding fragment" refers to a portion of an FcRn binding molecule, e.g., a portion of an Fc region, that is sufficient to confer FcRn binding.

As used herein, the terms, "one-armed," "one armed," "one-arm," "one arm," or "OA" refers to an FcRn/antigen-binding molecule comprising an FcRn binding molecule linked to only one antigen-binding domain. In some embodiments, "one-armed," "one armed," "one-arm," "one arm," or "OA" refers to an FcRn/antigen-binding molecule comprising an Fc region comprising the Fc domains of two heavy chains, wherein one of the Fc domains of the two heavy chains is linked to an antigen binding domain and the other Fc domain of the two heavy chains is not linked to an antigen binding domain. In some embodiments, the antigen binding domain is linked to the C-terminus of one of the Fc domains of the two heavy chains. In some embodiments, the antigen binding domain is linked to the N-terminus of one of the Fc domains of the two heavy chains. In some embodiments, the antigen binding domain is linked to a position other than the N-terminus or the C-terminus of one of the Fc domains of the two heavy chains. The linkage can be covalent or non-covalent. In some embodiments, the antigen binding domain is fused to the C-terminus of one of the Fc domains of the two heavy chains. In some embodiments, the antigen binding domain is fused to the N-terminus of one of the Fc domains of the two heavy chains. In some embodiments, the antigen binding domain is fused to a position other than the N-terminus or the C-terminus of one of the Fc domains of the two heavy chains.

As used herein, the terms, "two-armed," "two armed," "two-arm," "two arm," or "TA" refers to an FcRn/antigen-binding molecule comprising an FcRn binding molecule linked to two antigen-binding domains. In some embodiments, "two-armed," "two armed," "two-arm," "two arm," or "TA" refers to an FcRn/antigen-binding molecule comprising an Fc region comprising the Fc domains of two heavy chains, wherein each of the Fc domains of the two heavy chains is linked to an antigen binding domain. In some embodiments, an antigen binding domain is linked to the C-terminus of each of the Fc domains of the two heavy chains. In some embodiments, an antigen binding domain is linked to the N-terminus of each of the Fc domains of the two heavy chains. In some embodiments, the antigen binding domains are linked to positions other than the N-terminus or the C-terminus of each of the Fc domains of the two heavy chains. In some embodiments, one of the antigen binding domains is linked to the N-terminus of one of the Fc domains of the two heavy chains and the other antigen binding domain is linked to the C-terminus of the other Fc domain of the two heavy chains. In some embodiments, one of the antigen binding domains is linked to a position other than the N-terminus or the C-terminus of one of the Fc domains of the two heavy chains and the other antigen binding domain is linked to the N-terminus of the other Fc domain of the two heavy chains. In some embodiments, one of the antigen binding domains is linked to a position other than the N-terminus or the C-terminus of one of the Fc domains of the two heavy chains and the other antigen binding domain is linked to the C-terminus of the other Fc domain of the two heavy chains. The linkage can be covalent or non-covalent. In some embodiments, an antigen binding domain is fused to the C-terminus of each of the Fc domains of the two heavy chains. In some embodiments, an antigen binding domain is fused to the N-terminus of each of the Fc domains of the two heavy chains. In some embodiments, the antigen binding domains are fused to positions other than the N-terminus or the C-terminus of each of the Fc domains of the two heavy chains. In some embodiments, one of the antigen binding domains is fused to the N-terminus of one of the Fc domains of the two heavy chains and the other antigen binding domain is fused to the C-terminus of the other Fc domain of the two heavy chains. In some embodiments, one of the antigen binding domains is fused to a position other than the N-terminus or the C-terminus of one of the Fc domains of the two heavy chains and the other antigen binding domain is fused to the N-terminus of the other Fc domain of the two heavy chains. In some embodiments, one of the antigen binding domains is fused to a position other than the N-terminus or the C-terminus of one of the Fc domains of the two heavy chains and the other antigen binding domain is fused to the C-terminus of the other Fc domain of the two heavy chains.

As used herein, the term "EU position" refers to the amino acid position in the EU numbering convention for the Fc region described in Edelman, G M et al. *Proc. Nat. Acad. USA*, 63, 78-85 (1969) and Kabat et al., in "Sequences of Proteins of Immunological Interest," *U.S. Dept. Health and Human Services*, 5$^{th}$ edition, 1991.

As used herein, the term, "antibody-mediated disorder" refers to any disorder wherein the symptoms of the disorder are caused by abnormal levels of one or more antibodies in a subject. As used herein, the term "autoantibody-mediated disorder" refers to any disease or disorder in which the underlying pathology is caused, at least in part, by pathogenic IgG autoantibodies.

As used herein, the term "treat," "treating," and "treatment" refer to therapeutic or preventative measures described herein. The methods of "treatment" employ administration of a polypeptide to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment. In some embodiments, the methods of "treatment" employ administration of a polypeptide to a subject having a disease or disorder, or predisposed to having such a disease or disorder, in order to prevent, cure, delay, reduce the severity of, or ameliorate the disease or disorder or recurring disease or disorder.

As used herein, the term "effective amount" in the context of the administration of a therapy to a subject refers to the amount of a therapy that achieves a desired prophylactic or therapeutic effect.

As used herein, the term "dose" or "dosing" refers to an amount of an agent administered to a subject in a single administration.

As used herein, the terms "fixed dose" or "flat dose" both refer to a dose that does not vary based upon a characteristic (e.g., body mass, e.g., within a set range; sex; age, e.g., within a set range; etc.) of the subject.

As used herein, the term, "equivalent dose" refers to a dose of a first and a second therapeutic agent wherein the number of molecules of the first and second agents is about the same. In some embodiments, an equivalent dose is an equimolar dose. As used herein, the term "equimolar dose" refers to a dose of a first and a second therapeutic agent wherein the number of moles of the first and second agent is the same. In some embodiments, the first agent is a FcRn/antigen-binding molecule and the second agent is efgartigimod. In some embodiments, equivalent dose is calculated using the observed molecular weight of the first and second agents. In some embodiments, equivalent dose is calculated using the predicted molecular weight of the first and second agents. In some embodiments, equivalent dose is calculated using the observed molecular weight of the first agent and the predicted molecular weight of the second agent. In some embodiments, equivalent dose is calculated using the predicted molecular weight of the first agent and the observed molecular weight of the second agent.

As used herein, the terms "pharmacodynamics," and "PD," refer to the biological effect of a therapeutic agent on an organism. In some embodiments, the biological effect is modulation of the amount of circulating IgG in an organism administered a therapeutic agent. In some embodiments, the biological effect is modulation of the amount of circulating albumin in an organism administered a therapeutic agent. As used herein, the term "improved pharmacodynamics" or "improved PD" refers to the improvement of a desired biological effect in an organism administered a therapeutic agent. In some embodiments, the improved pharmacodynamics includes reduction of the amount of circulating IgG in the subject. In some embodiments, the improved pharmacodynamics includes maintenance of the amount of circulating albumin in the subject. In some embodiments, the improved pharmacodynamics includes reduction of the amount of circulating IgG in the subject as well as maintenance of the amount of circulating albumin in the subject. In some embodiments, the therapeutic agent is an FcRn/antigen-binding molecule.

As used herein, the terms "pharmacokinetics," and "PK," refer to the effect of an organism on a therapeutic agent administered to the organism. In some embodiments, the effect is metabolization and/or clearance of the therapeutic agent. In some embodiments, PK refers to the rate of metabolization and/or clearance of the therapeutic agent. As used herein, the term "improved pharmacokinetics" or "improved PK" refers to the improvement of a desired effect of an organism on a therapeutic agent administered to the organism. In some embodiments, the improved pharmacokinetics includes increase of the half-life ($T_{1/2}$), clearance, or area under the curve (AUC) of the therapeutic agent in the subject. In some embodiments, the therapeutic agent is an FcRn/antigen-binding molecule.

As used herein, the term "subject" or "patient" or "participant" includes any human or non-human animal. In an embodiment, the subject or patient or participant is a human or non-human mammal. In an embodiment, the subject or patient or participant is a human.

As used herein, the term "about" or "approximately" when referring to a measurable value, such as a dosage, encompasses variations of ±20%, ±15%, ±10%, ±5%, ±1%, or ±0.1% of a given value or range, as are appropriate to perform the methods disclosed herein.

As used herein, the term "molecular weight" can refer to a "predicted molecular weight" or an "observed molecular weight." The "predicted molecular weight" of a protein is a sum of the molecular weights of all the amino acids in the protein. In certain circumstances the "predicted molecular weight" can differ from the "observed molecular weight" of a molecule. In some embodiments, these differences can occur in a protein because of changes in glycosylation, glycanation, ubiquitination, phosphorylation, or protein cleavage of the protein or complexes of additional proteins with a given protein.

FcRn/Antigen Binding Molecules

The disclosure provides FcRn/antigen-binding molecules or fragments thereof. In some embodiments, the FcRn/antigen-binding molecules disclosed herein comprise an FcRn binding molecule and at least one antigen-binding domain. The FcRn binding molecule may be any FcRn binding molecule described herein. Similarly, the antigen-binding domain may be any antigen-binding domain described herein. In some embodiments, the FcRn/antigen-binding molecule comprises only one antigen-binding domain (e.g., one-armed FcRn/antigen-binding molecule). In some embodiments, the FcRn/antigen-binding molecule comprises two antigen-binding domains (e.g., two-armed FcRn/antigen-binding molecule).

In some embodiments, the antigen-binding domain is linked to the C-terminus of the FcRn binding molecule. In some embodiments, the antigen-binding domain is linked to the N-terminus of the FcRn binding molecule. In some embodiments, the antigen-binding domain is linked to the FcRn binding molecule at a position other than the C-terminus or the N-terminus. The antigen-binding domain may be covalently linked or non-covalently linked to the FcRn binding molecule.

In some embodiments, the antigen-binding domain is fused to the C-terminus of the FcRn binding molecule. In some embodiments, the antigen-binding domain is fused to the N-terminus of the FcRn binding molecule. In some embodiments, the antigen-binding domain is fused to the FcRn binding molecule at a position other than the C-terminus or the N-terminus.

In some embodiments, one antigen binding domain is linked or fused to the N-terminus of the FcRn binding molecule and another antigen binding domain is linked or fused to the C-terminus of the FcRn binding molecule. In some embodiments, one antigen binding domain is linked or fused to a position other than the N-terminus or the C-terminus of one of the FcRn binding molecule and another antigen binding domain is linked or fused to the N-terminus of the FcRn binding molecule. In some embodiments, one antigen binding domain is linked or fused to a position other than the N-terminus or the C-terminus of one of the FcRn binding molecule and another antigen binding domain is linked or fused to the C-terminus of the FcRn binding molecule.

In some embodiments, the FcRn binding molecule is an Fc region, e.g., a variant Fc region. In some embodiments, antigen-binding domain is linked or fused to the C-terminus of one of the Fc domains of the variant Fc region. In some embodiments, the antigen-binding domain is linked or fused to the N-terminus of the one of the Fc domains of the variant Fc region. In some embodiments, the antigen-binding domain is linked or fused to the FcRn binding molecule at a position other than the C-terminus or the N-terminus.

In some embodiments, one antigen binding domain is linked or fused to the C-terminus of one of the Fc domains of the variant Fc region and another antigen binding domain is linked or fused to the C-terminus of the other Fc domain of the variant Fc region. In some embodiments, one antigen binding domain is linked or fused to the N-terminus of one of the Fc domains of the variant Fc region and another antigen binding domain is linked or fused to the N-terminus of the other Fc domain of the variant Fc region. In some embodiments, one antigen binding domain is linked or fused to the N-terminus of one of the Fc domains of the variant Fc region and another antigen binding domain is linked or fused to the C-terminus of the other Fc domain of the variant Fc region. In some embodiments, one antigen binding domain is linked or fused to a position other than the N-terminus or the C-terminus of one of the Fc domains of the variant Fc region and another antigen binding domain is linked or fused to the N-terminus of the other Fc domain of the variant Fc region. In some embodiments, one antigen binding domain is linked or fused to a position other than the N-terminus or the C-terminus of one of the Fc domains of the variant Fc region and another antigen binding domain is linked or fused to the C-terminus of the other Fc domain of the variant Fc region.

In some embodiments, the antigen-binding domain may be linked or fused directly to the N-terminus or the C-terminus of an FcRn binding molecule. In some embodiments, the antigen-binding domain is linked to the N-terminus or the C-terminus of an FcRn binding molecule via a linker. In some embodiments, the linker is a non-cleavable linker.

In some embodiments, the antigen-binding domain may be linked (e.g., fused) directly to the N-terminus or the C-terminus of an Fc domain. In some embodiments, antigen-binding domain is linked to the N-terminus or the C-terminus of an Fc domain via a linker. The linker may be any suitable linker, including those described herein.

FcRn Binding Molecules

FcRn binding molecules disclosed herein include any molecule that binds to FcRn, including, but not limited to, any anti-FcRn antibody, any anti-FcRn binding region, or any Fc domain or Fc region.

In some embodiments, the FcRn binding molecules are FcRn antagonists which include any molecule that binds to and inhibits FcRn, including, but not limited to, any anti-FcRn antibody, any anti-FcRn binding region, or any Fc domain or Fc region.

In some embodiments, the FcRn binding molecules disclosed herein comprise two, three, or four FcRn binding regions, such as an Fc region.

In some embodiments, the FcRn binding molecules disclosed herein comprise one or more Fc regions, or FcRn binding fragment thereof, in combination with one or more antigen-binding domains (e.g., an sdAb, a Fab fragment, an scFv, or an antibody mimetic).

Any Fc region can be altered to produce a variant Fc region as disclosed herein. In general, an Fc region, or FcRn binding fragment thereof, is from a human immunoglobulin. It is understood, however, that the Fc region may be derived from an immunoglobulin of any other mammalian species, including for example, a camelid species, a rodent (e.g., a mouse, rat, rabbit, guinea pig) or non-human primate (e.g., chimpanzee, macaque) species. Moreover, the Fc region or FcRn binding portion thereof may be derived from any immunoglobulin class, including IgM, IgG, IgD, IgA, and IgE, and any immunoglobulin isotype, including IgG1, IgG2, IgG3, and IgG4. In an embodiment, the Fc region is an IgG Fc region (e.g., a human IgG region). In an embodiment, the Fc region is an IgG1 Fc region (e.g., a human IgG1 region). In an embodiment, the Fc region is a chimeric Fc region comprising portions of several different Fc regions. Suitable examples of chimeric Fc regions are set forth in US 2011/0243966A1, which is incorporated herein by reference in its entirety. A variety of Fc region gene sequences (e.g., human constant region gene sequences) are available in the form of publicly accessible deposits.

An Fc region can be further truncated or internally deleted to produce a minimal FcRn binding fragment thereof. The ability of an Fc-region fragment to bind to FcRn can be determined using any art recognized binding assay e.g., ELISA.

To enhance the manufacturability of FcRn binding molecules, and FcRn/antigen-binding molecules containing same, as disclosed herein, it is preferable that the constituent Fc regions do not comprise any non-disulfide bonded cysteine residues. Accordingly, in an embodiment, the Fc regions do not comprise a free cysteine residue.

In some embodiments, any Fc variant, or FcRn binding fragment thereof, that specifically binds to FcRn with increased affinity and reduced pH dependence relative to the native Fc region can be used herein. In an embodiment, the variant Fc region comprises amino acid alterations, substitutions, insertions, and/or deletions that confer the desired characteristics. In some embodiments, the FcRn binding molecule comprises a variant Fc region, or FcRn binding fragment thereof, which binds to FcRn with a higher affinity at pH 5.5 as compared to a corresponding wild-type Fc region. In some embodiments, the FcRn binding molecule comprises a variant Fc region, or FcRn binding fragment thereof, which binds to FcRn with a higher affinity at pH 6.0 and/or at pH 7.4 as compared to a corresponding wild-type Fc region. In some embodiments, the FcRn binding molecule comprises a variant Fc region, or FcRn binding fragment thereof, which binds to FcRn with a higher affinity at both acidic and neutral pH as compared to a corresponding wild-type Fc region.

In some embodiments, the variant Fc region is derived from the Fc region of any native immunoglobulin. In some embodiments, the native immunoglobulin is a human immunoglobulin. In some embodiments, the immunoglobulin is IgA, IgD, IgE, or IgG. In some embodiments, the immunoglobulin is IgG. In some embodiments, the immunoglobulin is human IgA, human IgD, human IgE, or human IgG. In some embodiments, the immunoglobulin is human IgG. In some embodiments, the IgG is IgG1, IgG2, IgG3, or IgG4. In some embodiments, the human IgG is human IgG1, human IgG2, human IgG3, or human IgG4. In some embodiments, the variant Fc region varies from the human IgG1 Fc region. In some embodiments, the human IgG1 Fc region comprises a G1m1(a), G1m2(x), G1m3(f), or G1m17(z) allotype.

In some embodiments, the FcRn binding molecule is an FcRn antagonist.

In some embodiments, the variant Fc region, or FcRn binding fragment thereof comprises or consists of at least one Fc domain. In some embodiments, the variant Fc region comprises or consists of two Fc domains. In some embodiments, the Fc domains are the same. In some embodiments, the Fc domains are different. In certain embodiments, at least one of the variant Fc domains or FcRn binding fragments described herein comprises at least one amino acid or at least two amino acids selected from the following: 237M; 238A; 239K; 248I; 250A; 250F; 250I; 250M; 250Q; 250S; 250V; 250W; 250Y; 252F; 252W; 252Y; 254T; 255E; 256D; 256E; 256Q; 257A; 257G; 257I; 257L; 257M; 257N; 257S; 257T; 257V; 258H; 265A; 270F; 286A; 286E; 289H; 297A; 298G; 303A; 305A; 307A; 307D; 307F; 307G; 307H; 307I; 307K; 307L; 307M; 307N; 307P; 307Q; 307R; 307S; 307V; 307W; 307Y; 308A; 308F; 308I; 308L; 308M; 308P; 308Q; 308T; 309A; 309D; 309E; 309P; 309R; 311A; 311H; 311I; 312A; 312H; 314K; 314R; 315A; 315H; 317A; 325G; 332V; 334L; 360H; 376A; 378V; 380A; 382A; 384A; 385D; 385H; 386P; 387E; 389A; 389S; 424A; 428A; 428D; 428F; 428G; 428H; 428I; 428K; 428L; 428N; 428P; 428Q; 428S; 428T; 428V; 428W; 428Y; 433K; 434A; 434F; 434H; 434S; 434W; 434Y; 436H; 436I and 436F, wherein the positions are defined in accordance with EU numbering. EU numbering refers to the convention for the Fc region described in Edelman, G. M. et al., Proc. Natl. Acad. Sci. USA, 63: 78-85 (1969); and Kabat et al., in "Sequences of Proteins of Immunological Interest", U.S. Dept. Health and Human Services, 5$^{th}$ edition, 1991. In some embodiments, at least one of the variant Fc domains or FcRn binding fragments described herein comprises 2, 3, 4 or 5 amino acids selected from the following: 237M; 238A; 239K; 248I; 250A; 250F; 250I; 250M; 250Q; 250S; 250V; 250W; 250Y; 252F; 252W; 252Y; 254T; 255E; 256D; 256E; 256Q; 257A; 257G; 257I; 257L; 257M; 257N; 257S; 257T; 257V; 258H; 265A; 270F; 286A; 286E; 289H; 297A; 298G; 303A; 305A; 307A; 307D; 307F; 307G; 307H; 307I; 307K; 307L; 307M; 307N; 307P; 307Q; 307R; 307S; 307V; 307W; 307Y; 308A; 308F; 308I; 308L; 308M; 308P; 308Q; 308T; 309A; 309D; 309E; 309P; 309R; 311A; 311H; 311I; 312A; 312H; 314K; 314R; 315A; 315H; 317A; 325G; 332V; 334L; 360H; 376A; 378V; 380A; 382A; 384A; 385D; 385H; 386P; 387E; 389A; 389S; 424A; 428A; 428D; 428F; 428G; 428H; 428I; 428K; 428L; 428N; 428P; 428Q; 428S; 428T; 428V; 428W; 428Y; 433K; 434A; 434F; 434H; 434S; 434W; 434Y; 436H; 436I and 436F, wherein the positions are defined in accordance with EU numbering and wherein any combinations are contemplated.

In certain embodiments, at least one of the variant Fc domains or FcRn binding fragments described herein comprises at least one non-naturally occurring amino acid or at least two non-naturally occurring amino acids selected from the following: 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, at least one of the variant Fc domains may comprise a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217, the contents of which are incorporated by reference herein in their entirety).

In certain embodiments, at least one of the variant Fc domains comprises at least one non-naturally occurring amino acid or comprises at least two non-naturally occurring amino acids selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R, 243W, 243L, 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, at least one of the variant Fc domains may comprise additional and/or alternative non-naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217, the contents of which are incorporated by reference herein in their entirety).

Other known Fc domain variants that may be used in the compositions disclosed herein include without limitations those disclosed in Ghetie et al, 1997, Nat. Biotech. 15:637-40; Duncan et al, 1988, Nature 332:563-564; Lund et al, 1991, J. Immunol, 147:2657-2662; Lund et al, 1992, Mol. Immunol, 29:53-59; Alegre et al, 1994, Transplantation 57:1537-1543; Hutchins et al, 1995, Proc Natl. Acad Sci USA, 92: 11980-11984; Jefferis et al, 1995, Immunol Lett., 44: 111-117; Lund et al, 1995, Faseb J., 9: 115-119; Jefferis et al, 1996, Immunol Lett., 54: 101-104; Lund et al, 1996, J. Immunol, 157:4963-4969; Armour et al, 1999, Eur J Immunol 29:2613-2624; Idusogie et al, 2000, J. Immunol, 164: 4178-4184; Reddy et al, 2000, J. Immunol, 164: 1925-1933; Xu et al, 2000, Cell Immunol, 200: 16-26; Idusogie et al, 2001, J. Immunol, 166:2571-2575; Shields et al, 2001, J Biol. Chem., 276:6591-6604; Jefferis et al, 2002, Immunol Lett., 82:57-65; Presta et al, 2002, Biochem Soc Trans., 30:487-490); U.S. Pat. Nos. 5,624,821; 5,885,573; 5,677, 425; 6,165,745; 6,277,375; 5,869,046; 6,121,022; 5,624, 821; 5,648,260; 6,528,624; 6,194,551; 6,737,056; 6,821, 505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351, the contents of which are incorporated by reference herein in their entirety.

In an embodiment, the variant Fc region, or FcRn binding fragment thereof comprises or consists of two Fc domains. In an embodiment, the variant Fc region, or FcRn binding fragment thereof, comprises at least one Fc domain comprising amino acids Y, T, E, K, and F at EU positions 252, 254, 256, 433, and 434, respectively. In an embodiment, the variant Fc region, or FcRn binding fragment thereof, comprises at least one Fc domain comprising amino acids Y, T, E, K, F, and Y at EU positions 252, 254, 256, 433, 434, and 436, respectively. In an embodiment, the variant Fc region, or FcRn binding fragment thereof, comprises one Fc domain comprising amino acids Y, T, E, K, and F at EU positions 252, 254, 256, 433, and 434, respectively, and a second Fc domain comprising amino acid K and F at EU positions 433 and 434, respectively. In an embodiment, the variant Fc region, or FcRn binding fragment thereof, comprises one Fc domain comprising amino acids Y, T, E, K, F, and Y at EU positions 252, 254, 256, 433, 434, and 436, respectively, and a second Fc domain comprising amino acid K and F at EU positions 433 and 434, respectively. In an embodiment, the variant Fc region, or FcRn binding fragment thereof consists of two Fc domains, both of which comprise amino acids Y, T, E, K, and F at EU positions 252, 254, 256, 433, and 434, respectively. In an embodiment, the variant Fc region, or FcRn binding fragment thereof, consists of two Fc domains, both of which comprise amino acids Y, T, E, K, F, and Y at EU positions 252, 254, 256, 433, 434, and 436, respectively.

In certain embodiments, at least one of the variant Fc domains or FcRn binding fragments described herein comprises a combination of amino acids selected from the following:
  (i) Q and L at EU positions 250 and 428, respectively;
  (ii) P and A at EU positions 308 and 434, respectively;
  (iii) P and Y at EU positions 308 and 434, respectively; or
  (iv) Y, E and Y at EU positions 252, 286 and 434, respectively.

In certain embodiments, at least one of the variant Fc domains or FcRn binding fragments described herein comprises at least one amino acid substitution selected from: G237M; P238A; S239K; K248I; T250A; T250F; T250I; T250M; T250Q; T250S; T250V; T250W; T250Y; M252F; M252W; M252Y; S254T; R255E; T256D; T256E; T256Q; P257A; P257G; P257I; P257L; P257M; P257N; P257S; P257T; P257V; E258H; D265A; D270F; N286A; N286E; T289H; N297A; S298G; V303A; V305A; T307A; T307D; T307F; T307G; T307H; T307I; T307K; T307L; T307M; T307N; T307P; T307Q; T307R; T307S; T307V; T307W; T307Y; V308A; V308F; V308I; V308L; V308M; V308P; V308Q; V308T; V309A; V309D; V309E; V309P; V309R; Q311A; Q311H; Q311I; D312A; D312H; L314K; L314R; N315A; N315H; K317A; N325G; I332V; K334L; K360H; D376A; A378V; E380A; E382A; N384A; G385D; G385H; Q386P; P387E; N389A; N389S; S424A; M428A; M428D; M428F; M428G; M428H; M428I; M428K; M428L; M428N; M428P; M428Q; M428S; M428T; M428V; M428W; M428Y; H433K; N434A; N434F; N434H; N434S; N434W; N434Y; Y436H; Y436I and Y436F, wherein the positions are defined in accordance with EU numbering. In some embodiments, at least one of the variant Fc domains or FcRn binding fragments described herein comprises 2, 3, 4 or 5 amino acid substitutions selected from the following: G237M; P238A; S239K; K248I; T250A; T250F; T250I;

T250M; T250Q; T250S; T250V; T250W; T250Y; M252F; M252W; M252Y; S254T; R255E; T256D; T256E; T256Q; P257A; P257G; P257I; P257L; P257M; P257N; P257S; P257T; P257V; E258H; D265A; D270F; N286A; N286E; T289H; N297A; S298G; V303A; V305A; T307A; T307D; T307F; T307G; T307H; T307I; T307K; T307L; T307M; T307N; T307P; T307Q; T307R; T307S; T307V; T307W; T307Y; V308A; V308F; V308I; V308L; V308M; V308P; V308Q; V308T; V309A; V309D; V309E; V309P; V309R; Q311A; Q311H; Q311I; D312A; D312H; L314K; L314R; N315A; N315H; K317A; N325G; I332V; K334L; K360H; D376A; A378V; E380A; E382A; N384A; G385D; G385H; Q386P; P387E; N389A; N389S; S424A; M428A; M428D; M428F; M428G; M428H; M428I; M428K; M428L; M428N; M428P; M428Q; M428S; M428T; M428V; M428W; M428Y; H433K; N434A; N434F; N434H; N434S; N434W; N434Y; Y436H; Y436I and Y436F, wherein the positions are defined in accordance with EU numbering, and wherein any combinations of substitutions are contemplated.

In certain embodiments, at least one of the variant Fc domains or FcRn binding fragments described herein comprises a combination of amino acid substitutions selected from the following:

(i) M252Y, S254T, T256E, H433K and N434F;
(ii) T250Q and M428L;
(iii) V308P and N434A;
(iv) V308P and N434Y; or
(v) M252Y, N286E and N434Y.

In an embodiment, one, two, or more mutations (e.g., amino acid substitutions) are introduced into the hinge region of a polypeptide described herein, such that the number of cysteine residues in the hinge region is altered (e.g., increased or decreased) as described in, e.g., U.S. Pat. No. 5,677,425, herein incorporated by reference in its entirety. The number of cysteine residues in the hinge region may be altered to, e.g., facilitate assembly of the light and heavy chains, or to alter (e.g., increase or decrease) the stability of the polypeptide.

In an embodiment, one, two, or more amino acid mutations (e.g., substitutions, insertions, or deletions) are introduced into an Fc region, Fc domain, or FcRn-binding fragment thereof to alter (e.g., decrease or increase) half-life of the polypeptide in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In certain embodiments, one, two, or more amino acid mutations (e.g., substitutions, insertions, or deletions) are introduced into a Fc region, Fc domain, or FcRn-binding fragment thereof to decrease the half-life of the polypeptide in vivo. In other embodiments, one, two, or more amino acid mutations (e.g., substitutions, insertions, or deletions) are introduced into a Fc region, Fc domain, or FcRn-binding fragment thereof to increase the half-life of the antibody in vivo. In an embodiment, the Fc region or Fc domain may have one or more amino acid mutations (e.g., substitutions) in the second constant (CH2) domain (residues 231-340 of human IgG1) and/or the third constant (CH3) domain (residues 341-447 of human IgG1), numbered according to the EU numbering system. In an embodiment, the constant region of the IgG1 of a polypeptide described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant Fc domain, referred to "as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In an embodiment, the polypeptide comprises an IgG constant region comprising one, two, three, or more amino acid substitutions of amino acid residues at positions 251-257, 285-290, 308-314, 385-389, and 428-436, numbered according to the EU numbering system.

In an embodiment, one, two, or more mutations (e.g., amino acid substitutions) are introduced into a Fc region, Fc domain, or FcRn-binding fragment thereof (e.g., a CH2 domain (residues 231-340 of human IgG1) and/or a CH3 domain (residues 341-447 of human IgG1, numbered according to the EU numbering system) and/or a hinge region (residues 216-230, numbered according to the EU numbering system)) of a polypeptide described herein, to increase or decrease the affinity of the antibody for an Fc receptor (e.g., an activated Fc receptor) on the surface of an effector cell. Mutations in the Fc region, Fc domain, or FcRn-binding fragment thereof that decrease or increase the affinity of an antibody for an Fc receptor and techniques for introducing such mutations into the Fc receptor or fragment thereof are known to one of skill in the art. Examples of mutations in the Fc region, Fc domain, or FcRn-binding fragment thereof that can be made to alter the affinity of the variant Fc region, or FcRn binding fragment thereof for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In an embodiment, one, two, or more amino acid substitutions are introduced into a Fc region, Fc domain, or FcRn binding fragment thereof to alter the effector function(s) of the polypeptide. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the polypeptide has an altered affinity for an effector ligand but retains the antigen-binding ability of the parent polypeptide. The effector ligand to which affinity is altered can be, for example, an Fc receptor. This approach is described in further detail in U.S. Pat. Nos. 5,624,821 and 5,648,260, each of which is herein incorporated by reference in its entirety. In an embodiment, one or more amino acid substitutions may be introduced into the Fc region or Fc domain of a polypeptide described herein to remove potential glycosylation sites on the Fc region or Fc domain, which may reduce Fc receptor binding (see, e.g., Shields R L et al., (2001) J Biol Chem 276: 6591-604, which is herein incorporated by reference in its entirety). In an embodiment, one or more of the following mutations in the constant region of a polypeptide described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A330L substitution; an I332E substitution; or a P396L substitution, numbered according to the EU numbering system.

In an embodiment, a mutation selected from the group consisting of D265A, P329A, and a combination thereof, numbered according to the EU numbering system, may be made in the constant region of a polypeptide described herein. In an embodiment, a mutation selected from the group consisting of L235A, L237A, and a combination thereof, numbered according to the EU numbering system, may be made in the constant region of a polypeptide described herein. In an embodiment, a mutation selected from the group consisting of S267E, L328F, and a combination thereof, numbered according to the EU numbering system, may be made in the constant region of a polypeptide described herein. In an embodiment, a mutation selected from the group consisting of S239D, I332E, optionally A330L, and a combination thereof, numbered according to the EU numbering system, may be made in the constant region of a polypeptide described herein. In an embodiment, a mutation selected from the group consisting of L235V, F243L, R292P, Y300L, P396L, and a combination thereof, numbered according to the EU numbering system, may be made in the constant region of a polypeptide described herein. In an embodiment, a mutation selected from the group consisting of S267E, L328F, and a combination thereof, numbered according to the EU numbering system, may be made in the constant region of a polypeptide described herein.

In an embodiment, an Fc region, Fc domain, or FcRn binding fragment thereof described herein comprises the constant region of an IgG1 with an N297Q or N297A amino acid substitution, numbered according to the EU numbering system. In an embodiment, an Fc region, Fc domain, or FcRn binding fragment thereof described herein comprises the constant region of an IgG1 with a mutation selected from the group consisting of D265A, P329A, and a combination thereof, numbered according to the EU numbering system. In an embodiment, an Fc region, Fc domain, or FcRn binding fragment thereof described herein comprises the constant region of an IgG1 with a mutation selected from the group consisting of L234A, L235A, and a combination thereof, numbered according to the EU numbering system. In another embodiment, an Fc region, Fc domain, or FcRn binding fragment thereof described herein comprises the constant region of an IgG1 with a mutation selected from the group consisting of L234F, L235F, N297A, and a combination thereof, numbered according to the EU numbering system. In an embodiment, amino acid residues in the constant region of an Fc region, Fc domain, or FcRn binding fragment thereof described herein in the positions corresponding to positions L234, L235, and D265 in a human IgG1 heavy chain, numbered according to the EU numbering system, are not L, L, and D, respectively. This approach is described in detail in International Publication No. WO 14/108483, which is herein incorporated by reference in its entirety. In an embodiment, the amino acids corresponding to positions L234, L235, and D265 in a human IgG1 heavy chain are F, E, and A;

or A, A, and A, respectively, numbered according to the EU numbering system.

In an embodiment, the amino acids at positions 433, 434, and 436 of the heavy chain constant region, according to the EU numbering system, are K, F, and Y, respectively. In an embodiment, the amino acids at positions 252, 254, and 256 of the heavy chain constant region, according to the EU numbering system, are Y, T, and E, respectively. In an embodiment, the amino acids at positions 428 and 434 of the heavy chain constant region, according to the EU numbering system, are L and S, respectively. In an embodiment, the amino acid at positions 309, 311, and 434 of the heavy chain constant region, according to the EU numbering system, are D, H, and S, respectively.

In an embodiment, the polypeptide does not have amino acids Y, T, E, K, and F at EU positions 252, 254, 256, 433, and 434, respectively.

In an embodiment, one or more amino acids selected from amino acid residues 329, 331, and 322 in the constant region of a polypeptide described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In an embodiment, one or more amino acid residues within amino acid positions 231 to 238 in the N-terminal region of the CH2 domain of a polypeptide described herein are altered to thereby alter the ability of the antibody to fix complement, numbered according to the EU numbering system. This approach is described further in International Publication No. WO 94/29351, which is herein incorporated by reference in its entirety. In an embodiment, the Fc region or Fc domain of a polypeptide described herein is modified to increase the ability of the antibody to mediate antibody dependent cellular cytotoxicity (ADCC) and/or to increase the affinity of the polypeptide for an Fc receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In an embodiment, any of the constant region mutations or modifications described herein can be introduced into one or both heavy chain constant regions of a polypeptide described herein having two heavy chain constant regions. In an embodiment, any of the constant region mutations or modifications described herein can be introduced into the heavy chain constant region of a polypeptide described herein having one heavy chain constant region.

In an embodiment, the instant disclosure provides a polypeptide comprising one, two or three binding sites for human FcRn, that specifically binds to FcRn and functions as an antagonist.

In an embodiment, the amino acid sequence of the Fc domains of the variant Fc region comprises the amino acid sequence of SEQ ID NO: 1. In an embodiment, the amino acid sequence of the Fc domains of the variant Fc region consists of the amino acid sequence of SEQ ID NO: 1. In an embodiment, the amino acid sequence of the Fc domains of the variant Fc region comprises the amino acid sequence of SEQ ID NO: 2. In an embodiment, the amino acid sequence of the Fc domains of the variant Fc region consists of the amino acid sequence of SEQ ID NO: 2. In an embodiment, the amino acid sequence of the Fc domains of the variant Fc region comprises the amino acid sequence of SEQ ID NO:

3. In an embodiment, the amino acid sequence of the Fc domains of the variant Fc region consists of the amino acid sequence of SEQ ID NO: 3.

In an embodiment, the FcRn binding molecule comprises a variant Fc region, wherein the variant Fc region comprises two Fc domains, wherein the amino acid sequence of each of the Fc domains is independently selected from SEQ ID NO: 1, SEQ ID NO: 2, or SEQ ID NO: 3.

In certain embodiments, the variant Fc region is a heterodimer, where the constituent Fc domains are different from each other. Methods of producing Fc heterodimers are known in the art (see, e.g., U.S. Pat. No. 8,216,805, which is incorporated by reference herein in its entirety). In an embodiment, the FcRn binding molecule consists of a variant Fc region, wherein the variant Fc region consists of two Fc domains which form a heterodimer, wherein the amino acid sequence of each of the Fc domains is independently selected from SEQ ID NO: 1, SEQ ID NO: 2, or SEQ ID NO: 3. In an embodiment, the FcRn binding molecule consists of or comprises a variant Fc region, wherein the variant Fc region consists of or comprises two Fc domains which form a heterodimer, wherein the amino acid sequence of the first Fc domain consists of or comprises the amino acid sequence of SEQ ID NO: 1, and the amino acid sequence of the second Fc domain consists of or comprises the amino acid sequence of SEQ ID NO: 2 or SEQ ID NO: 3. In an embodiment, the FcRn binding molecule consists of or comprises a variant Fc region, wherein the variant Fc region consists of or comprises two Fc domains which form a heterodimer, wherein the amino acid sequence of the first Fc domain consists of or comprises the amino acid sequence of SEQ ID NO: 2, and the amino acid sequence of the second Fc domain consists of or comprises the amino acid sequence of SEQ ID NO: 1 or SEQ ID NO: 3. In an embodiment, the FcRn binding molecule consists of or comprises a variant Fc region, wherein the variant Fc region consists of or comprises two Fc domains which form a heterodimer, wherein the amino acid sequence of the first Fc domain consists of or comprises the amino acid sequence of SEQ ID NO: 3, and the amino acid sequence of the second Fc domain consists of or comprises the amino acid sequence of SEQ ID NO: 1 or SEQ ID NO: 2.

In an embodiment, the FcRn binding molecule comprises a variant Fc region, wherein the variant Fc region consists of or comprises two Fc domains which form a homodimer, wherein the amino acid sequence of each of the Fc domains consists of or comprises the amino acid sequence of SEQ ID NO: 1.

In an embodiment, the FcRn binding molecule comprises a variant Fc region, wherein the variant Fc region consists of or comprises two Fc domains which form a homodimer, wherein the amino acid sequence of each of the Fc domains consists of or comprises the amino acid sequence of SEQ ID NO: 2.

In an embodiment, the FcRn binding molecule comprises a variant Fc region, wherein the variant Fc region consists of or comprises two Fc domains which form a homodimer, wherein the amino acid sequence of each of the Fc domains consists of or comprises the amino acid sequence of SEQ ID NO: 3.

In an embodiment, the FcRn binding molecule comprises a variant Fc region, wherein the variant Fc region comprises or consists of efgartigimod (CAS Registry No. 1821402-21-4). The term "efgartigimod" as used herein is interchangeable with "efgartigimod alfa" and "ARGX-113." In some embodiments, efgartigimod is efgartigimod alfa-fcab.

In an embodiment, the variant Fc region is modified to promote heterodimerization. Such modifications are known in the art and any suitable means to promote heterodimerization may be used to generate the FcRn/antigen-binding molecules described herein. In some embodiments, the variant Fc region comprises one or more mutations of amino acid residues forming the interface of the CH3 domain of the Fc domains. In some embodiments, the variant Fc region comprises knob-into-hole mutations (see, e.g., Intl. Publ. WO 2006/028936, incorporated by reference in its entirety). The mispairing of Ig heavy chains is reduced in this technology by mutating selected amino acids forming the interface of the CH3 domains in IgG. At positions within the CH3 domain at which the two heavy chains interact directly, one or more amino acids with a small side chain (hole) is/are introduced into the sequence of one heavy chain and one or more amino acids with a large side chain (knob) into the counterpart interacting residue location(s) on the other heavy chain. The Fc domains of an Fc region can be composed of immunoglobulin chains of the same subclass (e.g., IgG1 or IgG3) or different subclasses (e.g., IgG1 and IgG3, or IgG3 and IgG4).

In some embodiments, the variant Fc region comprises or consists of two Fc domains in which one of the Fc domains comprises amino acid W at EU position 366. In some embodiments, the variant Fc region comprises or consists of two Fc domains in which one of the Fc domains comprises amino acid S, A, and V at EU positions 366, 368, and 407, respectively. In some embodiments, the variant Fc region comprises or consists of two Fc domains in which one Fc domain comprises amino acid W at EU position 366, and the other Fc domain comprises amino acid S, A, and V at EU positions 366, 368, and 407, respectively.

In some embodiments, the variant Fc region comprises or consists of two Fc domains in which one Fc domain comprises amino acids E and D at EU positions 370 and 409, respectively, and the other Fc domain comprises amino acid K at EU positions 357 and 399. In some embodiments, the variant Fc region comprises or consists of two Fc domains in which one Fc domain comprises amino acids H and A at EU positions 364 and 405, respectively, and the other Fc domain comprises amino acids T and F at EU positions 349 and 394, respectively. In some embodiments, the variant Fc region comprises or consists of two Fc domains in which one Fc domain comprises amino acids V, Y, A, and V at EU positions 350, 351, 405, and 407, respectively, and the other Fc domain comprises amino acids V, L, L, and W at EU positions 350, 366, 392, and 394, respectively. In some embodiments, the variant Fc region comprises or consists of two Fc domains in which one Fc domain comprises amino acids D, M, and A at EU positions 360, 399, and 407, respectively, and the other Fc domain comprises amino acids R, R, V, and V at EU positions 345, 347, 366, and 409, respectively. In some embodiments, the variant Fc region comprises or consists of two Fc domains in which one Fc domain comprises amino acid D at EU positions 409 and 392, and the other Fc domain comprises amino acid K at EU positions 399 and 356. In some embodiments, the variant Fc region comprises or consists of two Fc domains in which one Fc domain comprises amino acids E, W, and C at EU positions 360, 409, and 349, respectively, and the other Fc domain comprises amino acids R, V, T, and C at EU positions 347, 399, 405, and 354, respectively. In some embodiments, the variant Fc region comprises or consists of two Fc domains in which one Fc domain comprises amino acids E and W at EU positions 370 and 409, respectively, and the other Fc domain comprises amino acids N, V, and T at EU positions 357, 399, and 405, respectively.

In an embodiment, the FcRn binding molecule consists of a variant Fc region, wherein the variant Fc region comprises or consists of two Fc domains which form a heterodimer, wherein the amino acid sequence of the first Fc domain is selected from an amino acid sequence comprising or consisting of SEQ ID NO: 4, SEQ ID NO: 5, and SEQ ID NO: 6 and/or the amino acid sequence of the second Fc domain is selected from an amino acid sequence comprising or consisting of SEQ ID NO: 7, SEQ ID NO: 8, and SEQ ID NO: 9. In an embodiment, the FcRn binding molecule consists of a variant Fc region, wherein the variant Fc region comprises or consists of two Fc domains which form a heterodimer, wherein the amino acid sequence of the first Fc domain is selected from an amino acid sequence comprising or consisting of SEQ ID NO: 7, SEQ ID NO: 8, and SEQ ID NO: 9 and/or the amino acid sequence of the second Fc domain is selected from an amino acid sequence comprising or consisting of SEQ ID NO: 4, SEQ ID NO: 5, and SEQ ID NO: 6. In an embodiment, the FcRn binding molecule consists of a variant Fc region, wherein the variant Fc region comprises or consists of two Fc domains which form a heterodimer, wherein the amino acid sequence of the first Fc domain comprises or consists of SEQ ID NO: 4 and the amino acid sequence of the second Fc domain comprises or consists of SEQ ID NO: 7. In an embodiment, the FcRn binding molecule consists of a variant Fc region, wherein the variant Fc region comprises or consists of two Fc domains which form a heterodimer, wherein the amino acid sequence of the first Fc domain comprises or consists of SEQ ID NO: 5 and the amino acid sequence of the second Fc domain comprises or consists of SEQ ID NO: 8. In an embodiment, the FcRn binding molecule consists of a variant Fc region, wherein the variant Fc region comprises or consists of two Fc domains which form a heterodimer, wherein the amino acid sequence of the first Fc domain comprises or consists of SEQ ID NO: 6 and the amino acid sequence of the second Fc domain comprises or consists of SEQ ID NO: 9. In some embodiments, the FcRn binding molecule is an FcRn antagonist.

TABLE 1

Amino acid sequences of variant Fc regions

| SEQ ID NO: | Amino Acid Sequence |
|---|---|
| 1 | CPPCPAPELLGGPSVFLFPPKPKDTLYITREPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALKFHYTQKSLSLSPG |
| 2 | DKTHTCPPCPAPELLGGPSVFLFPPKPKDTLYITREPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLTCLVKGFYPSDIAVEWESNGQPENNYKTTPPVLDSDGS FFLYSKLTVDKSRWQQGNVFSCSVMHEALKFHYTQKSLSLSPGK |
| 3 | DKTHTCPPCPAPELLGGPSVFLFPPKPKDTLYITREPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLTCLVKGFYPSDIAVEWESNGQPENNYKTTPPVLDSDGS FFLYSKLTVDKSRWQQGNVFSCSVMHEALKFHYTQKSLSLSPG |
| 4 | CPPCPAPELLGGPSVFLFPPKPKDTLYITREPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSRDELTKN QVSLWCLVKGFYPSDIAVEWESNGQPENNYKTTPPVLDSDGSFFLY SKLTVDKSRWQQGNVFSCSVMHEALKFHYTQKSLSLSPG |
| 5 | DKTHTCPPCPAPELLGGPSVFLFPPKPKDTLYITREPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLWCLVKGFYPSDIAVEWESNGQPENNYKTTPPVLDSDG SFFLYSKLTVDKSRWQQGNVFSCSVMHEALKFHYTQKSLSLSPG |
| 6 | DKTHTCPPCPAPELLGGPSVFLFPPKPKDTLYITREPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLWCLVKGFYPSDIAVEWESNGQPENNYKTTPPVLDSDG SFFLYSKLTVDKSRWQQGNVFSCSVMHEALKFHYTQKSLSLSPGK |
| 7 | CPPCPAPELLGGPSVFLFPPKPKDTLYITREPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSRDELTKN QVSLSCAVKGFYPSDIAVEWESNGQPENNYKTTPPVLDSDGSFFLV SKLTVDKSRWQQGNVFSCSVMHEALKFHYTQKSLSLSPG |
| 8 | DKTHTCPPCPAPELLGGPSVFLFPPKPKDTLYITREPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLSCAVKGFYPSDIAVEWESNGQPENNYKTTPPVLDSDGS FFLVSKLTVDKSRWQQGNVFSCSVMHEALKFHYTQKSLSLSPG |

TABLE 1-continued

Amino acid sequences of variant Fc regions

| SEQ ID NO: | Amino Acid Sequence |
|---|---|
| 9 | DKTHTCPPCPAPELLGGPSVFLFPPKPKDTLYITREPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLSCAVKGFYPSDIAVEWESNGQPENNYKTTPPVLDSDGS FFLVSKLTVDKSRWQQGNVFSCSVMHEALKFHYTQKSLSLSPGK |

In some embodiments, the variant Fc region comprises a first Fc domain comprising amino acids Y, T, E, K, and F at EU positions 252, 254, 256, 433, and 434, respectively, and a second Fc domain comprising amino acids K and F at EU positions 433 and 434, respectively. In some embodiments, the first Fc domain comprises the amino acid sequence of SEQ TD NO: 1. In some embodiments, the first Fc domain comprises the amino acid sequence of SEQ TD NO: 2. In some embodiments, the first Fc domain comprises the amino acid sequence of SEQ TD NO: 3.

In some embodiments, the variant Fc region comprises a first Fc domain comprising amino acids Y, T, E, W, K, and F at EU positions 252, 254, 256, 366, 433, and 434, respectively, and a second Fc domain comprising amino acids 5, A, V, K, and F at EU positions 366, 368, 407, 433, and 434, respectively. In some embodiments, the first Fc domain comprises the amino acid sequence of SEQ ID NO: 4. In some embodiments, the first Fc domain comprises the amino acid sequence of SEQ ID NO: 5. In some embodiments, the first Fc domain comprises the amino acid sequence of SEQ ID NO: 6.

In some embodiments, the variant Fc region comprises a first Fc domain comprising amino acids Y, T, E, S, A, V, K, and F at EU positions 252, 254, 256, 366, 368, 407, 433, and 434, respectively, and a second Fc domain comprising amino acids W, K, and F at EU positions 366, 433, and 434, respectively. In some embodiments, the first Fc domain comprises the amino acid sequence of SEQ ID NO: 7. In some embodiments, the first Fc domain comprises the amino acid sequence of SEQ ID NO: 8. In some embodiments, the first Fc domain comprises the amino acid sequence of SEQ ID NO: 9.

In an embodiment, the anti-FcRn antibody is rozanolixizumab (UCB7665), nipocalimab (M281), orilanolimab (ALXN1830/SYNT001), or batoclimab (IMVT-1401/RVT1401/HBM9161).

In an embodiment, an antibody that specifically binds to FcRn and inhibits the binding of the Fc region of immunoglobulin to FcRn is nipocalimab, also known as M281. Nipocalimab is a full-length "Fc dead" IgG1 monoclonal antibody. Nipocalimab has been administered as an intravenous infusion in Phase 2/3 clinical trials for the treatment of myasthenia gravis (MG) and warm autoimmune hemolytic anemia (WAIHA), and in Phase 2 clinical trials for the treatment of hemolytic disease of fetus and newborn (HDFN), systemic lupus erythematosus (SLE), rheumatoid arthritis (RA), and Sjögren's syndrome (SS). Nipocalimab comprises the light chain (SEQ ID NO: 128) and heavy chain (SEQ ID NO: 129) sequences set forth in Table 2 below (VL of SEQ ID NO: 128 and VH of SEQ ID NO: 129 are underlined):

TABLE 2

Heavy chain and light chain sequences of nipocalimab

| SEQ ID NO: | Amino Acid Sequence |
|---|---|
| 128 | <u>QSALTQPASVSGSPGQSITISCTGTGSDVGSYNLVSWYQQHPGKAP KLMIYGDSERPSGVSNRFSGSKSGNTASLTISGLQAEDEADYYCSSY AGSGIYVFGTGTKVTVLGQPKAAPSVTLFPPSSEELQANKATLVCLI</u>SDFYPGAVTVAWKADSSPVKAGVETTTPSKQSNNKYAASSYLSLT PEQWKSHKSYSCQVTHEGSTVEKTVAPTECS |
| 129 | <u>EVQLLESGGGLVQPGGSLRLSCAASGFTFSTYAMGWVRQAPGKGL EWVSSIGASGSQTRYADSVKGRFTISRDNSKNTLYLQMNSLRAEDT AVYYCARLAIGDSYWGQGTMVTVSSA</u>STKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKKVEPKSCDKTHTCPPCP APELLGGPSVFLFPPKPKDTLMISRTPEVTCVVVDVSHEDPEVKFN WYVDGVEVHNAKTKPREEQYASTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPG |

In an embodiment, an antibody that specifically binds to FRn and inhibits the binding of the Fc region of immunoglobulin to FcRn is rozanolixizumab, also known as UCB 7665. Rozanolixizumab is a full-length humanized IgG4 monoclonal antibody. Rozanolixizumab has been administered as a subcutaneous infusion in clinical trials for MG, immune thrombocytopenia (ITP), chronic inflammatory demyelinating polyneuropathy (CTDP), autoimmune encephalitis (AIE), and myelin oligodendrocyte glycoprotein antibody-associated disease (MOG-AD). Rozanolixizumab comprises the light chain (SEQ TD NO: 130) and heavy chain (SEQ ID NO: 131) sequences set forth in Table 3 below (VL of SEQ ID NO: 130 and VH of SEQ TD NO: 131 are underlined):

TABLE 3

Heavy chain and light chain sequences of rozanolixizumab

| SEQ ID NO: | Amino Acid Sequence |
|---|---|
| 130 | DIQMTQSPSSLSASVGDRVTITCKSSQSLVGASGKTYLYWLFQKPG KAPKRLIYLVSTLDSGIPSRFSGSGSGTEFTLTISSLQPEDFATYYCLQ GTHFPHTFGQGTKLEIKRTVAAPSVFIFPPSDEQLKSGTASVVCLLN NFYPREAKVQWKVDNALQSGNSQESVTEQDSKDSTYSLSSTLTLS KADYEKHKVYACEVTHQGLSSPVTKSFNRGEC |
| 131 | EVPLVESGGGLVQPGGSLRLSCAVSGFTFSNYGMVWVRQAPGKGL EWVAYIDSDGDNTYYRDSVKGRFTISRDNAKSSLYLQMNSLRAED TAVYYCTTGIVRPFLYWGQGTLVTVSSASTKGPSVFPLAPCSRSTSE STAALGCLVKDYFPEPVTVSWNSGALTSGVHTFPAVLQSSGLYSLS SVVTVPSSSLGTKTYTCNVDHKPSNTKVDKRVESKYGPPCPPCPAP EFLGGPSVFLFPPKPKDTLMISRTPEVTCVVVDVSQEDPEVQFNWY VDGVEVHNAKTKPREEQFNSTYRVVSVLTVLHQDWLNGKEYKCK VSNKGLPSSIEKTISKAKGQPREPQVYTLPPSQEEMTKNQVSLTCLV KGFYPSDIAVEWESNGQPENNYKTTPPVLDSDGSFFLYSRLTVDKS RWQEGNVFSCSVMHEALHNHYTQKSLSLSLGK |

In an embodiment, an antibody that specifically binds to FcRn and inhibits the binding of the Fc region of immunoglobulin to FcRn is orilanolimab, also known as SYNT001/ALXN1830. Orilanolimab is another full-length humanized IgG4 monoclonal antibody. Orilanolimab has been administered as an intravenous infusion in Phase 2 clinical trials for treatment of WAIHA and pemphigus. Orilanolimab comprises the light chain (SEQ ID NO: 132) and heavy chain (SEQ TD NO: 133) sequences set forth in Table 4 below (VL of SEQ ID NO: 132 and VH of SEQ ID NO: 133 are underlined):

TABLE 4

Heavy chain and light chain sequences of orilanolimab

| SEQ ID NO: | Amino Acid Sequence |
|---|---|
| 132 | DIQMTQSPSSLSASVGDRVTITCKASDHINNWLAWYQQKPGQAPR LLISGATSLETGVPSRFSGSGTGKDYTLTISSLQPEDFATYYCQQYW STPYTFGGGTKVEIKRTVAAPSVFIFPPSDEQLKSGTASVVCLLNNF YPREAKVQWKVDNALQSGNSQESVTEQDSKDSTYSLSSTLTLSKA DYEKHKVYACEVTHQGLSSPVTKSFNRGEC |
| 133 | QVQLVQSGAELKKPGASVKLSCKASGYTFTSYGISWVKQATGQGL EWIGEIYPRSGNTYYNEKFKGRATLTADKSTSTAYMELRSLRSEDS AVYFCARSTTVRPPGIWGTGTTVTVSSASTKGPSVFPLAPCSRSTSE STAALGCLVKDYFPEPVTVSWNSGALTSGVHTFPAVLQSSGLYSLS SVVTVPSSSLGTKTYTCNVDHKPSNTKVDKRVESKYGPPCPPCPAP EFLGGPSVFLFPPKPKDTLMISRTPEVTCVVVDVSQEDPEVQFNWY VDGVEVHNAKTKPREEQFNSTYRVVSVLTVLHQDWLNGKEYKCK VSNKGLPSSIEKTISKAKGQPREPQVYTLPPSQEEMTKNQVSLTCLV KGFYPSDIAVEWESNGQPENNYKTTPPVLDSDGSFFLYSRLTVDKS RWQEGNVFSCSVMHEALHNHYTQKSLSLSLG |

In an embodiment, an antibody that specifically binds to FcRn and inhibits the binding of the Fc region of immunoglobulin to FcRn is batoclimab, also known as IMVT1401/RVT1401/HBM9161. Batoclimab is another full-length "Fc dead" IgG1 monoclonal antibody. Batoclimab has been administered as a subcutaneous injection in Phase 2 clinical trials for treatment of MG, ITP, Graves' ophthalmopathy, thyroid eye disease, and neuromyelitis optica spectrum disorder (NMOSD). Batoclimab comprises the light chain (SEQ ID NO: 134) and heavy chain (SEQ ID NO: 135) sequences set forth in Table 5 below (VL of SEQ ID NO: 134 and VH of SEQ ID NO: 135 are underlined):

TABLE 5

Heavy chain and light chain sequences of batoclimab

| SEQ ID NO: | Amino Acid Sequence |
|---|---|
| 134 | SYVLTQSPSVSVAPGQTARITCGGNNIGSKSVHWYQQKPGQAPVL<br>VVYDDSDRPSGIPERFSASNSGNTATLTISRVEAGDEADYYCQVWD<br>SSSDHVVFGGGTKLTVLGQPKAAPSVTLFPPSSEELQANKATLVCLI<br>SDFYPGAVTVAWKADSSPVKAGVETTTPSKQSNNKYAASSYLSLT<br>PEQWKSHRSYSCQVTHEGSTVEKTVAPTECS |
| 135 | QLLLQESGPGLVKPSETLSLTCTVSGGSLSSSFSYWVWIRQPPGKGL<br>EWIGTIYYSGNTYYNPSLKSRLTISVDTSKNHFSLKLSSVTAADTAV<br>YYCARRAGILTGYLDSWGQGTLVTVSSASTKGPSVFPLAPSSKSTS<br>GGTAALGCLVKDYFPEPVTVSWNSGALTSGVHTFPAVLQSSGLYS<br>LSSVVTVPSSSLGTQTYICNVNHKPSNTKVDKRVEPKSCDKTHTCP<br>PCPAPEAAGGPSVFLFPPKPKDTLMISRTPEVTCVVVDVSHEDPEVK<br>FNWYVDGVEVHNAKTKPREEQYNSTYRVVSVLTVLHQDWLNGK<br>EYKCKVSNKALPAPIEKTISKAKGQPREPQVYTLPPSREEMTKNQV<br>SLTCLVKGFYPSDIAVEWESNGQPENNYKTTPPVLDSDGSFFLYSK<br>LTVDKSRWQQGNVFSCSVMHEALHNHYTQKSLSLSPG |

Antigen-Binding Domains

In an aspect, antigen-binding domains are provided by the present disclosure. In some embodiments, the FcRn/antigen-binding molecules disclosed herein comprise one or more FcRn binding molecules in combination with one or more antigen-binding domains. In some embodiments, the FcRn/antigen-binding molecules disclosed herein comprise one or more Fc regions, or FcRn binding fragments thereof, in combination with one or more antigen-binding domains. In some embodiments, the antigen-binding domain is a polypeptide derived from an antibody including, but not limited to, an sdAb (e.g., a VHH fragment), a Fab fragment, an scFv, a VH, or a VL. In some embodiments, the antigen-binding domain is a synthetic antigen-binding protein or antibody mimetic protein including, but not limited to, an anticalin or a DARPin.

In some embodiments, the antigen-binding domain further comprises one or more amino acids added at its C-terminus. In some embodiments, the antigen-binding domain further comprises one or more amino acids added at the C-terminus selected from A, AG, GG, and PP. In some embodiments, the C-terminus of VHH is the amino acid sequence VTVSS (SEQ ID NO: 91). In some embodiments, the C-terminus of VHH consists of the amino acid sequence VTVSS (SEQ ID NO: 91).

The antigen-binding domain may bind to any antigen. In some embodiments, the antigen is a non-human antigen, e.g., a protein or fragment thereof that is not normally expressed by humans and not normally found in humans. In some embodiments, the non-human antigen is a protein or fragment thereof that is not normally expressed by humans but may be found in a human. Examples of non-human antigens that may be found in a human include proteins or fragments thereof expressed by pathogens, such as bacterial or viral proteins or fragments thereof. These pathogenic proteins or fragments thereof may be found in a human due to infection and/or immunization. Thus, in some embodiments, the non-human antigen that may be found in a human is a viral antigen. In some embodiments, the non-human antigen is a non-human antigen that is not found in a human. Examples of non-human antigens that are not found in a human include proteins or fragments thereof that are not pathogenic and have no human counterpart, such as, for example hen egg lysozyme (HEL) or ovalbumin.

In some embodiments, the antigen is a human antigen, e.g., a protein or fragment thereof normally expressed by humans. In some embodiments the human antigen is selected from HSA or IgE.

In some embodiments, the antigen-binding domain specifically binds to HSA. In some embodiments, the antigen-binding domain specifically binds to HSA and is selected from a Fab fragment, an scFv, an sdAb, HSA, and HSA-binding fragments thereof. In some embodiments, the antigen-binding domain specifically binds to HSA and is an sdAb, such as a VHH fragment. In some embodiments, HSA comprises an amino acid sequence at least 95% identical to the amino acid sequence provided in GenBank Accession No.: AAA98797.1. In some embodiments HSA comprises the amino acid sequence provided in GenBank Accession No.: AAA98797.1.

In some embodiments, the antigen-binding domain is a VHH fragment comprising the CDR1, CDR2, and CDR3 amino acid sequences of a VHH fragment comprising an amino acid sequence selected from SEQ ID NOs: 43-74, 84-90, and 120-127.

In some embodiments, the antigen-binding domain is a VHH fragment comprising or consisting of a combination of CDR1, CDR2, and CDR3 wherein 1, 2, 3, 4, or 5 amino acids differ in at least one of the amino acid sequences selected from SEQ ID NOs: 10, 11 and 12; 13, 11, and 12; 14, 11, and 12; 15, 11, and 12; 16, 11, and 12; 17, 11, and 12; 10, 18, and 12; 10, 19, and 12; 10, 20, and 12; 10, 21, and 12; 10, 22, and 12; 10, 23, and 12; 10, 24, and 12; 10, 25, and 12; 10, 26, and 12; 10, 27, and 12; 10, 28, and 12; 10, 29, and 12; 10, 30, and 12; 10, 31, and 12; 10, 32, and 12; 10, 33, and 12; 10, 11, and 34; 10, 11, and 35; 10, 11, and 36; 10, 11 and 37; 10, 11, and 38; 10, 11, and 39; 10, 11, and 40; 15, 11, and 36; 15, 21, and 12; 10, 41, and 12; 10, 20, and 36; 111, 11, and 12; 112, 11, and 12; 10, 113, and 12; 10, 114, and 12; 10, 11, and 115; 10, 11, and 116; 10, 11, and 117; 118, 11, and 119; 75, 76, and 77; 75, 76, and 78; 75, 76, and 79; 75, 76, and 80; 75, 76, and 81; 75, 76, and 82; and 75, 76, and 83.

In some embodiments, the antigen-binding domain is a VHH fragment comprising or consisting of a combination of CDR1, CDR2, and CDR3 selected from: SEQ ID NOs: 10, 11 and 12; 13, 11, and 12; 14, 11, and 12; 15, 11, and 12; 16, 11, and 12; 17, 11, and 12; 10, 18, and 12; 10, 19, and 12; 10, 20, and 12; 10, 21, and 12; 10, 22, and 12; 10, 23, and 12; 10, 24, and 12; 10, 25, and 12; 10, 26, and 12; 10, 27, and 12; 10, 28, and 12; 10, 29, and 12; 10, 30, and 12; 10, 31, and 12; 10, 32, and 12; 10, 33, and 12; 10, 11, and 34; 10, 11, and 35; 10, 11, and 36; 10, 11 and 37; 10, 11, and 38; 10, 11, and 39; 10, 11, and 40; 15, 11, and 36; 15, 21, and 12; 10, 41, and 12; 10, 20, and 36; 111, 11, and 12; 112, 11, and 12; 10, 113, and 12; 10, 114, and 12; 10, 11, and 115; 10, 11, and 116; 10, 11, and 117; 118, 11, and 119; 75, 76, and 77; 75, 76, and 78; 75, 76, and 79; 75, 76, and 80; 75, 76, and 81; 75, 76, and 82; and 75, 76, and 83, wherein one or more amino acids within one or more of the CDRs is substituted with an alanine or a histidine.

In some embodiments, the antigen-binding domain is a VHH fragment comprising or consisting of a combination of CDR1, CDR2, and CDR3 selected from SEQ ID NOs: 10, 11 and 12; 13, 11, and 12; 14, 11, and 12; 15, 11, and 12; 16, 11, and 12; 17, 11, and 12; 10, 18, and 12; 10, 19, and 12; 10, 20, and 12; 10, 21, and 12; 10, 22, and 12; 10, 23, and 12; 10, 24, and 12; 10, 25, and 12; 10, 26, and 12; 10, 27, and 12; 10, 28, and 12; 10, 29, and 12; 10, 30, and 12; 10, 31, and 12; 10, 32, and 12; 10, 33, and 12; 10, 11, and 34; 10, 11, and 35; 10, 11, and 36; 10, 11 and 37; 10, 11, and 38; 10, 11, and 39; 10, 11, and 40; 15, 11, and 36; 15, 21, and 12; 10, 41, and 12; 10, 20, and 36; 111, 11, and 12; 112, 11, and 12; 10, 113, and 12; 10, 114, and 12; 10, 11, and 115; 10, 11, and 116; 10, 11, and 117; 118, 11, and 119; 75, 76, and 77; 75, 76, and 78; 75, 76, and 79; 75, 76, and 80; 75, 76, and 81; 75, 76, and 82; and 75, 76, and 83.

In some embodiments, the antigen-binding domain is a VHH fragment comprising or consisting of an amino acid sequence at least 70%, 75%, 80%, 85%, 90%, 95%, 96%, 97%, 98%, or 99% identical to an amino acid sequence selected from SEQ ID NOs: 42-74, 84-90, and 120-127. In some embodiments, the antigen-binding domain is a VHH fragment comprising or consisting of an amino acid sequence selected from SEQ ID NOs: 42-74, 84-90, and 120-127.

Linkers

The antigen-binding domain may be linked to the N-terminus or the C-terminus of an FcRn binding molecule (e.g., an Fc domain). Alternatively, the antigen-binding domain may to linked at a position other than the N-terminus or the C-terminus an FcRn binding molecule (e.g., an Fc domain). Preferably, the antigen-binding domain is linked to the C-terminus of an FcRn binding molecule (e.g., an Fc domain).

In some embodiments, the antigen-binding domain may be non-covalently linked to the FcRn binding molecule. In some embodiments, the antigen-binding domain may be covalently linked to the FcRn binding molecule.

In some embodiments, the antigen-binding domain may be linked (e.g., fused) directly to the N-terminus or the C-terminus of an FcRn binding molecule. In some embodiments, the antigen-binding domain is linked to the N-terminus or the C-terminus of an FcRn binding molecule via a linker. In some embodiments, the linker is a non-cleavable linker.

In some embodiments, the antigen-binding domain may be linked (e.g., fused) directly to the N-terminus or the C-terminus of an Fc domain. In some embodiments, the antigen-binding domain is linked to the N-terminus or the C-terminus of an Fc domain via a linker. In some embodiments, the linker is a non-cleavable linker. As used herein, the term "non-cleavable linker" refers to a linker that is not readily cleaved by one or more of a given enzyme, chemical agent, or photo-irradiation. In some embodiments, the enzyme is a protease.

In some embodiments, the linker is a synthetic compound linker such as, for example, a chemical cross-linking agent. Non-limiting examples of suitable cross-linking agents that are available on the market include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES).

As described above, Fc domains disclosed herein may comprise a portion of a hinge region. As such, the antigen-binding domain may be linked to the N-terminus of an Fc domain via this hinge region. In some embodiments, one or more amino acids are included between the C-terminus of the antigen-binding domain and the N-terminus of the Fc domain. In some embodiments, the one or more amino acids included between the C-terminus of the antigen-binding domain and the N-terminus of the Fc domain are amino acids of a natural hinge region. In some embodiments, the C-terminus of the antigen-binding domain is fused to the N-terminus of the Fc domain via a hinge region or a portion thereof. In some embodiments, the hinge region is and IgG hinge region, such as a human IgG hinge region.

In some embodiments, the linker is a peptide linker. Examples of peptide linkers are well known and those of skill in the art could select a suitable peptide linker for use in linking an antigen-binding domain to an FcRn binding molecule, e.g., an Fc domain.

Peptide linkers may be of any length. In some embodiments, the length and amino acid composition of the linker peptide sequence can be optimized to vary the orientation and/or proximity of the polypeptide domains to one another to achieve a desired activity of the FcRn/antigen-binding molecule. In some embodiments, the peptide linker is between about 1 and about 100 amino acids in length, between about 8 and about 40 amino acids in length, or between about 15 amino acids and about 25 amino acids in length. In some embodiments, the peptide linker is between 1 and 100 amino acids in length, between 8 and 40 amino acids in length, or between 15 and 25 amino acids in length. In some embodiments, the peptide linker is about 8 amino acid in length, about 9 amino acids in length, about 10 amino acids in length, about 11 amino acids in length, about 12 amino acids in length, about 13 amino acids in length, about 14 amino acids in length, about 15 amino acids in length, about 16 amino acids in length, about 17 amino acids in length, about 18 amino acids in length, about 19 amino acids in length, about 20 amino acids in length, about 21 amino acids in length, about 22 amino acids in length, about 23 amino acids in length, about 24 amino acids in length, about 25 amino acids in length, about 26 amino acids in length, about 27 amino acids in length, about 28 amino acids in length, about 29 amino acids in length, about 30 amino acids in length, about 31 amino acids in length, about 32 amino acids in length, about 33 amino acids in length, about 34 amino acids in length, about 35 amino acids in length, about 36 amino acids in length, about 37 amino acids in length, about 38 amino acids in length, about 39 amino acids in length, or about 40 amino acids in length. In some embodiments, the peptide linker is 8 amino acids in length, 9 amino acids in length, 10 amino acids in length, 11 amino acids in length, 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, or 40 amino acids in length.

In some embodiments, the peptide linker contains only glycine and/or serine residues (e.g., glycine-serine linker or GS linker). Examples of such peptide linkers include: Gly(x) Ser, where x is 0 to 6; or Ser Gly(x), where x is 0 to 6; (Gly Gly Gly Gly Ser)n, wherein n is an integer of one or more; and (Ser Gly Gly Gly Gly)n, wherein n is an integer of one or more. In some embodiments, the peptide linker includes an amino acid sequence selected from the group consisting of: (GGGGS)n and (SGGGG)n, where n is 1 to 8. In some embodiments, the linker peptides are modified such that the amino acid sequence GSG (that occurs at the junction of traditional Gly/Ser linker peptide repeats) is not present. For example, in some embodiments, the peptide linker includes an amino acid sequence selected from the group consisting of: (GGGXX)nGGGGS and GGGGS(XGGGS)n, where X is any amino acid that can be inserted into the sequence and not result in a polypeptide including the sequence GSG, and n is 0 to 4. In some embodiments, the sequence of a linker peptide is (GGGX1X2)nGGGGS and X1 is P and X2 is S and n is 0 to 4. In some other embodiments, the sequence of a linker peptide is (GGGX1X2)nGGGGS and X1 is G and X2 is Q and n is 0 to 4. In some other embodiments, the sequence of a linker peptide is (GGGX1X2)nGGGGS and X1 is G and X2 is A and n is 0 to 4. In yet other embodiments, the sequence of a linker peptide is GGGGS (XGGGS)n, and X is P and n is 0 to 4. In some embodiments, a linker peptide of the disclosure comprises or consists of the amino acid sequence (GGGGA)$_2$GGGGS. In some embodiments, a linker peptide comprises or consists of the amino acid sequence (GGGGQ)$_2$GGGGS. In another embodiment, a linker peptide comprises or consists of the amino acid sequence (GGGPS)$_2$GGGGS. In another embodiment, a linker peptide comprises or consists of the amino acid sequence GGGGS(PGGGS)$_2$. In yet a further embodiment, a linker peptide comprises or consists of the amino acid sequence GSGGS or SGGSGS. In some embodiments, a linker peptide comprises or consists of the amino acid sequence GGGGSGGGGSGGGGSGGGGS (SEQ ID NO: 136), GGGGSGGGGS (SEQ ID NO: 181), or GGGGSGGGGSGGGGSGGGGSGGGGSGGGGS (SEQ ID NO: 182).

In some embodiments, the peptide linker is a GS linker of about 20 or about 30 amino acids in length. In some embodiments, the peptide linker is a GS linker of 20 or 30 amino acids in length.

Heavy Chain Molecules

In some embodiments, FcRn/antigen-binding molecules can comprise a first heavy chain described herein. In some embodiments, the first heavy chain comprises an Fc domain and an antigen binding domain joined by a linker. In some embodiments, FcRn/antigen-binding molecules can further comprise second heavy chain described herein. In some embodiments, the second heavy chain comprises an Fc domain and an antigen binding domain joined by a linker. In some embodiments, the second heavy chain comprises an Fc domain. In some embodiments, the first and second heavy chains are the same. In some embodiments, the first and second heavy chains are different.

In some embodiments, the first and second heavy chains have the same Fc domain. In some embodiments, the first and second heavy chains have different Fc domains. In some embodiments, the first and second heavy chains both comprise an antigen binding domain. In some embodiments, the antigen binding domains on the first and second heavy chains are the same. In some embodiments, the antigen binding domains on the first and second heavy chains are different. In some embodiments, the first heavy chain comprises an Fc domain and an antigen binding domain, while the second heavy chain comprises an Fc but does not comprise an antigen binding domain. In some embodiments, the first heavy chain comprises an Fc domain and an antigen binding domain, while the second heavy chain comprises an Fc domain but does not comprise an antigen binding domain or a linker. In some embodiments, the first heavy chain comprises an Fc domain, an antigen binding domain and a linker, while the second heavy chain comprises an Fc domain but does not comprise an antigen binding domain or a linker.

In some embodiments, the antigen binding domain is linked to the N-terminus of the Fc domain. In some embodiments, the antigen binding domain is linked to the C-terminus of the Fc domain. In some embodiments, the antigen binding domain is linked to a position other than the N-terminus or the C-terminus of the Fc domain.

In some embodiments, the antigen binding domain is fused to the N-terminus of the Fc domain. In some embodiments, the antigen binding domain is fused to the C-terminus of the Fc domain. In some embodiments, the antigen binding domain is fused to a position other than the N-terminus or the C-terminus of the Fc domain.

In some embodiments, the antigen binding domain is linked to the N-terminus of the Fc domain by a linker. In some embodiments, the antigen binding domain is linked to the C-terminus of the Fc domain by a linker. In some embodiments, the antigen binding domain is linked to a position other than the N-terminus or the C-terminus of the Fc domain by a linker.

In some embodiments, the antigen binding domain is fused to the N-terminus of the Fc domain by a peptide linker. In some embodiments, the antigen binding domain is fused to the C-terminus of the Fc domain by a peptide linker. In some embodiments, the antigen binding domain is fused to a position other than the N-terminus or the C-terminus of the Fc domain by a peptide linker.

In some embodiments, the Fc domain comprises an amino acid sequence at least 70%, 75%, 80%, 85%, 90%, 95%, 96%, 97%, 98%, or 99% identical to the amino acid sequence of any one of SEQ ID NOs: 1-9. In some embodiments, the Fc domain consists of an amino acid sequence at least 70%, 75%, 80%, 85%, 90%, 95%, 96%, 97%, 98%, or 99% identical to the amino acid sequence of any one of SEQ ID NOs: 1-9.

In some embodiments, the Fc domain comprises the amino acid sequence of any one of SEQ ID NOs: 1-9. In some embodiments, the Fc domain consists of the amino acid sequence of any one of SEQ ID NOs: 1-9.

In some embodiments, the first and second heavy chains comprise the same Fc domain. In some embodiments, both the first and second heavy chains comprise an Fc domain comprising an amino acid sequence at least 70%, 75%, 80%, 85%, 90%, 95%, 96%, 97%, 98%, or 99% identical to the amino acid sequence of any one of SEQ ID NOs: 1-3. In some embodiments, both the first and second heavy chains comprise an Fc domain consisting of an amino acid sequence at least 70%, 75%, 80%, 85%, 90%, 95%, 96%, 97%, 98%, or 99% identical to the amino acid sequence of any one of SEQ ID NOs: 1-3. In some embodiments, both the first and second heavy chains comprise an Fc domain comprising the amino acid sequence of any one of SEQ ID NOs: 1-3. In some embodiments, both the first and second heavy chains comprise an Fc domain consisting of the amino acid sequence of any one of SEQ ID NOs: 1-3.

In some embodiments, the first and second heavy chains comprise different Fc domains. In some embodiments, the first heavy chain comprises an Fc domain comprising an amino acid sequence at least 70%, 75%, 80%, 85%, 90%, 95%, 96%, 97%, 98%, or 99% identical to the amino acid sequence of any one of SEQ ID NOs: 4-6 and the second heavy chain comprises an Fc domain comprising an amino acid sequence at least 70%, 75%, 80%, 85%, 90%, 95%, 96%, 97%, 98%, or 99% identical to the amino acid sequence of any one of SEQ ID NOs: 7-9. In some embodiments, the first heavy chain comprises an Fc domain consisting of an amino acid sequence at least 70%, 75%, 80%, 85%, 90%, 95%, 96%, 97%, 98%, or 99% identical to the amino acid sequence of any one of SEQ ID NOs: 4-6 and the second heavy chain comprises an Fc domain consisting of an amino acid sequence at least 70%, 75%, 80%, 85%, 90%, 95%, 96%, 97%, 98%, or 99% identical to the amino acid sequence of any one of SEQ ID NOs: 7-9. In some embodiments, the first heavy chain comprises an Fc domain comprising the amino acid sequence of any one of SEQ ID NOs: 4-6 and the second heavy chain comprises an Fc domain comprising the amino acid sequence of any one of SEQ ID NOs: 7-9. In some embodiments, when the first heavy chain comprises an Fc domain comprising the amino acid sequence of SEQ ID NO: 4 or a variant thereof, the second heavy chain comprises an Fc domain comprising SEQ ID NO: 7 or a variant thereof. In some embodiments, when the first heavy chain comprises an Fc domain comprising the amino acid sequence of SEQ ID NO: 5 or a variant thereof, the second heavy chain comprises an Fc domain comprising SEQ ID NO: 8 or a variant thereof. In some embodiments, when the first heavy chain comprises an Fc domain comprising the amino acid sequence of SEQ ID NO: 6 or a variant thereof, the second heavy chain comprises an Fc domain comprising SEQ ID NO: 9 or a variant thereof.

In some embodiments, the first and second heavy chains further comprise a peptide linker. In some embodiments, the first and second heavy chains further comprise the same peptide linker. In some embodiments, the first and second heavy chains further comprise different peptide linkers. In some embodiments, the first heavy chain comprises an Fc domain, a peptide linker, and an antigen binding domain and the second heavy chain comprises an Fc domain but no peptide linker or antigen binding domain. The peptide linkers encoded by the first and heavy chains can be any described herein. In some embodiments, the linker comprises the amino acid sequence of SEQ ID NO: 136, 180, or 181.

In some embodiments, the FcRn/antigen-binding molecule comprises an amino acid sequence selected from Table 6 or a variant thereof.

TABLE 6

| Clone | Sequence | SEQ ID NO: |
|---|---|---|
| #1 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRAFGMSWVRQAPGKGPEWVSSI SGSGSDTLYADSVKGRFTISRDNSKNTLYLQMNSLRPEDTAVYYCTIGGSLSRSSQGTLVTVSS | 137 |
| #2 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSAGMSWVRQAPGKGPEWVSSI SGSGSDTLYADSVKGRFTISRDNSKNTLYLQMNSLRPEDTAVYYCTIGGSLSRSSQGTLVTVSS | 138 |
| #3 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFAMSWVRQAPGKGPEWVSSI SGSGSDTLYADSVKGRFTISRDNSKNTLYLQMNSLRPEDTAVYYCTIGGSLSRSSQGTLVTVSS | 139 |
| #4 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKNGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMAWVRQAPGKGPEWVSSI SGSGSDTLYADSVKGRFTISRDNSKNTLYLQMNSLRPEDTAVYYCTIGGSLSRSSQGTLVTVSS | 140 |
| #5 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMAWVRQAPGKGPEWVSSI SGSGSDTLYADSVKGRFTISRDNSKNTLYLQMNSLRPEDTAVYYCTIGGSLSRSSQGTLVTVSS | 141 |
| #6 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMAWVRQAPGKGPEWVSAI SGSGSDTLYADSVKGRFTISRDNSKNTLYLQMNSLRPEDTAVYYCTIGGSLSRSSQGTLVTVSS | 142 |
| #7 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWINGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSA SGSGSDTLYADSVKGRFTISRDNSKNTLYLQMNSLRPEDTAVYYCTIGGSLSRSSQGTLVTVSS | 143 |
| #8 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI AGSGSDTLYADSVKGRFTISRDNSKNTLYLQMNSLRPEDTAVYYCTIGGSLSRSSQGTLVTVSS | 144 |
| #9 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SASGSDTLYADSVKGRFTISRDNSKNTLYLQMNSLRPEDTAVYYCTIGGSLSRSSQGTLVTVSS | 145 |
| #10 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGAGSDTLYADSVKGRFTISRDNSKNTLYLQMNSLRPEDTAVYYCTIGGSLSRSSQGTLVTVSS | 146 |

TABLE 6-continued

| Clone | Sequence | SEQ ID NO: |
|---|---|---|
| #11 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSASDTLYADSVKGRFTISRDNSKNTLYLQMNSLRPEDTAVYYCTIGGSLSRSSQGTLVTVSS | 147 |
| #12 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGADTLYADSVKGRFTISRDNSKNTLYLQMNSLRPEDTAVYYCTIGGSLSRSSQGTLVTVSS | 148 |
| #13 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSATLYADSVKGRFTISRDNSKNTLYLQMNSLRPEDTAVYYCTIGGSLSRSSQGTLVTVSS | 149 |
| #14 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDALYADSVKGRFTISRDNSKNTLYLQMNSLRPEDTAVYYCTIGGSLSRSSQGTLVTVSS | 150 |
| #15 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTAYADSVKGRFTISRDNSKNTLYLQMNSLRPEDTAVYYCTIGGSLSRSSQGTLVTVSS | 151 |
| #16 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLAADSVKGRFTISRDNSKNTLYLQMNSLRPEDTAVYYCTIGGSLSRSSQGTLVTVSS | 152 |
| #17 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYAASVKGRFTISRDNSKNTLYLQMNSLRPEDTAVYYCTIGGSLSRSSQGTLVTVSS | 153 |
| #18 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADAVKGRFTISRDNSKNTLYLQMNSLRPEDTAVYYCTIGGSLSRSSQGTLVTVSS | 154 |
| #19 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSAKGRFTISRDNSKNTLYLQMNSLRPEDTAVYYCTIGGSLSRSSQGTLVTVSS | 155 |
| #20 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLVAGRFTISRDNSKNTLYLQMNSLRPEDTAVYYCTIGGSLSRSSQGTLVTVSS | 156 |

TABLE 6-continued

| Clone | sequence | SEQ ID NO: |
|---|---|---|
| #21 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKGRFTISRDNSKNTLYLQMNSLRPEDTAVYYCTIAGSLSRSSQGTLVTVSS | 157 |
| #22 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKARFTISRDNSKNTLYLQMNSLRPEDTAVYYCTIAGSLSRSSQGTLVTVSS | 158 |
| #23 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKGRFTISRDNSKNTLYLQMNSLRPEDTAVYYCTIGASLSRSSQGTLVTVSS | 159 |
| #24 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKGRFTISRDNSKNTLYLQMNSLRPEDTAVYYCTIGGSLSRSSQGTLVTVSS | 160 |
| #25 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKGRFTISRDNSKNTLYLQMNSLRPEDTAVYYCTIGGSASRSSQGTLVTVSS | 161 |
| #26 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKGRFTISRDNSKNTLYLQMNSLRPEDTAVYYCTIGGSLARSSQGTLVTVSS | 162 |
| #27 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKGRFTISRDNSKNTLYLQMNSLRPEDTAVYYCTIGGSLARSSQGTLVTVSS | 163 |
| #28 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSGSDTLYADSVKGRFTISRDNSKNTLYLQMNSLRPEDTAVYYCTIGGSLASSQGTLVTVSS | 164 |
| #29 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFAMSWVRQAPGKGPEWVSSI SGSGSDTLYADSVKGRFTISRDNSKNTLYLQMNSLRPEDTAVYYCTIGGALSRSSQGTLVTVSS | 165 |
| #30 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFAMSWVRQAPGKGPEWVSSI SASGSDTLYADSVKGRFTISRDNSKNTLYLQMNSLRPEDTAVYYCTIGGSLSRSSQGTLVTVSS | 166 |

TABLE 6-continued

| Clone | Sequence | SEQ ID NO: |
|---|---|---|
| #31 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI AASGSDTLYADSVKGRFTISRDNSKNTLYLQMNSLRPEDTAVYYCTIGGSLSRSSQGTLVTVSS | 167 |
| #32 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI AGSGSDTLYADSVKGRFTISRDNSKNTLYLQMNSLRPEDTAVYYCTIGGALSRSSQGTLVTVSS | 168 |
| #33 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSHGMSWVRQAPGKGPEWVSSI SGSGSDTLYADSVKGRFTISRDNSKNTLYLQMNSLRPEDTAVYYCTIGGSLSRSSQGTLVTVSS | 169 |
| #34 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGHSWVRQAPGKGPEWVSSI SGSGSDTLYADSVKGRFTISRDNSKNTLYLQMNSLRPEDTAVYYCTIGGSLSRSSQGTLVTVSS | 170 |
| #35 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTFRSFGMSWVRQAPGKGPEWVSSI SGSHSDTLYADSVKGRFTISRDNSKNTLYLQMNSLRPEDTAVYYCTIGGSLSRSSQGTLVTVSS | 171 |
| #36 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWINGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTERSFGMSWVRQAPGKGPEWVSSI SGSGSDTHYADSVKGRFTISRDNSKNTLYLQMNSLRPEDTAVYYCTIGGSLSRSSQGTLVTVSS | 172 |
| #37 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTERSFGMSWVRQAPGKGPEWVSSI SGSGSDTLYADSVKGRFTISRDNSKNTLYLQMNSLRPEDTAVYYCTIHGSLSRSSQGTLVTVSS | 173 |
| #38 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTERSFGMSWVRQAPGKGPEWVSSI SGSGSDTLYADSVKGRFTISRDNSKNTLYLQMNSLRPEDTAVYYCTIGHSLSRSSQGTLVTVSS | 174 |
| #39 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQ QGNVFSCSVMHEALKFHYTQKSLSLSPGGGGSGGGGSGGGGSEVQLLESGGGLVQPGGSLRLSCAASGFTERSFGMSWVRQAPGKGPEWVSSI SGSGSDTLYADSVKGRFTISRDNSKNTLYLQMNSLRPEDTAVYYCTIGGSHSRSSQGTLVTVSS | 175 |

TABLE 6-continued

| Clone | Sequence | SEQ ID NO: |
|---|---|---|
| #40 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCCSVMHEALKFHYTQKSLSLSPGGGGSGGGGSGGGGSEVQLLESGGGLVQPGGSLRLSCAASGFTFRSFHMSWVRQAPGKGPEWVSSISGSGSDTLYADSVKGRFTISRDNSKNTLYLQMNSLRPEDTAVYYCTIGGHLSRSSQGTLVTVSS | 176 |
| #41 | DKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCCSVMHEALKFHYTQKSLSLSPGGGGSGGGGSGGGGSEVQLLESGGGLVQPGGSLRLSCAASGFTFRSAGMSWVRQAPGKGPEWVSSISGSGSDTLYADSVKGRFTISRDNSKNTLYLQMNSLRPEDTAVYYCTIGGSLSRSSQGTLVTVSSA | 180 |

In some embodiments, the FcRn/antigen-binding molecule comprises or consists of an amino acid sequence at least 70%, 75%, 80%, 85%, 90%, 95%, 96%, 97%, 98%, or 99% identical to the amino acid sequence of any one of SEQ ID NOs: 137-176 and 180. In some embodiments, the FcRn/antigen-binding molecule comprises or consists of the amino acid sequence of any one of SEQ ID NOs: 137-176 and 180.

In some embodiments, the FcRn/antigen-binding molecule comprises the amino acid sequence of any one of SEQ ID NOs: 137-176 and 180 or a variant thereof and one or more amino acids added at the C-terminus. In some embodiments, the FcRn/antigen-binding molecule comprises the amino acid sequence of any one of SEQ ID NOs: 137-176 and 180 or a variant thereof and one or more amino acids added at the C-terminus selected from A, AG, GG, and PP.

In some embodiments, the first heavy chain of the FcRn/antigen-binding molecule comprises or consists of an amino acid sequence at least 70%, 75%, 80%, 85%, 90%, 95%, 96%, 97%, 98%, or 99% identical to the amino acid sequence of any one of SEQ ID NOs: 137-176 and 180 and the second heavy chain of the FcRn/antigen-binding molecule does not comprise an antigen binding domain. In some embodiments, the second heavy chain of the FcRn/antigen-binding molecule comprises an Fc domain, but does not comprise an antigen binding domain. Optionally, the second heavy chain of the FcRn/antigen-binding molecule comprises or consists of an amino acid sequence at least 70%, 75%, 80%, 85%, 90%, 95%, 96%, 97%, 98%, or 99% identical to the amino acid sequence of SEQ ID NO: 8.

In some embodiments, the first heavy chain of the FcRn/antigen-binding molecule comprises or consists of the amino acid sequence of any one of SEQ ID NOs: 137-176 and 180 and the second heavy chain of the FcRn/antigen-binding molecule does not comprise an antigen binding domain. In some embodiments, the second heavy chain of the FcRn/antigen-binding molecule comprises an Fc domain, but does not comprise an antigen binding domain. Optionally, the second heavy chain of the FcRn/antigen-binding molecule comprises or consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 137 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 137 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 137 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 137 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 138 and the second heavy chain of the FcRn/antigen-binding molecule comprises an Fc domain comprising the amino acid sequence of SEQ ID NO: 8, but does not comprise an antigen binding domain. In some embodiments, the first heavy chain the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 138 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 138 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 138 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 139 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 139 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 139 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 139 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 140 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 140 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 140 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 140 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 141 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 141 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 141 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 141 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 142 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 142 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 142 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 142 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 143 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 143 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 143 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 143 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 144 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 144 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 144 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 144 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 145 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 145 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 145 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 145 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 146 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 146 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 146 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 146 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 147 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 147 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 147 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 147 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 148 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 148 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 148 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 148 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 149 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 149 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 149 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 149 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 150 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 150 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 150 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 150 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 151 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 151 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 151 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 151 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 152 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 152 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 152 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 152 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 153 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 153 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 153 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 153 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 154 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 154 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 154 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 154 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 155 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 155 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 155 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 155 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 156 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 156 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 156 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 156 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 157 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 157 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 157 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 157 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 158 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 158 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 158 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 158 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 159 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 159 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 159 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 159 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 160 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 160 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 160 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 160 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 161 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 161 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 161 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 161 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 162 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 162 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 162 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 162 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 163 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 163 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 163 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 163 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 164 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 164 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 164 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 164 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 165 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 165 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 165 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 165 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 166 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 166 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 166 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 166 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 167 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 167 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 167 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 167 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 168 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 168 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 168 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 168 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 169 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 169 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 169 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 169 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 170 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 170 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 170 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 170 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 171 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 171 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 171 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 171 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 172 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 172 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 172 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 172 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 173 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 173 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 173 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 173 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 174 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 174 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 174 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 174 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 175 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 175 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 175 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 175 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 176 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 176 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 176 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 176 and the second heavy chain of the FcRn/antigen-binding molecule consists of the amino acid sequence of SEQ ID NO: 8.

In some embodiments, the first heavy chain of the FcRn/antigen-binding molecule comprises an amino acid sequence at least 70%, 75%, 80%, 85%, 90%, 95%, 96%, 97%, 98%, or 99% identical to the amino acid sequence of SEQ ID NO: 180 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of an amino acid sequence at least 70%, 75%, 80%, 85%, 90%, 95%, 96%, 97%, 98%, or 99% identical to the amino acid sequence of SEQ ID NO: 180 and the second heavy chain of the FcRn/antigen-binding molecule consists of the amino acid sequence of SEQ ID NO: 8.

In some embodiments, the first heavy chain of the FcRn/antigen-binding molecule comprises the amino acid sequence of SEQ ID NO: 180 and the second heavy chain of the FcRn/antigen-binding molecule comprises an Fc domain comprising the amino acid sequence of SEQ ID NO: 8, but does not comprise an antigen binding domain. In some embodiments, the first heavy chain of the FcRn/antigen-binding molecule consists of the amino acid sequence of SEQ ID NO: 180 and the second heavy chain of the FcRn/antigen-binding molecule consists of the amino acid sequence of SEQ ID NO: 8.

In some embodiments, the FcRn/antigen-binding molecule comprises the amino acid sequence of any one of SEQ ID NOs: 137-176 and 180 or a variant thereof as described herein and one or more amino acids added at the C-terminus. In some embodiments, the FcRn/antigen-binding molecule comprises the amino acid sequence of any one of SEQ ID NOs: 137-176 and 180 or a variant thereof as described herein and one or more amino acids added at the C-terminus selected from A, AG, GG, and PP.

Polynucleotides, Vectors, and Methods of Production

The disclosure also provides polynucleotides encoding the FcRn/antigen-binding molecules disclosed herein or fragments thereof. In some embodiments, the polynucleotide encodes an antigen-binding domain of the disclosure. In some embodiments, the polynucleotide encodes an FcRn binding molecule of the disclosure. In some embodiments, the polynucleotide encodes an Fc region of the disclosure. In some embodiments, the polynucleotide encodes an Fc domain of the disclosure. In some embodiments, the polynucleotide encodes one or more of an antigen-binding domain, an FcRn binding molecule, and a linker. In some embodiments, the polynucleotide encodes an antigen-binding domain and an FcRn binding molecule, and optionally a linker. In some embodiments, the polynucleotide encodes one or more of an antigen-binding domain, an Fc region, and a linker. In some embodiments, the polynucleotide encodes an antigen-binding domain and an Fc region, and optionally a linker. In some embodiments, the polynucleotide encodes an FcRn/antigen-binding molecule comprising one or more antigen-binding domains and an Fc region. In some embodiments, the polynucleotide encodes one or more of an antigen-binding domain, an Fc domain, and a linker. In some embodiments, the polynucleotide encodes an antigen-binding domain and an Fc domain, and optionally a linker. In some embodiments, the polynucleotide encodes an FcRn/antigen-binding molecule comprising one or more antigen-binding domains and one or more Fc domains. In some embodiments, the polynucleotide encodes one or more heavy chains of the disclosure.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecules having less than about 15%, 10%, 5%, 2%, 1%, 0.5%, or 0.1% (in particular, less than about 10%) of other material, e.g., cellular material, culture medium, other nucleic acid molecules, chemical precursors and/or other chemicals. In an embodiment, a nucleic acid molecule(s) encoding a polypeptide described herein is isolated or purified.

In an aspect, provided herein are polynucleotides comprising a nucleotide sequence encoding an FcRn binding molecule or FcRn/antigen-binding molecule described herein. In another aspect, provided herein are polynucleotides comprising a nucleotide sequence encoding an antigen binding domain described herein. In another aspect, provided herein are polynucleotides comprising a nucleotide sequence encoding an FcRn/antigen-binding molecule described herein. In another aspect, provided herein are polynucleotides comprising a nucleotide sequence encoding an FcRn/HSA binding molecule described herein.

The polynucleotides can comprise nucleotide sequences encoding an sdAb (e.g., a VHH fragment), a Fab fragment, an scFv, a VH, or a VL comprising FRs and CDRs of antigen-binding domains described herein. The polynucleotides can also comprise nucleotide sequences encoding an antibody mimetic as described herein. In some embodiments, the polynucleotides can comprise nucleotide sequences encoding a VHH fragment comprising FR and CDRs of antigen-binding domains described herein. In some embodiments, the polynucleotides can comprise nucleotide sequences encoding a light chain comprising VL FRs and CDRs of antigen binding domains described herein or nucleotide sequences encoding a heavy chain comprising VH FRs and CDRs of antigen binding domains described herein and/or an Fc domain as described herein. In an embodiment, a polynucleotide encodes a VH, VL, heavy chain, and/or light chain of an antigen binding domain described herein. In an embodiment, a polynucleotide encodes the first VH and the first VL of an antigen binding domain described herein. In an embodiment, a polynucleotide encodes the second VH and the second VL of an antigen-binding domain described herein. In an embodiment, a polynucleotide encodes the first heavy chain and the first light chain of an antigen-binding domain described herein. In an embodiment, a polynucleotide encodes the second heavy chain and the second light chain of an antigen-binding domain described herein. In an embodiment, a polynucleotide encodes the VH and/or the VL, or the heavy chain and/or the light chain, of an antigen-binding domain described herein.

In some embodiments, the polynucleotides can comprise nucleotide sequences encoding a first heavy chain described herein. In some embodiments, the first heavy chain comprises an Fc domain and an antigen binding domain joined by a linker. In some embodiments, polynucleotides can comprise nucleotide sequences encoding a second heavy chain described herein. In some embodiments, the second heavy chain comprises an Fc domain and an antigen binding domain joined by a linker. In some embodiments, the first and second heavy chains are the same. In some embodiments, the first and second heavy chains are different.

In some embodiments, the first and second heavy chains have the same Fc domain. In some embodiments, the first and second heavy chains have different Fc domains. In some embodiments, the first and second heavy chains both comprise an antigen binding domain. In some embodiments, the antigen binding domains on the first and second heavy chains are the same. In some embodiments, the antigen binding domains on the first and second heavy chains are different. In some embodiments, the second heavy chain comprises an Fc domain but does not comprise an antigen binding domain, while the first heavy chain comprises an Fc domain and an antigen binding domain. In some embodiments, the second heavy chain comprises an Fc domain but does not comprise an antigen binding domain or a linker, while the first heavy chain comprises an Fc domain and an antigen binding domain. In some embodiments, the second heavy chain comprises an Fc domain but does not comprise an antigen binding domain or a linker, while the first heavy chain comprises an Fc domain and an antigen binding domain and a linker.

In some embodiments, the polynucleotides comprise a nucleotide sequence that encodes an Fc domain comprising an amino acid sequence at least 70%, 75%, 80%, 85%, 90%, 95%, 96%, 97%, 98%, or 99% identical to the amino acid sequence of any one of SEQ ID NOs: 1-9. In some embodiments, the polynucleotides consist of a nucleotide sequence that encodes an Fc domain comprising an amino acid sequence at least 70%, 75%, 80%, 85%, 90%, 95%, 96%, 97%, 98%, or 99% identical to the amino acid sequence of any one of SEQ ID NOs: 1-9.

In some embodiments, the polynucleotides comprise a nucleotide sequence that encodes an Fc domain comprising the amino acid sequence of any one of SEQ ID NOs: 1-9. In some embodiments, the polynucleotides comprise a nucleotide sequence that encodes an Fc domain consisting of the amino acid sequence of any one of SEQ ID NOs: 1-9.

In some embodiments, the polynucleotides comprise nucleotide sequences that encode two or more Fc domains. In some embodiments, the polynucleotides comprise nucleotide sequences that encode two Fc domains. In some embodiments, the polynucleotides comprise a first nucleotide sequence that encodes a first Fc domain and a second nucleotide sequence that encodes a second Fc domain. In some embodiments, the first nucleotide sequence and the second nucleotide sequence are comprised in distinct nucleic acid molecules. In some embodiments, the first nucleotide sequence and the second nucleotide sequence are comprised in the same nucleic acid molecule.

In some embodiments, the first and second nucleotide sequence encode the same Fc domain. In some embodiments, both the first and second nucleotide sequence encode an Fc domain comprising an amino acid sequence at least 70%, 75%, 80%, 85%, 90%, 95%, 96%, 97%, 98%, or 99% identical to the amino acid sequence of any one of SEQ ID NOs: 1-3. In some embodiments, both the first and second nucleotide sequence encode an Fc domain consisting of an amino acid sequence at least 70%, 75%, 80%, 85%, 90%, 95%, 96%, 97%, 98%, or 99% identical to the amino acid sequence of any one of SEQ ID NOs: 1-3. In some embodiments, both the first and second nucleotide sequence encode an Fc domain comprising the amino acid sequence of any one of SEQ ID NOs: 1-3. In some embodiments, both the first and second nucleotide sequence encode an Fc domain consisting of the amino acid sequence of any one of SEQ ID NOs: 1-3.

In some embodiments, the first and second nucleotide sequence encode different Fc domains. In some embodiments, the first nucleotide sequence encodes an Fc domain comprising an amino acid sequence at least 70%, 75%, 80%, 85%, 90%, 95%, 96%, 97%, 98%, or 99% identical to the amino acid sequence of any one of SEQ ID NOs: 4-6 and the second nucleotide sequence encodes an Fc domain comprising an amino acid sequence at least 70%, 75%, 80%, 85%, 90%, 95%, 96%, 97%, 98%, or 99% identical to the amino acid sequence of any one of SEQ ID NOs: 7-9. In some embodiments, the first nucleotide sequence encodes an Fc domain consisting of an amino acid sequence at least 70%, 75%, 80%, 85%, 90%, 95%, 96%, 97%, 98%, or 99% identical to the amino acid sequence of any one of SEQ ID NOs: 4-6 and the second nucleotide sequence encodes an Fc domain consisting of an amino acid sequence at least 70%, 75%, 80%, 85%, 90%, 95%, 96%, 97%, 98%, or 99% identical to the amino acid sequence of any one of SEQ ID NOs: 7-9. In some embodiments, the first nucleotide sequence encodes an Fc domain comprising the amino acid sequence of any one of SEQ ID NOs: 4-6 and the second nucleotide sequence encodes an Fc domain comprising the amino acid sequence of any one of SEQ ID NOs: 7-9. In some embodiments, the first nucleotide sequence encodes an Fc domain consisting of the amino acid sequence of any one of SEQ ID NOs: 4-6 and the second nucleotide sequence encodes an Fc domain consisting of the amino acid sequence of any one of SEQ ID NOs: 7-9. In some embodiments, when the first nucleotide sequence encodes the amino acid sequence of SEQ ID NO: 4 or a variant thereof, the second nucleotide sequence encodes SEQ ID NO: 7 or a variant thereof. In some embodiments, when the first nucleotide sequence encodes the amino acid sequence of SEQ ID NO: 5 or a variant thereof, the second nucleotide sequence encodes SEQ ID NO: 8 or a variant thereof. In some embodiments, when the first nucleotide sequence encodes the amino acid sequence of SEQ ID NO: 6 or a variant thereof, the second nucleotide sequence encodes SEQ ID NO: 9 or a variant thereof.

In some embodiments, the first and second nucleotide sequence also encode an antigen binding domain. In some embodiments, the first and second nucleotide sequence encode the same antigen binding domain. In some embodiments, the first and second nucleotide sequence encode different antigen binding domains. In some embodiments, the first nucleotide sequence encodes an Fc domain and an antigen binding domain and the second nucleotide sequence encodes an Fc domain but no antigen binding domain. The antigen binding domains encoded by the first and/or second nucleotide sequences can be any described herein.

In some embodiments, the first and second nucleotide sequence also encode a peptide linker. In some embodiments, the first and second nucleotide sequence encode the same peptide linker. In some embodiments, the first and second nucleotide sequence encode different peptide linkers. In some embodiments, the first nucleotide sequence encodes an Fc domain, a peptide linker, and an antigen binding domain and the second nucleotide sequence encodes an Fc domain but no peptide linker or antigen binding domain. In some embodiments, the first nucleotide sequence encodes an antigen binding domain, a peptide linker, and an Fc domain and the second nucleotide sequence encodes an Fc domain but no peptide linker or antigen binding domain. The peptide linkers encoded by the first and/or second nucleotide sequences can be any described herein. In some embodiments, the linker comprises the amino acid sequence of SEQ ID NO: 136, 181, or 182.

In some embodiments, the polynucleotide comprises a nucleotide sequence that encodes a protein comprising or consisting of an amino acid sequence at least 70%, 75%, 80%, 85%, 90%, 95%, 96%, 97%, 98%, or 99% identical to the amino acid sequence of any one of SEQ ID NOs: 137-176 and 180.

In some embodiments, the polynucleotide comprises a nucleotide sequence that encodes a protein comprising or consisting of the amino acid sequence of any one of SEQ ID NOs: 137-176 and 180.

In some embodiments, the first nucleotide sequence encodes a protein comprising or consisting of an amino acid sequence at least 70%, 75%, 80%, 85%, 90%, 95%, 96%, 97%, 98%, or 99% identical to the amino acid sequence of any one of SEQ ID NOs: 137-176 and 180 and the second nucleotide sequence encodes an Fc domain, but does not encode an antigen binding domain. Optionally, the second nucleotide sequence encodes a protein comprising an amino acid sequence at least 70%, 75%, 80%, 85%, 90%, 95%, 96%, 97%, 98%, or 99% identical to the amino acid sequence of SEQ ID NO: 8.

In some embodiments, the first nucleotide sequence encodes a protein comprising the amino acid sequence of any one of SEQ ID NOs: 137-176 and 180 and the second nucleotide sequence encodes an Fc domain, but does not encode an antigen binding domain. Optionally, the second nucleotide sequence encodes a protein comprising the amino acid sequence of SEQ ID NO: 8. In some embodiments, the first nucleotide sequence comprises a nucleotide sequence that encodes a protein consisting of the amino acid sequence of any one of SEQ ID NOs: 137-176 and 180 and the second nucleotide sequence encodes an Fc domain, but does not encode an antigen binding domain. Optionally, the second nucleotide sequence encodes a protein consisting of the amino acid sequence of SEQ ID NO: 8.

Also provided herein are polynucleotides encoding a polypeptide as provided above that are optimized, e.g., by codon/RNA optimization, replacement with heterologous signal sequences, and elimination of mRNA instability elements. Methods to generate optimized nucleic acids for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In an embodiment, it can be desirable to alter one or more codons to encode a conservative mutation, e.g., a similar amino acid with similar chemical structure and properties and/or function as the original amino acid.

The polynucleotides can be obtained, and the nucleotide sequence of the polynucleotides determined, by any method known in the art. Nucleotide sequences encoding proteins described herein, and modified versions of these antibodies can be determined using methods well known in the art, i.e., nucleotide codons known to encode particular amino acids are assembled in such a way to generate a nucleic acid that encodes the protein. Such a polynucleotide encoding the protein can be assembled from chemically synthesized oligonucleotides (e.g., as described in Kutmeier G et al., (1994) *BioTechniques* 17: 242-6, herein incorporated by reference in its entirety), which, briefly, involves the synthesis of overlapping oligonucleotides containing portions of the sequence encoding the antibody, annealing, and ligating of those oligonucleotides, and then amplification of the ligated oligonucleotides by PCR.

Alternatively, a polynucleotide encoding a protein described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the polypeptide of interest. Such PCR amplification methods can be used to obtain nucleic acids comprising the sequence encoding the polypeptide. The amplified nucleic acids can be cloned into vectors for expression in host cells and for further cloning.

If a clone containing a nucleic acid encoding a particular polypeptide is not available, but the sequence of the polypeptide is known, a nucleic acid encoding the polypeptide can be chemically synthesized or obtained from a suitable source (e.g., a cDNA library generated from, or nucleic acid, preferably poly A+ RNA, isolated from any tissue or cells expressing the polypeptide described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the polypeptide. Amplified nucleic acids generated by PCR can then be cloned into replicable cloning vectors using any method well known in the art.

DNA encoding proteins described herein can be readily isolated and sequenced using conventional procedures. Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce the proteins described herein.

Also provided are polynucleotides that hybridize under high stringency, intermediate or lower stringency hybridization conditions to polynucleotides that encode a protein described herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions is known to those of skill in the art and has been described, see, e.g., Ausubel F M et al., eds., (1989) *Current Protocols in Molecular Biology*, Vol. I, Green Publishing Associates, Inc. and John Wiley & Sons, Inc., New York at pages 6.3.1-6.3.6 and 2.10.3, which is herein incorporated by reference in its entirety.

In an aspect, provided herein are cells (e.g., host cells) expressing (e.g., recombinantly) a protein described herein, and related polynucleotides and expression vectors. Provided herein are vectors (e.g., expression vectors) comprising polynucleotides comprising nucleotide sequences encoding a protein described herein for recombinant expression in host cells, preferably in mammalian cells (e.g., CHO cells). Also provided herein are host cells comprising such vectors for recombinantly expressing proteins described herein. In an aspect, provided herein are methods for producing a protein described herein, comprising expressing the polypeptide from a host cell.

Recombinant expression of a protein described herein generally involves construction of an expression vector containing a polynucleotide that encodes the polypeptide. Once a polynucleotide encoding a polypeptide described herein has been obtained, the vector for the production of the polypeptide can be produced by recombinant DNA technology using techniques well known in the art. Thus, methods for preparing a protein by expressing a polynucleotide containing a polypeptide encoding nucleotide sequence are described herein. Methods which are well known to those skilled in the art can be used to construct expression vectors containing polypeptide coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding containing a polypeptide described herein, operably linked to a promoter. Such vectors can, for example, include a nucleotide sequence encoding a first heavy chain of the disclosure (see, e.g., International Publication Nos. WO 86/05807 and WO 89/01036; and U.S. Pat. No. 5,122,464, which are herein incorporated by reference in their entireties), and a second heavy chain of the disclosure can be cloned into such a vector for expression of the first heavy chain, the second heavy chain, or both the first and second heavy chains.

In an embodiment, a vector comprises a polynucleotide encoding an sdAb, Fab fragment, scFv, VHH fragment, VH, VL, heavy chain, and/or light chain of a polypeptide described herein. In another embodiment, a vector comprises a polynucleotide encoding the VH and the VL of a polypeptide described herein. In another embodiment, a vector comprises a polynucleotide encoding the heavy chain and the light chain of a polypeptide described herein.

An expression vector can be transferred to a cell (e.g., host cell) by conventional techniques and the resulting cells can then be cultured by conventional techniques to produce a polypeptide described herein or a fragment thereof. Thus, provided herein are host cells containing a polynucleotide encoding containing a polypeptide described herein or fragments thereof, or a heavy or light chain thereof, or fragment thereof, or a single chain antibody described herein, operably linked to a promoter for expression of such sequences in the host cell.

In an embodiment, a host cell comprises a polynucleotide comprising one of the first nucleotide sequences and one of the second nucleotide sequences described above. In another embodiment, a host cell comprises a first polynucleotide comprising one of the first nucleotide sequences described above, and a second polynucleotide comprising one of the first nucleotide sequences described above. In another embodiment, a host cell comprises a first vector comprising one of the first nucleotide sequences and one of the second nucleotide sequences described above. In another embodiment, a host cell comprises a first vector comprising one of the first nucleotide sequences and one of the second nucleotide sequences described above, and a second vector comprising a second polynucleotide comprising one of the first nucleotide sequences described above.

In some embodiments, an FcRn/antigen-binding molecule expressed by a first host cell is associated with an FcRn/antigen-binding molecule expressed by a second host cell to form a two-armed FcRn/antigen-binding molecule. In some embodiments, an FcRn/antigen-binding molecule expressed by a first host cell is associated with an FcRn binding molecule expressed by a second host cell to form a one-armed FcRn/antigen-binding molecule. In some embodiments, provided herein are populations of host cells comprising such first host cells and such second host cells.

In some embodiments, provided herein is a population of vectors comprising a first vector comprising a polynucleotide encoding an FcRn/antigen-binding molecule, and a second vector comprising a polynucleotide encoding an FcRn/antigen-binding molecule. In some embodiments, provided herein is a population of vectors comprising a first vector comprising a polynucleotide encoding an FcRn/antigen-binding molecule, and a second vector comprising a polynucleotide encoding an FcRn binding molecule. In some embodiments, provided herein is a population of vectors comprising a first vector comprising a polynucleotide encoding an FcRn/antigen-binding molecule and a polynucleotide encoding an FcRn/antigen-binding molecule. In some embodiments, provided herein is a population of vectors comprising a first vector comprising a polynucleotide encoding two FcRn/antigen-binding molecules.

A variety of host-expression vector systems can be utilized to express polypeptides described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express a polypeptide described herein in situ. These include but are not limited to microorganisms such as bacteria (e.g., *E. coli* and *B. subtilis*) transformed with, e.g., recombinant bacteriophage DNA, plasmid DNA, or cosmid DNA expression vectors containing FcRn/antigen-binding molecule coding sequences; yeast (e.g., *Saccharomyces* and *Pichia*) transformed with, e.g., recombinant yeast expression vectors containing FcRn/antigen binding molecule coding sequences; insect cell systems infected with, e.g., recombinant virus expression vectors (e.g., baculovirus) containing FcRn/antigen-binding molecule coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing FcRn/antigen-binding molecule coding sequences; or mammalian cell systems (e.g., COS (e.g., COS1 or COS), CHO, BHK, MDCK, HEK 293, NS0, PER.C6, VERO, CRL7030, HsS78Bst, HeLa, NIH 3T3, HEK-293T, HepG2, SP210, R1.1, B-W, L-M, BSC1, BSC40, YB/20, and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In an embodiment, cells for expressing FcRn/antigen-binding molecules described herein are Chinese hamster ovary (CHO) cells, for example CHO cells from the CHO GS System™ (Lonza). In an embodiment, the heavy chain and/or light chain produced by a CHO cell may have an N-terminal glutamine or glutamate residue replaced by pyroglutamate. In an embodiment, cells for expressing polypeptides described herein are human cells, e.g., human cell lines. In an embodiment, a mammalian expression vector is pOptiVEC™ or pcDNA3.3. In an embodiment, bacterial cells such as *Escherichia coli*, or eukaryotic cells (e.g., mammalian cells), are used for the expression of a recombinant polypeptide. For example, mammalian cells such as CHO cells, in conjunction with a vector such as the major intermediate early gene promoter element from human cytomegalovirus, are an effective expression system for antibodies (Foecking M K & Hofstetter H (1986) *Gene* 45: 101-5; and Cockett M I et al., (1990) *Biotechnology* 8(7): 662-7, each of which is herein incorporated by reference in its entirety). In an embodiment, polypeptides described herein are produced by CHO cells or NS0 cells. In an embodiment, the expression of nucleotide sequences encoding polypeptides described herein which comprise two, three, or four binding sites for human FcRn is regulated by a constitutive promoter, inducible promoter, or tissue specific promoter.

In bacterial systems, a number of expression vectors can be advantageously selected depending upon the use intended for the molecule being expressed. For example, when a large quantity of such a polypeptide is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) *EMBO J* 2: 1791-1794), in which the coding sequence can be ligated individually into the vector in frame with the lac Z coding region so that a fusion protein is produced; pIN vectors (Inouye S & Inouye M (1985) *Nuc Acids Res* 13: 3101-3109; Van Heeke G & Schuster S M (1989) *J Biol Chem* 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (see, e.g., Logan J & Shenk T (1984) *PNAS* 81(12): 3655-9, which is herein incorporated by reference in its entirety). Specific initiation signals can also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) *Methods Enzymol.* 153: 516-544, which is herein incorporated by reference in its entirety).

In addition, a host cell strain can be chosen which modulates the expression of the inserted sequences or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, MDCK, HEK 293, NIH 3T3, W138, BT483, Hs578T, HTB2, BT2O, and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10, and HsS78Bst cells. In an embodiment, proteins described herein are produced in mammalian cells, such as CHO cells.

In an embodiment, a polypeptide described herein comprises a portion of an antibody with reduced fucose content or no fucose content. Such proteins can be produced using techniques known to one skilled in the art. For example, the proteins can be expressed in cells deficient in or lacking the ability to fucosylate. In an example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express a protein described herein can be engineered. In an embodiment, a cell provided herein stably expresses an antigen-binding domain, an FcRn/antigen-binding molecule, or an FcRn binding molecule which associate to form a one-armed or two-armed polypeptide described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for one to two days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method can advantageously be used to engineer cell lines which express a polypeptide comprising two, three, or four binding sites for human FcRn described herein or a fragment thereof. Such engineered cell lines can be particularly useful in the screening and evaluation of compositions that interact directly or indirectly with the polypeptide.

A number of selection systems can be used, including but not limited to the herpes simplex virus thymidine kinase (Wigler M et al., (1977) *Cell* 11(1): 223-32), hypoxanthineguanine phosphoribosyltransferase (Szybalska E H & Szybalski W (1962) *PNAS* 48(12): 2026-2034) and adenine phosphoribosyltransferase (Lowy I et al., (1980) *Cell* 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) *PNAS* 77(6): 3567-70; O'Hare K et al., (1981) *PNAS* 78: 1527-31); gpt, which confers resistance to mycophenolic acid (Mulligan R C & Berg P (1981) *PNAS* 78(4): 2072-6); neo, which confers resistance to the aminoglycoside G-418 (Wu G Y & Wu C H (1991) *Biotherapy* 3: 87-95; Tolstoshev P (1993) *Ann Rev Pharmacol Toxicol* 32: 573-596; Mulligan R C (1993) *Science* 260: 926-932; and Morgan R A & Anderson W F (1993) *Ann Rev Biochem* 62: 191-217; Nabel G J & Felgner P L (1993) *Trends Biotechnol* 11(5): 211-5); and hygro, which confers resistance to hygromycin (Santerre R F et al., (1984) *Gene* 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), *Current Protocols in Molecular Biology*, John Wiley & Sons, NY (1993); Kriegler M, *Gene Transfer and Expression, A Laboratory Manual*, Stockton Press, NY (1990); and in Chapters 12 and 13, Dracopoli N C et al., (eds.), *Current Protocols in Human Genetics*, John Wiley & Sons, NY (1994); Colbère-Garapin F et al., (1981) *J Mol Biol* 150: 1-14, all of which are herein incorporated by reference in their entireties.

The expression levels of a polypeptide can be increased by vector amplification (for a review, see, Bebbington C R & Hentschel C C G, The use of vectors based on gene amplification for the expression of cloned genes in mammalian cells in DNA cloning, p. 163-188. In DNA Cloning, Vol III, A Practical Approach. D. M. Glover (Ed.) (Academic Press, New York, 1987), which is herein incorporated by reference in its entirety). When a marker in the vector system is amplifiable, increase in the level of inhibitor present in culture of host cell will increase the number of copies of the marker gene. Since the amplified region is associated with the gene of interest, production of the polypeptide will also increase (Crouse G F et al., (1983) *Mol Cell Biol* 3: 257-66, which is herein incorporated by reference in its entirety).

The host cell can be co-transfected with two or more expression vectors described herein. The two vectors can contain identical selectable markers which enable equal expression of polypeptides, such as a first heavy chain and a second heavy chain polypeptide. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both polypeptides. The coding sequences can comprise cDNA or genomic DNA. The expression vector can be monocistronic or multicistronic. A multicistronic nucleic acid construct can encode 2, 3, 4, 5, 6, 7, 8, 9, 10, or more genes/nucleotide sequences, or in the range of 2-5, 5-10, or 10-20 genes/nucleotide sequences. For example, a bicistronic nucleic acid construct can comprise, in the following order, a promoter, a first gene and a second gene. In such an expression vector, the transcription of both genes can be driven by the promoter, whereas the translation of the mRNA from the first gene can be by a cap-dependent scanning mechanism, and the translation of the mRNA from the second gene can be by a cap-independent mechanism, e.g., by an IRES.

Once a polypeptide described herein has been produced by recombinant expression, it can be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins. Further, the polypeptides described herein can be fused to heterologous polypeptide sequences described herein or otherwise known in the art to facilitate purification.

In an embodiment, a polypeptide described herein is isolated or purified. In an embodiment, an isolated polypeptide is one that is substantially free of other polypeptides with different antigenic specificities than the isolated polypeptide. For example, in certain embodiments, a preparation of a protein described herein is substantially free of cellular material and/or chemical precursors. The language "substantially free of cellular material" includes preparations of a polypeptide in which the polypeptide is separated from cellular components of the cells from which it is isolated or recombinantly produced. Thus, a polypeptide that is substantially free of cellular material includes preparations of polypeptide having less than about 30%, 20%, 10%, 5%, 2%, 1%, 0.5%, or 0.1% (by dry weight) of heterologous protein (also referred to herein as a "contaminating protein") and/or variants of a polypeptide, for example, different post-translational modified forms of a polypeptide or other different versions of a polypeptide (e.g., polypeptide fragments). When the polypeptide is recombinantly produced, it is also generally substantially free of culture medium, i.e., culture medium represents less than about 20%, 10%, 2%, 1%, 0.5%, or 0.1% of the volume of the protein preparation. When the polypeptide is produced by chemical synthesis, it is generally substantially free of chemical precursors or other chemicals, i.e., it is separated from chemical precursors or other chemicals, which are involved in the synthesis of the protein. Accordingly, such preparations of the protein have less than about 30%, 20%, 10%, or 5% (by dry weight) of chemical precursors or compounds other than the molecule of interest. In an embodiment, polypeptides described herein are isolated or purified.

A polypeptide described herein can be produced by any method known in the art for the synthesis of proteins, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) *Molecular Cloning: A Laboratory Manual*, Cold Spring Harbor Laboratory Press; Sambrook J et al., (1989), *Molecular Cloning: A Laboratory Manual*, Second Edition, Cold Spring Harbor Laboratory Press; Sambrook J et al., (2001) *Molecular Cloning: A Laboratory Manual*, Cold Spring Harbor Laboratory Press, Cold Spring Harbor, NY; Ausubel F M et al., *Current Protocols in Molecular Biology*, John Wiley & Sons (1987 and annual updates); *Current Protocols in Immunology*, John Wiley & Sons (1987 and annual updates); Gait (ed.) (1984) *Oligonucleotide Synthesis: A Practical Approach*, IRL Press; Eckstein (ed.) (1991) *Oligonucleotides and Analogues: A Practical Approach*, IRL Press; Birren B et al., (eds.) (1999) *Genome Analysis: A Laboratory Manual*, Cold Spring Harbor Laboratory Press, all of which are herein incorporated by reference in their entireties.

In an embodiment, a polypeptide described herein is prepared, expressed, created, or isolated by any means that involves creation, e.g., via synthesis, genetic engineering of DNA sequences. In an embodiment, such a polypeptide comprises sequences (e.g., DNA sequences or amino acid sequences) that do not naturally exist within the antibody germline repertoire of an animal or mammal (e.g., human) in vivo.

Pharmaceutical Compositions

In an aspect, the instant disclosure provides pharmaceutical compositions comprising an FcRn/antigen-binding molecule as disclosed herein for use in methods of treating an antibody-mediated disorder (e.g., an autoantibody-mediated disorder). In certain embodiments, these compositions comprise an FcRn/antigen-binding molecule comprising an FcRn binding molecule and an antigen-binding domain. In some embodiments, the FcRn binding molecule is an FcRn antagonist. In some embodiments, the FcRn antagonist comprises or consists of a variant Fc region, or FcRn binding fragment thereof that inhibits the binding of an Fc region of immunoglobulin to FcRn. In general, these FcRn antagonists inhibit the binding of Fc-containing agents (e.g., antibodies and immunoadhesins) to FcRn in vivo, which results in an increased rate of degradation of the Fc-containing agents and, concomitantly, a reduced serum level of these agents.

In some embodiments, FcRn/antigen-binding molecules of the current disclosure have a molecular weight ranging from about 50 kDa, which is about one-third the molecular weight of full-length IgG (MW ca. 150 kDa), to about 140 kDa. In some embodiments, the FcRn/antigen-binding molecule has a molecular weight from about 60 kDa to about 104 kDa. In some embodiments, the FcRn/antigen-binding molecule has a molecular weight from 60 kDa to 104 kDa. In some embodiments, the FcRn/antigen-binding molecule has a molecular weight of about 60 kDa. In some embodiments, the FcRn/antigen-binding molecule has a molecular weight of about 104 kDa. In some embodiments, the FcRn/antigen-binding molecule has a molecular weight of 60 kDa. In some embodiments, the FcRn/antigen-binding molecule has a molecular weight of 104 kDa.

In some embodiments, FcRn/antigen-binding molecules of the current disclosure have a predicted molecular weight ranging from about 50 kDa, which is about one-third the molecular weight of full-length IgG (MW ca. 150 kDa), to about 140 kDa. In some embodiments, the FcRn/antigen-binding molecule has a predicted molecular weight from about 60 kDa to about 104 kDa. In some embodiments, the FcRn/antigen-binding molecule has a predicted molecular weight from 60 kDa to 104 kDa. In some embodiments, the FcRn/antigen-binding molecule has a predicted molecular weight of about 60 kDa. In some embodiments, the FcRn/antigen-binding molecule has a predicted molecular weight of about 104 kDa. In some embodiments, the FcRn/antigen-binding molecule has a predicted molecular weight of 60 kDa. In some embodiments, the FcRn/antigen-binding molecule has a predicted molecular weight of 104 kDa.

The formulations disclosed herein include bulk drug compositions useful in the manufacture of pharmaceutical compositions (e.g., compositions that are suitable for administration to a subject or patient) which can be used in the preparation of unit dosage forms. In an embodiment, a composition of the invention is a pharmaceutical composition. Such compositions comprise a prophylactically or therapeutically effective amount of one or more prophylactic or therapeutic agents (e.g., an FcRn/antigen-binding molecule) of the invention (or other prophylactic or therapeutic agent), and a pharmaceutically acceptable carrier.

In some embodiments the pharmaceutical compositions are formulated for administration to a subject via any suitable route of administration including, but not limited to, intramuscular, intravenous, intradermal, intraperitoneal, subcutaneous, epidural, nasal, oral, rectal, topical, inhalation, buccal (e.g., sublingual), and transdermal administration. In an embodiment, the pharmaceutical compositions are formulated to be suitable for intravenous administration to a subject. In an embodiment, the pharmaceutical compositions are formulated to be suitable for subcutaneous administration to a subject.

Methods of Treatment

The disclosure also provides methods for treating an antibody-mediated disorder (e.g., an autoantibody-mediated disorder) in a subject comprising administering to the subject a therapeutically effective amount of an FcRn/antigen-binding molecule according to the disclosure or a pharmaceutical composition comprising the same.

In some embodiments, the antibody-mediated disorder is an autoimmune disease. In some embodiments, the autoimmune disease is selected from the group consisting of allogenic islet graft rejection, alopecia areata, ankylosing spondylitis, antiphospholipid syndrome, autoimmune Addison's disease, Alzheimer's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, immune thrombocytopenia (ITP or idiopathic thrombocytopenic purpura, idiopathic thrombocytopenia purpura, immune mediated thrombocytopenia, or primary immune thrombocytopenia), autoimmune urticaria, Behcet's disease, bullous pemphigoid (BP), cardiomyopathy, Castleman disease, celiac sprue-dermatitis, chronic fatigue immune disfunction syndrome, chronic inflammatory demyelinating polyneuropathy (CIDP), Churg-Strauss syndrome, cicatricial pemphigoid, CREST syndrome, cold agglutinin disease, Crohn's disease, dilated cardiomyopathy, discoid lupus, epidermolysis bullosa acquisita, essential mixed cryoglobulinemia, factor VIII deficiency, fibromyalgia-fibromyositis, glomerulonephritis, Graves' disease, Guillain-Barre syndrome, Goodpasture's syndrome, graft-versus-host disease (GVHD), Hashimoto's thyroiditis, hemophilia A, idiopathic inflammatory myopathies (IIMs), idiopathic membranous neuropathy, idiopathic pulmonary fibrosis, IgA neuropathy, IgM polyneuropathies, immune-mediated necrotizing myopathy (IMNM), juvenile arthritis, Kawasaki disease, lichen planus, lichen sclerosus, lupus erythematosus, lupus nephritis, Meniere's disease, mixed connective tissue disease, mucous membrane pemphigoid, multiple sclerosis, Type 1 diabetes mellitus, multifocal motor neuropathy (MMN), myasthenia gravis (MG), generalized myasthenia gravis (gMG), myositis, paraneoplastic bullous pemphigoid, pemphigoid gestationis, pemphigus vulgaris (PV), pemphigus foliaceus (PF), pernicious anemia, polyarteritis nodosa, polychrondritis, polyglandular syndromes, polymyalgia rheumatica, polymyositis, dermatomyositis (DM), necrotizing autoimmune myopathy (NAM), AntiSynthetase Syndrome (ASyS), primary agammaglobulinemia, primary biliary cirrhosis, psoriasis, psoriatic arthritis, relapsing polychondritis, Raynaud's phenomenon, Reiter's syndrome, rheumatoid arthritis, sarcoidosis, scleroderma, Sjögren's syndrome, solid organ transplant rejection, stiff-person syndrome, systemic lupus erythematosus, Takayasu's arteritis, toxic epidermal necrolysis (TEN), Stevens-Johnson syndrome (SJS), temporal arteritis/giant cell arteritis, thrombotic thrombocytopenia purpura, ulcerative colitis, uveitis, dermatitis herpetiformis vasculitis, anti-neutrophil cytoplasmic antibody-associated vasculitides, vitiligo, and Wegener's granulomatosis.

In an embodiment, the FcRn/antigen-binding molecule antagonizes FcRn binding to an antibody Fc region. In an embodiment, the FcRn/antigen-binding molecule does not antagonize FcRn binding to albumin.

The disclosure provides methods of reducing serum IgG in a subject comprising administering to the subject a therapeutically effective amount of an FcRn/antigen-binding molecule according to the disclosure or a pharmaceutical composition comprising the same. In an embodiment, at least one of the IgG subtypes is reduced in a subject following administration of the FcRn/antigen-binding molecule. In some embodiments, IgG1, IgG2, IgG3, IgG4, or any combination thereof is reduced. In some embodiments, the administration of the FcRn/antigen-binding molecule is a single administration (e.g., a single therapeutic administration) of the FcRn/antigen-binding molecule. In an embodiment, the level of serum IgG is decreased in the subject following administration of the FcRn/antigen-binding molecule compared to a baseline level of serum IgG.

In an embodiment, a total serum IgG reduction of at least about 40% compared to baseline serum IgG level is obtained. In an embodiment, a total serum IgG reduction of at least about 45% compared to baseline serum IgG level is obtained. In an embodiment, a total serum IgG reduction of at least about 50% compared to baseline serum IgG level is obtained. In an embodiment, a total serum IgG reduction of at least about 55% compared to baseline serum IgG level is obtained. In an embodiment, a total serum IgG reduction of at least about 60% compared to baseline serum IgG level is obtained. In an embodiment, a total serum IgG reduction of at least about 65%, about 70%, about 75%, or about 80% compared to baseline serum IgG level is obtained. In an embodiment, a total serum IgG reduction of at least about 65% compared to baseline serum IgG level is obtained. In an embodiment, a total serum IgG reduction of at least about 70% compared to baseline serum IgG level is obtained. In an embodiment, a total serum IgG reduction of at least about 75% compared to baseline serum IgG level is obtained. In an embodiment, a total serum IgG reduction of at least about 80% compared to baseline serum IgG level is obtained.

In an embodiment, the level of serum IgG is decreased in the subject following administration of the FcRn/antigen-binding molecule compared to a baseline level of serum IgG. In an embodiment, a total serum IgG reduction of about 40% compared to baseline serum IgG level is obtained. In an embodiment, a total serum IgG reduction of about 45% compared to baseline serum IgG level is obtained. In an embodiment, a total serum IgG reduction of at about 50% compared to baseline serum IgG level is obtained. In an embodiment, a total serum IgG reduction of about 55% compared to baseline serum IgG level is obtained. In an embodiment, a total serum IgG reduction of about 60% compared to baseline serum IgG level is obtained. In an embodiment, a total serum IgG reduction of about 65%, about 70%, about 75%, or about 80% compared to baseline serum IgG level is obtained. In an embodiment, a total serum IgG reduction of about 65% compared to baseline serum IgG level is obtained. In an embodiment, a total serum IgG reduction of about 70% compared to baseline serum IgG level is obtained. In an embodiment, a total serum IgG reduction of about 75% compared to baseline serum IgG level is obtained. In an embodiment, a total serum IgG reduction of about 80% compared to baseline serum IgG level is obtained.

In an embodiment, the level of FcRn is not decreased in the subject following administration of the FcRn/antigen-binding molecule compared to a baseline level of FcRn. In an embodiment, an FcRn reduction of less than about 1%, 2%, 3%, 4%, or 5% compared to baseline FcRn level is observed. In an embodiment, an FcRn reduction of less than about 10% compared to baseline FcRn level is observed.

In an embodiment, the level of albumin is not decreased in the subject following administration of the FcRn/antigen-binding molecule compared to a baseline level of albumin. In an embodiment, an albumin reduction of less than about 1%, 2%, 3%, 4%, or 5% compared to baseline albumin level is observed. In an embodiment, an albumin reduction of less than about 10% compared to baseline albumin level is observed.

In an embodiment, the total IgG, FcRn/antigen-binding molecule, FcRn, or albumin in a serum sample of the patient is analyzed using a bioanalytical method. In an embodiment, the total IgG, FcRn/antigen-binding molecule, FcRn, or albumin in a serum sample of the patient is analyzed using ELISA or automated diagnostic analyzer (IVD). In an embodiment, the total IgG, FcRn/antigen-binding molecule, FcRn, or albumin in a serum sample of the patient is analyzed using ELISA. In an embodiment, the total IgG, FcRn/antigen-binding molecule, FcRn, or albumin in a serum sample of the patient is analyzed using automated diagnostic analyzer (IVD). In an embodiment, the total FcRn in a blood sample of the patient is analyzed using a bioanalytical method, preferably flow cytometry, microscopy, or an immunoblot.

In some embodiments, the reduction of total serum IgG is measured by area under the percentage of reduction curve (AUEC). In some embodiments, the reduction of total serum IgG is measured by clearance of total serum IgG (CL).

In some embodiments, clearance of total serum IgG is increased in a subject following administration of the FcRn/antigen-binding molecule. In some embodiments, clearance of total serum IgG in a subject following a single therapeutic administration of the FcRn/antigen-binding molecule is comparable to the clearance of total serum IgG in a subject following a single therapeutic administration of efgartigimod. In some embodiments, clearance of total serum IgG in a subject following a single therapeutic administration of the FcRn/antigen-binding molecule is similar or the same as the clearance of total serum IgG in a subject following a single therapeutic administration of efgartigimod. In some embodiments, clearance of total serum IgG is increased in a subject following a single therapeutic administration of the FcRn/antigen-binding molecule compared to clearance of total serum IgG following a single therapeutic administration of efgartigimod. In some embodiments, clearance of total serum IgG is increased by at least 5%, at least 10%, at least 15%, at least 20%, at least 25%, at least 30%, at least 40%, at least 50%, at least 60%, at least 70%, at least 80%, at least 90%, at least 100%, at least 125%, at least 150%, or at least 200% in a subject following a single therapeutic administration of the FcRn/antigen-binding molecule compared to clearance of total serum IgG following a single therapeutic administration of efgartigimod.

In some embodiments, clearance of total serum IgG in a subject following a single administration of the FcRn/antigen-binding molecule is comparable to the clearance of total serum IgG in a subject following a single administration of an equivalent amount of efgartigimod. In some embodiments, clearance of total serum IgG in a subject following a single administration of the FcRn/antigen-binding molecule is similar or the same as the clearance of total serum IgG in a subject following a single administration of an equivalent amount of efgartigimod. In some embodiments, clearance of total serum IgG is increased in a subject following a single administration of the FcRn/antigen-binding molecule compared to clearance of total serum IgG following a single administration of an equivalent amount of efgartigimod. In some embodiments, clearance of total serum IgG is increased by at least 5%, at least 10%, at least 15%, at least 20%, at least 25%, at least 30%, at least 40%, at least 50%, at least 60%, at least 70%, at least 80%, at least 90%, at least 100%, at least 125%, at least 150%, or at least 200% in a subject following a single administration of the FcRn/antigen-binding molecule compared to clearance of total serum IgG following a single administration of an equivalent amount of efgartigimod.

In some embodiments, clearance of the FcRn/antigen-binding molecule is decreased in a subject following a single therapeutic administration of the FcRn/antigen-binding molecule compared to clearance of efgartigimod following a single therapeutic administration of efgartigimod. In some embodiments, clearance of the FcRn/antigen-binding molecule is decreased by at least 1-fold, at least 1.5-fold, at least 2-fold, at least 3-fold, at least 4-fold, at least 5-fold, at least 6-fold, at least 7-fold, at least 8-fold, at least 9-fold, at least 10-fold, at least 12-fold, at least 15-fold, or at least 20-fold in a subject following a single therapeutic administration of the FcRn/antigen-binding molecule compared to clearance of efgartigimod following a single therapeutic administration of efgartigimod.

In some embodiments, clearance of the FcRn/antigen-binding molecule is decreased in a subject following a single administration of the FcRn/antigen-binding molecule compared to clearance of efgartigimod following a single administration of an equivalent amount of efgartigimod. In some embodiments, clearance of the FcRn/antigen-binding molecule is decreased by at least 1-fold, at least 1.5-fold, at least 2-fold, at least 3-fold, at least 4-fold, at least 5-fold, at least 6-fold, at least 7-fold, at least 8-fold, at least 9-fold, at least 10-fold, at least 12-fold, at least 15-fold, or at least 20-fold in a subject following a single administration of the FcRn/antigen-binding molecule compared to clearance of efgartigimod following a single administration of an equivalent amount of efgartigimod.

In some embodiments, clearance of the FcRn/antigen-binding molecule is less than about 0.2, about 0.19, about 0.18, about 0.17, about 0.16, about 0.15, about 0.14, about 0.13, about 0.12, about 0.11, about 0.1, about 0.09, about 0.08, about 0.07, about 0.06 or about 0.05 l/h in a subject following a single administration of the FcRn/antigen-binding molecule. In some embodiments, clearance of the FcRn/antigen-binding molecule is less than 0.2, 0.19, 0.18, 0.17, 0.16, 0.15, 0.14, 0.13, 0.12, 0.11, 0.1, 0.09, 0.08, 0.07, 0.06 or 0.05 l/h in a subject following a single administration of the FcRn/antigen-binding molecule. In some embodiments, clearance of the FcRn/antigen-binding molecule is the range of about 0.05 to about 0.2 l/h following a single administration of the FcRn antagonist. In some embodiments, clearance of the FcRn/antigen-binding molecule is about 0.2, about 0.19, about 0.18, about 0.17, about 0.16, about 0.15, about 0.14, about 0.13, about 0.12, about 0.11, about 0.1, about 0.09, about 0.08, about 0.07, about 0.06 or about 0.05 l/h in a subject following a single administration of the FcRn/antigen-binding molecule. In some embodiments, clearance of the FcRn/antigen-binding molecule is in the range of 0.05 to 0.2 l/h following a single administration of the FcRn antagonist. In some embodiments, clearance of the FcRn/antigen-binding molecule is 0.2, 0.19, 0.18, 0.17, 0.16, 0.15, 0.14, 0.13, 0.12, 0.11, 0.1, 0.09, 0.08, 0.07, 0.06 or 0.05 l/h in a subject following a single administration of the FcRn/antigen-binding molecule.

In some embodiments, $t_{1/2,z}$ of the FcRn/antigen-binding molecule is increased in a subject following a single therapeutic administration of the FcRn/antigen-binding molecule compared to $t_{1/2,z}$ of efgartigimod following a single therapeutic administration of efgartigimod. In some embodiments, $t_{1/2,z}$ of the FcRn/antigen-binding molecule is increased by at least 0.5-fold, at least 1-fold, at least 1.5-fold, at least 2-fold, at least 3-fold, at least 4-fold, at least 5-fold, at least 6-fold, at least 7-fold, at least 8-fold, at least 9-fold, at least 10-fold, at least 12-fold, at least 15-fold, or at least 20-fold in a subject following a single therapeutic administration of the FcRn/antigen-binding molecule compared to $t_{1/2,z}$ of efgartigimod following a single therapeutic administration of efgartigimod.

In some embodiments, $t_{1/2,z}$ of the FcRn/antigen-binding molecule is increased in a subject following a single administration of the FcRn/antigen-binding molecule compared to $t_{1/2,z}$ of efgartigimod following a single administration of an equivalent amount of efgartigimod. In some embodiments, $t_{1/2,z}$ of the FcRn/antigen-binding molecule is increased by at least 0.5-fold, at least 1-fold, at least 1.5-fold, at least 2-fold, at least 3-fold, at least 4-fold, at least 5-fold, at least 6-fold, at least 7-fold, at least 8-fold, at least 9-fold, at least 10-fold, at least 12-fold, at least 15-fold, or at least 20-fold in a subject following a single administration of the FcRn/antigen-binding molecule compared to $t_{1/2,z}$ of efgartigimod following a single administration of an equivalent amount of efgartigimod.

In some embodiments, $t_{1/2,z}$ of the FcRn/antigen-binding molecule is greater than about 3 days, about 3.5 days, about 4 days, about 4.5 days, about 5 days, about 5.5 days, about 6 days, about 6.5 days, about 7 days, about 7.5 days, about 8 days, about 8.5 days, about 9 days, about 9.5 days, about 10 days, about 10.5 days, about 11 days, about 11.5 days, about 12 days, about 12.5 days, about 13 days, about 13.5 days, about 14 days, about 14.5 days, about 15 days, about 15.5 days, about 16 days, about 16.5 days, about 17 days, about 17.5 days, about 18 days, about 18.5 days, about 19 days, about 19.5 days, about 20 days, about 20.5 days, about 21 days, about 21.5 days, about 22 days, about 22.5 days, about 23 days, about 23.5 days, about 24 days, about 24.5 days, about 25 days, about 25.5 days, about 26 days, about 26.5 days, about 27 days, about 27.5 days, about 28 days, about 28.5 days, about 29 days, about 29.5 days, or about 30 days in a subject following a single administration of the FcRn/antigen-binding molecule.

In some embodiments, $t_{1/2,z}$ of the FcRn/antigen-binding molecule is greater than 3 days, 3.5 days, 4 days, 4.5 days, 5 days, 5.5 days, 6 days, 6.5 days, 7 days, 7.5 days, 8 days, 8.5 days, 9 days, 9.5 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days, 19.5 days, 20 days, 20.5 days, 21 days, 21.5 days, 22 days, 22.5 days, 23 days, 23.5 days, 24 days, 24.5 days, 25 days, 25.5 days, 26 days, 26.5 days, 27 days, 27.5 days, 28 days, 28.5 days, 29 days, 29.5 days, or 30 days in a subject following a single administration of the FcRn/antigen-binding molecule.

In some embodiments, $t_{1/2,z}$ of the FcRn/antigen-binding molecule is in the range of about 3 days to about 30 days. In some embodiments, $t_{1/2,z}$ of the FcRn/antigen-binding molecule is about 3 days, about 3.5 days, about 4 days, about 4.5 days, about 5 days, about 5.5 days, about 6 days, about 6.5 days, about 7 days, about 7.5 days, about 8 days, about 8.5 days, about 9 days, about 9.5 days, about 10 days, about 10.5 days, about 11 days, about 11.5 days, about 12 days, about 12.5 days, about 13 days, about 13.5 days, about 14 days, about 14.5 days, about 15 days, about 15.5 days, about 16 days, about 16.5 days, about 17 days, about 17.5 days, about 18 days, about 18.5 days, about 19 days, about 19.5 days, about 20 days, about 20.5 days, about 21 days, about 21.5 days, about 22 days, about 22.5 days, about 23 days, about 23.5 days, about 24 days, about 24.5 days, about 25 days, about 25.5 days, about 26 days, about 26.5 days, about 27 days, about 27.5 days, about 28 days, about 28.5 days, about 29 days, about 29.5 days, or about 30 days in a subject following a single administration of the FcRn/antigen-binding molecule.

In some embodiments, $t_{1/2,z}$ of the FcRn/antigen-binding molecule is in the range of 3 days to 30 days. In some embodiments, $t_{1/2,z}$ of the FcRn/antigen-binding molecule is 3 days, 3.5 days, 4 days, 4.5 days, 5 days, 5.5 days, 6 days, 6.5 days, 7 days, 7.5 days, 8 days, 8.5 days, 9 days, 9.5 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days, 19.5 days, 20 days, 20.5 days, 21 days, 21.5 days, 22 days, 22.5 days, 23 days, 23.5 days, 24 days, 24.5 days, 25 days, 25.5 days, 26 days, 26.5 days, 27 days, 27.5 days, 28 days, 28.5 days, 29 days, 29.5 days, or 30 days in a subject following a single administration of the FcRn/antigen-binding molecule.

In some embodiments, one-armed FcRn/antigen-binding molecules of the disclosure sweep antigens more efficiently than two-armed FcRn/antigen-binding molecules (such as, e.g., a full-length antibody). In some embodiments, a one-armed FcRn/antigen-binding molecule sweeps antigens more efficiently than a corresponding two-armed FcRn/antigen-binding molecule. Put another way, removal of one arm of a two-armed FcRn/antigen-binding molecule, in some embodiments, results in a molecule that sweeps antigen more efficiently than the two-armed FcRn/antigen-binding molecule.

As used herein, "sweep" refers to the ability of a molecule to remove antigen from serum. "Sweeping" may be performed by molecules (such as, e.g., antibodies) having both pH-sensitive antigen binding and at least a threshold level of binding to FcRn at neutral or physiological pH. For example, sweeping molecules may bind to an antigen via an antigen-binding domain and bind to FcRn via an Fc region, leading to cellular internalization of the antigen/sweeping antibody complex. The antigen may then be released from the complex in an acidic endosome and be degraded. In some embodiments, a sweeping molecule, no longer bound to the antigen, may then be released (e.g., by exocytosis) by the cell back into the serum.

In an embodiment, the FcRn/antigen-binding molecule is administered to the subject simultaneously or sequentially with an additional therapeutic agent. In an embodiment, the additional therapeutic agent is an anti-inflammatory agent. In an embodiment, the additional therapeutic agent is a corticosteroid. In an embodiment, the additional therapeutic agent is rituximab, daclizumab, basiliximab, muromonab-CD3, infliximab, adalimumab, omalizumab, efalizumab, natalizumab, tocilizumab, eculizumab, golimumab, canakinumab, ustekinumab, or belimumab. In an embodiment, the additional therapeutic agent is a leucocyte depleting agent.

In an embodiment, the additional therapeutic agent is a B-cell depleting agent. In an embodiment, the B-cell depleting agent is an antibody. In an embodiment, the B-cell depleting antibody is an antibody that specifically binds to CD10, CD19, CD20, CD21, CD22, CD23, CD24, CD37, CD53, CD70, CD72, CD74, CD75, CD77, CD79a, CD79b, CD80, CD81, CD82, CD83, CD84, CD85, or CD86.

In some embodiments, the FcRn/antigen-binding molecule is administered intravenously. In some embodiments, the FcRn/antigen-binding molecule is administered intravenously once weekly, once every two weeks, once every three weeks, once every four weeks, once monthly, or once every six weeks.

In some embodiments, the FcRn/antigen-binding molecule is administered subcutaneously. In some embodiments, the FcRn/antigen-binding molecule is administered subcutaneously once weekly, once every two weeks, once every three weeks, once every four weeks, once monthly, or once every six weeks.

EXAMPLES

The following examples are offered by way of illustration, and not by way of limitation.

Example 1: Pharmacokinetics/Pharmacodynamics of Anti-HSA-ABDEG in Cynomolgus Monkeys The MHC class I-related receptor, FcRn, plays a central role in regulating the serum levels of IgG (Ghetie et al., (1996) *Immunology Today* 18(12): 592-8) and albumin (Chaudhury et al., (2003) *Journal of Experimental Medicine* 197(3): 315-22) and is ubiquitously expressed e.g., in endothelial, epithelial, and hematopoietic such as monocytes, macrophages, dendritic cells, and B cells. The Fc portion of IgG binds with high affinity to FcRn at an acidic pH (<6.5) but not at a physiological pH (7.4) (Rodewald R., (1976) *Journal of Cell Biology* 71(2): 666-9). A mutated, human IgG1-derived antibody (MST-HN) binds with higher affinity and reduced pH dependence to FcRn and competes effectively with wild-type IgGs for FcRn-mediated transport resulting in a rapid decrease of IgG levels in mice (Vaccaro et al., (2005) *Nature Biotechnology* 23(10): 1283-8). In humans, such FcRn blockers (or "ABDEGs," for antibodies that enhance IgG degradation) may be desirable in multiple therapeutic situations, e.g., clearance of autoreactive antibodies in autoimmune diseases such as systemic lupus erythematosus, myasthenia gravis, and immune thrombocytopenic purpura (ITP) or other antibody-mediated diseases.

Efgartigimod is a human IgG1 Fc-fragment that utilizes the ABDEG Fc engineering technology. Its presumed in vivo mechanism of action is the constitutive blockage of FcRn-mediated IgG recycling leading to IgG degradation. The effectiveness of efgartigimod depends in large part on its pharmacokinetic properties. For this reason, it is desired to explore methods to further improve the half-life of the efgartigimod molecule which could allow the use of lower dose and/or less frequent administrations. An effective mean of improving the pharmacokinetic properties is by binding to long-lived plasma proteins. Albumin is the most abundant protein in plasma, has a half-life of 19 days in humans, and could represent an optimal carrier for therapeutic peptides/proteins.

Figure 1:
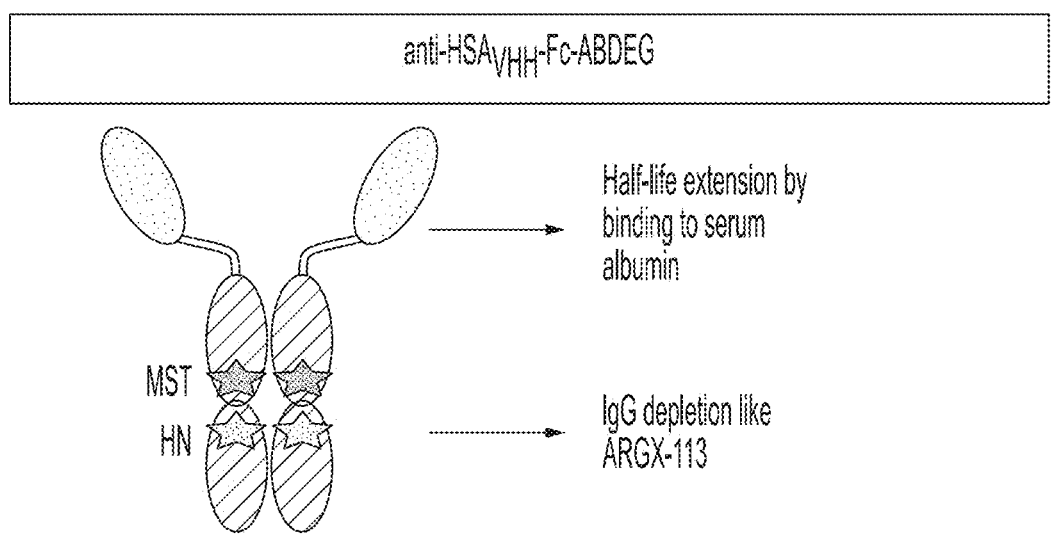
FIG. 1 is a schematic of a representative two-armed (TA) Fc-ABDEG molecule equipped with an anti-HSAvHH fused at the N-termini of both Fc domains.

It was opted to fuse an HSA-targeting VHH fragment, Alb23 (SEQ ID NO: 42), at the N-termini of both Fc domains of efgartigimod (TA-Alb23-Fc-ABDEG) in an effort to further extend the half-life of efgartigimod and retard its clearance (FIG. 1). Alb23 is described in WO 2012/175400, incorporated herein by reference in its entirety. The full-length sequence of TA-Alb23-Fc-ABDEG is:

(SEQ ID NO: 177)
EVQLLESGGGLVQPGGSLRLSCAASGFTFRSFGMSWVRQAPGKGPEWVS

SISGSGSDTLYADSVKGRFTISRDNSKNTLYLQMNSLRPEDTAVYYCTI

GGSLSRSSQGTLVTVSSDKTHTCPPCPAPELLGGPSVFLFPPKPKDTLY

ITREPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLD

SDGSFFLYSKLTVDKSRWQQGNVFSCSVMHEALKFHYTQKSLSLSPG.

The aim of the study was the assessment of the pharmacokinetic and pharmacodynamic properties of TA-Alb23-

Fc-ABDEG, after single intravenous administration of 5 mg/kg or 20 mg/kg to cynomolgus monkeys.

Besides the measurement of TA-Alb23-Fc-ABDEG in cynomolgus serum, the determination of anti-drug antibodies (ADA) against TA-Alb23-Fc-ABDEG was performed to investigate any impact on drug exposure. The fusion of an anti-HSA VHH fragment to the N-terminus of both Fc domains of Fc-ABDEG molecule was expected to extend the half-life and efficacy (altered PD profile (endogenous IgG reduction)) of this Fc-ABDEG (TA-Alb23-Fc-ABDEG) compared to efgartigimod.

Male cynomolgus monkeys (*Macaca fascicularis*) were divided in 2 test groups, group 1 and group 2, consisting of 3 monkeys each with an approximately equal mean body weight (pseudo-random body weight stratification procedure) and naïve history. Both group 1 and group 2 were treated with a single intravenous bolus injection (vena cephalica of the right arm) of TA-Alb23-Fc-ABDEG, respectively 20 and 5 mg/kg b.w. The selection of dose levels for this study was based earlier studies using efgartigimod.

Blood samples were collected for PK/PD/immunogenicity measurements at: test day 1 (TD1) (pre-dose), TD1 (prior to dosing), TD1 (5 min), TD2 (24 hrs post dosing), TD3, TD4, TD6, TD8, TD11, TD15, TD18, TD22, TD29, TD36, and TD43. The whole blood was collected in serum separator tubes and the blood samples were allowed to clot at room temperature for approx. 30 minutes before centrifugation. Immediately after centrifugation the serum samples were aliquoted in 3×150 µL aliquots and stored at −70° C. or colder until shipment for analysis.

Pharmacokinetics were assessed by measuring TA-Alb23-Fc-ABDEG serum concentrations using a sandwich ELISA method. Briefly, mouse anti-ABDEG antibody was coated on a 96-well immunoplate and non-specific binding sites were blocked. Next, 100% serum samples were diluted to the concentration range of quantitation (or at least the minimum required dilution (MRD)) and added on the immunoplate together with fresh calibration standards and a set of quality control (QC) samples. At the end, TA-Alb23-Fc-ABDEG levels were visualized by the subsequent additions of an HRP-conjugated goat anti-human Fc F(ab')2 and the chromogenic substrate tetramethylbenzidine (TMB). The enzymatic reaction was stopped with sulfuric acid and optical density values at 450 nm were recorded using a Tecan plate reader.

Pharmacodynamics were assessed by measuring total cynomolgus monkey IgG serum levels using a sandwich ELISA method. Briefly, polyclonal anti-monkey IgG antibody (gamma chain specific) was coated on a 96-well immunoplate and nonspecific binding sites were blocked. Next, 100% serum samples were diluted to the concentration range of quantification and added on the immunoplate together with fresh calibration standards and a set of quality control (QC) samples. The total levels of serum Rabbit IgG were detected and visualized by the subsequent additions of an HRP-conjugated goat anti-Rabbit Fc F(ab')2 and the chromogenic substrate tetramethylbenzidine (TMB). The enzymatic reaction was stopped with sulfuric acid and optical density values at 450 nm were recorded using a Tecan plate reader.

Immunogenicity against the human IgG1 part, ABDEG substitutions, or anti-HSA moiety of the molecule was measured by using a sandwich ELISA method. Briefly, TA-Alb23-Fc-ABDEG was coated on a 96-well immunoplate and nonspecific binding sites were blocked. Dilutions of the serum samples from several post-administration timepoints of the cynomolgus monkey study were applied. Anti-drug antibodies (ADAs) were detected and visualized by the subsequent additions of an RP-conjugated anti-monkey IgG monoclonal antibody (gamma chain specific) and the chromogenic substrate tetramethylbenzidine (TMB). Optical density values were recorded using a Tecan plate reader.

Figure 2:
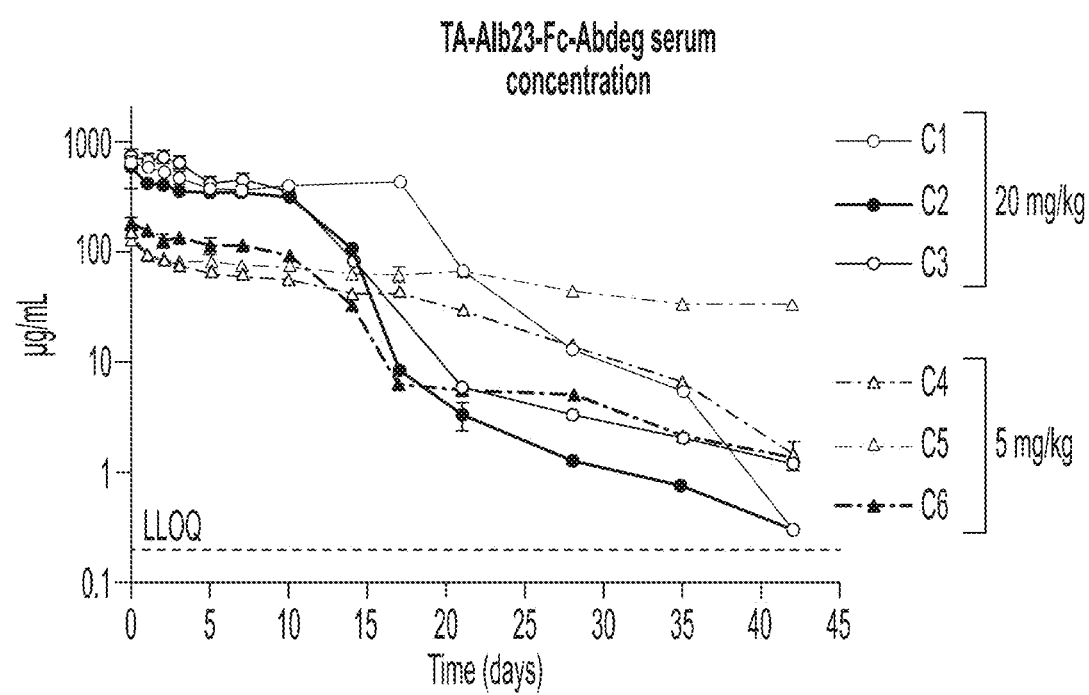
FIG. 2 shows pharmacokinetic profiles of individual cynomolgus monkeys treated with one intravenous (IV) dose of an Fc-ABDEG molecule equipped with one anti-HSAvHH (Alb23) fused at the N-terminus of each Fc domain (TA-Alb23-Fc-ABDEG); C1-3: 20 mg/kg, C4-6: 5 mg/kg. TA-Alb23-Fc-ABDEG concentration values were plotted over time. The datapoints show the mean±SD of 2 duplicates (n=2 duplicates, 2× study sample dilutions in duplicate) as a result per post-administration timepoint.

The pharmacokinetic data revealed a clear improvement of the Fc-ABDEG half-life by conjugation to an anti-HSA VHH fragment (Alb23), ranging between 13.4 and 54 days in the different groups, with an average of 26.5 days and 28.2 days for the 20 mg/kg and 5 mg/kg dose, respectively (FIG. 2). An overview of the evaluated pharmacokinetic parameters (half-life ($T_{1/2}$), $C_{max}$, Area Under Curve (AUC), and dose proportional factor (DPF)), per dose group or single animal, is presented in Table S1 and Table S2, respectively. The DPF calculations were based on the acquired AUC values. The AUC was calculated by GraphPad Prism 7 where the baseline was set as y=0 and peaks that go below the baseline or less than 10% of the distance from minimum to maximum Y were ignored. The half-life was calculated by GraphPad Prism 7 as well, using a two-phase decay model until day 10 (ADA as of day 14). The average half-life, $C_{max}$, and AUC per dose group, as shown in Table S1, were calculated based on the average TA-Alb23-Fc-ABDEG serum concentration (n=2 duplicates, 1× duplicate per study sample dilution) per post-administration timepoint of the individual monkeys per dose group (values indicated in Table S2).

TABLE S1

Average pharmacokinetic parameters of TA-Alb23-Fc-ABDEG per dose group

| Group | Administration | $C_{max}$ (µg/mL) | AUC (h · µg/mL) | $T_{1/2}$ (d) | DPF |
|---|---|---|---|---|---|
| 1 | TA-Alb23-Fc-ABDEG (20 mg/kg IV) | 664 ± 90 | 6638 ± 1997 | 27* | 0.9 |
| 2 | TA-Alb23-Fc-ABDEG (5 mg/kg IV) | 155 ± 30 | 1851 ± 532 | 28 ± 23 | 1.0 |

The results show the mean ± SD of 1 triplicate (n = 1 triplicate, 3 monkeys per dose group) per PK parameter.
*Only one value included since for monkeys c1 and c3 no accurate two-phase decay fit could be established (see Table S2).

TABLE S2

Pharmacokinetic parameters of TA-Alb23-Fc-ABDEG per individual animal

| Group | Administration | Animal | $C_{max}$ (µg/mL) | AUC (d.µg/mL) | AUC (h.µg/mL) | $T_{1/2}$ (d)* | $T_{1/2}$ (h)* |
|---|---|---|---|---|---|---|---|
| 1 | TA-Alb23-Fc-ABDEG | C1 | 671 ± 81.1 | 8695 | 208680 | ND** | ND** |

TABLE S2-continued

Pharmacokinetic parameters of TA-Alb23-Fc-ABDEG per individual animal

| Group | Administration | Animal | $C_{max}$ (μg/mL) | AUC (d.μg/mL) | AUC (h.μg/mL) | $T_{1/2}$ (d)* | $T_{1/2}$ (h)* |
|---|---|---|---|---|---|---|---|
| | (20 mg/kg IV) | C2 | 570.7 ± 187.4 | 4708 | 112992 | 26.5 | 636 |
| | | C3 | 749.6 ± 90.3 | 6510 | 156240 | ND** | ND** |
| 2 | TA-Alb23-Fc-ABDEG (5 mg/kg IV) | C4 | 153.3 ± 4.3 | 1465 | 35160 | 13.4 | 322 |
| | | C5 | 126.0 ± 3.5 | 2458 | 58992 | 54.4 | 1306 |
| | | C6 | 186.7 ± 19.9 | 1629 | 39096 | 16.9 | 406 |

The results show the mean ± SD of 2 duplicates (n = 2 duplicates, 2× study sample dilutions in duplicate) per PK parameter.
*$T_{1/2}$ was determined using a two-phase decay, until day 10 (ADA as of day 14).
**The two-phase decay fittings were ambiguous, and no accurate $T_{1/2}$ value could be obtained.

The PK profile of TA-Alb23-Fc-ABDEG post intravenous administration showed a drastically increased half-life of the Fc-ABDEG molecule compared to efgartigimod. The calculated Cmax values are in the range of what is to be expected when considering the estimated mean blood volume of the Macaque Cynomolgus, which is 65 mL/kg. The predicted Cmax for the 20 and 5 mg/kg dose group were 559 and 140 μg/mL, respectively. The half-life for the TA-Alb23-Fc-ABDEG molecule is 26.5 days and 28.2 days for the 20 mg/kg and 5 mg/kg dose group respectively, while for efgartigimod, this is around 1.5 days. A clear decrease in TA-Alb23-Fc-ABDEG serum levels is observed in most animals as of day 10, which correlates with detectable levels of anti-drug antibodies as of that moment. The AUC values showed to increase linear with the administrated dose as this is demonstrated by a DPF of 0.9 between the 5 mg/kg and 20 mg/kg group.

The IgG decrease is small but dose-dependent; no pharmacodynamic effect is observed at a dose of 5 mg/kg. An IgG clearance effect could be observed at a dose of 20 mg/kg of TA-Alb23-Fc-ABDEG; maximally 25% reduction in IgG levels compared to baseline values (when C3 was excluded). Moreover, the time to reach a maximum PD effect ($T_{min}$) is quite long. It takes 21 and 28 days for 5 mg/kg and 20 mg/kg dose groups, respectively.

Figure 3A:
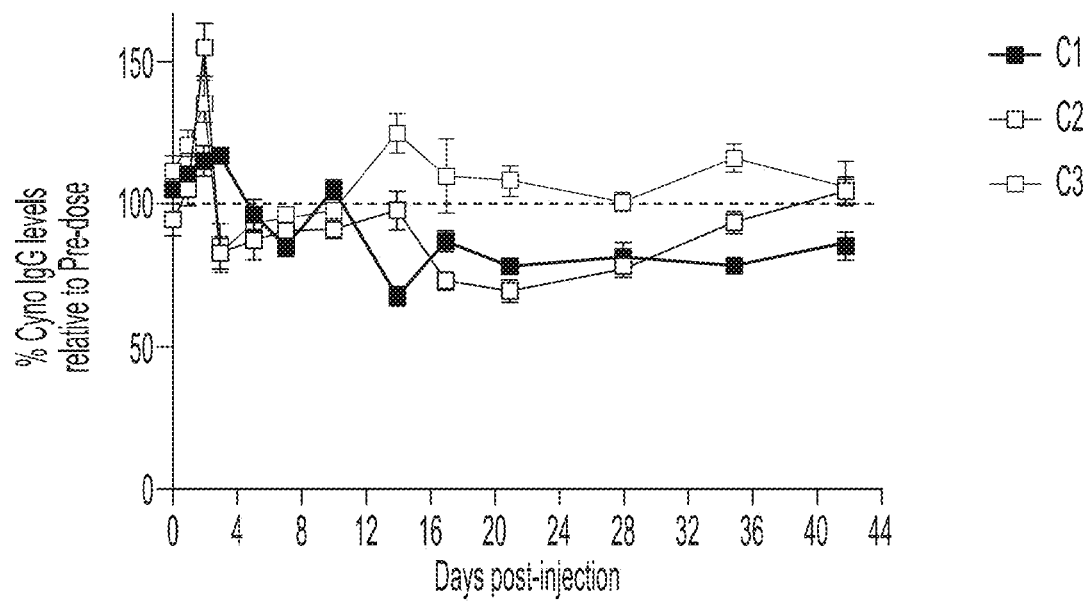
FIGS. 3A-3B show pharmacodynamic profiles of individual cynomolgus monkeys treated with one IV dose of TA-Alb23-Fc-ABDEG; -C1-3: 20 mg/kg (FIG. 3A), -C4-6: 5 mg/kg (FIG. 3B). % Cynomolgus total serum IgG levels relative to pre-dose were plotted over time. The datapoints show the mean±SD of 2 duplicates (n=2 duplicates, 2× study sample dilutions in duplicate) as a result per post-administration timepoint.
Figure 3B:
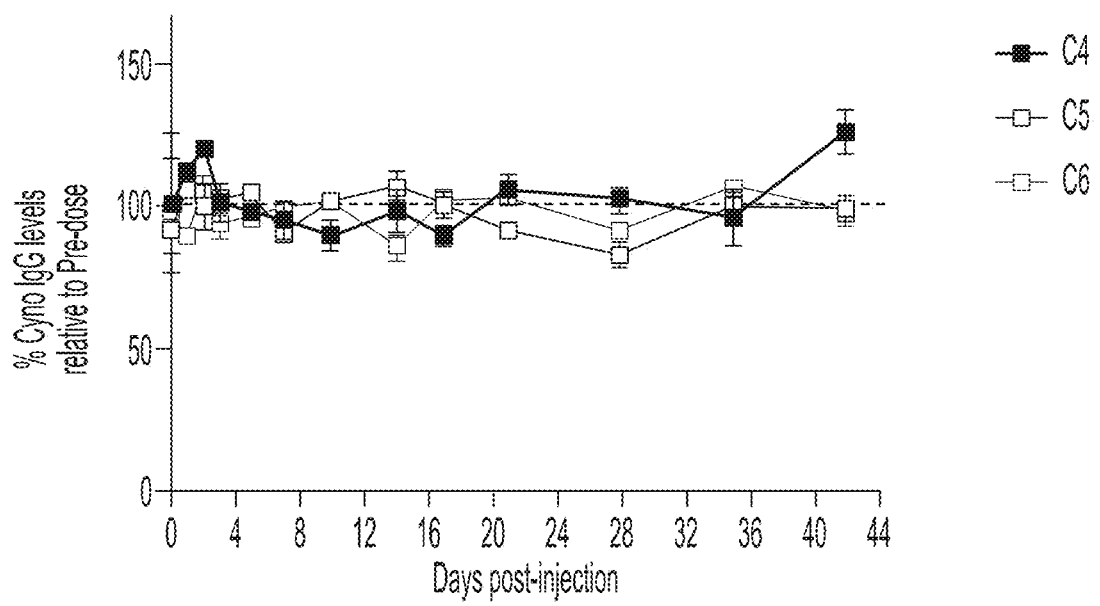

The total IgG levels in cynomolgus serum after a single dose of 5 or 20 mg/kg b.w. TA-Alb23-Fc-ABDEG are shown relative to pre-dose level, in FIGS. 3A-3B. The pharmacodynamic parameters of the different animals are shown in Table S3 and Table S4.

TABLE S3

Pharmacodynamic parameters of TA-Alb23-Fc-ABDEG per individual animal

| Group | Administration | Animal | $C_{min}$ (% to pre-dose) | Average $C_{min}$ (% to pre-dose) | $T_{min}$ (days) |
|---|---|---|---|---|---|
| 1 | TA-Alb23-Fc-ABDEG (20 mg/kg IV) | C1 | 68.0 | 74.1 ± 9.2 | 14 |
| | | C2 | 69.7 | *68.8 ± 1.2 | 21 |
| | | C3 | 84.7* | | 3 |
| 2 | TA-Alb23-Fc-ABDEG (5 mg/kg IV) | C4 | 89.6 | 86.0 ± 3.6 | 17 |
| | | C5 | 82.5 | | 28 |
| | | C6 | 86.0 | | 14 |

The results show the mean ± SD of 2 duplicates (n = 2 duplicates, 2× study sample dilutions in duplicate) per PD parameter.
*C3 excluded from analysis.

TABLE S4

Average pharmacodynamic parameters of TA-Alb23-Fc-ABDEG per dose group

| Administration | $C_{min}$ (% to pre-dose) | $T_{min}$ (days) |
|---|---|---|
| 20 mg/kg TA-Alb23-Fc-ABDEG | 74.1 ± 9.2 | 12.7 ± 9.1 |
| | *68.8 ± 1.2 | *17.5 ± 4.9 |
| 5 mg/kg TA-Alb23-Fc-ABDEG | 86.0 ± 3.6 | 19.7 ± 7.4 |

The results show the mean ± SD of 1 triplicate (n = 1 triplicate, 3 monkeys per dose group) per PD parameter.
*C3 excluded from analysis.

Figure 4:
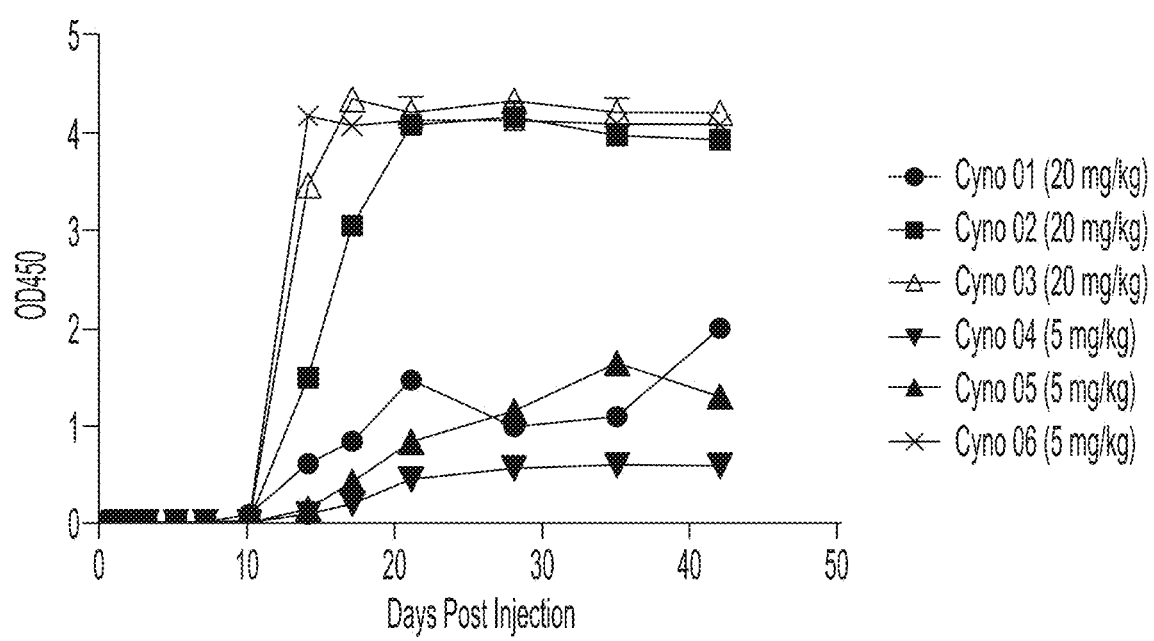
FIG. 4 shows TA-Alb23-Fc-ABDEG ADA development profiles of individual cynomolgus monkeys treated with one IV dose of TA-Alb23-Fc-ABDEG; C1-3: 20 mg/kg, C4-6: 5 mg/kg. The developing immune response was plotted over time. The datapoints show the mean±SD of 1 duplicate (n=1 duplicate, 1× study sample dilution in duplicate) as a result per post-administration timepoint.

All animals treated with TA-Alb23-Fc-ABDEG developed anti-drug antibodies as of day 10. The immune response of the animals is shown in FIG. 4. An increase in OD450 can be detected when antibodies, against the human IgG1 part, ABDEG substitutions, or the anti-HSA moiety of the molecule, are present in the cynomolgus serum study samples. ADA development was observed in all the animals as of 10 days post injection of the TA-Alb23-Fc-ABDEG molecule in both dosing groups. C2, C3, and C6 showed significantly higher OD signal, more pronounced immune response than the other monkeys, and since they do not originate from the same dose group, it is assumedly not related to the administered TA-Alb23-Fc-ABDEG dose (5 mg/kg vs 20 mg/kg).

The aim of the study was to determine the pharmacokinetic, pharmacodynamic, and immunogenic properties of a two-armed N-terminal anti-HSA-Fc-ABDEG (TA-Alb23-Fc-ABDEG) after single intravenous bolus injection of 5 mg/kg and 20 mg/kg in cynomolgus monkeys. It was predicted that the addition of two anti-HSA VHH fragments at the N-terminus of Fc-ABDEG would extend the half-life and efficacy of the molecule compared to efgartigimod. In this study, the PK profile of TA-Alb23-Fc-ABDEG demonstrated an increased half-life of the Fc-ABDEG molecule as compared to efgartigimod. The half-life for the TA-Alb23-Fc-ABDEG molecule is 26.5 days and 28.2 days for the 20 mg/kg and 5 mg/kg dose group respectively, while for efgartigimod this is around 1.5 days. However, the TA-Alb23-Fc-ABDEG molecule had a minimal effect on the endogenous cynomolgus serum IgGs in both administration groups (maximum reduction observed was 25% compared to pre-dose levels; 20 mg/kg dose group). This is in strong contrast with the data of other studies in cynomolgus monkeys where administration of 20 mg/kg efgartigimod resulted in at least 50% decrease of total serum IgGs within the first 10 days post injection. In vitro testing suggests that the functionality of the TA-Alb23-Fc-ABDEG is lower compared to efgartigimod. Furthermore, an accelerated TA-Alb23-Fc-ABDEG clearance is observed in most animals as of day 10, which corresponds with the detectable levels of anti-drug antibodies as of that time point.

Figure 5:
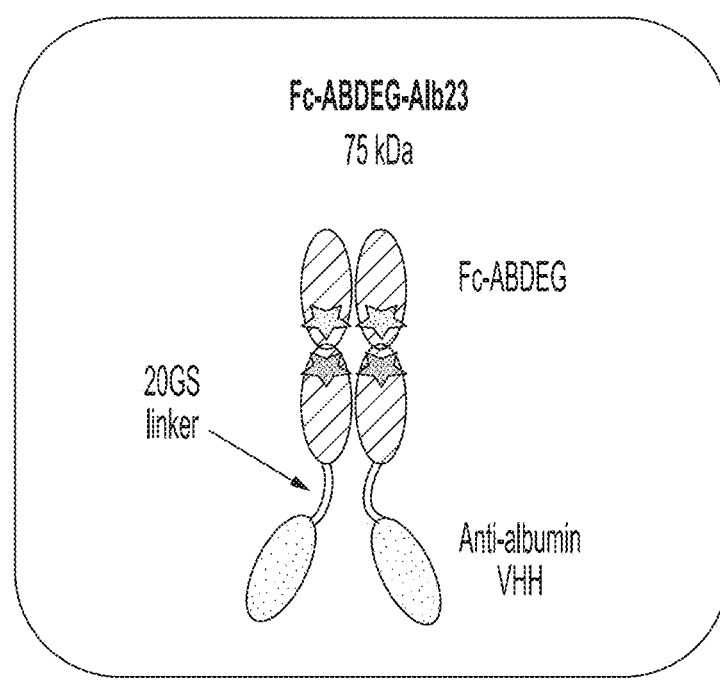
FIG. 5 is a schematic of a representative TA Fc-ABDEG molecule equipped with an anti-HSAvHH (Alb23) fused at the C-termini of both Fc domains.

Example 2: Pharmacokinetics/Pharmacodynamics of Fc-ABDEG-Anti-HSA in Cynomolgus Monkeys As described in Example 1, efgartigimod (Fc-ABDEG fragment) fused at its N-terminus with HSA-targeting VHH fragment Alb23 (Alb23-Fc-ABDEG with two Alb23 albumin-binding arms on N-termini) demonstrated an increased half-life in cynomolgus monkeys but no appreciable pharmacodynamic effect on clearance of endogenous cynomolgus IgGs. It was postulated that positioning of anti-HSA VHH fragments on the N-terminus of Fc-ABDEG might prevent the Fc-ABDEG portion of the molecule from occupying FcRn and, therefore, may lead to a less efficient competition with endogenous IgG for binding to FcRn. Therefore, for this study, efgartigimod was fused with two Alb23 VHHs at the C-termini of efgartigimod (TA-Fc-ABDEG-Alb23) (FIG. 5). The full-length sequence of TA-Fc-ABDEG-Alb23 is:

(SEQ ID NO: 178)
DKTHTCPPCPAPELLGGPSVFLFPPKPKDTLYITREPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALKFHYTQKSLSLSPGGGGSGGGGSGGGGSGGGG

SEVQLLESGGGLVQPGGSLRLSCAASGFTFRSFGMSWVRQAPGKGPEWV

SSISGSGSDTLYADSVKGRFTISRDNSKNTLYLQMNSLRPEDTAVYYCT

IGGSLSRSSQGTLVTVSS.

Earlier, prolonged PK with TA-Fc-ABDEG-Alb23 (anti-HSA VHH fragments on C-termini) was observed in human FcRn and human albumin transgenic AlbuMus mice. Importantly, in the same model, Fc-ABDEG-Alb23 also demonstrated a pronounced PD effect on clearance of circulating preloaded human IgG, in contrast to TA-Alb23-Fc-ABDEG (anti-HSA VHH fragments on N-termini). These finding enabled further investigations of TA-Fc-ABDEG-Alb23 (anti-HSA VHH fragments on C-termini) in cynomolgus monkeys.

The procedures that were applied on animals in this study were reviewed and approved by PharmaLegacy Laboratories IACUC. Briefly, a total of 6 naïve female cynomolgus monkeys (2.5-5 kg) were randomly assigned into 2 groups. The monkeys were single-dosed IV via cephalic or saphenous vein with 30 or 75 mg/kg TA-Fc-ABDEG-Alb23. Blood samples were collected before (pre-dose) and after the treatment during 4 weeks for PD, PK, ADA, albumin assays, as well as for hematology, clinical biochemistry, and coagulation analysis, according to the schedule described in Table S5.

TABLE S5

Sample collection summary

| Sample | Time points | Used for |
|---|---|---|
| Serum | Pre-dose D-7, D-1, −5 min, and 5 min, 2, 6, 24, 48, 72, 120, 168, 240, 336, 408, 504, 648 hrs post dose | PD |
| Serum | Same schedule as PD | PK |
| Serum | Pre-dose D-7, and 72, 168, 336, 648 hrs post dose | ADA |
| Serum | Same schedule as PD | Albumin test |
| Whole blood | Pre-dose D-7, −5 min, and 6 24, 336, 648 hrs post dose | Hematology: WBC, RBC, HCT, MCV, RDW, HGB, MCH, MCHC, PLT, MPV, MON, NEUT, LYM, ESO, BAS |
| Serum | Pre-dose D-7, −5 min, and 6 24, 336, 648 hrs post dose | Clinical Chemistry: ALT, AST, ALP, GGT, CK, CRE, TP, ALB, GLB, A/G, TBIL, CHOL, TG, GLU, UREA, Ca, P, Na, K, Cl, HDL, LDL |
| Plasma | Pre-dose D-7, −5 min, and 6 24, 336, 648 hrs post dose | Coagulation: APTT, PT, TT, Fib, D-dimer |

Pharmacodynamics were assessed by measuring total cynomolgus monkey IgG serum levels using a qualified sandwich ELISA. Briefly, recombinant mouse anti-monkey IgG (Southern Biotech, cat #4700-01, 1° H3418-SH51) were coated at 0.5 μg/mL on a 96-well immunoplates. Study serum samples were diluted 1:500000 and incubated on the coated immunoplates together with a fresh 10-point cynomolgus monkey IgG calibration curve (MyBioSource, cat #MBS135162, LOT CY-GF-816) and 3 frozen quality control (QC) samples: HQC, dilution QC (100% cynomolgus monkey serum diluted 1:500000), and LQC for 2 hours in a temperature controlled shaking incubator at 22° C. IgGs were detected for 1 hour by a mouse anti-monkey IgG HRP-conjugated (Southern Biotech, cat #4700-05, 1° H3418-YG59D). The plates were developed by adding tetramethylbenzidine (TMB) substrate for approximately 15 minutes. The enzymatic reaction was stopped with sulfuric acid and optical density values at 450 nm were recorded using a Tecan plate reader. Pooled cynomolgus monkey serum was used. The ELISA method was fully qualified in-house with regard to calibration range, precision, accuracy, specificity, dilution linearity, and drug interference.

Concentrations of TA-Fc-ABDEG-Alb23 in monkey serum were determined using a sandwich Electrochemiluminescence Immunoassay (ECLIA) method. Briefly, after blocking nonspecific binding sites, streptavidin coated 96-well MSD SECTOR plates were coated with biotinylated mouse anti-ABDEG for 1 h. Next, 100% study serum samples were diluted to the concentration range of quantitation or at least the minimum required dilution (MRD) and incubated on the immunoplate together with a fresh 12-point calibration curve with TA-Fc-ABDEG-Alb23 (Evitria, #903724.1, E17404, 12214-SEC) from 200000 ng/mL to 390 ng/mL in 100% pooled monkey serum and two sets of frozen QC samples (HQC, MQC, and LQC) in a temperature controlled shaking incubator at 22° C. for 1 hour. TA-Fc-ABDEG-Alb23 was detected by the subsequent addition of a sulfo-tagged VHH fragment for 30 minutes. Levels of TA-Fc-ABDEG-Alb23 were developed after a 5-minute incubation step in 1×MSD READ buffer using an MSD reader. The applied ECLIA method was fit-for-purpose qualified in-house with regard to calibration range, precision, accuracy, matrix effect, selectivity, dilutional linearity and stability. The MRD of this method was set on 1:50 and the sensitivity (LLOQ) was 390.6 ng/mL in 100% serum.

The non-compartmental PK analysis (NCA) was performed using Phoenix® WinNonlin® version 8.3 (Copyright © 1998-2020, Certara L.P., USA). NCA analysis was performed on the individual plasma concentrations per animal. In Phoenix® WinNonlin® the NCA calculation method "Linear Up Log Down" and dose option "IV Bolus" was applied.

The presence of an immune response against TA-Fc-ABDEG-Alb23 was measured by using a sandwich ELISA. Briefly, TA-Fc-ABDEG-Alb23 was coated at 1 µg/mL on 96-well immunoplates and non-specific binding sites were blocked with 1% Casein-PBS (G-Bioscience, Part #097B, Lot #212206). 1:10000 dilutions of cynomolgus monkey serum at pre-dose and post-dose in 0.1% Casein-PBS were applied and incubated on a shaking incubator for 1 h. The plates were washed, and mouse anti-monkey IgG-HRP (Southern Biotech, #4700-05, clone SB108a, H3418-YG59D) at 1:10000 dilution was added and incubated for 1 h. The plates were developed by adding TMB substrate for 10 minutes. The enzymatic reaction was stopped with sulfuric acid and optical density values at 450 nm were recorded using a Tecan plate reader.

Albumin concentrations in serum were determined using bromocresol green (BCG) colorimetric assay. Briefly, 3 µL of 100% study serum samples was mixed with 300 µL of BCG reagent (0.05 M Succinic acid buffer, 2.4 g/L Brij™ 35, 1.8e-4 M BCG) and incubated for 1 minute at 37° C. Albumin levels were measured by a microplate absorbance reader at 600 nm. Study samples were analyzed together with an albumin standard at 49.6 g/L and a set of QC samples with human albumin (Wako Diagnostics/Chemicals) at 10, 27, 44, and 60 g/L. Serum albumin concentration was calculated by the following formula: albumin concentration (g/L)=((OD sample−OD blank)/(OD standard−OD blank))×concentration of standard (g/L). TA-Fc-ABDEG-Alb23 showed no interference in this assay.

Figure 6A:
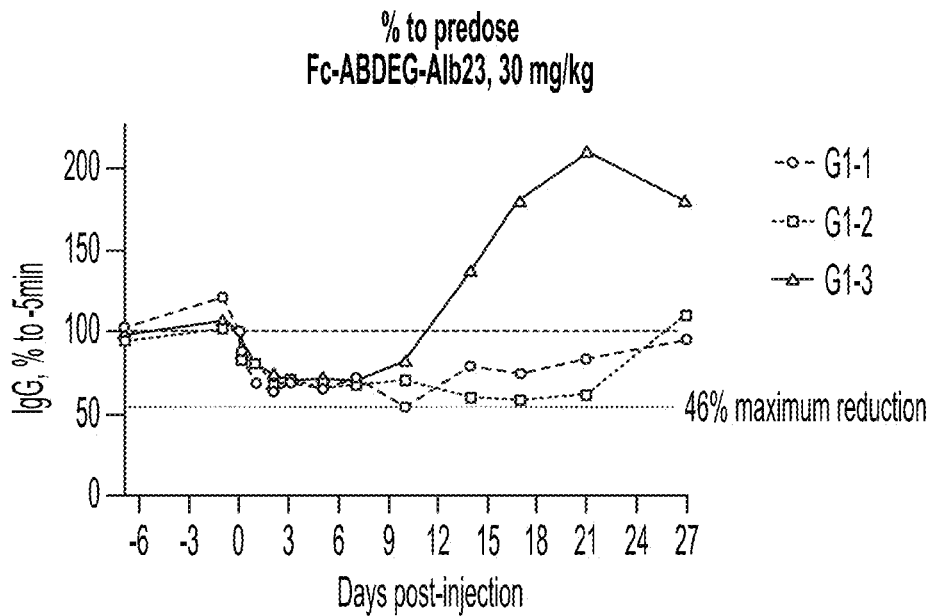
FIGS. 6A-6B show total circulating IgG levels of individual cynomolgus monkeys after a single IV bolus injection with an Fc-ABDEG molecule equipped with an anti-HSAvHH (Alb23) fused at the C-termini of both Fc domains via a 20GS linker (TA-Fc-ABDEG-Alb23). On day 0, monkeys in group 1 (G1-1, G1-2, and G1-3) received a 30 mg/kg dose of TA-Fc-ABDEG-Alb23 (FIG. 6A), and monkeys in group 2 (G2-1, G2-2, and G2-3) received a 75 mg/kg dose of TA-Fc-ABDEG-Alb23 (FIG. 6B). Percentages relative to pre-dose on day 0 at −5 min were plotted over time during the course of the study (days post-injection). The dashed lines represent 100% of total serum IgG at the baseline (day 0, −5 min) before TA-Fc-ABDEG-Alb23 injection. The dotted lines represent maximum IgG level reduction observed in individual monkeys in each study group. The graphs show means±SD of study samples analyzed in duplicates (technical replicates).
Figure 6B:
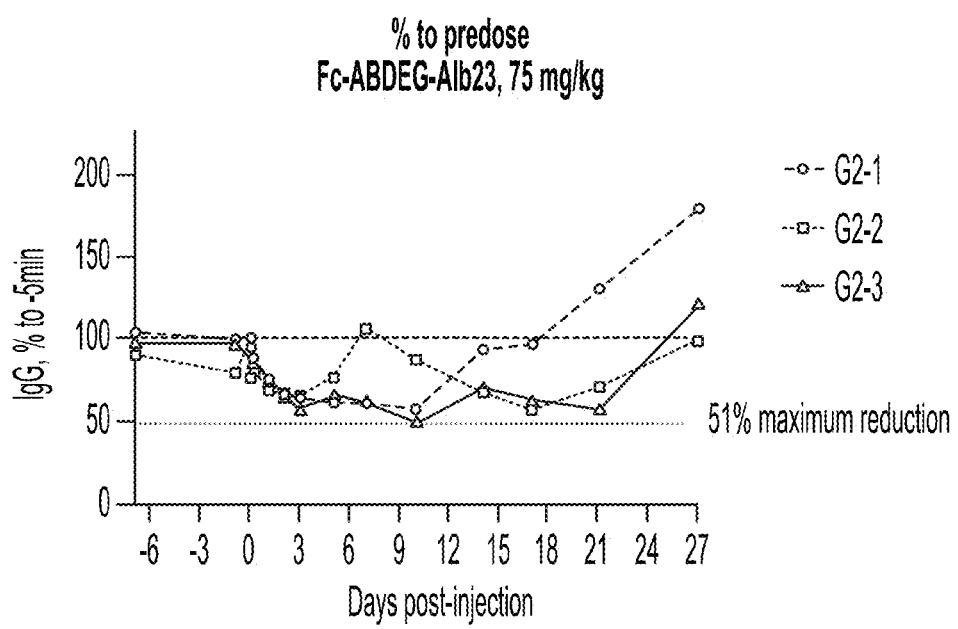

To evaluate pharmacodynamic effects of TA-Fc-ABDEG-Alb23 after a single IV administration at 30 and 75 mg/kg doses, the levels of total circulating IgG in serum samples were determined at baseline (pre-dose) and post-dose according to the bleeding scheme in Table S5. The obtained IgG concentrations were plotted as percentage to pre-dose at 5 min (day 0, −5 min) prior to TA-Fc-ABDEG-Alb23 administration (FIGS. 6A-6B). TA-Fc-ABDEG-Alb23 demonstrated a pronounced PD effect on the clearance of total circulating IgG with an observed maximum total IgG reduction of 46% and 51%, defined as IgG $C_{min}$, in individual monkeys in the dose groups of 30 and 75 mg/kg, respectively (FIGS. 6A-6B, Table S6). Average total serum IgG $C_{min}$ in the dose groups of 30 and 75 mg/kg were 60.9±7.7% and 54.2±4.5%, respectively, with the average time to $C_{min}$ ($T_{min}$) being 11.3±5.1 and 12.3±4.0 days, respectively. Overall, for 4 (G1-1, G1-2, G2-2, and G2-3) out of 6 monkeys dosed with TA-Fc-ABDEG-Alb23, IgG levels remained decreased with a return to baseline observed only between day 21 and 27.

Potential role of ADA developed in the monkeys after TA-Fc-ABDEG-Alb23 administration cannot be excluded and should be taken into account when interpreting PD effects on total circulating IgG. Two monkeys, G1-3 and G2-1 displayed an increase in IgG levels after day 10 post-injection, making it difficult to observe and conclude on a duration of PD effects in those monkeys. Monkey G2-2 showed an unexpected profile of IgG depletion: between day 5 and 7 IgG levels increased back to the baseline levels, after which IgG levels decreased again. The reason for this deviating profile is not clear and could be related to ADA development.

G1-1, G1-2, and G1-3, and G2-1, G2-2, and G2-3 were dosed with TA-Fc-ABDEG-Alb23 at 30 or 75 mg/kg doses, respectively. IgG $C_{min}$ shows a minimum level of total circulating IgG (deepest PD response) detected in an individual monkey post TA-Fc-ABDEG-Alb23 administration, presented as % to pre-dose (% to day 0 −5 min). IgG $T_{min}$ shows a day of the study when IgG $C_{min}$ was observed (Table S6).

TABLE S6

Summary of pharmacodynamic parameters of TA-Fc-ABDEG-Alb23 in cynomolgus monkeys

| Group | TA-Fc-ABDEG-Alb23, dose, route | Animal ID | IgG $C_{min}$, % | Group mean IgG $C_{min}$ ± SD, % | IgG $T_{min}$, days | Group mean IgG $T_{min}$ ± SD, days |
|---|---|---|---|---|---|---|
| 1 | 30 mg/kg, IV | G1-1 | 54.6 | 60.9 ± 7.7 | 10 | 11.3 ± 5.1 |
|   |   | G1-2 | 58.6 |   | 17 |   |
|   |   | G1-3 | 69.4 |   | 7 |   |
| 2 | 75 mg/kg, IV | G2-1 | 56.9 | 54.2 ± 4.5 | 10 | 12.3 ± 4.0 |
|   |   | G2-2 | 56.8 |   | 17 |   |
|   |   | G2-3 | 49 |   | 10 |   |

Figure 7A:
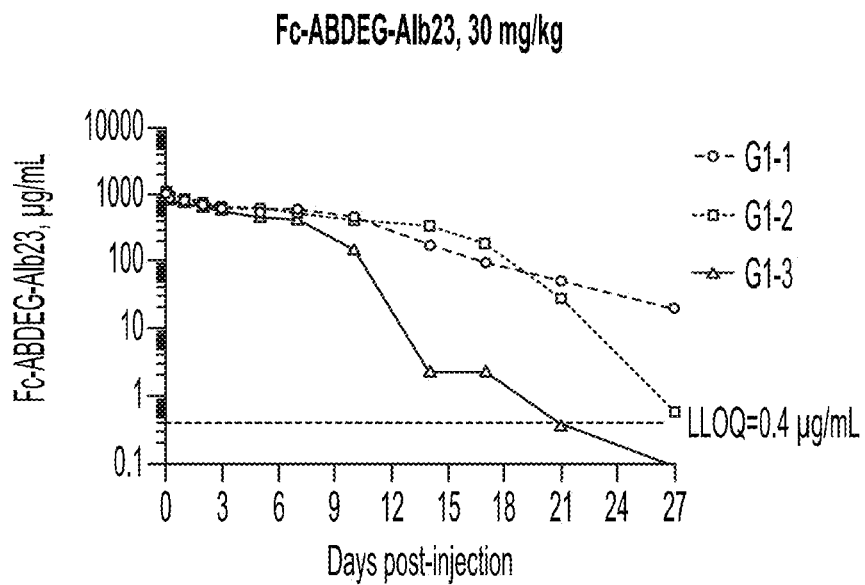
FIGS. 7A-7B show TA-Fc-ABDEG-Alb23 pharmacokinetic profiles after single IV bolus injection in cynomolgus monkeys. On day 0, monkeys in group 1 (G1-1, G1-2, and G1-3) received a 30 mg/kg dose of TA-Fc-ABDEG-Alb23, and monkeys in group 2 (G2-1, G2-2, and G2-3) received a 75 mg/kg dose of TA-Fc-ABDEG-Alb23. TA-Fc-ABDEG-Alb23 levels in µg/mL for individual monkeys were plotted over time during the course of the study (days post-injection) for 30 mg/kg (FIG. 7A) and for 75 mg/kg (FIG. 7B) dose groups. The dashed lines represent the sensitivity level of the TA-Fc-ABDEG-Alb23 PK ELISA with the LLOQ of 0.4 µg/mL. The datapoints show the mean±SD of a study sample analyzed in duplicates (technical replicates).
Figure 7B:
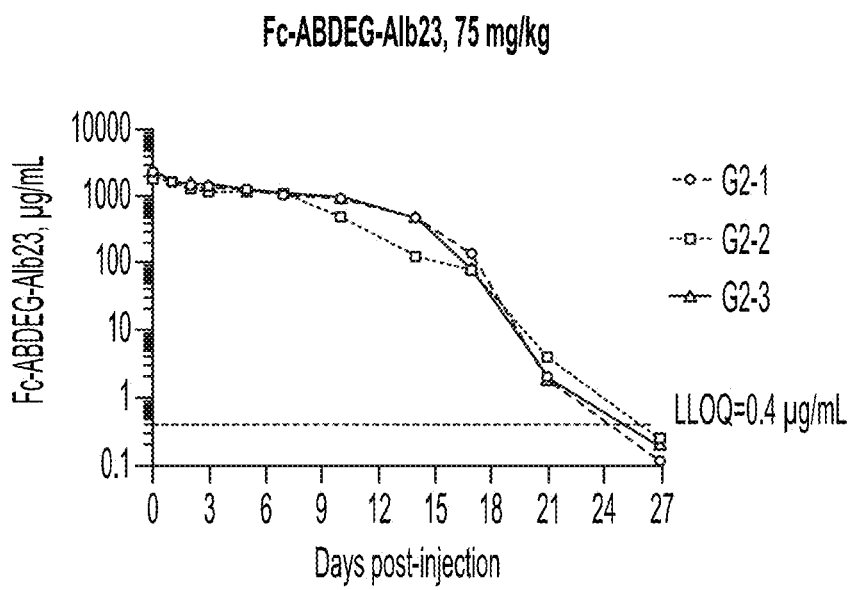

To evaluate the PK profile of TA-Fc-ABDEG-Alb23 after a single IV administration at 30 and 75 mg/kg doses, TA-Fc-ABDEG-Alb23 levels were determined in serum post-dose samples according to the bleeding scheme in Table S5. The obtained TA-Fc-ABDEG-Alb23 concentrations were plotted over time during the course of the study (FIGS. 7A-7B). For the 30 mg/kg dosing group, 2 out of 3 monkeys showed a steep non-linear decrease of TA-Fc-ABDEG- Alb23 levels starting on day 7 for G1-3 and day 14 for G1-2. All monkeys of the 75 mg/kg dosing group showed similar steep declines of TA-Fc-ABDEG-Alb23 levels starting as of days 7 for G2-2 and as of day 10 for G2-1 and G2-3. TA-Fc-ABDEG-Alb23 concentrations were still quantifiable in serum of all monkeys on day 21. The observed sudden non-linear elimination from circulation of Fc-ABDEG-Alb23 starting somewhat one week after the injection in both dose groups can presumably by mediated by ADA. ADA was analyzed and is discussed in detail below.

Since the majority of TA-Fc-ABDEG-Alb23 concentrations in serum where ADA was detected (FIGS. 8A-8B) resulted in abnormal time-concentrations with the mentioned unexpected steep concentration decline, it was considered justified to omit ADA-positive values from NCA analysis. For comparison of exposure in case of invalid $AUC_{inf}$, the partial AUC from 0 to 10 days, $AUC_{(0-10)}$, was calculated. For Animal G2-2, the 10-day value had to be extrapolated, since $t_{last}$ was 5 days. Values for $C_{max}$, $AUC_{(0-10)}$, and $t_{1/2,z}$ (terminal half-life) are summarized in Table S7. $C_{max}$ and $AUC_{(0-10)}$ both increased with dose in a dose proportional manner, since the ratios of mean $C_{max}$ and mean $AUC_{(0-10)}$ at 75 mg/kg over 30 mg/kg were 2.4 for $C_{max}$ and 2.5 for $AUC_{(0-10)}$, close to the 2.5 ratio of the doses, and there was no relevant difference between mean dose-normalized values. Measured values for $C_{max}$ were in good agreement with calculated $C_{max}$ values (991 µg/mL and 2479 µg/mL for 30 and 75 mg/kg, respectively) expected for the administered doses when considering the circulating blood volume in cynomolgus macaques as 55 mL/kg (range 55-75 mL/kg). A mean terminal half-life of approximately 10 days was found for both doses. Variability of terminal half-life is moderate to high, although this may be caused by the short observation time due to ADA at later time points. Since for all animals $AUC_{\% \ extr}$ is >20% $AUC_{inf}$ is considered unreliable and should not be used.

G1-1, G1-2, and G1-3, and G2-1, G2-2, and G2-3 were dosed with TA-Fc-ABDEG-Alb23 at 30 or 75 mg/kg doses, respectively. $C_{max}$ was measured by PK ELISA at 5 min post-injection. For comparison of exposure, the partial AUC from 0 to 10 days, $AUC_{(0-10)}$, was calculated. $t_{1/2,z}$ is a terminal elimination phase half-life (Table S7).

Figure 9A:
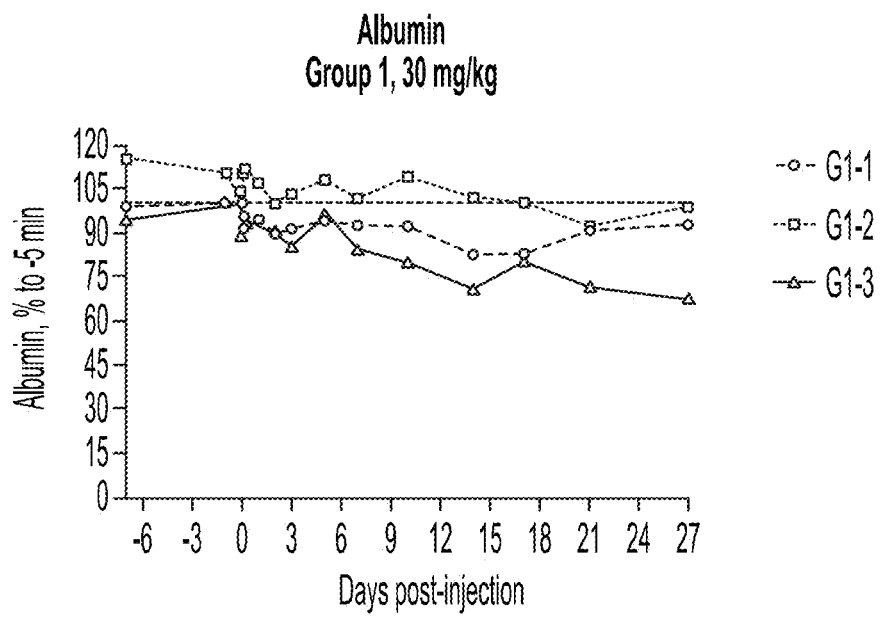
FIGS. 9A-9B show serum albumin levels after injection of TA-Fc-ABDEG-Alb23 (analyzed with BCG assay in 96-well plate format). On day 0, monkeys in group 1 (G1-1, G1-2, and G1-3) received a 30 mg/kg dose of TA-Fc-ABDEG-Alb23 (FIG. 9A), and monkeys in group 2 (G2-1, G2-2, and G2-3) received a 75 mg/kg dose of TA-Fc-ABDEG-Alb23 (FIG. 9B). Percentages relative to pre-dose (day 0 at −5 min) were plotted over time during the course of the study (days post-injection). The dashed lines represent 100% of albumin on day 0, 5 min before TA-Fc-ABDEG-Alb23 injection. The datapoints show the mean±SD of a study sample analyzed in duplicates (technical replicates).
Figure 9B:
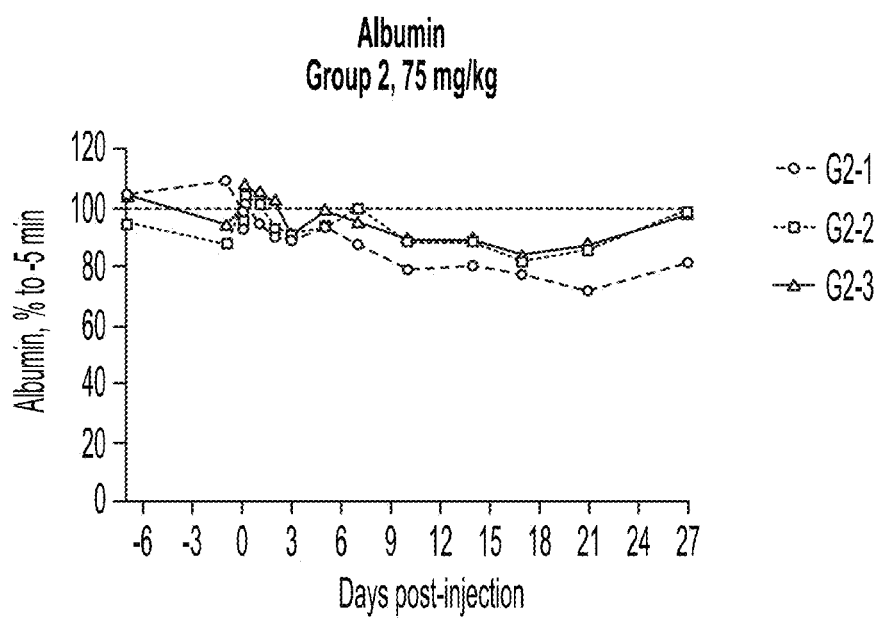

To evaluate a potential impact of TA-Fc-ABDEG-Alb23 on albumin levels after the administration to cynomolgus monkeys, total serum albumin levels were measured throughout the study with BCG assay in 96-well plate format at baseline (pre-dose) and post-dose according to the scheme in Table S5. Obtained albumin concentrations were plotted as percentage to pre-dose on day 0, −5 min prior TA-Fc-ABDEG-Alb23 administration (FIGS. 9A-9B). For 2 out of 3 animals (30 mg/kg group), monkeys G1-1 and G1-3, serum albumin levels showed a maximum decline (albumin $C_{min}$) to 82% and 67% to pre-dose on days 14 and 27, respectively (Table S8). This decline did not return to baseline at the end of the study. Monkey G1-2 (75 mg/kg group) also showed an overall decline of albumin in comparison to the pre-dose levels with the lowest level being detected on day 21. The monkeys in 75 mg/kg group showed a decline of albumin levels down to 72%, 82%, and 84% to pre-dose on days 21, 17, and 17 for G2-1, G2-2, and G2-3, respectively. For monkeys G2-2 and G2-3, albumin levels returned to baseline on day 27, in contrast to G2-1.

Additionally, albumin concentrations were analyzed as a part of the blood biochemistry panel at pre-dose (day −7, day 0 −5 min) and post-dose (day 0 6 h, day 1, day 14, day 27) with the same BCG kit but using an automated bioanalyzer. Maximum decline of albumin levels in this format of BCG assay was observed on day 14 (Tables S9 and S10). Overall, both BCG assay formats (96-well plate and bioanalyzer) showed similar trends in the declines of albumin levels after TA-Fc-ABDEG-Alb23 administration, as compared on day 14.

TABLE S8

Summary of the observed albumin levels as measured with BCG assay in 96-well plate format

| Group | Fc-ABDEG-Alb23, dose | Animal ID | Albumin $C_{min}$, % | Albumin $T_{min}$, days |
|---|---|---|---|---|
| 1 | 30 mg/kg i.v. | G1-1 | 82 | 14 |
|   |   | G1-2 | 93 | 21 |
|   |   | G1-3 | 67 | 27 |

TABLE S7

Summary of pharmacokinetic parameters of TA-Fc-ABDEG-Alb23 in cynomolgus monkeys

| Group | Fc-ABDEG-Alb23, dose, route | Animal ID | $C_{max}$ µg/ml Individ, ± SD | $C_{max}$ µg/ml Group mean ± SD | $AUC_{(0-10)}$, day*µg/ml Individ, ± SD | $AUC_{(0-10)}$, day*µg/ml Group mean ± SD | $t_{1/2,z}$, days Individ, ± SD | $t_{1/2,z}$, days Group mean ± SD |
|---|---|---|---|---|---|---|---|---|
| 1 | 30 mg/kg i.v. | G1-1 | 1106 ± 20 | 1044 ± 117 | 6209 | 5696 ± 817 | 15 | 9.7 ± 5.3 |
|   |   | G1-2 | 1117 ± 48 |   | 6124 |   | 9.3 |   |
|   |   | G1-3 | 909 ± 24 |   | 4754 |   | 4.5 |   |
| 2 | 75 mg/kg i.v. | G2-1 | 2647 ± 66 | 2466 ± 371 | 14488 | 13945 ± 1400 | 13 | 10 ± 3.7 |
|   |   | G2-2 | 2039 ± 54 |   | 12356 |   | 6.1 |   |
|   |   | G2-3 | 2712 ± 33 |   | 14993 |   | 12 |   |

Figure 8A:
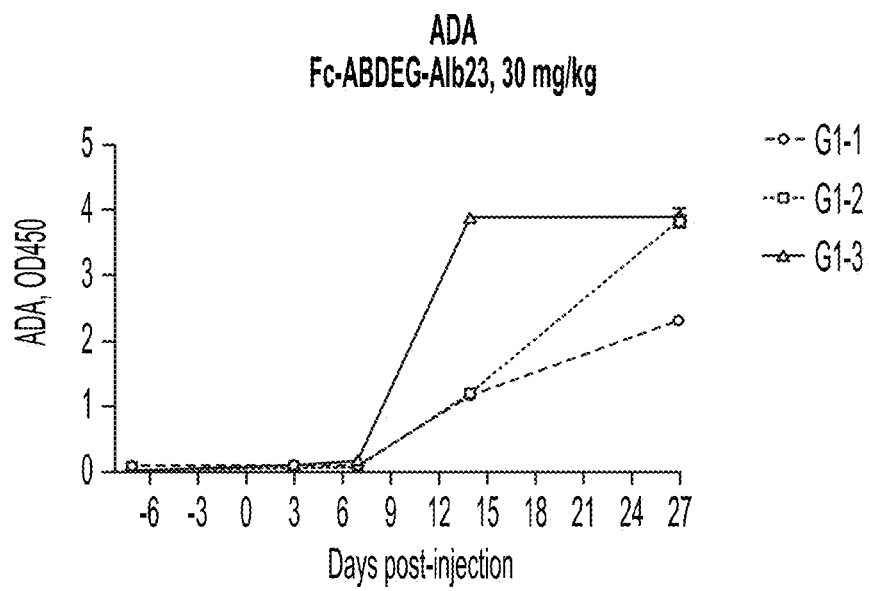
FIGS. 8A-8B show ADA response after a single IV bolus injection of TA-Fc-ABDEG-Alb23 in cynomolgus monkeys. On day 0, monkeys in group 1 (G1-1, G1-2, and G1-3) received a 30 mg/kg dose of TA-Fc-ABDEG-Alb23 (FIG. 8A), and monkeys in group 2 (G2-1, G2-2, and G2-3) received a 75 mg/kg dose of TA-Fc-ABDEG-Alb23 (FIG. 8B). ADA response against TA-Fc-ABDEG-Alb23 was analyzed by ELISA and OD450 values were plotted over time during the course of the study (days post-injection).
Figure 8B:
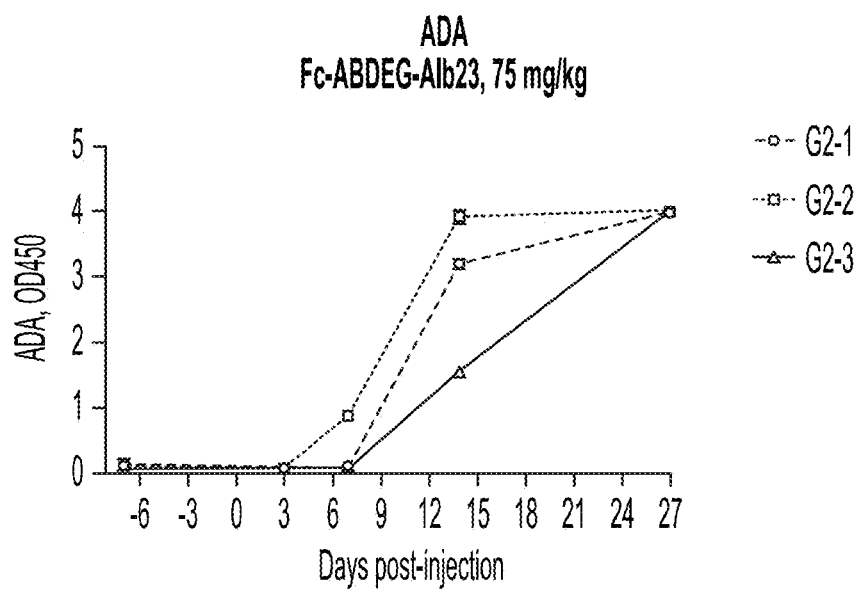

To evaluate immune response to TA-Fc-ABDEG-Alb23 during the course of the study, presence of ADA was analyzed by a sandwich ELISA with 1:10000 diluted serum samples (FIGS. 8A-8B). ADA against TA-Fc-ABDEG-Alb23 were observed in all monkeys included in the study as of day 7-14. No increase in the level of ADA response was observed with the higher dose of TA-Fc-ABDEG-Alb23 with this method. Noticeably, the highest ADA signal was detected in monkey G1-3 on day 14 as compared to the other monkeys in the 30 mg/kg dose group. Monkey G2-2 showed the earliest detected response among all animals in this study with ADA already on day 7 post-injection.

TABLE S8-continued

Summary of the observed albumin levels as measured with BCG assay in 96-well plate format

| Group | Fc-ABDEG-Alb23, dose | Animal ID | Albumin $C_{min}$, % | Albumin $T_{min}$, days |
|---|---|---|---|---|
| 2 | 75 mg/kg i.v. | G2-1 | 72 | 21 |
|   |   | G2-2 | 82 | 17 |
|   |   | G2-3 | 84 | 17 |

In Table S8, G1-1, G1-2, and G1-3, and G2-1, G2-2, and G2-3 were dosed with TA-Fc-ABDEG-Alb23 at 30 or 75 mg/kg doses, respectively. Albumin $C_{min}$ shows a minimum level of serum albumin detected in an individual monkey post TA-Fc-ABDEG-Alb23 administration, presented as percentage to pre-dose (00 to day 0 −5 min). Albumin $T_{min}$ shows a day of the study when albumin $C_{min}$ was observed.

TABLE S9

Comparison of the results from BCG assay in two different formats: 96-well plate and bioanalyzer

| | 96-well plate, mg/ml | | | | | | Bioanalyzer, mg/ml | | | | | |
|---|---|---|---|---|---|---|---|---|---|---|---|---|
| Monkeys | Day −7 | −5 min | 6 h | Day 1 | Day 14 | Day 27 | Day −7 | −5 min | 6 h | Day 1 | Day 14 | Day 27 |
| G1-1 | 36.3 | 36.7 | 35.1 | 34.6 | 30.1 | 34.1 | 45.6 | 45.9 | 45.6 | 43.4 | 38.1 | 39.6 |
| G1-2 | 32.6 | 28.2 | 31.6 | 30.4 | 28.8 | 27.9 | 43.2 | 43.2 | 43.9 | 42.2 | 39.6 | 39.2 |
| G1-3 | 32.7 | 34.6 | 32.0 | 32.7 | 24.4 | 23.3 | 41.6 | 40.8 | 40.4 | 40.4 | 32.5 | 32.0 |
| G2-1 | 41.3 | 39.6 | 40.7 | 37.4 | 31.8 | 32.2 | 46.7 | 43.3 | 45.1 | 43.3 | 35.6 | 38.9 |
| G2-2 | 31.6 | 33.3 | 34.7 | 34.0 | 29.4 | 33.0 | 39.7 | 34.8 | 38.0 | 36.3 | 32.0 | 34.5 |
| G2-3 | 37.4 | 35.8 | 38.0 | 37.8 | 32.1 | 35.0 | 43.5 | 43.8 | 43.4 | 42.2 | 37.3 | 40.5 |

In Table S9, absolute concentrations (mg/mL) at pre-dose (day −7, day 0 −5 min) and post-dose (day 0 6 h, day 1, day 14, day 27) are shown as measured using both techniques, 96-well plate or bioanalyzer. On Day 14, maximal reduction of albumin was detected among the time points used in blood biochemistry panel (bioanalyzer).

TABLE S10

Comparison of the results from BCG assay in two different formats: 96-well plate and bioanalyzer

| | 96-well plate, % | | | | | | Bioanalyzer, % | | | | | |
|---|---|---|---|---|---|---|---|---|---|---|---|---|
| Monkeys | Day −7 | −5 min | 6 h | Day 1 | Day 14 | Day 27 | Day −7 | −5 min | 6 h | Day 1 | Day 14 | Day 27 |
| G1-1 | 98.9 | 100.0 | 95.7 | 94.4 | 82.0 | 92.8 | 99.3 | 100.0 | 99.3 | 94.6 | 83.0 | 86.3 |
| G1-2 | 115.3 | 100.0 | 111.9 | 107.6 | 101.9 | 98.7 | 100.0 | 100.0 | 101.6 | 97.7 | 91.7 | 90.7 |
| G1-3 | 94.5 | 100.0 | 92.7 | 94.7 | 70.7 | 67.3 | 102.0 | 100.0 | 99.0 | 99.0 | 79.7 | 78.4 |
| G2-1 | 104.4 | 100.0 | 102.8 | 94.7 | 80.4 | 81.4 | 107.9 | 100.0 | 104.2 | 100.0 | 82.2 | 89.8 |
| G2-2 | 95.0 | 100.0 | 104.4 | 102.1 | 88.4 | 99.0 | 114.1 | 100.0 | 109.2 | 104.3 | 92.0 | 99.1 |
| G2-3 | 104.3 | 100.0 | 106.0 | 105.6 | 89.5 | 97.8 | 99.3 | 100.0 | 99.1 | 96.3 | 85.2 | 92.5 |

In Table S10, percent to pre-dose (day 0 −5 min) is shown for pre-dose (day −7, day 0 −5 min) and post-dose (day 0 6 h, day 1, day 14, day 27) time points measured using both techniques, 96-well plate or bioanalyzer. On Day 14 maximal reduction of albumin was detected among the time points used in blood biochemistry panel (bioanalyzer).

The aim of the study was to evaluate PD effects on clearance of total serum IgG and PK of a single dose of TA-Fc-ABDEG-Alb23 (30 or 75 mg/kg) in cynomolgus monkeys, as well as to exploratory evaluate its safety and tolerability. TA-Fc-ABDEG-Alb23, fused on its C-terminus with two albumin binding Alb23 VHH fragments demonstrated a pronounced PD effect on clearance of total circulating IgG, in contrast to the previously evaluated TA-Alb23-Fc-ABDEG (two Alb23 placed on the N-terminus of Fc-ABDEG). No improved PD effect in terms of the depth and duration of IgG clearance was observed with the higher dose of TA-Fc-ABDEG-Alb23.

In terms of PK, a dose-related increase in $C_{max}$ and exposure was demonstrated by TA-Fc-ABDEG-Alb23; $C_{max}$ and $AUC_{(0-10)}$ both increased with dose in a dose proportional manner. Measured values for $C_{max}$ were in good agreement with calculated $C_{max}$ values for cynomolgus macaques. A mean terminal half-life of approximately 10 days was found for both doses, which is appreciably longer than the half-life of efgartigimod in cynomolgus monkeys (1-2 days or 16-44 hours). High variability in the PK profiles of TA-Fc-ABDEG-Alb23 by day 14 is probably related to ADA. All animals were shown to be ADA-positive when profiles started deviating, making it difficult to determine a true elimination rate of TA-Fc-ABDEG-Alb23.

The decrease in serum albumin was observed in all the monkeys in this study, independently of the treatment dose, with the maximum effects being ~20-30% decrease from baseline. Some variations in the results were observed when different formats of the BCG assay were used. Nevertheless, the main trends in the decline of albumin were conserved in this study.

Example 3: Generation of pH-Dependent Anti-Albumin VHH Fragments

Previous experiments explored the pharmacodynamics and pharmacokinetics of two-armed Alb23 VHH at the N-terminus or C-terminus of Fc-ABDEG. Generation and characterization of pH-dependent anti-albumin VHH fragments are described here.

Briefly, two llamas were immunized with human and mouse serum albumin and phage display libraries were generated (VHH/scFv). Selection was performed with phage binding at pH 5.5 and elution at pH 7.4 (trypsin as control) with HSA and MSA. Screening was conducted by ELISA/Biacore and Biacore (human, mouse, and cynomolgus monkey serum albumin).

One clone, 2H11, showed good pH-dependency, no cross-reactivity with mouse and cynomolgus serum albumin, does not bind to isolated DII, and does not compete with Alb23. 2H11 was subjected to alanine scanning of all three CDRs. The resulting variant VHH fragments were produced as two-armed Fc-ABDEG-20GS-Cterm fusions and analyzed by FcRn ELISA QC; Biacore (3000) with human, cynomolgus, and mouse albumin on chip (selection criteria: binding at pH 5.5 remains, binding at pH 7.4 reduced); and Biacore T200 with Fc-ABDEG-VHH on chip (selection criteria: lowest affinity at pH 7.4, highest at pH 5.5).

Mutations in the CDR3 region of 2H11 increased pH-dependency via reducing binding at pH 7.4 while maintaining good binding at pH 5.5. 2H11 binding to HSA was also affected by CDR3 alanine scanning; a panel of variants displaying different binding at pH 7.4 vs. pH 5.5 was identified.

Data from selected 2H11 variants is provided in Table S11.

TABLE S11

Analysis of 2H11 variants fused at the C-terminus of Fc-ABDEG with albumin on a chip (Biacore 3000)

| | HSA | | | | |
|---|---|---|---|---|---|
| Clone | Kd pH5.5, 1/s | R0 pH5.5, RU | Kd pH 7.4, 1/s | R0 pH7.4, RU | R0 5.5/7.4 |
| 2H11 parental | 1.60E−04 | 351 | 7.2E−04 | 115 | 3 |
| 2H11-v15 | 1.74E−03 | 235 | 2.5E−03 | 0.635 | 370 |
| 2H11-v3 | 1.35E−04 | 164 | 2.9E−03 | 8.24 | 19.9 |
| 2H11-v12 | 9.72E−05 | 93.9 | 1.2E−03 | 6.32 | 14.9 |
| 2H11-v9 | 0.0389* | 77.9 | 1.1E−02* | 0.26 | 300 |
| 2H11-v16 | 3.01E−03 | 8.91 | 1.93E−03 | 0.571 | 16 |
| 2H11-v8 | 1.39E−03 | 1.16 | NA | 0.57 | 2 |

*Difference in off-rate noted.

Sequences for the 2H11 parent VHH fragment and select variants, as well as Alb23 VHH fragment, are provided below in Tables S12 and S13.

TABLE S12

CDR sequences of VHH fragments binding to albumin

| Clone | CDR1 | SEQ ID NO. | CDR2 | SEQ ID NO. | CDR3 | SEQ ID NO. |
|---|---|---|---|---|---|---|
| 2H11 parental | SNTMG | 75 | AITWSGGTTYYADSVKG | 76 | EGPKWEPWNGIYHPADFGS | 77 |
| 2H11-v9 | SNTMG | 75 | AITWSGGTTYYADSVKG | 76 | EGPKWEPWAGIYHPADFGS | 78 |
| 2H11-v8 | SNTMG | 75 | AITWSGGTTYYADSVKG | 76 | EGPKWEPANGIYHPADFGS | 79 |
| 2H11-v15 | SNTMG | 75 | AITWSGGTTYYADSVKG | 76 | EGPKWEPWNGIYHPAAFGS | 80 |
| 2H11-v3 | SNTMG | 75 | AITWSGGTTYYADSVKG | 76 | EGAKWEPWNGIYHPADFGS | 81 |
| 2H11-v12 | SNTMG | 75 | AITWSGGTTYYADSVKG | 76 | EGPKWEPWNGIAHPADFGS | 82 |
| 2H11-v16 | SNTMG | 75 | AITWSGGTTYYADSVKG | 76 | EGPKWEPWNGIYHPADAGS | 83 |
| Alb23 | SFGMS | 10 | SISGSGSDTLYADSVKG | 11 | GGSLSR | 12 |

TABLE S13

Albumin-binding VHH fragment sequences

| Clone | VHH | SEQ ID NO. |
|---|---|---|
| 2H11 parental | ELQVVESGGGLVQAGGSLRLSCAASGRTFRSNTMGWFRQAPGKEREFVAAITWSGGTTYYADSVKGRFAISGDNAKNTVYLQMNSLKPEDTAVYYCAAEGPKWEPWNGIYHPADFGSWGQGTQVTVSS | 84 |
| 2H11-v9 | ELQVVESGGGLVQAGGSLRLSCAASGRTFRSNTMGWFRQAPGKEREFVAAITWSGGTTYYADSVKGRFAISGDNAKNTVYLQMNSLKPEDTAVYYCAAEGPKWEPWAGIYHPADFGSWGQGTQVTVSS | 85 |
| 2H11-v8 | ELQVVESGGGLVQAGGSLRLSCAASGRTFRSNTMGWFRQAPGKEREFVAAITWSGGTTYYADSVKGRFAISGDNAKNTVYLQMNSLKPEDTAVYYCAAEGPKWEPANGIYHPADFGSWGQGTQVTVSS | 86 |

TABLE S13-continued

Albumin-binding VHH fragment sequences

| Clone | VHH | SEQ ID NO. |
|---|---|---|
| 2H11-v15 | ELQVVESGGGLVQAGGSLRLSCAASGRTFRSNTMGWFRQAPGKEREFVAAITWSGGTTYYADS VKGRFAISGDNAKNTVYLQMNSLKPEDTAVYYCAAEGPKWEPWNGIYHPAAFGSWGQGTQVT VSS | 87 |
| 2H11-v3 | ELQVVESGGGLVQAGGSLRLSCAASGRTFRSNTMGWFRQAPGKEREFVAAITWSGGTTYYADS VKGRFAISGDNAKNTVYLQMNSLKPEDTAVYYCAAEGAKWEPWNGIYHPADFGSWGQGTQVT VSS | 88 |
| 2H11-v12 | ELQVVESGGGLVQAGGSLRLSCAASGRTFRSNTMGWFRQAPGKEREFVAAITWSGGTTYYADS VKGRFAISGDNAKNTVYLQMNSLKPEDTAVYYCAAEGPKWEPWNGIAHPADFGSWGQGTQVT VSS | 89 |
| 2H11-v16 | ELQVVESGGGLVQAGGSLRLSCAASGRTFRSNTMGWFRQAPGKEREFVAAITWSGGTTYYADS VKGRFAISGDNAKNTVYLQMNSLKPEDTAVYYCAAEGPKWEPWNGIYHPADAGSWGQGTQVT VSS | 90 |
| Alb23 | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGSLSRSSQGTLVTVSS | 42 |

Example 4: Evaluation of Different GS-Linker Lengths in Fc-ABDEG-Alb23 Molecules Previous experiments illustrated the improvement in pharmacodynamics by placing two VHH fragments at the C-terminus of Fc-ABDEG instead of the N-terminus. The current study was conducted to evaluate the effect if a linker between the Fc-ABDEG and the C-terminal anti-HSA VHH fragment is required to obtain a functional molecule. A list of the different ABDEG-based molecules tested is provided below in Table S14.

TABLE S14

ABDEG-based molecules used in this study

| Full name | Description |
|---|---|
| TA-Fc-ABDEG-Alb23 | Two Alb23 VHH fragments fused via 20 GS linker to C-terminus of Fc-ABDEG |
| TA-Fc-ABDEG-Alb23 (mod) | Two Alb23 VHH fragments fused via 20 GS linker to C-terminus of Fc-ABDEG containing functionally neutral point mutation |
| TA-Fc-ABDEG-0GS-Alb23 (mod) | Two Alb23 VHH fragments fused directly (no linker) to C-terminus of Fc-ABDEG containing functionally neutral point mutation |

Methods

Briefly, a total of 16 (male (12) and female (4)) AlbuMus mice at approximately 15 weeks were randomly assigned into 4 groups. AlbuMus mice are double-humanized for serum albumin/neonatal Fc receptor mouse model (hFcRn+/+, hAlb+/+). Fcgrt and hAlb are knocked-in and expressed under the endogenous mouse promotor. Mice were single-dosed IP with human IgG (tracer IgG) prior to administration of test items. On day 0, mice were injected IV (200 µL injection volume, reference weight 30 g) according to the designated group and doses in Table S15. 30 mg/kg doses for TA-Fc-ABDEG-Alb23 (mod), TA-Fc-ABDEG-Alb23 and TA-Fc-ABDEG-0GS-Alb23 (mod) were selected based on MW of the test items (~75 kDa).

All animals were pre-weighed before dosing and dosed according to their body weights. Blood samples were collected before dosing of the test article (pre-dose, d0, −1 h) and after treatment for PD, PK, ADA and albumin read-outs during 14 days (see Table S15) (for all timepoints). Blood samples were processed to serum and added to a 96-well plate (polypropylene) per group.

TABLE S15

Groups and dosing regimen

| Group | N | Test Article | Dose, mg/kg | Administration route | Blood sampling times |
|---|---|---|---|---|---|
| A | 4 | PBS | — | IV, single dose | −1 h, 5 min, 1 d, 2 d, 3 d, 4 d, 7 d, 9 d, 14 d |
| B | 4 | TA-Fc-ABDEG-Alb23 (mod) | 30 | IV, single dose | −1 h, 5 min, 1 d, 2 d, 3 d, 4 d, 7 d, 9 d, 14 d |
| C | 4 | TA-Fc-ABDEG-Alb23 | 30 | IV, single dose | −1 h, 5 min, 1 d, 2 d, 3 d, 4 d, 7 d, 9 d, 14 d |
| D | 4 | TA-Fc-ABDEG-0GS-Alb23 (mod) | 30 | IV, single dose | −1 h, 5 min, 1 d, 2 d, 3 d, 4 d, 7 d, 9 d, 14 d |

Mice were injected with tracer IgGs and hIVIg prior to administration of test items to reconstitute IgG levels. On day 0, mice were injected with test articles according to the designated group and followed up over the course of 14 days.

Tracer IgG serum levels were determined using a sandwich ELISA. A Nunc MaxiSorp F-bottom plate (Thermo Fisher Scientific, Cat. 44-24004-21) was coated overnight (4° C.) with a specific antigen for the tracer IgG and non-specific binding sites were blocked with 1% casein-PBS (Bio-Rad, Cat. #1610783). Study serum samples were diluted 1/100 and 1/4000 (depending on time post-injection) and incubated on the immunoplate together with a fresh 11-point hIgG1 (Evitria ##32101.1—SEC) calibration curve and 3 quality control (QC) samples (HQC, MQC, LQC) for 1 hour. IgG tracer was bound and detected for 1 hour by a goat anti-hIgG, Fc-specific (abcam #98595). The plate was developed by adding 3,3',5,5'-tetramethylbenzidine (TMB) substrate for approximately 7 minutes. The enzymatic reaction was stopped with sulfuric acid ($H_2SO_4$) and optical density values at 450 nm were recorded using a Tecan plate reader. For data analysis, the obtained values were back-calculated on a 11-point calibrator curve in GraphPad Prism (log (agonist) vs. response—Variable slope (four parameters), Least squares fit). Tracer IgG concentrations were plotted in absolute values measured (µg/mL) and percentage to pre-dose (1 h prior to test article injection, day 0, -1 h).

Human IgG serum levels were determined using a sandwich ELISA. A Nunc MaxiSorp F-bottom plate (Thermo Fisher Scientific, Cat. 44-24004-21) was coated overnight (4° C.) with mouse anti-human lambda light chain (Sigma-Aldrich L6522, clone HP-6054) and non-specific binding sites are blocked with 1% casein-PBS (Bio-Rad, Cat. #1610783). Study serum samples were diluted 1/5000 and 1/1000 (depending on time post-injection) and incubated on the immunoplate together with a fresh 11-point hIgG (IVIg, CSL Behring (Privigen Lot. P100071321)) calibration curve and 3 quality control (QC) samples (HQC, MQC, LQC) for 1 hour. hIgG were bound and detected for 1 hour by a goat anti-human IgG, Fc-specific (abcam #98595). The plate was developed by adding 3,3',5,5'-tetramethylbenzidine (TMB) substrate for approximately 9 minutes. The enzymatic reaction was stopped with sulfuric acid ($H_2SO_4$) and optical density values at 450 nm were recorded using a Tecan plate reader. For data analysis, the obtained values were back-calculated on a 11-point calibrator curve in GraphPad Prism (log(agonist) vs. response—Variable slope (four parameters), Least squares fit). hIgG were plotted in absolute values measured (µg/mL) and percentage to pre-dose (1 h prior to test article injection, day 0, -1 h).

Concentrations of ABDEG-based molecules, comprising TA-Fc-ABDEG-Alb23, TA-Fc-ABDEG-Alb23 (mod) and TA-Fc-ABDEG-0GS-Alb23 (mod), were determined using a sandwich ELISA method. Briefly, Nunc MaxiSorp F-bottom plates (Thermo Fisher Scientific, Cat. 44-24004-21) were coated overnight (4° C.) with neutravidin (Thermo Fisher Scientific, Lot VI312512) and nonspecific binding sites were blocked with 1% casein-PBS (G Biosciences, Part #097B, Lot #210104). anti-ABDEG-biotin (10× molar excess) was captured for 1 hour. Next, 100% study serum samples were diluted to the concentration range of quantitation or at least the minimum required dilution (MRD). The calibration curve and quality control (QC) samples (HQC, MQC and LQC) with ABDEG-based drug molecules were spiked in 100% AlbuMus serum and pre-incubated for 30 min. at room temperature RT before applying MRD 100. Samples were incubated on the immunoplate together with a fresh calibration curve and two sets of QC samples (HQC, MQC and LQC) for 2 hours. ABDEG-based drug molecules were detected by the subsequent addition of goat anti-Human IgG-Fc (HRP) (Abcam #ab98595, Lot GR3345397-1) for 1 hour. Plates were developed by adding TMB substrate for approximately 20 minutes. The enzymatic reaction was stopped with 0.5M $H_2SO_4$ and optical density values at 450 nm were recorded using a Tecan plate reader. For data analysis, the obtained values were back-calculated on a 11-point calibrator curve in GraphPad Prism (Nonlinear regression; Asymmetric Sigmoidal, 5PL, X is concentration). Concentrations were plotted in absolute values measured (µg/mL) for each tested molecule.

Immune response against the test items was measured by using a sandwich ELISA. TA-Fc-ABDEG-Alb23 (mod), TA-Fc-ABDEG-0GS-Alb23 (mod), and TA-Fc-ABDEG-Alb23 were coated at 1 µg/mL on a 96-well immunoplate and non-specific binding sites were blocked. A 1/100 dilution of mouse serum (pre-dose and post-dose serum samples) was applied. Samples were incubated for 1 h and detected by an HRP-conjugated goat anti-mouse Fab2 (HRP Peroxidase AffiniPure F(ab')2 Fragment Goat Anti-Mouse IgG, F(ab')2 Fragment Specific, Jackson ImmunoResearch, Cat. 115-036-072) for 1 h on a shaking incubator. The signal was developed by adding TMB substrate for 7 minutes. The enzymatic reaction was stopped with $H_2SO_4$ and optical density values at 450 nm were recorded using a Tecan plate reader.

Albumin levels in serum samples were assessed by using a sandwich ELISA. Ninety-six-well ELISA plates were coated with 1.0 µg/mL of Goat anti-Human Albumin (Sigma, A1151) and incubated O/N at 4° C. Non-specific binding sites were blocked with 1×PBS with 1% (w/v) casein for 1 h at room temperature. Study serum samples were diluted 1/1,000,000 and incubated on the immunoplate together with a fresh 11-point HSA (Sigma-A3782) calibration curve and 3 quality control (QC) samples (HQC, MQC, LQC) for 1 hour. Bound HSA was detected using an RP-conjugated polyclonal goat anti-HSA antibody (Bethyl, A80-129P). ELISAs were developed by adding 100 µL of TMB substrate and the enzymatic reaction was stopped with $H_2SO_4$. Optical density values at 450 nm were recorded using a Tecan plate reader. For data analysis, the obtained values were back-calculated on an 11-point calibrator curve in GraphPad Prism (log(agonist) vs. response—Variable slope (four parameters), Least squares fit). Albumin concentrations were plotted in absolute values measured (µg/mL) and percentage to pre-dose (1 h prior to test article injection, day 0, -1 h).

Results

Figure 10A:
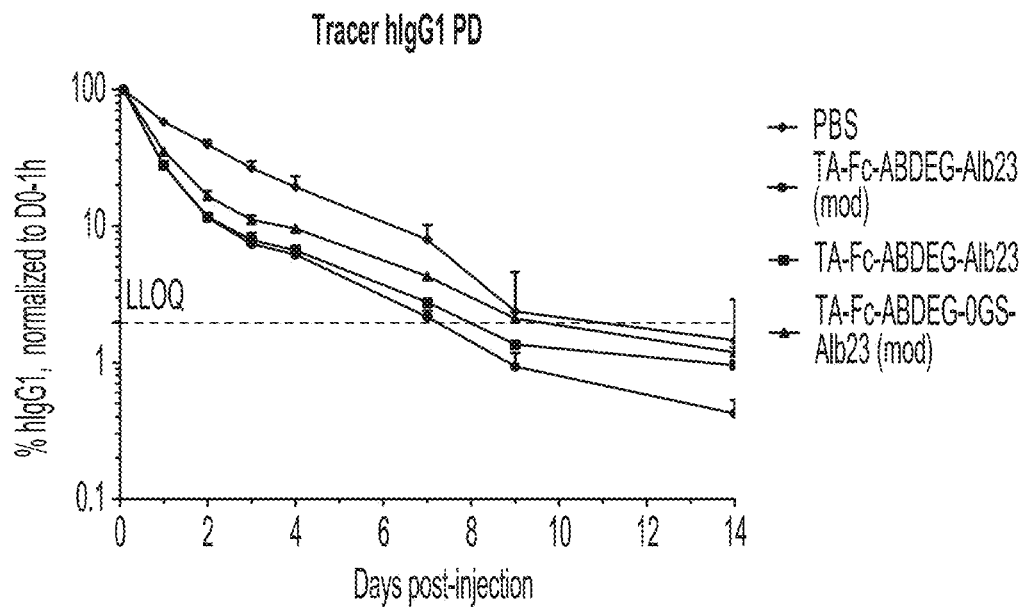
FIGS. 10A-10B show normalized tracer IgG1 after a single IV administration of TA-Fc-ABDEG molecules with an anti-HSA VHH fragment fused at the C-termini of both Fc domains with or without a 20GS linker (TA-Fc-ABDEG-Alb23, TA-Fc-ABDEG-Alb23 (mod), and TA-Fc-ABDEG-0GS-Alb23 (mod); see Table S15 for description of constructs) at a dose of 30 mg/kg in AlbuMus mice.

To assess the efficacy of the three tested ABDEG-equipped drugs to deplete IgG, the PD effect over time was measured. The measured tracer IgG concentrations were plotted as percentage to pre-dose at 1 h prior to test article injection (d0, -1 h) per treatment group (FIG. 10A). Two mice and 1 mouse from groups injected with TA-Fc-ABDEG-Alb23 and TA-Fc-ABDEG-0GS-Alb23 (mod) respectively, were excluded due to poor injection quality. A clear ABDEG effect was observed for all test articles compared to the PBS control group starting at day 1. Overall, TA-Fc-ABDEG-0GS-Alb23 (mod) shows a less robust PD effect compared to its 20GS counterpart and TA-Fc-ABDEG-Alb23. TA-Fc-ABDEG-Alb23 (mod) and TA-Fc-ABDEG-Alb23 show a similar IgG depletion efficacy. Measured levels of tracer IgG were below the LLOQ of the ELISA read-out starting day 7, by which accurate read-out is no longer ensured.

Figure 10B:
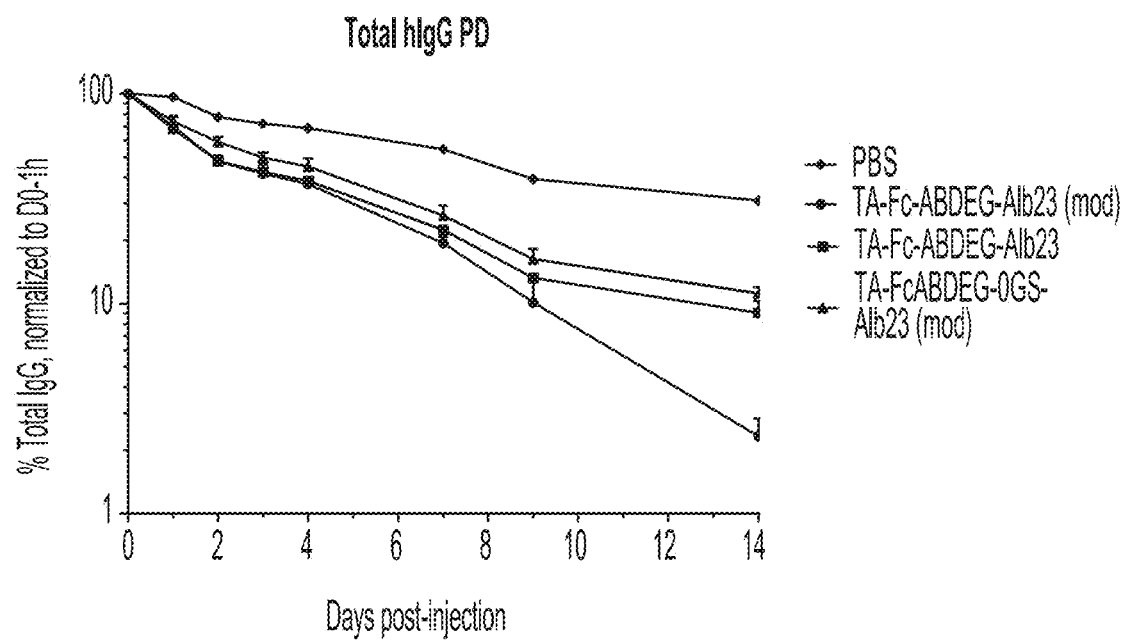

To assess the efficacy of the three tested ABDEG-equipped drugs to deplete IgG, the PD effect over time was measured by a second tracer antibody (hIVIg). The measured concentrations were plotted as percentage to pre-dose at 1 h prior to test article injection (d0, −1 h) per treatment group (FIG. 10B). As above, 2 mice and 1 mouse from groups injected with TA-Fc-ABDEG-Alb23 and TA-Fc-ABDEG-0GS-Alb23 (mod), respectively, were excluded due to poor injection quality. The total serum IgG tracer read-out confirms all conclusions on hIgG1 tracer PD effect: indication of slightly worse PD effect observed for TA-Fc-ABDEG-0GS-Alb23 (mod) and similar IgG depletion by TA-Fc-ABDEG-Alb23 (mod) and TA-Fc-ABDEG-Alb23.

Figure 11:
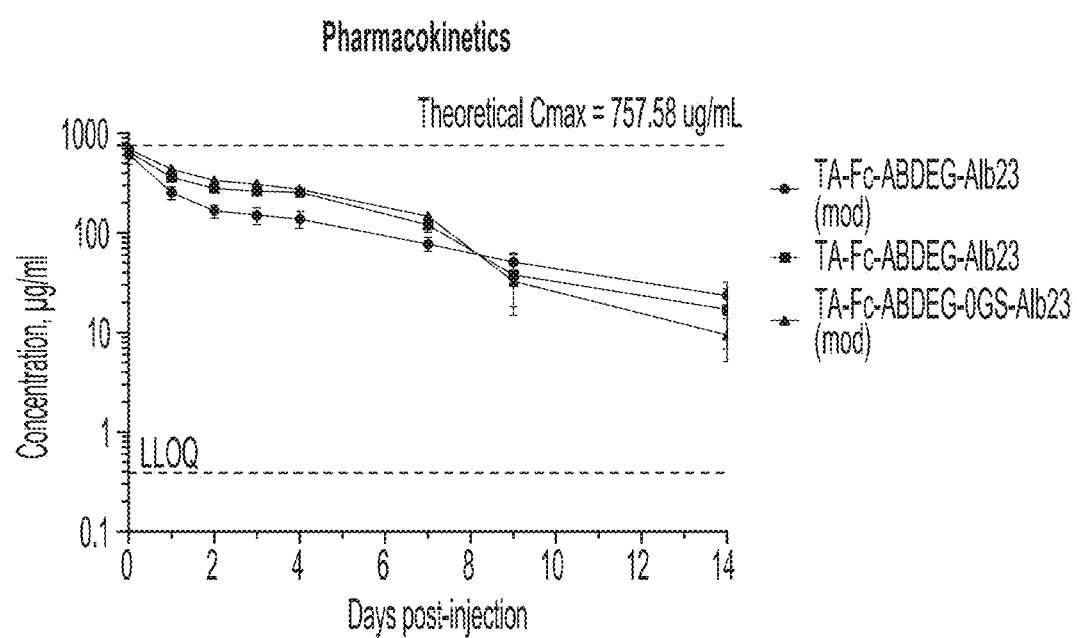
FIG. 11 shows serum PK of TA-Fc-ABDEG-Alb23 (mod), TA-Fc-ABDEG-Alb23, and TA-Fc-ABDEG-0GS-Alb23 (mod) after a single IV injection. Three groups of AlbuMus mice received a single 30 mg/kg dose of either TA-Fc-ABDEG-Alb23 (mod), TA-Fc-ABDEG-Alb23, or TA-Fc-ABDEG-0GS-Alb23 (mod). Serum concentrations of the test items were plotted as an average per group over time during the course of the study. The datapoints show the mean±SEM of 4 animals per group.
Figure 12:
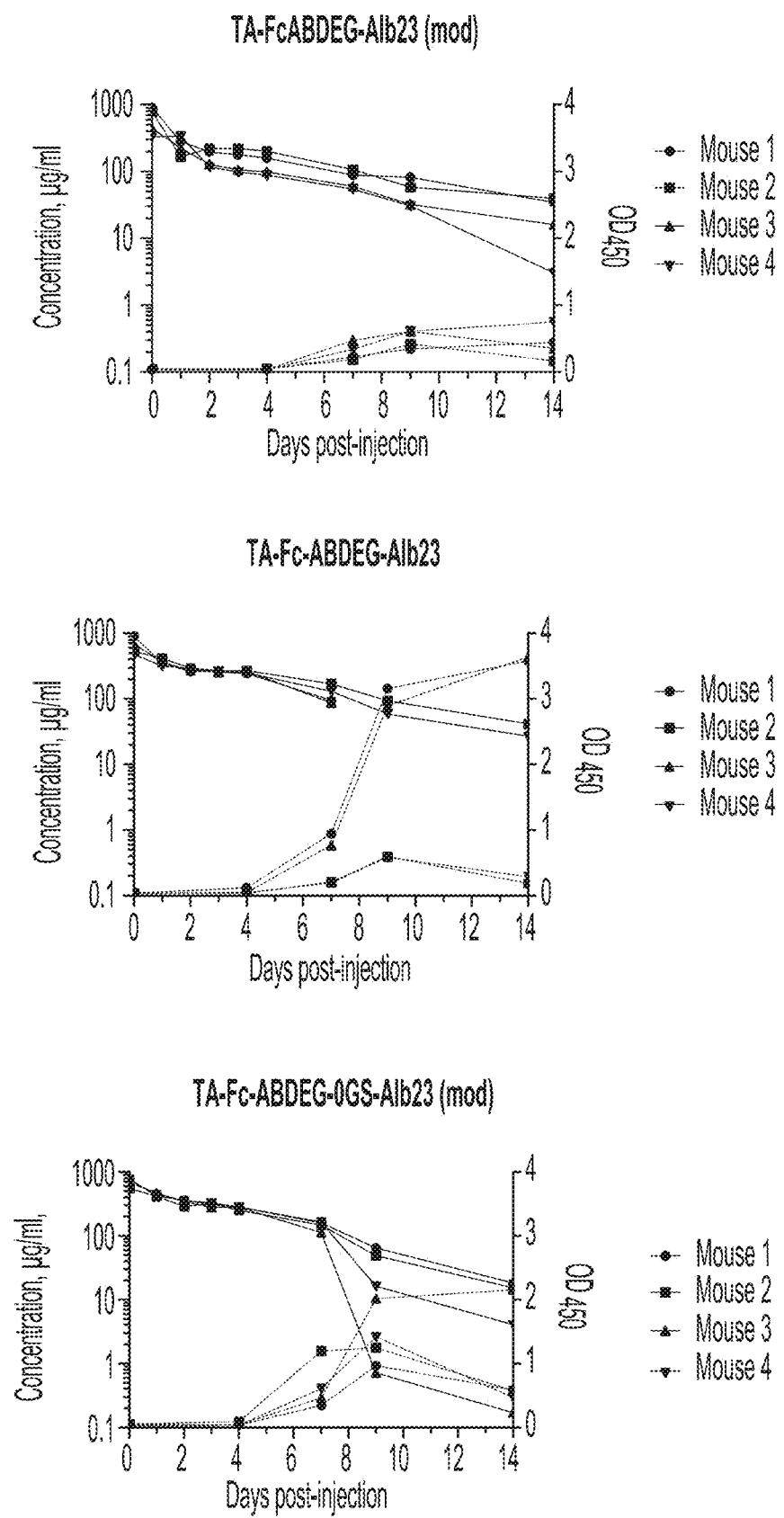
FIG. 12 shows ADA response after single IV injection of TA-Fc-ABDEG-Alb23 (mod), TA-Fc-ABDEG-Alb23, or TA-Fc-ABDEG-0GS-Alb23 (mod) in individual AlbuMus mice. On day 0, mice received TA-Fc-ABDEG-Alb23 (mod) (30 mg/kg), TA-Fc-ABDEG-Alb23 (30 mg/kg) or TA-Fc-ABDEG-0GS-Alb23 (mod) (30 mg/kg). ADA response (OD450, right Y-axis) was overlayed with the PK profiles (µg/mL, left Y-axis) per mouse, per group over time (days post-injection, X-axis). Each datapoint (PK and ADA) represents the mean of a study sample analyzed in duplicates (technical replicates).

To evaluate the PK profile of the test items after a single IV administration, their levels in mouse serum were determined post-dose according to the bleeding scheme in Table S15. The obtained values were plotted in μg/mL. No clear differences were observed in PK profile between TA-Fc-ABDEG-Alb23 and TA-Fc-ABDEG-0GS-Alb23 (mod). Starting day 7, a non-linear PK profile was observed, which points to an immunogenic response toward the human ABDEG injected at day 0. A seemingly faster and deeper drop was measured for TA-Fc-ABDEG-Alb23 (mod) at day 1, after which the PK profile is very similar to TA-Fc-ABDEG-Alb23 and TA-Fc-ABDEG-0GS-Alb23 (mod). For this test article, no interference of ADA on the PK profile was observed (FIG. 11). An overview of the influence of ADA development on PK profile of individual mice can be found in FIG. 12. Overall, no clear correlation was found between measured PD effect and serum half-life. For all tested molecules, concentrations were quantifiable in the serum during the entire study (14 days). A total of three mice showed a relatively low captured $C_{max}$ at 5 min post-injection. Animals were not excluded from analysis since no influence was observed on mean serum concentration per molecule.

Figure 13:
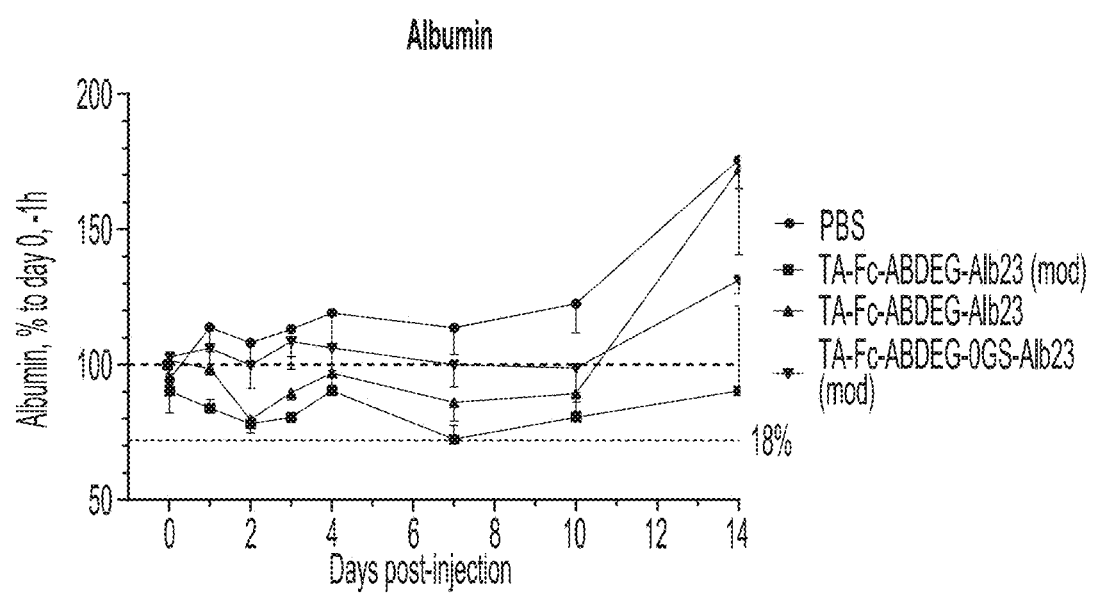
FIG. 13 shows normalized albumin levels (% pre-dose) after single IV injection of TA-Fc-ABDEG-Alb23 (mod) (30 mg/kg), TA-Fc-ABDEG-Alb23 (30 mg/kg), or TA-Fc-ABDEG-0GS-Alb23 (mod) (30 mg/kg) in AlbuMus mice. Albumin levels were plotted over time (days post-injection) as % relative to pre-dose (day 0, −1 h), averaged per group. The datapoints show the mean±SEM of 4 mice per group, per timepoint.

To evaluate a potential impact of TA-Fc-ABDEG-Alb23 (mod), TA-Fc-ABDEG-Alb23 and TA-Fc-ABDEG-0GS-Alb23 (mod) on albumin levels after the administration to AlbuMus mice, total human serum albumin levels were measured throughout the study at baseline (pre-dose) and post-dose according to the scheme in Table S15. Measured albumin concentrations were plotted as percentage to pre-dose (day 0, −1 h) prior test item administration (FIG. 13). No meaningful decreases in albumin levels were observed in control mice treated with PBS and TA-Fc-ABDEG-0GS-Alb23 (mod) (30 mg/kg) during the course of the study. Similar albumin decreases were observed in mice treated with TA-Fc-ABDEG-Alb23 (mod) (30 mg/kg) and TA-Fc-ABDEG-Alb23 (30 mg/kg). In more detail, serum albumin levels showed a maximal reduction of 18±5% to pre-dose at day 7 for the group injected with TA-Fc-ABDEG-Alb23 (mod). Albumin levels turned to baseline between day 10 and 14. An overshoot in albumin concentration was observed in all groups. Overall, the data indicates linker length might have an impact on albumin levels when comparing TA-Fc-ABDEG-Alb23 (mod) with TA-Fc-ABDEG-0GS-Alb23 (mod).

The aim of this study was to evaluate if a linker between Fc-ABDEG part and C-terminal anti-albumin VHH fragment is required for extended plasma half-life and efficient depletion of pre-loaded human IgG from circulation. PD and PK effects of ABDEG-Alb23 molecules with different linker lengths after single intravenous injection were tested in AlbuMus mice. A clear ABDEG effect was observed for all test articles compared to the PBS control group. PD effect mediated by TA-Fc-ABDEG-0GS-Alb23 (mod) at 30 mg/kg dose was less pronounced compared to TA-Fc-ABDEG-Alb23 (mod) and TA-Fc-ABDEG-Alb23. Development of ADA starting from day 7 was observed in this study. Albumin decreases were observed for TA-Fc-ABDEG-Alb23 (mod) and TA-Fc-ABDEG-Alb23, up to 18%, whereas no drop in albumin levels were noted for TA-Fc-ABDEG-0GS-Alb23 (mod). However, no major conclusions could be made due to a high variability in the albumin levels detected over time. Overall, no meaningful differences were observed between ABDEG-Alb23 molecules with different linker lengths with respect to PD effect and PK profile.

The impact of linker length between Fc-ABDEG and the C-terminal anti-albumin VHH fragment on function was further explored by measuring FcRn degradation using a cell-based assay in the presence or absence of albumin. Briefly, HEK FcRn WT GFP+ cells/well were seeded on a 96-well microplate overnight at 37° C. in growth medium (DMEM+10% FBS+P/S+L-glutamine). Fc-ABDEG-VHH molecules (500 nM) or anti-FcRn mAb1 (5 nM) were pre-incubated with 2000 nM human serum albumin (HSA) in a 1:4 ratio in treatment medium (DMEM+1% BSA+P/S+L-glutamine) for 30 minutes at 37° C., 5% $CO_2$ prior to adding to the cells. After incubation of the Fc-ABDEG-VHH/HSA mix or Fc-ABDEG-VHH with the cells, plates were then placed on ice and cells harvested by trypsin. Harvested cells were transferred to FACS plate and centrifuged. LD stain (1:800) was added in FACS buffer and incubated for 15 minutes at 4° C. Cells were washed, centrifuged, and resuspended in FACS buffer. GFP signal was measured and compared to untreated controls. An anti-FcRn mAb (anti-FcRn mAb1) comprising the light chain sequence of SEQ ID NO: 134 and the heavy chain sequence of SEQ ID NO: 135, which is known to decrease in albumin in patients, was included as a positive control.

Figure 14:
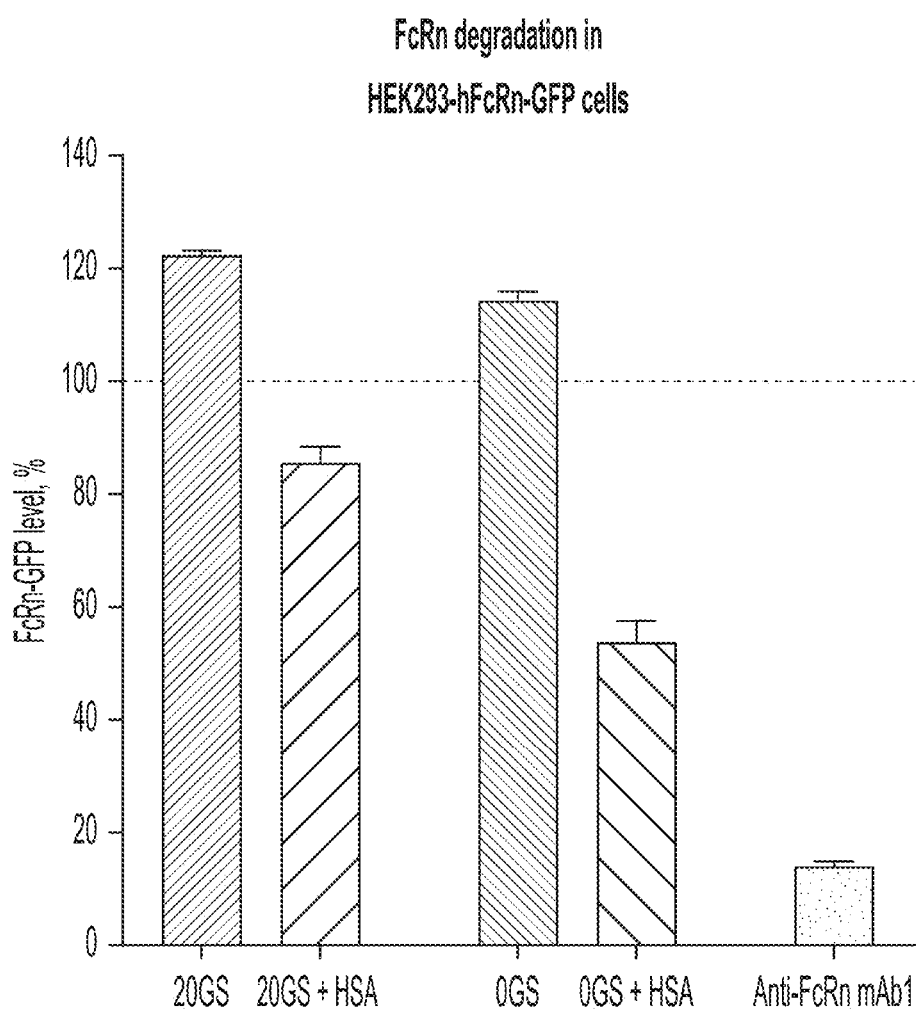
FIG. 14 shows the effect of linker length between the Fc-ABDEG and VHH fragments in a two-armed (TA)-Fc-ABDEG molecule with an albumin binding VHH fused at the C-termini of both Fc domains on FcRn degradation in HEK FcRn WT GFP+ cells in the presence or absence of human serum albumin (HSA). The presence of a 20GS linker in TA-Fc-ABDEG-Alb23 results in less FcRn degradation levels in vitro compared to TA-Fc-ABDEG-Alb23 with a 0GS linker (i.e., no linker). An anti-FcRn mAb known to increase FcRn degradation (anti-FcRn mAb1), was included as a positive control. Bars represent mean±SEM of two individual experiments each performed in two technical replicates.

Results are shown in FIG. 14, illustrating that the TA-Fc-ABDEG-0GS-Alb23 significantly increased FcRn degradation in the presence of HSA. This effect was ameliorated by inclusion of a 20GS linker between the Fc-ABDEG and Alb23 VHH fragments.

Example 5: In Vitro Characterization of OA-Fc-ABDEG-VHH Molecules

Figure 15:
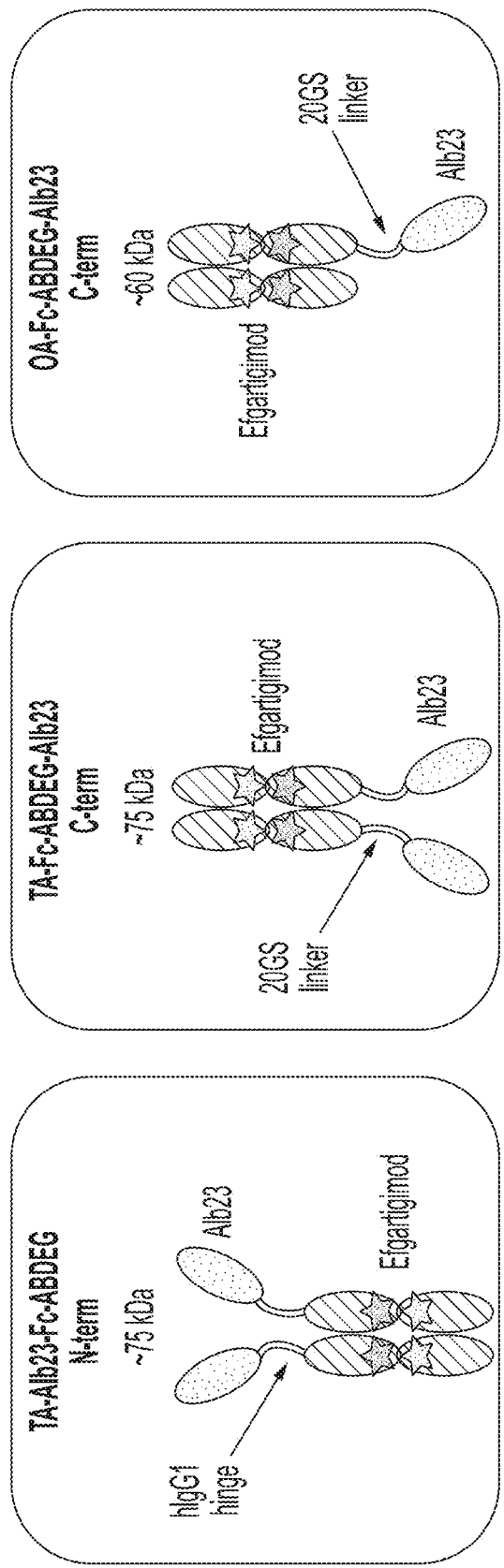
FIG. 15 shows schematics of representative two-armed and one-armed albumin binding VHH Fc-ABDEG molecules according to the invention.

Previous experiments illustrated the improvement in pharmacodynamics by placing two VHH fragments at the C-terminus of Fc-ABDEG instead of the N-terminus. However, the two-armed C-terminal VEG-Fc-ABDEG molecule (TA-Fc-ABDEG-Alb23) reduced serum albumin levels by about 20-30% when administered to cynomolgus monkeys (Example 2). One hypothesis is that the serum albumin decrease is due to crosslinking of FcRn. To explore this possibility, one-armed Fc-ABDEG-V2H molecules were developed to reduce valency and thus crosslinking. Such molecules could also reduce steric hindrance. The current experiment was conducted to compare in vitro characteristics of one-armed Fc-ABDEG-VHH molecules to two-armed Fc-ABDEG-VHH molecules. A list of the different ABDEG-based molecules tested is provided below in Table S16 and schematics of representative molecules are shown in FIG. 15.

TABLE S16

ABDEG-based molecules used in this study

| Full name | Description |
|---|---|
| TA-Fc-ABDEG-Alb23 | Two Alb23 VHH fragments fused via 20GS linker to C-terminus of Fc-ABDEG |
| OA-Fc-ABDEG-Alb23 | One Alb23 VHH fragment fused via 20GS linker to C-terminus of Fc-ABDEG |
| TA-Fc-ABDEG-2H11 | Two 2H11 VHH fragments fused via 20GS linker to C-terminus of Fc-ABDEG |
| OA-Fc-ABDEG-2H11 | One 2H11 VHH fragment fused via 20GS linker to C-terminus of Fc-ABDEG |
| TA-Fc-ABDEG-2H11v8 | Two 2H11-CDR3v8 VHH fragments fused via 20GS linker to C-terminus of Fc-ABDEG |
| OA-Fc-ABDEG-2H11v8 | One 2H11-CDR3v8 VHH fragment fused via 20GS linker to C-terminus of Fc-ABDEG |
| TA-Fc-ABDEG-2H11v9 | Two 2H11-CDR3v9 VHH fragments fused via 20GS linker to C-terminus of Fc-ABDEG |
| OA-Fc-ABDEG-2H11v9 | One 2H11-CDR3v9 VHH fragment fused via 20GS linker to C-terminus of Fc-ABDEG |
| TA-Alb23-Fc-ABDEG | Two Alb23 VHH fragments fused via a natural human IgG1 hinge to N-terminus of Fc-ABDEG |
| OA-Alb23-Fc-ABDEG | One Alb23 VHH fragment fused via a natural human IgG1 hinge to N-terminus of Fc-ABDEG |

Figure 16A:
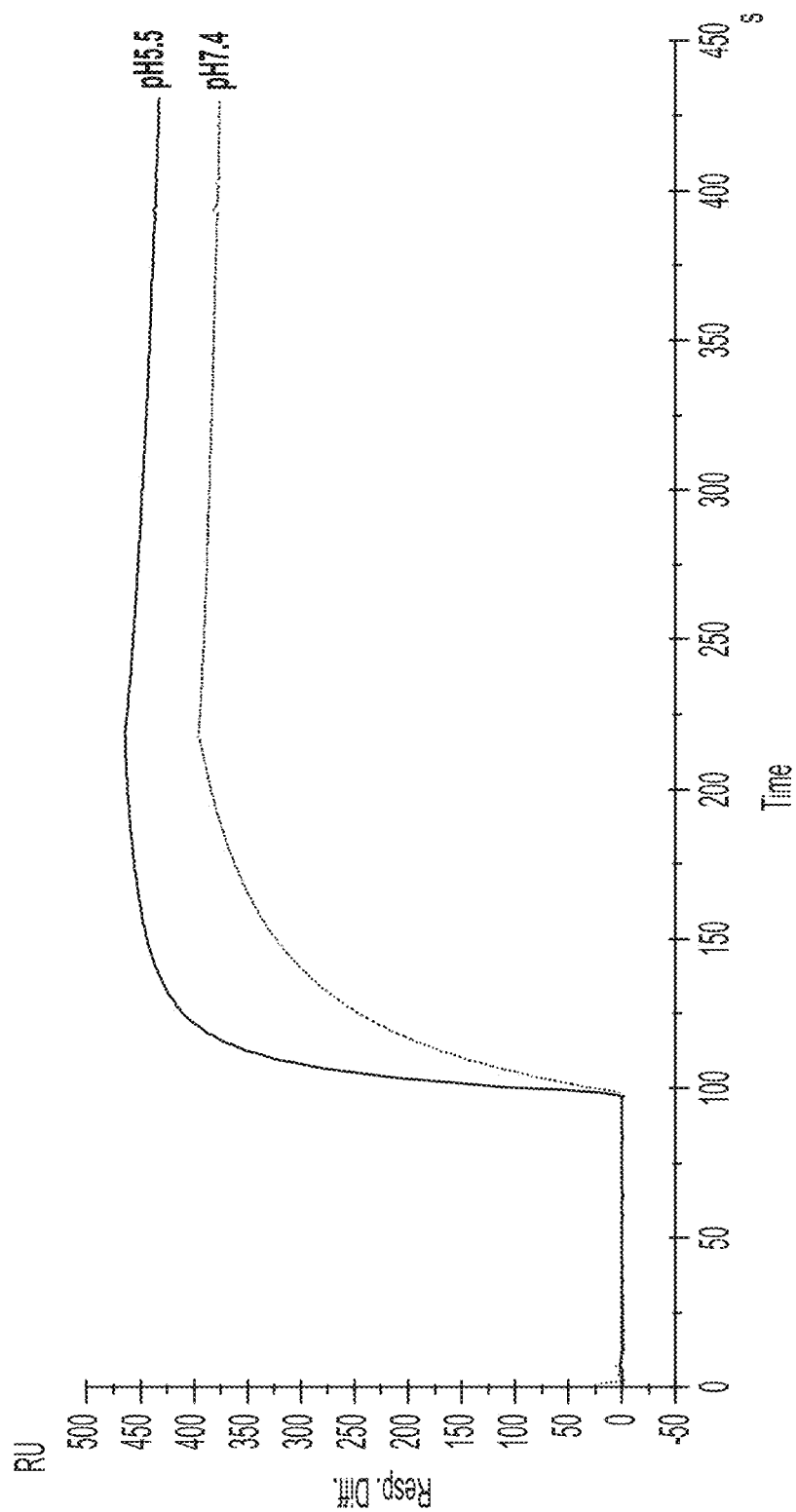
FIGS. 16A-16B show pH-dependent albumin binding profiles of a two-armed (TA)-Fc-ABDEG molecule with an albumin binding VHH fused at the C-termini of both Fc domains (TA-Fc-ABDEG-Alb23.
Figure 16B:
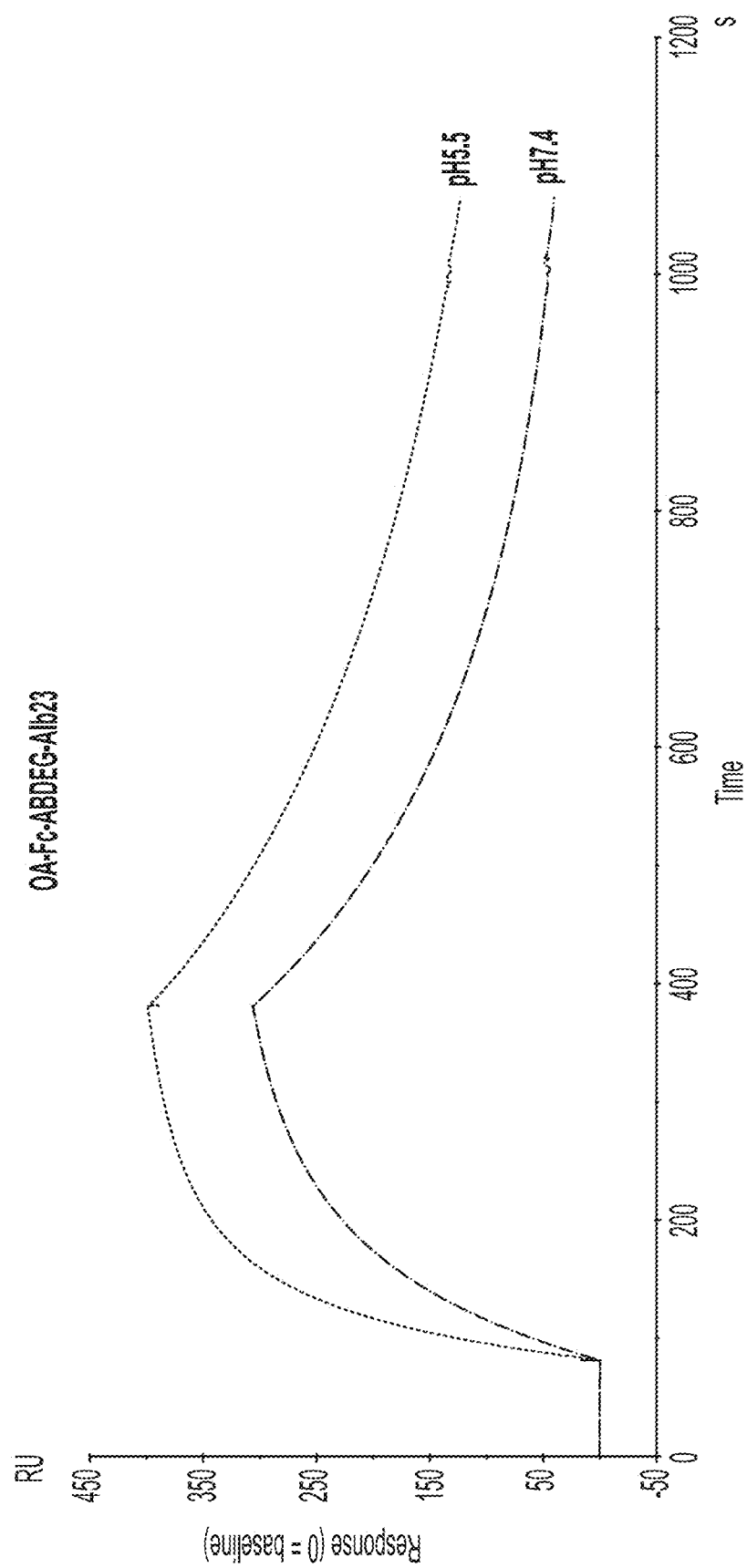

Previous studies illustrated the pH-dependent albumin binding of Alb23 VHH fragment fused to Fc-ABDEG at the C-terminus of both Fc domains (two-armed) (data not shown). The same is shown here for Fc-ABDEG molecules with one Alb23 VHH fragment fused to the C-terminus of one of the Fc domains (one-armed) using Biacore T200 (albumin coated, OA-Fc-ABDEG-VHH flown over). Data are presented in FIGS. 16A-16B.

To determine the effect of one-armed Fc-ABDEG-VHH on FcRn degradation, a cell-based FcRn degradation assay was used in the presence or absence of albumin. Briefly, HEK FcRn WT GFP+ cells/well were seeded on a 96-well microplate overnight at 37° C. in growth medium (DMEM+ 10% FBS+P/S+L-glutamine). Fc-ABDEG-VHH molecules were pre-incubated with human serum albumin (HSA) in a 1:4 ratio in treatment medium (DMEM+1% BSA+P/S+L-glutamine) for 30 minutes at 37° C., 5% $CO_2$ prior to adding to the cells. After incubation of the Fc-ABDEG-VHH/HSA mix or Fc-ABDEG-VHH with the cells, plates were then placed on ice and cells harvested by trypsin. Harvested cells were transferred to FACS plate and centrifuged. LD stain (1:800) was added in FACS buffer and incubated for 15 minutes at 4° C. Cells were washed, centrifuged, and resuspended in FACS buffer. GFP signal was measured and compared to untreated controls.

Figure 17A:
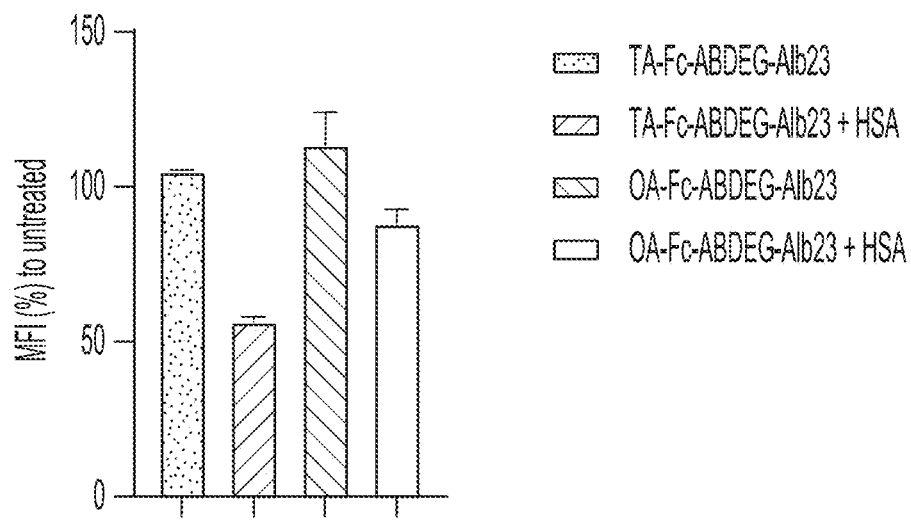
FIGS. 17A-17B show the effect of one-armed Fc-ABDEG-Alb23 molecules on FcRn degradation in the presence or absence of HSA.
Figure 17B:
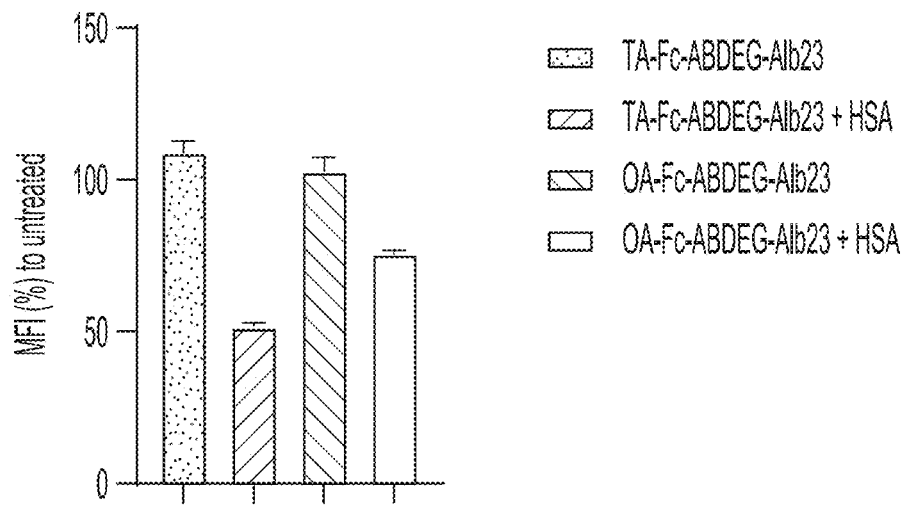
Figure 18:
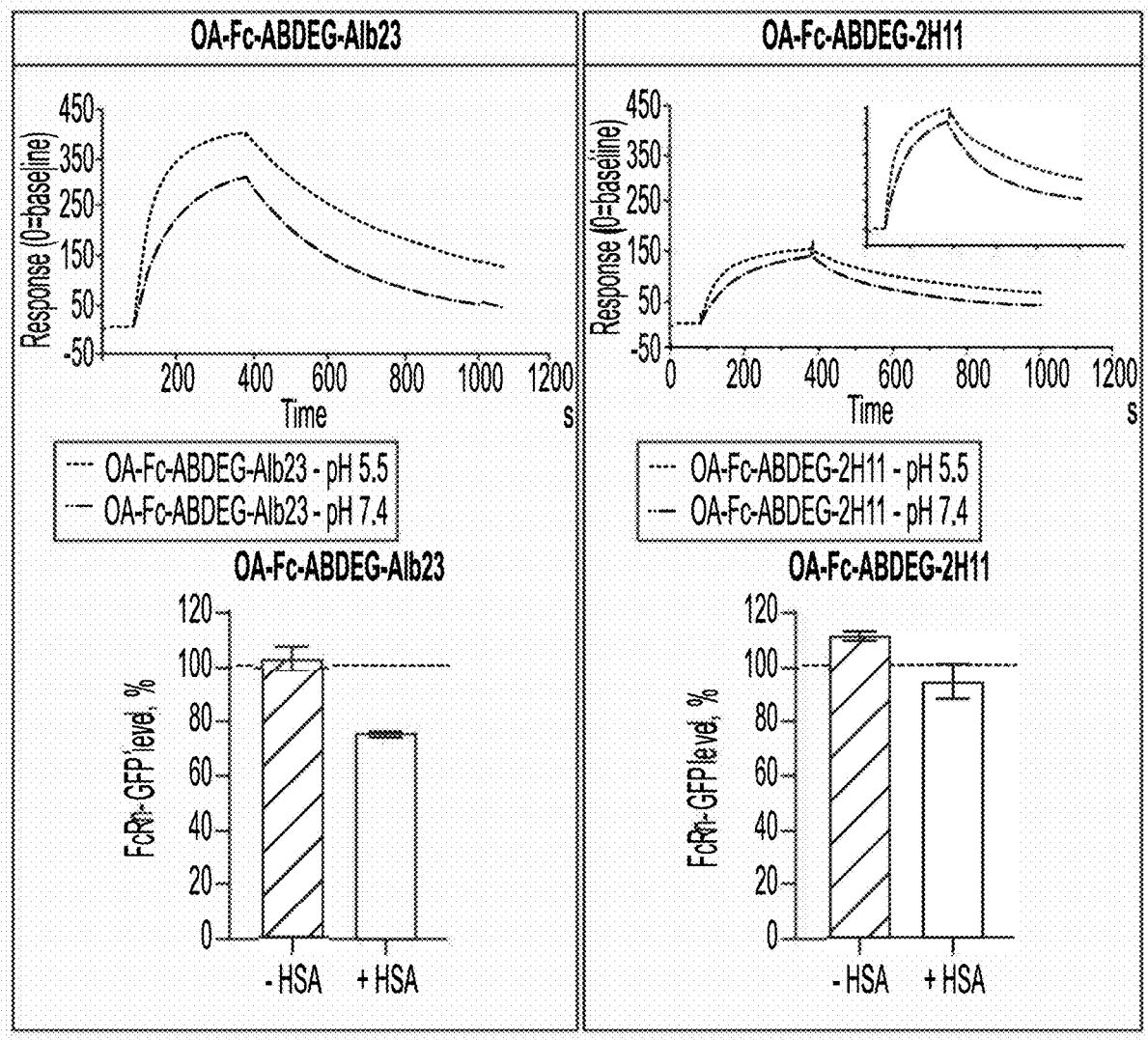
FIG. 18 shows the effect of one-armed Fc-ABDEG-2H11 molecules on FcRn degradation in the presence or absence of HSA. pH-dependent HSA binding profiles of each molecule are also shown to illustrate that use of VHH with reduced albumin-binding affinity reduces FcRn degradation. HEK FcRn WT GFP+ cells were incubated with 1 mg/mL Fc-ABDEG-VHH in the absence of HSA or in the presence of 3.3 mg/mL HSA. Bars represent mean±SD of two independent experiments performed in duplicate.
Figure 18:
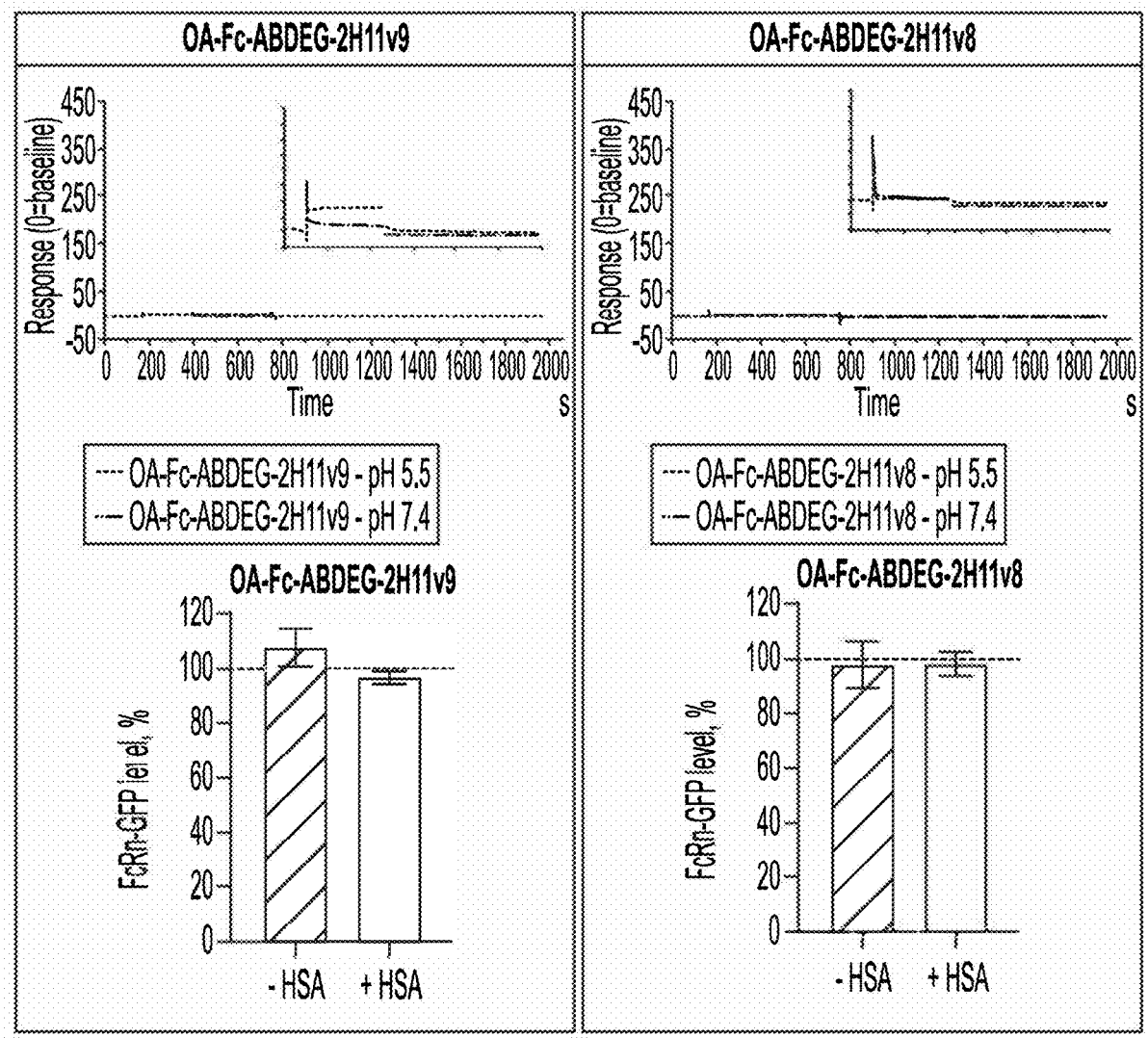

Results are shown in FIGS. 17A-17B illustrating that the FcRn degradation effect in the presence of albumin is ameliorated in one-armed constructs. Furthermore, decreased affinity to HSA (e.g., 2H11 and its variants) further ameliorated FcRn degradation as shown in FIG. 18.

Next, FcRn occupancy was tested using a cell-based FcRn occupancy assay in the presence or absence of albumin. Briefly, test articles (Fc-ABDEG-VHH molecules) were pre-incubated with HSA for 30 minutes at 37° C., pH 7.4 in FACS buffer. Cells (HEK FcRn mut or U937) were plated in a 96-well microplate. Cells were incubated with test article for two hours, shaking at 37° C., pH 7.4 in FACS buffer. Plates were then transferred immediately on ice and cells were collected by centrifugation at 4° C. Cells stained for viability in FACS buffer at pH 6 and then fixed/permeabilized in permeabilization buffer at pH 6. Fixed/permeabilized cells were then stained intracellularly with anti-FcRn-Fab AF647 to stain free FcRn by incubation for 30 minutes at 4° C., pH 6 in permeabilization buffer. Cells were analyzed by FACS, ensuring that they are kept on ice until immediately prior to analysis.

FcRn occupancy with BA-FG-ABDEG-VHH molecules in the presence or absence of albumin in HEK293-FcRn-L322A/L323A cells (HEK293 cells transfected with FcRn-L322A/L323A) is shown in Table S17. Data are presented as mean±SEM of 1-7 independent experiments performed in technical duplicates. N-terminally placed Alb23 showed impaired FcRn occupancy in the presence of albumin as compared to efgartigimod. C-terminally placed Alb23 improved FcRn occupancy of the constructs in the presence of albumin comparable to efgartigimod. Finally, slightly improved FcRn occupancy was observed for OA-Fc-AB-DEG-Alb23 molecules compared to TA-Fc-ABDEG-Alb23 construct.

TABLE S17

FcRn occupancy after incubation of with Fc-ABDEG-VHH molecules in the presence or absence of albumin in HEK293-FcRn-mut cells

| Name | Albumin | IC50 ± SEM, nM | % max occupancy ± SEM |
|---|---|---|---|
| Efgartigimod (n = 3) | + | 16.1 ± 3.1 | 57.7 ± 5.3 |
| Efgartigimod (n = 2) | − | 6.8 ± 1.4 | |
| TA-Alb23-Fc-ABDEG (n = 6) | + | 78.3 ± 2.9 | 43.4 ± 2.2 |
| TA-Alb23-Fc-ABDEG (n = 2) | − | 19.9 ± 0.3 | |
| OA-Alb23-Fc-ABDEG (n = 1) | + | 87.6 | 45.6 |
| OA-Alb23-Fc-ABDEG (n = 1) | − | 11.8 | — |
| TA-Fc-ABDEG-Alb23 (n = 7) | + | 33 ± 8.8 | 63.8 ± 2.3 |
| TA-Fc-ABDEG-Alb23 (n = 3) | − | 20.2 ± 4.8 | |
| OA-Fc-ABDEG-Alb23 (n = 2) | + | 11.5 ± 2.3 | 67.9 ± 0.2 |
| OA-Fc-ABDEG-Alb23 (n = 1) | − | 6.4 | |

FcRn occupancy with OA-Fc-ABDEG-VHH molecules in the presence and absence of albumin in U937 cells (which endogenously express FcRn) is shown in Table S18. Data are presented as mean±SEM of 1-4 independent experiments performed in technical duplicates. Similar to the results obtained with 1TEK293-FcRn-mut cells, N-terminally placed Alb23 showed impaired FcRn occupancy in the presence of albumin as compared to efgartigimod. C-terminally placed Alb23 improves FcRn occupancy in the presence of albumin comparable to efgartigimod. A slightly improved FcRn occupancy was observed for OA-Fc-ABDEG-VHH molecules compared to TA-Fc-ABDEG-Alb23 construct.

TABLE S18

FcRn occupancy after incubation of with Fc-ABDEG-VHH molecules in the presence of albumin in U937 cells

| Name | Albumin | IC50 ± SEM, nM | % max occupancy ± SEM |
|---|---|---|---|
| Efgartigimod (n = 2) | + | 4.8 ± 0.1 | 56.8 ± 6.4 |
| TA-Alb23-Fc-ABDEG (n = 4) | + | 389 ± 77 | 39.1 ± 4.1 |
| TA-Alb23-Fc-ABDEG (n = 1) | − | 7.5 | |
| OA-Alb23-Fc-ABDEG (n = 1) | + | 25.0 | 51.1 |
| OA-Alb23-Fc-ABDEG (n = 1) | − | 8.5 | |
| TA-Fc-ABDEG-Alb23 (n = 3) | + | 14.5 ± 3.5 | 69.7 ± 6.4 |
| OA-Fc-ABDEG-Alb23 (n = 3) | + | 5.2 ± 1.5 | 67.4 ± 4.8 |

Example 6: Pharmacokinetics/Pharmacodynamics of OA-Fc-ABDEG-Alb23 in Tg32-hFc Mice Previous experiments illustrated the improvement in pharmacodynamics by placing two VHH fragments at the C-terminus of Fc-ABDEG instead of the N-terminus. However, the two-armed C-terminal VHH-Fc-ABDEG molecule (TA-Fc-ABDEG-Alb23) reduced serum albumin levels by about 20-30% when administered to cynomolgus monkeys (Example 2). The current experiment was conducted to compare PK and PD of one-armed Fc-ABDEG-VHH molecules to two-armed Fc-ABDEG-VHH molecules. FTg32-hFc mice (B6.Cg-Tg(FCGRT)32DcrFcgrt$^{tm1Dcr}$ Ighg1$^{em2(IGHGH1)Mvw}$/MvwJ) were created and described by the Jackson Laboratories (JAX) (Low, B. E., et al., MAbs, 2020, 12(1):1829334). Low and colleagues used CRISPR/Cas9-mediated homology-directed repair to equip the human FcRn transgenic Tg32 mouse strain with a human IGHG1 Fc domain. This replacement resulted in mice that produce human IgG1 Fc-mouse IgG Fab$_2$ chimeric antibodies (chIgG1) at physiologically relevant levels in mice, which were shown to be further heightened by immunization in Low et al. chIgG1 antibodies contain human Fc (CH2-CH3) and hinge domains (replacing mouse IgG1 CH2-CH3 and hinge), while Fab arms are still of murine origin. Using this model, the pharmacodynamic effect of ABDEG can be measured on endogenous chIgG1 (without IgG preloading). The Tg32-hFc mouse model was previously evaluated for studying PK and PD properties of ABDEG-equipped molecule.

The first objective of this study was to evaluate PD and PK properties of one-armed Fc-ABDEG-Alb23 (OA-Fc-ABDEG-Alb23) binding serum albumin (human, mouse, cynomolgus monkey cross-reactive) after single intraperitoneal injection. The second goal of this study was to evaluate the effect of OA-Fc-ABDEG-Alb23 molecules on circulating albumin levels. Clearance of circulating chIgG1 (PD effect), as well as PK of the test items, levels of circulating albumin and anti-drug antibodies (ADA) were analyzed. A description of the different ABDEG-based molecules tested is provided above in Table S16 and schematics of representative molecules are shown in FIG. 15.

Methods

Briefly, a total of 19 naïve male Tg32-hFc mice were randomly assigned into 4 groups. The mice were single-dosed intraperitoneally (200 μL injection volume, reference weight 30 g) according to the designated group and doses in Table S19. 30 mg/kg doses for TA-Fc-ABDEG-Alb23 and TA-Alb23-Fc-ABDEG and 25 mg/kg for OA-Fc-ABDEG-Alb23 were selected based on MW of the test items (FIG. 15) to have equimolar doses thereof. All animals were pre-weighed before dosing and dosed according to their body weights. Blood samples were collected before dosing of the test article (pre-dose, d-3) and after treatment for PD, PK, ADA and albumin read-outs during 14 days (Table S19).

Blood samples were processed to serum and added to a 96-well plate (polypropylene) and stored at −80° C.

TABLE S19

Groups and dosing regimen

| Group | N | Test Article | Dose, mg/kg | Administration route | Blood sampling times |
|---|---|---|---|---|---|
| A | 4 | PBS | — | IP, single dose | −3 d, 0 d+1 h, 1 d, 2 d, 3 d, 4 d, 7 d, 10 d, 14 d |
| B | 5 | TA-Fc-ABDEG-Alb23 | 30 | IP, single dose | −3 d, 0 d+1 h, 1 d, 2 d, 3 d, 4 d, 7 d, 10 d, 14 d |
| C | 5 | TA-Alb23-Fc-ABDEG | 30 | IP, single dose | −3 d, 0 d+1 h, 1 d, 2 d, 3 d, 4 d, 7 d, 10 d, 14 d |
| D | 5 | OA-Fc-ABDEG-Alb23 | 25 | IP, single dose | −3 d, 0 d+1 h, 1 d, 2 d, 3 d, 4 d, 7 d, 10 d, 14 d |

ChIgG1 serum levels were determined using a sandwich ELISA. Briefly, a Nunc MaxiSorp F-bottom plate (Thermo Fisher Scientific, Cat. 44-24004-21) was coated overnight (4° C.) with neutravidin (Thermo Fisher Scientific, Lot VI312512) and non-specific binding sites are blocked with 1% casein-PBS (Bio-Rad, Cat. #1610783, Batch 64412107). A human biotinylated Fab clone (specifically binding WT Fc and not binding Fc with ABDEG mutations) was captured for 1 hour. Study serum samples were diluted 1/500 and 1/2000 and incubated on the immunoplate together with a fresh 11-point chIgG1 calibration curve (In-house produced) and 4 frozen quality control (QC) samples (HQC, MQC, LQC and dilution QC (100% naïve Tg32-hFc serum diluted 1/4000)) for 1 hour. ChIgG1s were bound and detected for 1 hour by a goat anti-mouse kappa HRP (Southern Biotech, 1050-05). The plate was developed by adding 3,3',5,5'-tetramethylbenzidine (TMB) substrate for approximately 16 minutes. The enzymatic reaction was stopped with sulfuric acid ($H_2SO_4$) and optical density values at 450 nm were recorded using a Tecan plate reader. All incubation steps were in a temperature controlled shaking incubator (22° C.). The ELISA method was tested for dilution linearity, precision, accuracy, robustness, and drug interference. For data analysis, the obtained values were back-calculated on a 11-point calibrator curve in GraphPad Prism (log(agonist) vs. response—Variable slope (four parameters), Least squares fit). ChIgG1 were plotted in absolute values measured (µg/mL) and percentage to pre-dose (3 days prior to test article injection, day-3).

Concentrations of ABDEG-based drug molecules, comprising TA-Fc-ABDEG-Alb23, TA-Alb23-Fc-ABDEG, and OA-Fc-ABDEG-Alb23, were determined using a sandwich ELISA method. Briefly, Nunc MaxiSorp F-bottom plates (Thermo Fisher Scientific, Cat. 44-24004-21) were coated overnight (4° C.) with anti-HN (ABDEG) hFab and non-specific binding sites were blocked with 1% casein-PBS (Bio-Rad, #1610783). Next, 100% study serum samples were diluted to the concentration range of quantitation or at least the minimum required dilution (MRD). The calibration curve and quality control (QC) samples (HQC, MQC, and LQC) with ABDEG-based drug molecules were spiked in 100% C57Bl/6 serum and pre-incubated for 30 min. at RT before applying MRD 100. Samples were incubated on the immunoplate together with a fresh calibration curve and two sets of QC samples (HQC, MQC, and LQC) for 1 hour. ABDEG-based drug molecules were detected by the addition of anti-HN-Biotin for 1 hour. Subsequent detection was done by Strep-RP (BD Biosciences, Cat. #554066) for 30 min. Plates were developed by adding TMB substrate for approximately 10 and 15 minutes for TA-Fc-ABDEG-Alb23, TA-Alb23-Fc-ABDEG, and OA-Fc-ABDEG-Alb23, respectively. The enzymatic reaction was stopped with 0.5M $H_2SO_4$ and optical density values at 450 nm, ref620 were recorded using a Tecan plate reader. All incubation steps were in a temperature controlled shaking incubator (22° C.). For data analysis, the obtained values were back-calculated on a 11-point calibrator curve in GraphPad Prism nonlinear regression; Asymmetric (five parameters), X is log(concentration).

Immune response against the test items was measured by using a sandwich ELISA. Briefly, TA-Fc-ABDEG-Alb23, TA-Alb23-Fc-ABDEG, and OA-Fc-ABDEG-Alb23 were coated at 1 µg/mL on a 96-well immunoplate and non-specific binding sites were blocked. A 1/100 dilution of mouse serum (pre-dose and post-dose serum samples) was applied. Samples were incubated for 1 h and detected by an HRP-conjugated goat anti-mouse Fab2 (HRP Peroxidase AffiniPure F(ab')2 Fragment Goat Anti-Mouse IgG, F(ab')2 Fragment Specific, Jackson ImmunoResearch, Lot. 147275, Cat. 115-036-072) for 1 h on a shaking incubator. The signal was developed by adding TMB substrate for 8 minutes. The enzymatic reaction was stopped with $H_2SO_4$ and optical density values at 450 nm were recorded using a Tecan plate reader.

Albumin levels in serum samples assessed by using a sandwich ELISA. Briefly, 96-well ELISA plates were coated with 1.0 µg/mL of a polyclonal anti-MSA antibody (Abcam, #ab19194) and incubated ON at 4° C. Non-specific binding sites were blocked with PBS with 1% (w/v) casein for 1 h at room temperature. Study serum samples were diluted 1/1,000,000 and incubated on the immunoplate together with a fresh 11-point MSA (Sigma-A3559) calibration curve and 3 quality control (QC) samples (HQC, MQC, LQC) for 1 hour. Bound MSA was detected using HRP-conjugated polyclonal anti-MSA antibody from goat (Abcam, #ab19195, 1:40000). ELISAs were developed by adding 100 µL of TMB substrate and the enzymatic reaction was stopped with $H_2SO_4$. Optical density values at 450 nm were recorded using a Tecan plate reader. The absorbance of the product at 450 nm is proportional to the amount of albumin analyte present in the sample and a four-parameter standard curve is generated. The albumin concentrations in the test samples were then quantified by interpolating their absorbance from the standard curve generated in parallel with the samples. After factoring sample dilutions, the albumin concentrations in the original sample were calculated. The obtained values were back-calculated on an 11-point calibrator curve in GraphPad Prism (log(agonist) vs. response—Variable slope (four parameters), Least squares fit). Albumin concentrations were plotted in absolute values measured (µg/mL) and percentage to pre-dose (3 days prior to test article injection, day-3).

Results

Figure 19A:
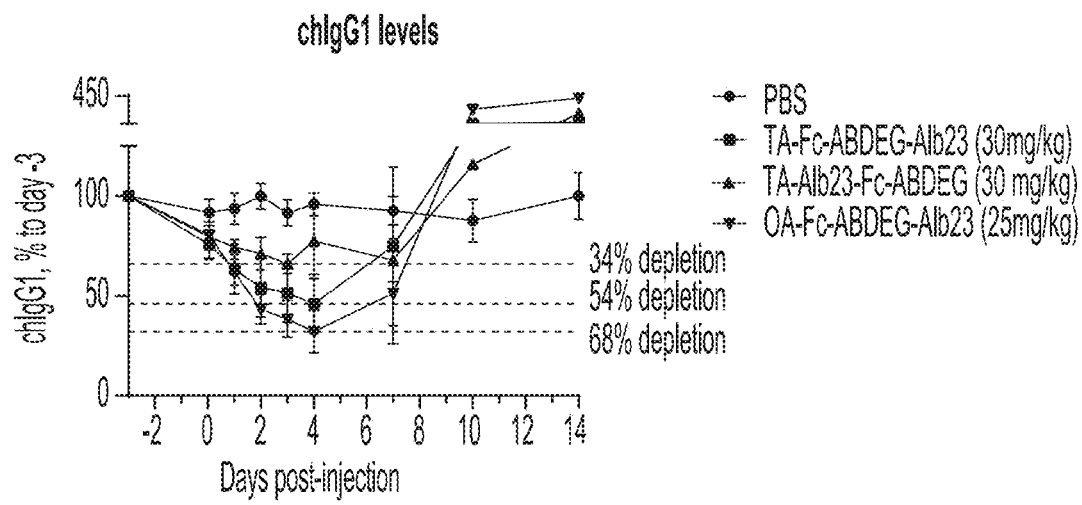
FIG. 19A shows normalized chimeric IgG1 (chIgG1) levels (% pre-dose) post-injection per group in Tg32-hFc mice dosed with various two-armed and one-armed albumin binding VHH Fc-ABDEG molecules. Four groups of Tg32-hFc mice received a single intraperitoneal (IP) injection of 30 mg/kg TA-Fc-ABDEG-Alb23 30 mg/kg TA-Alb23-Fc-ABDEG, 25 mg/kg OA-Fc-ABDEG-Alb23 (equimolar to 30 mg/kg of two-armed constructs), or PBS (control). Change in chIgG1 levels was plotted over time (days post-injection) as % to pre-dose on day-3. The datapoints show the mean±SEM of 4-5 mice per group per timepoint. Y-axis was presented by 2 segments: lower segment to better appreciate chIgG1 depletion at day 1 to 7, upper segment to observe timepoints with chIgG1 levels going above baseline. Broken lines represent maximum depletion levels of chIgG1 as a percent of baseline.

To assess the PD effects of the albumin-binding VHH molecules (two-armed vs one-armed), the levels of endogenous circulating chIgG1 were measured during the course of the study. The measured chIgG1 concentrations were plotted as percentage to pre-dose at 3 days prior to test article injection (day-3) per treatment group (FIG. 19A). Baseline levels of chIgG1 vary among mice and for most animals lie below the normal biological variation for reported IgG1 levels in WT mice.

As expected and in line with historical in vivo data, a clear depletion of chIgG1 was observed for TA-Fc-ABDEG-Alb23 (30 mg/kg), reaching a maximal depletion of 54.1±7.5% at day 4 post-injection. Previously, the PD effect of TA-Fc-ABDEG-Alb23 was demonstrated in Tg32-hFc mice with a maximum IgG clearance of 59.9±6.5% to pre-dose after a single IV injection of 30 mg/kg. A more pronounced PD effect was observed for the OA-Fc-ABDEG-VHH molecules: maximal IgG depletion of 68.0±4.7% for OA-Fc-ABDEG-Alb23 (25 mg/kg). The PBS control group showed steady chIgG1 levels over time.

A poor depletion of chIgG1 (22.7±8.4%) was observed for TA-Alb23-Fc-ABDEG (30 mg/kg). This is in line with the observed lack of PD effect of this molecule in cynomolgus monkeys (Example 1). In general, the levels of chIgG1 returned to baseline between day 7 and day 10, with an overshoot of chIgG1 levels over the baseline after day 10, which might be related to the development of ADA (discussed further below).

Figure 19B:
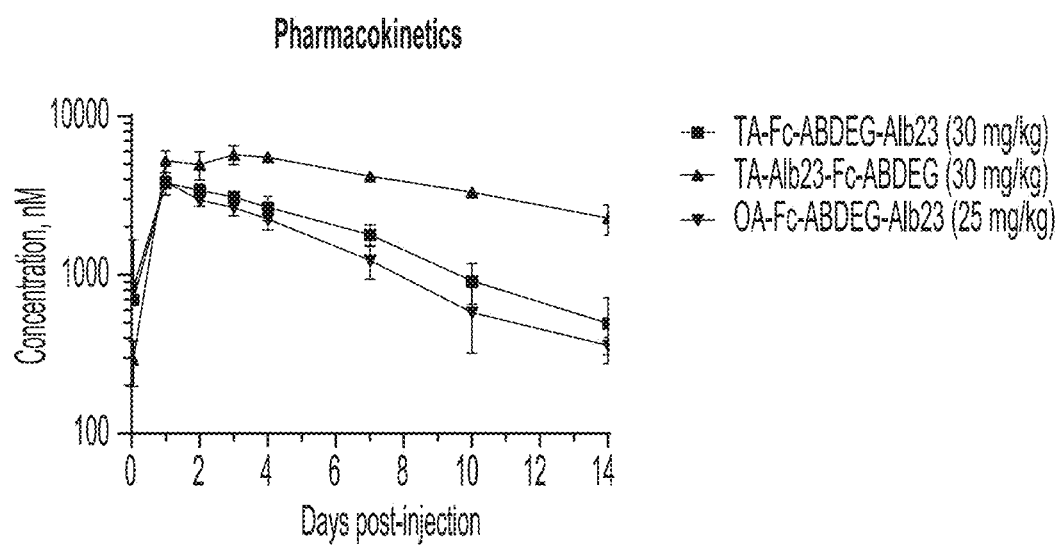
FIG. 19B shows serum PK of TA-Fc-ABDEG-Alb23, TA-Alb23-Fc-ABDEG, and OA-Fc-ABDEG-Alb23 after a single IP injection. Tg32-hFc mice received 30 mg/kg TA-Fc-ABDEG-Alb23, 30 mg/kg TA-Alb23-Fc-ABDEG, or 25 mg/kg OA-Fc-ABDEG-Alb23 (equimolar doses). Serum concentrations of the test items were plotted as an average per group over time during the course of the study. The datapoints show the mean±SEM of 5 animals per group.

To evaluate the PK profiles of the test items after a single IP administration, their levels in mouse serum were determined post-dose according to the bleeding scheme in Table S19. The obtained values were plotted in molar concentrations (nM) to correct for different mg/kg doses of the administered molecules due to different molecular weights (FIG. 19B). TA-Fc-ABDEG-Alb23 showed a steady PK profile over the entire course of the experiment. A similar steady PK profile was observed for OA-Fc-ABDEG-Alb23. These results indicate that Fc-ABDEG can be rescued with only one albumin binding VHH fragment.

TA-Alb23-Fc-ABDEG showed the best PK profile among the test items, which can be linked to its poor PD effect (poor FcRn occupancy) leading to the extended time in circulation. For all tested molecules, concentrations were quantifiable in the serum during the entire study (14 days). A formal calculation of PK parameters by means of non-compartmental analysis was not performed.

Figure 20:
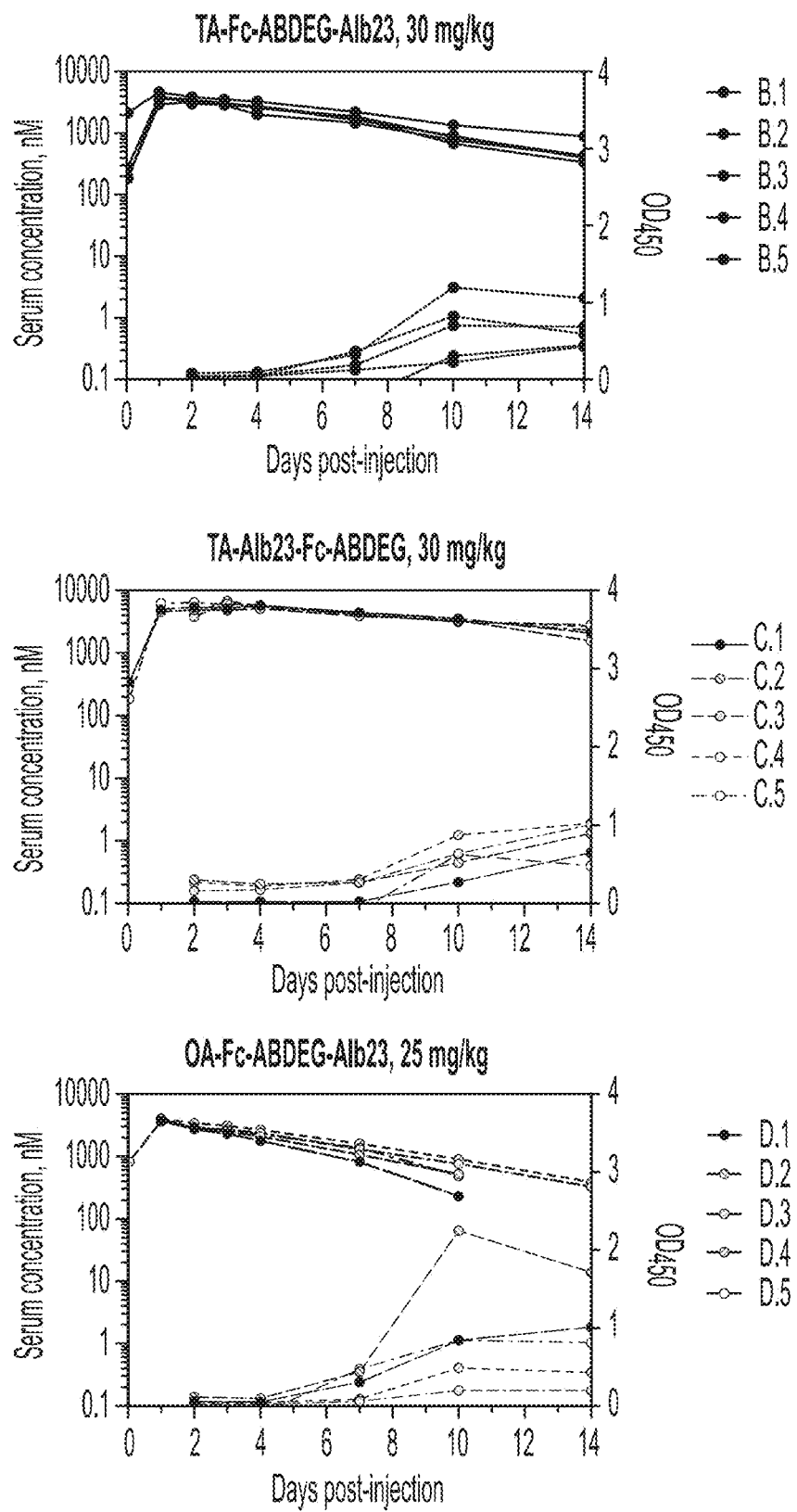
FIG. 20 shows ADA response after a single IP injection of TA-Fc-ABDEG-Alb23, TA-Alb23-Fc-ABDEG, or OA-Fc-ABDEG-Alb23 in individual Tg32-hFc mice. On day 0, mice received a single IP injection of TA-Fc-ABDEG-Alb23 (30 mg/kg), TA-Alb23-Fc-ABDEG (30 mg/kg), or OA-Fc-ABDEG-Alb23 (25 mg/kg). ADA response (OD450, right Y-axis) was overlayed with the PK profiles (nM, left Y-axis) per mouse, per group over time (days post-injection, X-axis). Each datapoint (PK and ADA) represents the mean±SEM of a study sample analyzed in duplicates (technical replicates).

An immunogenic response is likely to develop upon the injection of human molecules in mice. To assess the presence of ADAs in the course of the study, an ADA ELISA was performed. Mouse serum samples were diluted 1/100 and measured by a sandwich ELISA. FIG. 20 shows free ADA serum titers for all individual animals per group plotted against test items serum concentrations (PK).

Overall, the impact of ADAs on the PK profiles of the test items was not dramatic, as the PK profiles remained steady during the course of the study after ADA was detected. Additionally, development of ADA starting from day 7 can potentially influence the levels of circulating chIgG1 and should be taken into account for interpretation of the duration of ABDEG PD effect.

Figure 21:
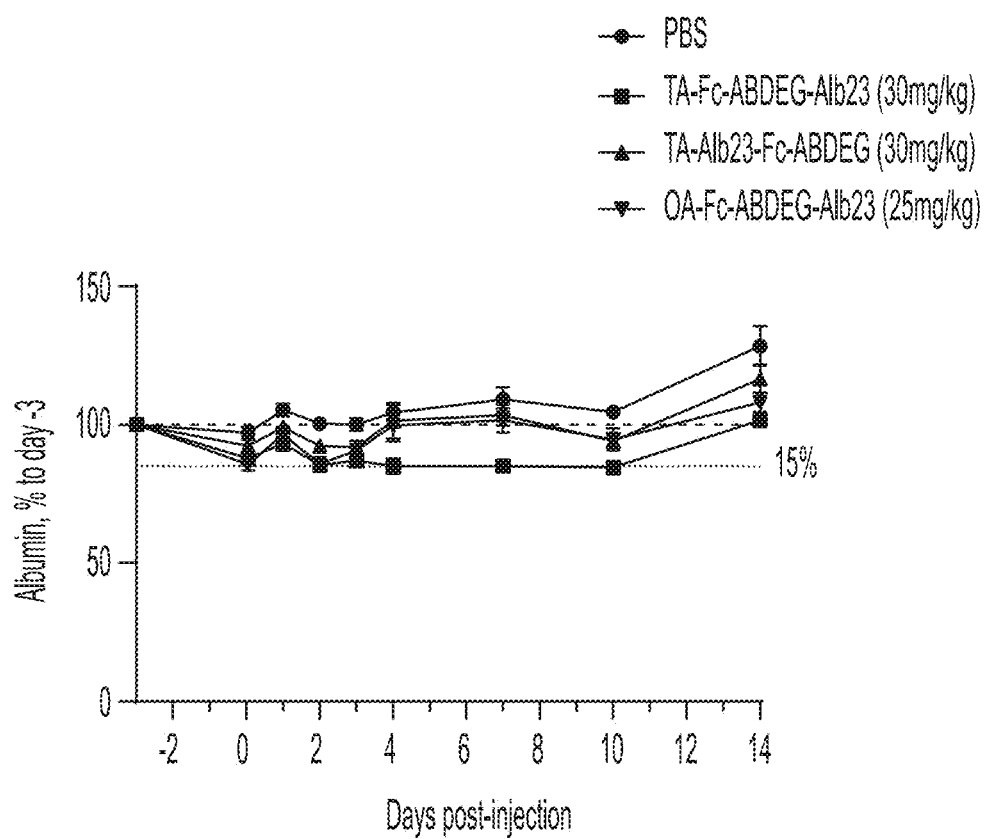
FIG. 21 shows normalized albumin levels (% pre-dose) post-injection per group. On day 0, Tg32-hFc mice received a single IP injection of TA-Fc-ABDEG-Alb23 (30 mg/kg), TA-Alb23-Fc-ABDEG (30 mg/kg), OA-Fc-ABDEG-Alb23 (25 mg/kg) or PBS (control). Albumin levels were plotted overtime (days post-injection) as % relative to pre-dose (day-3), averaged per group. The datapoints show the mean±SEM of 4-5 mice per group per timepoint.

To evaluate a potential impact of two-armed (TA) or one-armed (OA) Fc-ABDEG-VHH molecules on albumin levels after the administration to Tg32hFc mice, total serum albumin levels were measured throughout the study at baseline (pre-dose) and post-dose according to the scheme in Table S19. Measured albumin concentrations were plotted as percentage to pre-dose (day-3) prior to test item administration (FIG. 21). No pronounced decrease in albumin levels was observed in control mice treated with PBS during the course of the study. Albumin decreases were observed in mice treated with TA-Fc-ABDEG-Alb23 (30 mg/kg). In more detail, for this group, serum albumin levels showed a nadir of 15% to pre-dose from day 2 up to day 10. Albumin levels returned to baseline by the end of the study on day 14. A maximum reduction of 8% was observed 1 hour after injection in mice treated with TA-Alb23-Fc-ABDEG (30 mg/kg). Albumin levels turned back to baseline from day 3 onwards. Mice treated with OA-Fc-ABDEG-Alb23 showed similar albumin decreases 1 hour after test article injection (14%). However, the observed decline for OA-Fc-ABDEG-Alb23 was only transient and returned to baseline after 4 days. Overall, the most pronounced and prolonged decrease in albumin concentration was detected after treatment with TA-Fc-ABDEG-Alb23, confirming the previous findings in cynomolgus monkeys. This data is also reinforced by experimental data obtained in the FcRn degradation assay. TA-Fc-ABDEG-Alb23 was shown to reduce FcRn-GFP levels by 45-50%, while OA-Fc-ABDEG-2H11 and variants had no meaningful effect on FcRn levels (Example 5). The effect was less pronounced and transient with one-armed molecules.

The aim of this study was to evaluate whether one-armed Fc-ABDEG-VHH constructs conserve the extended plasma half-life and efficient depletion of chIgG1 from circulation in Tg32-hFc mice, compared to the TA-Fc-ABDEG-Alb23 with two albumin-binding VHH fragments (two-armed). The second goal of this study was to evaluate the effect of OA-Fc-ABDEG-VHH molecules on circulating albumin levels. Tg32-hFc mice have human FcRn transgene and produce human IgG1 Fc-mouse IgG Fab2 chimeric antibodies at physiologically relevant levels. A clear depletion of chIgG1 was observed after a single IP dose of TA-Fc-ABDEG-Alb23 and OA-Fc-ABDEG-Alb23 with a subsequent return to baseline later on. On average, a 14% deeper IgG depletion was observed for OA-Fc-ABDEG-Alb23. A very small depletion of chIgG1 was observed for TA-Alb23-Fc-ABDEG which is in line with historical cynomolgus monkey data. All 3 test items showed a steady PK profile over the course of the experiment. Serum PK profiles of OA-Fc-ABDEG-Alb23 were very comparable to TA-Fc-ABDEG-Alb23. This effect was observed despite containing only one albumin binding arm. Development of ADA starting from day 7 was observed for all molecules without impacting the PK. Effects on circulating mouse serum albumin were also evaluated. A 15% decrease in albumin concentration was observed for TA-Fc-ABDEG-Alb23. Levels returned to baseline by the end of the experiment. Only transient and less pronounced effect on albumin levels was observed for OA-Fc-ABDEG-Alb23. In conclusion, this experiment shows that incorporation of only one albumin-binding VHH fragment can substantially improve PK of Fc-ABDEG, allow Fc-ABDEG to mediate an efficient IgG depletion, and ameliorate the effects on circulating albumin levels observed with two-armed TA-Fc-ABDEG-Alb23.

Example 7: Pharmacokinetics/Pharmacodynamics of OA-Fc-ABDEG-VHH in AlbuMus Mice

The current experiment was conducted to compare PK and PD of one-armed Fc-ABDEG-VHH molecules to two-armed Fc-ABDEG-VHH molecules in the AlbuMus mouse model (hFcRn+/+, hSA+/+) instead of the Tg32-hFc mouse model (hFcRn+/+, chIgG1, MSA) used in Example 6.

Methods

Briefly, a total of 20 AlbuMus mice were randomly assigned into 4 groups. The mice were single-dosed intravenously according to the designated group and doses in Table S20. Tracer IgG was administered to all groups prior to administration of test items. 30 mg/kg doses for TA-Fc-ABDEG-Alb23 and TA-Alb23-Fc-ABDEG and 25 mg/kg for OA-Fc-ABDEG-Alb23 were selected based on MW of the test items (FIG. 15) to have equimolar doses thereof. All animals were pre-weighed before dosing and dosed according to their body weights. Blood samples were collected before dosing of the test article (pre-dose, d0, −2 h) and after treatment for PD, PK, ADA, and albumin read-outs during 7 days (Table S20).

Blood samples were processed to serum and added to a 96-well plate (polypropylene) and stored at −80° C.

TABLE S20

Groups and dosing regimen

| Group | N | Test Article | Dose, mg/kg | Administration route | Blood sampling times |
|---|---|---|---|---|---|
| A | 5 | PBS | — | IV, single dose | 0 d−2 h, 0 d+30 m, 1 d, 2 d, 4 d, 7 d |
| B | 5 | TA-Fc-ABDEG-Alb23 | 30 | IV, single dose | 0 d−2 h, 0 d+30 m, 1 d, 2 d, 4 d, 7 d |
| C | 5 | TA-Alb23-Fc-ABDEG | 30 | IV, single dose | 0 d−2 h, 0 d+30 m, 1 d, 2 d, 4 d, 7 d |
| D | 5 | OA-Fc-ABDEG-Alb23 | 25 | IV, single dose | −0 d−2 h, 0 d+30 m, 1 d, 2 d, 4 d, 7 d |

Tracer IgG1 serum levels were determined using a sandwich ELISA and were plotted as percentage to pre-dose (day prior to test article injection, day 0-2 h).

Concentrations of ABDEG-based drug molecules, comprising TA-Fc-ABDEG-Alb23, TA-Alb23-Fc-ABDEG, and OA-Fc-ABDEG-Alb23, were determined using a sandwich ELISA method. Briefly, Nunc MaxiSorp F-bottom plates (Thermo Fisher Scientific, Cat. 44-24004-21) were coated overnight (4° C.) with anti-HN and nonspecific binding sites were blocked with 1% casein-PBS (Bio-Rad, #1610783). Next, 100% study serum samples were diluted to the concentration range of quantitation or at least the minimum required dilution (MRD). The calibration curve and quality control (QC) samples (HQC, MQC, and LQC) with ABDEG-based drug molecules were spiked in 100% serum and pre-incubated for 30 min. at RT before applying MRD 100. Samples were incubated on the immunoplate together with a fresh calibration curve and two sets of QC samples (HQC, MQC, and LQC) for 1 hour. ABDEG-based drug molecules were detected by the addition of anti-HN (AB- DEG hFab-Biotin) for 1 hour. Subsequently, hFab5-Biotin was detected by Strep-HRP (BD Biosciences, Cat. #554066) for 30 min. Plates were developed by adding TMB substrate for approximately 10 and 15 minutes for TA-Fc-ABDEG-Alb23, TA-Alb23-Fc-ABDEG, and OA-Fc-ABDEG-Alb23, respectively. The enzymatic reaction was stopped with 0.5M $H_2SO_4$ and optical density values at 450 nm, ref620 were recorded using a Tecan plate reader. All incubation steps were in a temperature controlled shaking incubator (22° C.). For data analysis, the obtained values were back-calculated on a 11-point calibrator curve in GraphPad Prism nonlinear regression; Asymmetric (five parameters), X is log(concentration).

Immune response against the test items was measured by using a sandwich ELISA. Briefly, TA-Fc-ABDEG-Alb23, TA-Alb23-Fc-ABDEG, and OA-Fc-ABDEG-Alb23 were coated at 1 μg/mL on a 96-well immunoplate and non-specific binding sites were blocked. A 1/100 dilution of mouse serum (pre-dose and post-dose serum samples) was applied. Samples were incubated for 1 h and detected by an HRP-conjugated goat anti-mouse Fab2 (HRP Peroxidase AffiniPure F(ab')$_2$ Fragment Goat Anti-Mouse IgG, F(ab')2 Fragment Specific, Jackson ImmunoResearch, Lot. 147275, Cat. 115-036-072) for 1 h on a shaking incubator. The signal was developed by adding TMB substrate for 8 minutes. The enzymatic reaction was stopped with $H_2SO_4$ and optical density values at 450 nm were recorded using a Tecan plate reader.

Albumin levels in serum samples assessed by using a sandwich ELISA. Briefly, 96-well ELISA plates were coated with 1.0 μg/mL of a polyclonal anti-MSA antibody (Abcam, #ab19194) and incubated overnight at 4° C. Non-specific binding sites were blocked with PBS with 1% (w/v) casein for 1 h at room temperature. Study serum samples were diluted 1/1,000,000 and incubated on the immunoplate together with a fresh 11-point MSA (Sigma-A3559) calibration curve and 3 quality control (QC) samples (HQC, MQC, LQC) for 1 hour. Bound MSA was detected using HRP-conjugated polyclonal anti-MSA antibody from goat (Abcam, #ab19195, 1:40000). ELISAs were developed by adding 100 μL of TMB substrate and the enzymatic reaction was stopped with $H_2SO_4$. Optical density values at 450 nm were recorded using a Tecan plate reader. The absorbance of the product at 450 nm is proportional to the amount of albumin analyte present in the sample and a four-parameter standard curve was generated. The albumin concentrations in the test samples were then quantified by interpolating their absorbance from the standard curve generated in parallel with the samples. After factoring sample dilutions, the albumin concentrations in the original sample were calculated. The obtained values were back-calculated on an 11-point calibrator curve in GraphPad Prism (log(agonist) vs. response—Variable slope (four parameters), Least squares fit). Albumin concentrations were plotted in absolute values measured (μg/mL) and percentage to pre-dose (2 hours prior to test article injection, day 0, −2 h).

Results

Figure 22A:
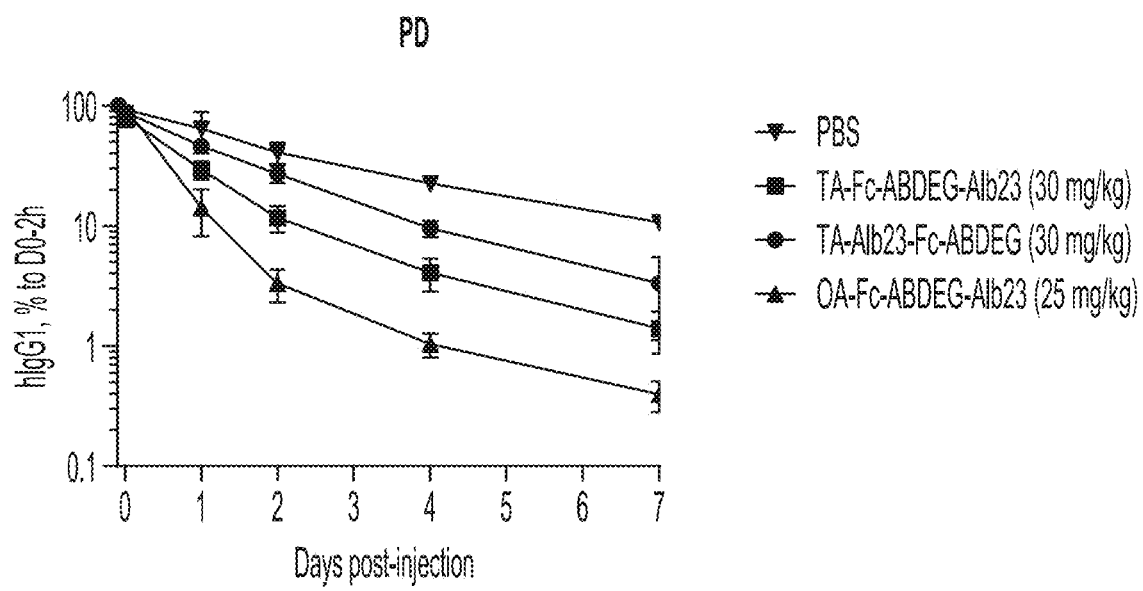
FIGS. 22A-22C show the PD/PK/serum albumin effect of TA-Fc-ABDEG-Alb23, TA-Alb23-Fc-ABDEG, and OA-Fc-ABDEG-Alb23 after a single IV injection in AlbuMus mice. Four groups of mice received 30 mg/kg TA-Fc-ABDEG-Alb23, 30 mg/kg TA-Alb23-Fc-ABDEG, 25 mg/kg OA-Fc-ABDEG-Alb23 (equimolar to 30 mg/kg of the two-armed constructs), or PBS on day 0. The datapoints show the mean±SEM of 5 mice per group per timepoint.

To assess the PD effects of the albumin-binding VHH molecules (two-armed vs one-armed), tracer IgG was administered to the mice prior to treatment with the test articles. The levels of tracer IgG were measured during the course of the study. The measured tracer IgG concentrations were plotted as percentage to pre-dose at 2 hours prior to test article injection (day 0, −2 h) per treatment group (FIG. 22A).

As expected and in line with data from Tg32-hFc mice, a clear depletion of IgG1 was observed for TA-Fc-ABDEG-Alb23 (30 mg/kg). A more pronounced PD effect was observed for OA-Fc-ABDEG-Alb23. A poor depletion of IgG1 was observed for TA-Alb23-Fc-ABDEG (30 mg/kg), in line with the observed lack of PD effect of this molecule in cynomolgus monkeys (Example 1) and in Tg32-hFc mice.

Figure 22B:
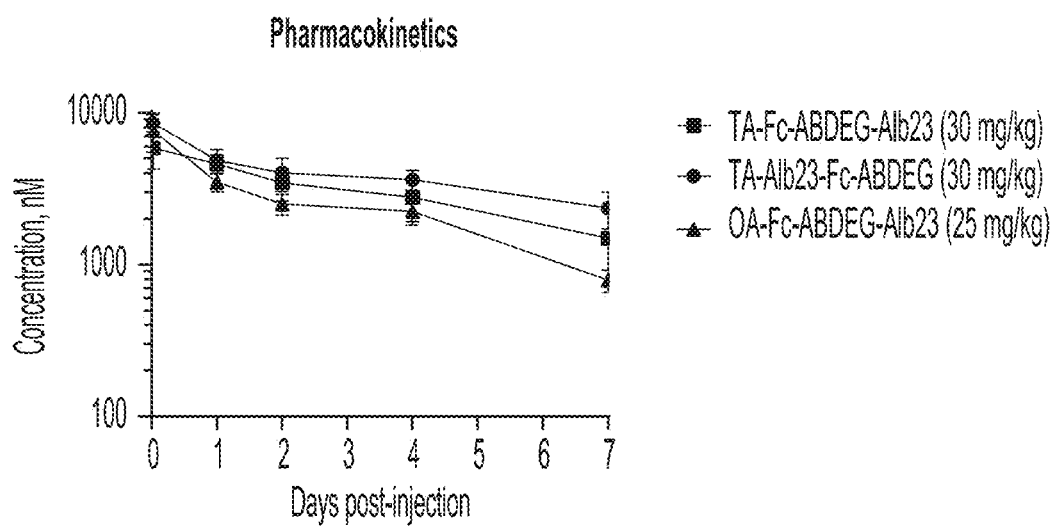

To evaluate the PK profiles of the test items after a single IV administration, their levels in mouse serum were determined post-dose according to the bleeding scheme in Table S20. The obtained values were plotted in molar concentrations (nM) to correct for different mg/kg doses of the administered molecules due to different molecular weights (FIG. 22B). These results corroborate the findings from Tg32-hFc mice that Fc-ABDEG can be rescued with only one albumin binding VHH fragment.

TA-Alb23-Fc-ABDEG showed the best PK profile among the test items, which can be linked to its poor PD effect (poor FcRn occupancy) leading to the extended time in circulation. For all tested molecules, concentrations were quantifiable in the serum during the entire study (7 days).

Figure 22C:
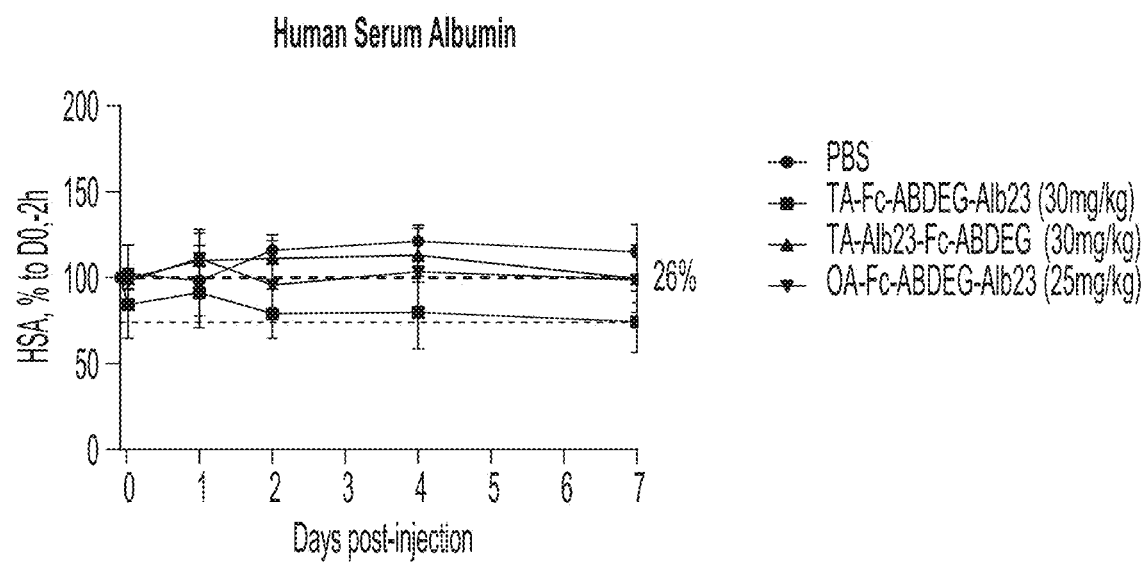

To evaluate a potential impact of two-armed (TA) or one-armed (OA) Fc-ABDEG-VHH molecules on albumin levels after the administration to AlbuMus mice, total serum albumin levels were measured throughout the study at baseline (pre-dose) and post-dose according to the scheme in Table S20. Measured albumin concentrations were plotted as percentage to pre-dose (day 0, −2 h) prior test item administration (FIG. 22C). No pronounced decrease in albumin levels was observed in control mice treated with PBS during the course of the study. Albumin decreases were observed in mice treated with TA-Fc-ABDEG-Alb23 (30 mg/kg). In more detail, for this group, serum albumin levels showed a nadir of 26% to pre-dose from day 2 up to day 7. No or transient (limited to the first 3 days) reduction in albumin levels were observed for OA-Fc-ABDEG-VHH molecules. Overall, the most pronounced and prolonged decrease in albumin concentration was detected after treatment with TA-Fc-ABDEG-Alb23, confirming the previous findings in cynomolgus monkeys and Th32-hFc mice. The effect was less pronounced and transient with one-armed molecules.

In conclusion, this experiment corroborates the results seen in Tg32-hFc mice that incorporation of only one albumin-binding VHH fragment can substantially improve PK of Fc-ABDEG, allow Fc-ABDEG to mediate an efficient IgG depletion, and ameliorate the effects on circulating albumin levels observed with two-armed TA-Fc-ABDEG-Alb23.

Example 8: Identification of Alb23 VHH Variants with Reduced Affinity to Albumin by Alanine/Histidine Scanning Based on previous data from clone 2H11 demonstrating that VHH fragments with low affinity for albumin do not result in FcRn degradation when fused to Fc-ABDEG seen with Alb23, alanine scanning and histidine scanning of Alb23 CDRs were conducted to identify Alb23 VHH variants with reduced affinity for albumin for further development. Alb23 VHH variant sequences are provided below in Tables S21 and S22.

TABLE S21

CDR Sequences of Alb23 variants

| Variant | CDR1 | SEQ ID NO. | CDR2 | SEQ ID NO. | CDR3 | SEQ ID NO. |
|---|---|---|---|---|---|---|
| Alb23 parental | SFGMS | 10 | SISGSGSDTLYADSVKG | 11 | GGSLSR | 12 |
| Alb23 S31A | AFGMS | 13 | SISGSGSDTLYADSVKG | 11 | GGSLSR | 12 |
| Alb23 F32A | SAGMS | 14 | SISGSGSDTLYADSVKG | 11 | GGSLSR | 12 |
| Alb23 G33A | SFAMS | 15 | SISGSGSDTLYADSVKG | 11 | GGSLSR | 12 |
| Alb23 M34A | SFGAS | 16 | SISGSGSDTLYADSVKG | 11 | GGSLSR | 12 |
| Alb23 S35A | SFGMA | 17 | SISGSGSDTLYADSVKG | 11 | GGSLSR | 12 |
| Alb23 S50A | SFGMS | 10 | AISGSGSDTLYADSVKG | 18 | GGSLSR | 12 |
| Alb23 I51A | SFGMS | 10 | SASGSGSDTLYADSVKG | 19 | GGSLSR | 12 |
| Alb23 S52A | SFGMS | 10 | SIAGSGSDTLYADSVKG | 20 | GGSLSR | 12 |
| Alb23 G53A | SFGMS | 10 | SISASGSDTLYADSVKG | 21 | GGSLSR | 12 |
| Alb23 S54A | SFGMS | 10 | SISGAGSDTLYADSVKG | 22 | GGSLSR | 12 |
| Alb23 G55A | SFGMS | 10 | SISGSASDTLYADSVKG | 23 | GGSLSR | 12 |
| Alb23 S56A | SFGMS | 10 | SISGSGADTLYADSVKG | 24 | GGSLSR | 12 |
| Alb23 D57A | SFGMS | 10 | SISGSGSATLYADSVKG | 25 | GGSLSR | 12 |
| Alb23 T58A | SFGMS | 10 | SISGSGSDALYADSVKG | 26 | GGSLSR | 12 |
| Alb23 L59A | SFGMS | 10 | SISGSGSDTAYADSVKG | 27 | GGSLSR | 12 |
| Alb23 Y60A | SFGMS | 10 | SISGSGSDTLAADSVKG | 28 | GGSLSR | 12 |
| Alb23 D62A | SFGMS | 10 | SISGSGSDTLYAASVKG | 29 | GGSLSR | 12 |
| Alb23 S63A | SFGMS | 10 | SISGSGSDTLYADAVKG | 30 | GGSLSR | 12 |
| Alb23 V64A | SFGMS | 10 | SISGSGSDTLYADSAKG | 31 | GGSLSR | 12 |
| Alb23 K65A | SFGMS | 10 | SISGSGSDTLYADSVAG | 32 | GGSLSR | 12 |
| Alb23 G66A | SFGMS | 10 | SISGSGSDTLYADSVKA | 33 | GGSLSR | 12 |
| Alb23 G99A | SFGMS | 10 | SISGSGSDTLYADSVKG | 11 | AGSLSR | 34 |
| Alb23 G100A | SFGMS | 10 | SISGSGSDTLYADSVKG | 11 | GASLSR | 35 |
| Alb23 S101A | SFGMS | 10 | SISGSGSDTLYADSVKG | 11 | GGALSR | 36 |
| Alb23 L102A | SFGMS | 10 | SISGSGSDTLYADSVKG | 11 | GGSASR | 37 |
| Alb23 S103A | SFGMS | 10 | SISGSGSDTLYADSVKG | 11 | GGSLAR | 38 |
| Alb23 R104A | SFGMS | 10 | SISGSGSDTLYADSVKG | 11 | GGSLSA | 39 |
| Alb23 S101T | SFGMS | 10 | SISGSGSDTLYADSVKG | 11 | GGTLSR | 40 |
| Alb23 G33A/S101A | SFAMS | 15 | SISGSGSDTLYADSVKG | 11 | GGALSR | 36 |
| Alb23 G33A/G53A | SFAMS | 15 | SISASGSDTLYADSVKG | 21 | GGSLSR | 12 |
| Alb23 S52A/G53A | SFGMS | 10 | SIAASGSDTLYADSVKG | 41 | GGSLSR | 12 |
| Alb23 S52A/S101A | SFGMS | 10 | SIAGSGSDTLYADSVKG | 20 | GGALSR | 36 |
| Alb23 F32H | SHGMS | 111 | SISGSGSDTLYADSVKG | 11 | GGSLSR | 12 |
| Alb23 M34H | SFGHS | 112 | SISGSGSDTLYADSVKG | 11 | GGSLSR | 12 |
| Alb23 G55H | SFGMS | 10 | SISGSHSDTLYADSVKG | 113 | GGSLSR | 12 |
| Alb23 L59H | SFGMS | 10 | SISGSGSDTHYADSVKG | 114 | GGSLSR | 12 |
| Alb23 G99H | SFGMS | 10 | SISGSGSDTLYADSVKG | 11 | HGSLSR | 115 |

TABLE S21-continued

CDR Sequences of Alb23 variants

| Variant | CDR1 | SEQ ID NO. | CDR2 | SEQ ID NO. | CDR3 | SEQ ID NO. |
|---|---|---|---|---|---|---|
| Alb23 G100H | SFGMS | 10 | SISGSGSDTLYADSVKG | 11 | GHSLSR | 116 |
| Alb23 L102H | SFGMS | 10 | SISGSGSDTLYADSVKG | 11 | GGSHSR | 117 |
| Alb23G33H/S101H | SFHMS | 118 | SISGSGSDTLYADSVKG | 11 | GGHLSR | 119 |

TABLE S22

Alb23 variant VHH sequences

| Clone | VHH | SEQ ID NO. |
|---|---|---|
| Alb23 parental | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS | 42 |
| Alb23 S31A | EVQLLESGGGLVQPGGSLRLSCAASGFTFRAFGMSWVRQAPGKGPEWVSSISGSGSDTLYADSVKGRFTISRDNSKNTLYLQMNSLRPEDTAVYYCTIGGSLSRSSQGTLVTVSS | 43 |
| Alb23 F32A | EVQLLESGGGLVQPGGSLRLSCAASGFTFRSAGMSWVRQAPGKGPEWVSSISGSGSDTLYADSVKGRFTISRDNSKNTLYLQMNSLRPEDTAVYYCTIGGSLSRSSQGTLVTVSS | 44 |
| Alb23 G33A | EVQLLESGGGLVQPGGSLRLSCAASGFTFRSFAMSWVRQAPGKGPEWVSSISGSGSDTLYADSVKGRFTISRDNSKNTLYLQMNSLRPEDTAVYYCTIGGSLSRSSQGTLVTVSS | 45 |
| Alb23 M34A | EVQLLESGGGLVQPGGSLRLSCAASGFTFRSFGASWVRQAPGKGPEWVSSISGSGSDTLYADSVKGRFTISRDNSKNTLYLQMNSLRPEDTAVYYCTIGGSLSRSSQGTLVTVSS | 46 |
| Alb23 S35A | EVQLLESGGGLVQPGGSLRLSCAASGFTFRSFGMAWVRQAPGKGPEWVSSISGSGSDTLYADSVKGRFTISRDNSKNTLYLQMNSLRPEDTAVYYCTIGGSLSRSSQGTLVTVSS | 47 |
| Alb23 S50A | EVQLLESGGGLVQPGGSLRLSCAASGFTFRSFGMSWVRQAPGKGPEWVAISGSGSDTLYADSVKGRFTISRDNSKNTLYLQMNSLRPEDTAVYYCTIGGSLSRSSQGTLVTVSS | 48 |
| Alb23 I51A | EVQLLESGGGLVQPGGSLRLSCAASGFTFRSFGMSWVRQAPGKGPEWVSASGSGSDTLYADSVKGRFTISRDNSKNTLYLQMNSLRPEDTAVYYCTIGGSLSRSSQGTLVTVSS | 49 |
| Alb23 S52A | EVQLLESGGGLVQPGGSLRLSCAASGFTFRSFGMSWVRQAPGKGPEWVSSIAGSGSDTLYADSVKGRFTISRDNSKNTLYLQMNSLRPEDTAVYYCTIGGSLSRSSQGTLVTVSS | 50 |
| Alb23 G53A | EVQLLESGGGLVQPGGSLRLSCAASGFTFRSFGMSWVRQAPGKGPEWVSSISAGSDTLYADSVKGRFTISRDNSKNTLYLQMNSLRPEDTAVYYCTIGGSLSRSSQGTLVTVSS | 51 |
| Alb23 S54A | EVQLLESGGGLVQPGGSLRLSCAASGFTFRSFGMSWVRQAPGKGPEWVSSISGAGSDTLYADSVKGRFTISRDNSKNTLYLQMNSLRPEDTAVYYCTIGGSLSRSSQGTLVTVSS | 52 |
| Alb23 G55A | EVQLLESGGGLVQPGGSLRLSCAASGFTFRSFGMSWVRQAPGKGPEWVSSISGSASDTLYADSVKGRFTISRDNSKNTLYLQMNSLRPEDTAVYYCTIGGSLSRSSQGTLVTVSS | 53 |
| Alb23 S56A | EVQLLESGGGLVQPGGSLRLSCAASGFTFRSFGMSWVRQAPGKGPEWVSSISGSGADTLYADSVKGRFTISRDNSKNTLYLQMNSLRPEDTAVYYCTIGGSLSRSSQGTLVTVSS | 54 |
| Alb23 D57A | EVQLLESGGGLVQPGGSLRLSCAASGFTFRSFGMSWVRQAPGKGPEWVSSISGSGSATLYADSVKGRFTISRDNSKNTLYLQMNSLRPEDTAVYYCTIGGSLSRSSQGTLVTVSS | 55 |
| Alb23 T58A | EVQLLESGGGLVQPGGSLRLSCAASGFTFRSFGMSWVRQAPGKGPEWVSSISGSGSDALYADSVKGRFTISRDNSKNTLYLQMNSLRPEDTAVYYCTIGGSLSRSSQGTLVTVSS | 56 |
| Alb23 L59A | EVQLLESGGGLVQPGGSLRLSCAASGFTFRSFGMSWVRQAPGKGPEWVSSISGSGSDTAYADSVKGRFTISRDNSKNTLYLQMNSLRPEDTAVYYCTIGGSLSRSSQGTLVTVSS | 57 |
| Alb23 Y60A | EVQLLESGGGLVQPGGSLRLSCAASGFTFRSFGMSWVRQAPGKGPEWVSSISGSGSDTLAADSVKGRFTISRDNSKNTLYLQMNSLRPEDTAVYYCTIGGSLSRSSQGTLVTVSS | 58 |
| Alb23 D62A | EVQLLESGGGLVQPGGSLRLSCAASGFTFRSFGMSWVRQAPGKGPEWVSSISGSGSDTLYAASVKGRFTISRDNSKNTLYLQMNSLRPEDTAVYYCTIGGSLSRSSQGTLVTVSS | 59 |
| Alb23 S63A | EVQLLESGGGLVQPGGSLRLSCAASGFTFRSFGMSWVRQAPGKGPEWVSSISGSGSDTLYADAVKGRFTISRDNSKNTLYLQMNSLRPEDTAVYYCTIGGSLSRSSQGTLVTVSS | 60 |

TABLE S22-continued

Alb23 variant VHH sequences

| Clone | VHH | SEQ ID NO. |
|---|---|---|
| Alb23 V64A | EVQLLESGGGLVQPGGSLRLSCAASGFTFRSFGMSWVRQAPGKGPEWVSSISGSGSDTLYADSA KGRFTISRDNSKNTLYLQMNSLRPEDTAVYYCTIGGSLSRSSQGTLVTVSS | 61 |
| Alb23 K65A | EVQLLESGGGLVQPGGSLRLSCAASGFTFRSFGMSWVRQAPGKGPEWVSSISGSGSDTLYADSV AGRFTISRDNSKNTLYLQMNSLRPEDTAVYYCTIGGSLSRSSQGTLVTVSS | 62 |
| Alb23 G66A | EVQLLESGGGLVQPGGSLRLSCAASGFTFRSFGMSWVRQAPGKGPEWVSSISGSGSDTLYADSV KARFTISRDNSKNTLYLQMNSLRPEDTAVYYCTIGGSLSRSSQGTLVTVSS | 63 |
| Alb23 G99A | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIAGSLSRSSQGTLVTVSS | 64 |
| Alb23 G100A | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGASLSRSSQGTLVTVSS | 65 |
| Alb23 S101A | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGALSRSSQGTLVTVSS | 66 |
| Alb23 L102A | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGSASRSSQGTLVTVSS | 67 |
| Alb23 S103A | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGSLARSSQGTLVTVSS | 68 |
| Alb23 R104A | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGSLSASSQGTLVTVSS | 69 |
| Alb23 S101T | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGTLSRSSQGTLVTVSS | 70 |
| Alb23 G33A/S101A | EVQLLESGGGLVQPGGSLRLSCAASGFTFRSFAMSWVRQAPGKGPEWVSSISGSGSDTLYADSV KGRFTISRDNSKNTLYLQMNSLRPEDTAVYYCTIGGALSRSSQGTLVTVSS | 71 |
| Alb23 G33A/G53A | EVQLLESGGGLVQPGGSLRLSCAASGFTFRSFAMSWVRQAPGKGPEWVSSISASGSDTLYADSV KGRFTISRDNSKNTLYLQMNSLRPEDTAVYYCTIGGSLSRSSQGTLVTVSS | 72 |
| Alb23 S52A/G53A | EVQLLESGGGLVQPGGSLRLSCAASGFTFRSFGMSWVRQAPGKGPEWVSSIAASGSDTLYADSV KGRFTISRDNSKNTLYLQMNSLRPEDTAVYYCTIGGSLSRSSQGTLVTVSS | 73 |
| Alb23 S52A/S101A | EVQLLESGGGLVQPGGSLRLSCAASGFTFRSFGMSWVRQAPGKGPEWVSSIAGSGSDTLYADSV KGRFTISRDNSKNTLYLQMNSLRPEDTAVYYCTIGGALSRSSQGTLVTVSS | 74 |
| Alb23 F32H | EVQLLESGGGLVQPGGSLRLSCAASGFTFRSHGMSWVRQAPGKGPEWVSSISGSGSDTLYADSV KGRFTISRDNSKNTLYLQMNSLRPEDTAVYYCTIGGSLSRSSQGTLVTVSS | 120 |
| Alb23 M34H | EVQLLESGGGLVQPGGSLRLSCAASGFTFRSFGHSWVRQAPGKGPEWVSSISGSGSDTLYADSV KGRFTISRDNSKNTLYLQMNSLRPEDTAVYYCTIGGSLSRSSQGTLVTVSS | 121 |
| Alb23 G55H | EVQLLESGGGLVQPGGSLRLSCAASGFTFRSFGMSWVRQAPGKGPEWVSSISGSHSDTLYADSV KGRFTISRDNSKNTLYLQMNSLRPEDTAVYYCTIGGSLSRSSQGTLVTVSS | 122 |
| Alb23 L59H | EVQLLESGGGLVQPGGSLRLSCAASGFTFRSFGMSWVRQAPGKGPEWVSSISGSGSDTHYADSV KGRFTISRDNSKNTLYLQMNSLRPEDTAVYYCTIGGSLSRSSQGTLVTVSS | 123 |
| Alb23 G99H | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIHGSLSRSSQGTLVTVSS | 124 |
| Alb23 G100H | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGHSLSRSSQGTLVTVSS | 125 |
| Alb23 L102H | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGSHSRSSQGTLVTVSS | 126 |
| Alb23G33H/ S101H | EVQLLESGGGLVQPGGSLRLSCAASGFTFRSFHMSWVRQAPGKGPEWVSSISGSGSDTLYADSV KGRFTISRDNSKNTLYLQMNSLRPEDTAVYYCTIGGHLSRSSQGTLVTVSS | 127 |

Figure 23:
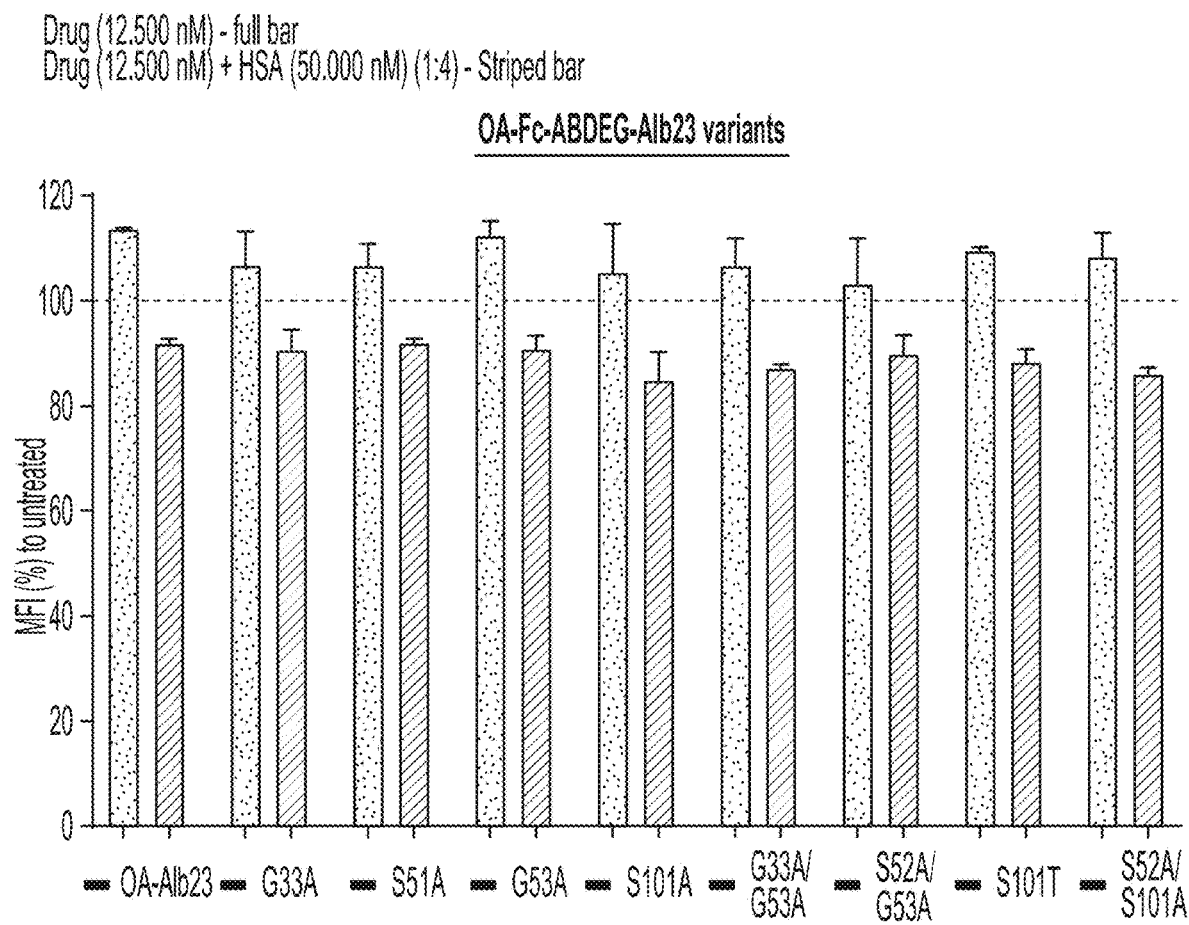
FIG. 23 shows the effect of one-armed Fc-ABDEG-Alb23 variant molecules on FcRn degradation in the presence or absence of HSA. HEK FcRn WT GFP+ cells were incubated with 12,500 nM Fc-ABDEG-VHH in the absence of HSA (solid bars) or in the presence of 50,000 nM HSA (striped bars). Bars represent mean±SEM of duplicate wells; result of two independent runs.

Initially, Alb23 alanine variants targeting position G33 in CDR1, positions S52 and G53 in CDR2, and position S101 in CDR3 were tested since these positions were predicted to bind directly to albumin based on co-crystallization data of Alb1 (which contains the same CDR sequences as Alb23) and serum albumin (Jian M, Molecular Basis For The Cross-Species Specificity Of The Anti-Serum Albumin VHH M79 (2020) Thesis, California State University, Fresno). Eight Alb23 variants were fused at the C-terminus of an Fc-ABDEG and were tested for their albumin binding affinity at pH 5.5 and pH 7.4 (Table S23), as well as for their effect on FcRn degradation (FIG. 23). These studies were conducted using Biacore (HSA coated, OA-Fc-ABDEG-VHH in solution) assays and FcRn degradation assays as previously described in the above Examples.

TABLE S23

Kinetic and steady-state albumin binding of OA-Fc-ABDEG-Alb23 variants

| | pH 7.4 | | pH 5.5 | |
|---|---|---|---|---|
| Name | Kinetic KD (M) | Steady KD (M) | Kinetic KD (M) | Steady KD (M) |
| OA-Fc-ABDEG-Alb23 | 6.91E−08 | 1.53E−07 | 1.66E−08 | 3.27E−08 |
| OA-Fc-ABDEG-Alb23-G33A | 1.5E−07 | 8.63E−07 | 1.24E−07 | 1.45E−07 |
| OA-Fc-ABDEG-Alb23-S52A | 1.67E−07 | 2.73E−08 | 3.42E−08 | 4.95E−08 |
| OA-Fc-ABDEG-Alb23-G53A | 7.88E−08 | 1.58E−07 | 2.06E−08 | 3.67E−08 |
| OA-Fc-ABDEG-Alb23-S101A | 2.55E−07 | 3.53E−08 | 5.43E−08 | 6.75E−08 |
| OA-Fc-ABDEG-Alb23-G33A/G53A | 4.99E−07 | 7.67E−07 | 9.02E−08 | 1.35E−07 |
| OA-Fc-ABDEG-Alb23-S52A/G53A | 2.04E−07 | 2.98E−07 | 4.77E−08 | 6.59E−08 |
| OA-Fc-ABDEG-Alb23-S101T | 2.06E−07 | 3.15E−07 | 5.49E−08 | 7.08E−08 |
| OA-Fc-ABDEG-Alb23-S52A/S101A | 5.01E−07 | 5.79E−07 | 9.56E−08 | 1.24E−07 |

Overall, none of the eight variants tested showed pronounce reduced affinity to HSA when compared against OA-Fc-ABDEG-Alb23 (parental). Variants OA-Fc-ABDEG-Alb23-G33A and OA-Fc-ABDEG-Alb23-S101A showed the most pronounced reduction in HSA binding affinity (Table S23). Similarly, no reduction in FcRn degradation was seen for any of the OA-Fc-ABDEG-Alb23 variants studied as compared to OA-Fc-ABDEG-Alb23 (parental) (FIG. 23).

Next, Alb23 alanine variants at different positions in all three CDRs plus one further double mutant (G33A/S101A) were explored. The on-rate and the off-rate for 22 Alb23 VHH variants were evaluated by SPR, using Biacore 8K+, in single cycle kinetics (SCK) protocol. Human, cynomolgus monkey, and mouse serum albumin proteins were immobilized on CM5 chips and the VHH variants were injected in-solution in a five step 2-fold dilution series (6.25 nM, 12.5 nM, 25 nM, 50 nM, and 100 nM in 1×HBS-EP+ pH 7.4) during 2 minutes at 30 µL/min. Buffer only and OA-Fc-ABDEG-Alb23 were included as controls. Data are presented below in Table S24.

TABLE S24

Albumin binding affinity of Alb23 VHH variants at pH 7.4

| | | humanSA | | cynoSA | | mouseSA | |
|---|---|---|---|---|---|---|---|
| | Samples | KD (nM) | Rmax (RU) | KD (nM) | Rmax (RU) | KD (nM) | Rmax (RU) |
| WT | VHH-Alb23_Parental (#1) | 2.37 | 174.5 | 2.68 | 173.3 | 28.65 | 167.0 |
| CDR1 | Alb23 S31A (#2) | 3.36 | 192.9 | 3.74 | 194.3 | 29.27 | 195.1 |
| | Alb23 F32A (#3) | nd | nd | nd | nd | nd | 2.4 |
| | Alb23 M34A (#4) | 174.77 | 225.1 | 182.44 | 222.3 | 148.57 | 46.7 |
| | Alb23 S35A (#5) | 4.95 | 192.4 | 5.24 | 185.5 | 37.57 | 174.5 |
| CDR2 | Alb23 S50A (#6) | 2.33 | 191.9 | 2.60 | 193.0 | 19.00 | 168.6 |
| | Alb23 I51A (#7) | 5.17 | 179.4 | 5.53 | 179.3 | 42.29 | 170.4 |
| | Alb23 S54A (#8) | 2.81 | 177.6 | 3.13 | 176.5 | 25.58 | 165.8 |
| | Alb23 S56A (#10) | 3.33 | 190.7 | 3.65 | 184.3 | 37.71 | 166.2 |
| | Alb23 D57A (#11) | 5.58 | 194.1 | 6.25 | 195.7 | 50.56 | 198.7 |
| | Alb23 T58A (#12) | 5.97 | 172.7 | 6.83 | 172.5 | 57.08 | 176.7 |
| | Alb23 L59A (#13) | 50.97 | 177.7 | 55.62 | 181.6 | 353.52 | 154.2 |
| | Alb23 Y60A (#14) | 4.28 | 185.3 | 4.58 | 179.0 | 42.25 | 162.4 |
| | Alb23 D62A (#15) | 3.07 | 179.0 | 3.48 | 177.9 | 36.49 | 198.6 |
| | Alb23 S63A (#16) | 3.57 | 188.8 | 3.92 | 182.5 | 40.02 | 179.9 |
| | Alb23 V64A (#17) | 2.90 | 188.9 | 4.11 | 176.9 | 31.94 | 172.5 |
| | Alb23 K65A (#18) | 5.36 | 183.4 | 3.18 | 190.5 | 52.34 | 153.3 |
| | Alb23 G66A (#19) | 3.97 | 175.4 | 5.84 | 184.9 | 39.45 | 164.3 |
| CDR3 | Alb23 G99A (#20) | 99.96 | 191.1 | 151.80 | 210.3 | 73.08 | 181.8 |
| | Alb23 G100A (#21) | 30.59 | 179.5 | 37.88 | 181.2 | 87.85 | 165.1 |
| | Alb23 S103A (#23) | 3.85 | 187.5 | 4.20 | 181.0 | 38.23 | 151.3 |
| | Alb23 R104A (#24) | 4.58 | 184.0 | 4.92 | 185.6 | 49.72 | 177.5 |
| | Alb23 G33A/S101A (#25) | 116.00 | 172.3 | 145.99 | 175.0 | 117.67 | 151.9 |

Six of the evaluated Alb23 VHH mutants bound to albumin with at least a 10-fold decrease in affinity compared to the parental Alb23 VHH fragment: F32A, M34A, L59A, G99A, G100A, and G33A/S101A (Table S24).

The F32A Alb23 VHH fragment was fused to the C-terminus of an Fc-ABDEG via a 30GS linker (referred to interchangeably herein as "OA-Fc-ABDEG-30GS-Alb23-F32A" or "ABDEG-30GS-Alb23-SM") and binding affinity of the one-armed construct to human albumin was compared to OA-Fc-ABDEG-Alb23 (parental). Kinetic parameters and/or affinity values were determined using the Langmuir 1:1 binding model or steady state model of OA-Fc-ABDEG-Alb23 variants binding to serum albumin at pH 7.4 and 5.5. Results from a representative individual run are shown in Table S25, showing greater than a 300-fold decrease in human albumin affinity of ABDEG-30GS-Alb23-SM compared to OA-Fc-ABDEG-Alb23.

TABLE S25

Albumin binding affinity of OA-Fc-ABDEG-Alb23-F32A variant

| Samples | pH | ka (1/Ms) | kd (1/s) | KD (µM) |
|---|---|---|---|---|
| OA-Fc-ABDEG-Alb23 | 5.5 | 2.79E+04 | 1.86E−03 | 0.0665 |
|  | 7.4 | 2.29E+04 | 3.36E−03 | 0.147 |
| ABDEG-30GS-Alb23-SM | 5.5 | 1.73E+04 | 3.51E−01 | 20.3 |
|  | 7.4 | N/A | N/A | 49 |

N/A: Not applicable

Example 9: Optimization of Linker Length

As shown in FIG. 14, inclusion of a 20GS linker in TA-Fc-ABDEG-Alb23 molecules was demonstrated to ameliorate FcRn degradation in the presence of HSA. The goal of this study was to explore optimal linker lengths in OA-Fc-ABDEG-Alb23 molecules.

FcRn degradation was measured as described in previous Examples. Briefly, HEK FcRn WT GFP+ cells/well were seeded on a 96-well microplate overnight at 37° C. in growth medium (DMEM+10% FBS+P/S+L-glutamine). Fc-ABDEG-VHH molecules (12500 nM) were pre-incubated with 50000 nM HSA in treatment medium (DMEM+1% BSA+P/S+L-glutamine) for 30 minutes at 37° C., 5% $CO_2$ prior to adding to the cells. After incubation of the Fc-ABDEG-VHH/HSA mix or Fc-ABDEG-VHH with the cells, plates were then placed on ice and cells harvested by trypsin. Harvested cells were transferred to FACS plate and centrifuged. LD stain (1:800) was added in FACS buffer and incubated for 15 minutes at 4° C. Cells were washed, centrifuged, and resuspended in FACS buffer. GFP signal was measured and compared to untreated controls.

Figure 24:
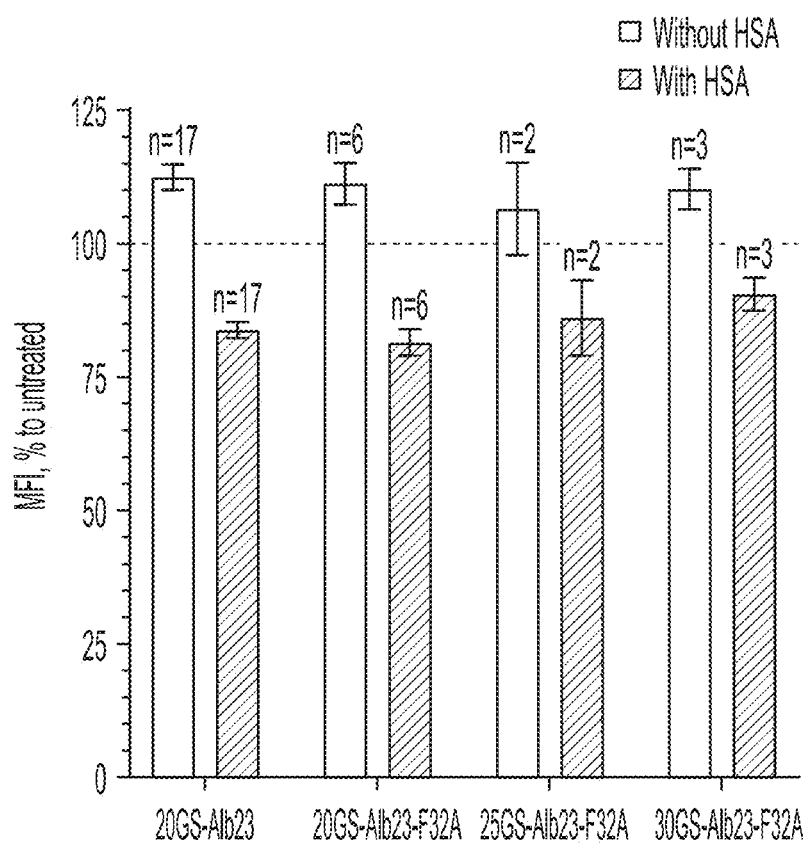
FIG. 24 shows the effect of OA-Fc-ABDEG-Alb23 with a 20GS linker, and OA-Fc-ABDEG-Alb23-F32A with 20, 25, and 30 GS linkers on FcRn degradation in the presence or absence of human serum albumin (HSA). HEK FcRn WT GFP+ cells were incubated with 12500 nM of the test molecules in the absence of HSA or in the presence of 50,000 nM HSA. Bars represent mean±SEM of individual experiments (indicated with n) each performed in two technical replicates.

Results are shown in FIG. 24. There was no difference in FcRn degradation between OA-Fc-ABDEG-20GS-Alb23 and OA-Fc-ABDEG-20GS-Alb23-F32A, demonstrating that use of an Alb23 variant with lower affinity to HSA had no effect on FcRn degradation. Inclusion of longer linker lengths (25GS and 30GS) showed improvement in FcRn degradation, with the 30GS linker performing better than either the 20GS linker or the 25 GS linker.

The effect of linker length on PD and PK was studied in AlbuMus Rag1KO mice. AlbuMus Rag1KO mice are double-humanized for serum albumin/neonatal Fc receptor, Rag1 knock-out mouse model (hFcRn+/+, hAlb+/+, Rag1−/−). Fcgrt and hAlb are knocked-in and expressed under the endogenous mouse promoter. Knock out of Rag1 produces immunodeficiency such that the mice do not develop ADA.

Eleven AlbuMus Rag1KO mice were assigned to one of three groups as shown below in Table S26. Mice were preloaded intraperitoneally with IVIg (200 mg/kg) and hIgG1 (20 mg/kg) on day −3 (due to low levels on endogenous mIgG in mouse model). OA-Fc-ABDEG-20GS-Alb23-F32A, OA-Fc-ABDEG-30GS-Alb23-F32A, or OA-Fc-ABDEG-3Rab (containing an irrelevant rabies virus-binding VHH fragment as a control) were administered on day 0. Blood samples were drawn on Day 0, 2 hours prior to administration of the test articles and again 1 hour after administration of the test articles, and on Days 1, 2, 4, 7, 11, and 14 post-administration.

TABLE S26

Groups and dosing regimen

| Group | Test article | Dose (mg/kg) | # animals | Route, frequency | Readouts |
|---|---|---|---|---|---|
| 1 | OA-Fc-ABDEG-3Rab | 25 | 3 | IP, single dose | PD |
| 2 | OA-Fc-ABDEG-20GS-Alb23-F32A | 25 | 4 |  | tracer/total, PK, HSA |
| 3 | OA-Fc-ABDEG-30GS-Alb23-F32A | 25 | 4 |  |  |

Figure 25A:
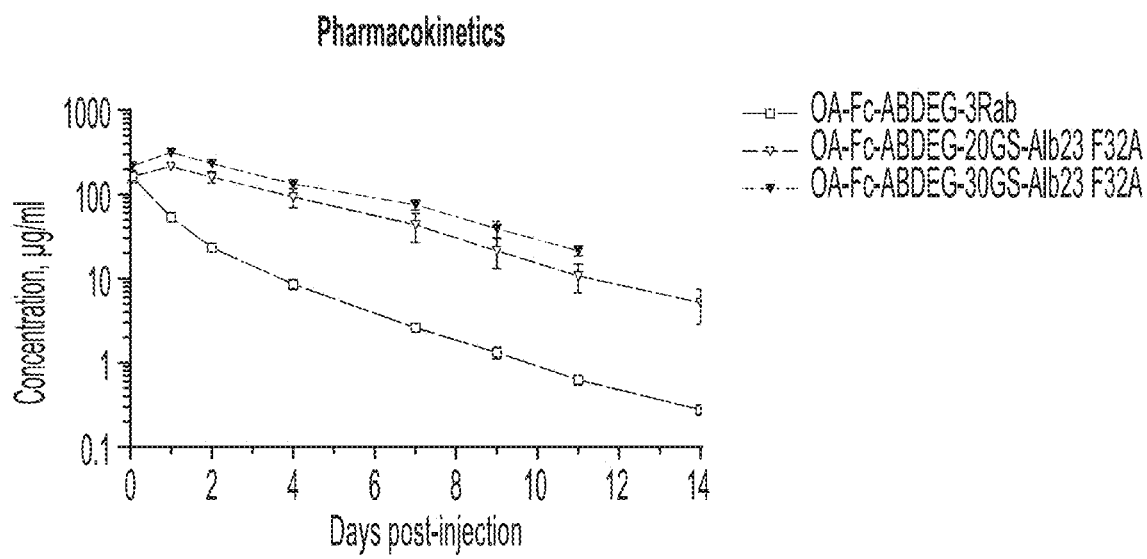
FIGS. 25A-25B show the PD/PK effect of OA-Fc-ABDEG-Alb23-F32A with a 20GS linker, OA-Fc-ABDEG-Alb23-F32A with a 30GS linker, and OA-Fc-ABDEG-3Rab. The datapoints show the mean±SD of 3-4 animals per group.
Figure 25B:
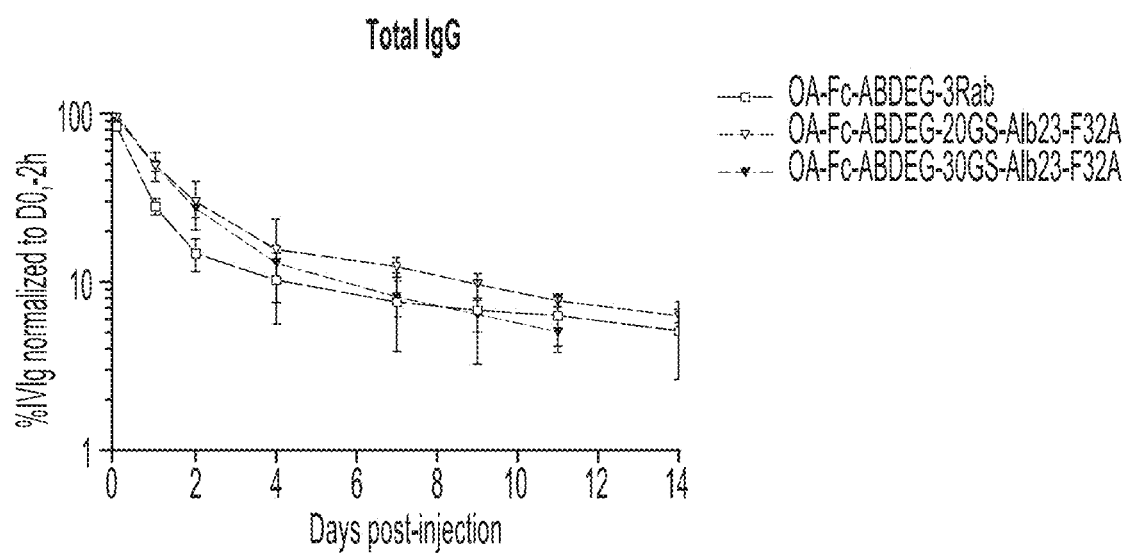

Results are shown in FIGS. 25A-25B. A slight improvement in PK (FIG. 25A) was seen with OA-Fc-ABDEG-30GS-Alb23-F32A when compared to OA-Fc-ABDEG-30GS-F32A, further supporting the benefit of using a 30GS linker over a 20GS linker. No difference in PD, as measured by percent reduction in total serum IgG, was seen when comparing the three test articles (FIG. 25B).

Example 10: Pharmacokinetics/Pharmacodynamics of OA-Fc-ABDEG-Alb23 Variants in AlbuMus Rag1KO Mice The current experiment was conducted to compare PK and PD of one-armed Fc-ABDEG-Alb23 variants to two-armed and one-armed Fc-ABDEG-Alb23 molecules in the AlbuMus Rag1KO mouse model (hFcRn+/+, hSA+/+, Rag1−/−).

Methods

Briefly, AlbuMus Rag1KO mice were randomly assigned into 7 groups (4-5 mice per group). The mice were single-dosed intraperitoneally (IP) according to the designated group and doses in Table S27. Tracer IgG was administered to all groups prior to administration of test items. 30 mg/kg dose for TA-Fc-ABDEG-Alb23 and 25 mg/kg for OA-Fc-ABDEG molecules were selected based on MW of the test items (FIG. 15) to have equimolar doses thereof. All animals were pre-weighed before dosing and dosed according to their body weights. Blood samples were collected before dosing of the test article (pre-dose, d0, −2 h) and after treatment for PD, PK, and albumin read-outs (Table S27).

Blood samples were processed to serum and added to a 96-well plate (polypropylene) and stored at −80° C.

TABLE S27

Groups and dosing regimen

| Group | N | Test Article | Dose, mg/kg | Administration route | Blood sampling times |
|---|---|---|---|---|---|
| A | 4-5 | PBS | — | IP, single dose | 0 d−2 h, 0 d+30 m, 1 d, 2 d, 4 d, 7 d, 11 d, 14 d, |
| B | 4-5 | ARGX-113 (efgartigimod) | 20 |  |  |

TABLE S27-continued

Groups and dosing regimen

| Group | N | Test Article | Dose, mg/kg | Administration route | Blood sampling times |
|---|---|---|---|---|---|
| C | 4-5 | OA-Fc-ABDEG-3Rab | 25 | | 16 d, 18 d, 21 d |
| D | 4-5 | OA-Fc-ABDEG-Alb23 | 25 | | |
| E | 4-5 | OA-Fc-ABDEG-Alb23-F32A | 25 | | |
| F | 4-5 | OA-Fc-ABDEG-Alb23-M34A | 25 | | |
| G | 4-5 | TA-Fc-ABDEG-Alb23 | 30 | | |

Total IgG serum levels and tracer IgG1 serum levels were determined using a sandwich ELISA and were plotted as percentage to pre-dose (2 hrs prior to test article injection, day 0-2 h).

Concentrations of ABDEG-based drug molecules: efgartigimod (ARGX-113), OA-Fc-ABDEG-3Rab, OA-Fc-ABDEG-Alb23, OA-Fc-ABDEG-Alb23-F32A, OA-Fc-ABDEG-Alb23-M34A, and TA-Fc-ABDEG-Alb23, were determined using a sandwich ELISA method. Briefly, Nunc MaxiSorp F-bottom plates (Thermo Fisher Scientific, Cat. 44-24004-21) were coated overnight (4° C.) with anti-HN and nonspecific binding sites were blocked with 1% casein-PBS (Bio-Rad, #1610783). Next, 100% study serum samples were diluted to the concentration range of quantitation or at least the minimum required dilution (MRD). The calibration curve and quality control (QC) samples (HQC, MQC, and LQC) with ABDEG-based drug molecules were spiked in 100% serum and pre-incubated for 30 min. at RT before applying MRD 100. Samples were incubated on the immunoplate together with a fresh calibration curve and two sets of QC samples (HQC, MQC, and LQC) for 1 hour. ABDEG-based drug molecules were detected by the addition of anti-HN (ABDEG hFab-Biotin) for 1 hour. Subsequently, hFab5-Biotin was detected by Strep-HRP (BD Biosciences, Cat. #554066) for 30 min. Plates were developed by adding TMB substrate for approximately 10 and 15 minutes for TA-Fc-ABDEG-Alb23, TA-Alb23-Fc-ABDEG, and OA-Fc-ABDEG-Alb23, respectively. The enzymatic reaction was stopped with 0.5M $H_2SO_4$ and optical density values at 450 nm, ref620 were recorded using a Tecan plate reader. All incubation steps were in a temperature controlled shaking incubator (22° C.). For data analysis, the obtained values were back-calculated on a 11-point calibrator curve in GraphPad Prism nonlinear regression; Asymmetric (five parameters), X is log(concentration).

Albumin levels in serum samples assessed by using a sandwich ELISA. Briefly, 96-well ELISA plates were coated with 1.0 μg/mL of a polyclonal anti-MSA antibody (Abcam, #ab19194) and incubated overnight at 4° C. Non-specific binding sites were blocked with PBS with 1% (w/v) casein for 1 h at room temperature. Study serum samples were diluted 1/1,000,000 and incubated on the immunoplate together with a fresh 11-point MSA (Sigma-A3559) calibration curve and 3 quality control (QC) samples (HQC, MQC, LQC) for 1 hour. Bound MSA was detected using RP-conjugated polyclonal anti-MSA antibody from goat (Abcam, #ab19195, 1:40000). ELISAs were developed by adding 100 μL of TMB substrate and the enzymatic reaction was stopped with $H_2SO_4$. Optical density values at 450 nm were recorded using a Tecan plate reader. The absorbance of the product at 450 nm is proportional to the amount of albumin analyte present in the sample and a four-parameter standard curve was generated. The albumin concentrations in the test samples were then quantified by interpolating their absorbance from the standard curve generated in parallel with the samples. After factoring sample dilutions, the albumin concentrations in the original sample were calculated. The obtained values were back-calculated on an 11-point calibrator curve in GraphPad Prism (log(agonist) vs. response—Variable slope (four parameters), Least squares fit). Albumin concentrations were plotted in absolute values measured (μg/mL) and percentage to pre-dose (2 hours prior to test article injection, day 0, -2 h).

Results

To assess PD, tracer hIgG1 was administered to the mice prior to treatment with the test articles. The levels of tracer hIgG1 and total IgG were measured during the course of the study. The measured total IgG concentrations (FIG. 26A) and tracer hIgG1 concentrations (FIG. 26B) were plotted as percentage to pre-dose at 2 hours prior to test article injection (day 0, -2 h) per treatment group.

As expected from previous data, a clear depletion of total IgG and tracer hIgG1 was observed for TA-Fc-ABDEG-Alb23 (30 mg/kg). A more pronounced PD effect was observed for all OA-Fc-ABDEG constructs regardless of the VHH attached. PD of the OA-Fc-ABDEG molecules was similar to that seen in the efgartigimod (ARGX-113) group.

To evaluate the PK profiles of the test items after a single IV administration, their levels in mouse serum were determined post-dose according to the bleeding scheme in Table S27. The obtained values were plotted in molar concentrations (nM) to correct for different mg/kg doses of the administered molecules due to different molecular weights (FIG. 26C). Non-compartmental analysis of PK data are provided in Table S28. Values below LLOQ were excluded (efgartigimod—0.97 nM; OA-Fc-ABDEG constructs—0.51 nM).

TABLE S28

PK parameters of OA-Fc-ABDEG-Alb23 variants in AlbuMus Rag1KO mice

| Test articles | | $T_{1/2z}$ (day) | $T_{max}$ (day) | $C_{max}$ (nM) | $AUC_{last}$ (d*nM) | $AUC_{INF\_pred}$ (d*nM) | $T_{1/2,MRT}$ (day) | $CL_{F\_pred}$ (L/day/kg) | $Vz_{F\_pred}$ (L/kg) |
|---|---|---|---|---|---|---|---|---|---|
| Efgartigimod | Mean | 1.503 | 1 | 2007 | 2539 | 2540 | 0.766 | 1.16 | 0.346 |
| (ARGX-113) | CV % | 40.4 | 0.04-1 | 9.6 | 13.3 | 13.3 | 11 | 13 | 45.1 |
| OA-Fc- | Mean | 2.159 | 0.04 | 1978 | 2947 | 2949 | 1.662 | 0.156 | 0.497 |
| ABDEG-3Rab | CV % | 8.3 | 0.04-1 | 89.6 | 41.8 | 41.8 | 24.7 | 50.7 | 56.3 |
| OA-Fc- | Mean | 2.777 | 1 | 3496 | 15962 | 16036 | 2.828 | 0.026 | 0.103 |
| ABDEG-Alb23 | CV % | 13.1 | 1-1 | 24.7 | 36 | 36.2 | 4.5 | 32.8 | 27.2 |

TABLE S28-continued

PK parameters of OA-Fc-ABDEG-Alb23 variants in AlbuMus Rag1KO mice

| Test articles | | $T_{1/2,z}$ (day) | $T_{max}$ (day) | $C_{max}$ (nM) | $AUC_{last}$ (d*nM) | $AUC_{INF\_pred}$ (d*nM) | $T_{1/2,MRT}$ (day) | $CL_{F\_pred}$ (L/day/kg) | $Vz_{F\_pred}$ (L/kg) |
|---|---|---|---|---|---|---|---|---|---|
| OA-Fc-ABDEG-Alb23-F32A | Mean | 2.794 | 1 | 3882 | 17670 | 17751 | 2.905 | 0.023 | 0.095 |
| | CV % | 10.6 | 1-1 | 29.1 | 35.1 | 35 | 4 | 27.6 | 31.2 |
| OA-Fc-ABDEG-Alb23-M34A | Mean | 3.083 | 1 | 3744 | 18996 | 19110 | 2.998 | 0.022 | 0.096 |
| | CV % | 19.1 | 1-1 | 22.5 | 30.8 | 30.8 | 8.3 | 41.3 | 32.6 |
| TA-Fc-ABDEG-Alb23 | Mean | 4.478 | 1.5 | 3633 | 27302 | 28721 | 4.931 | 0.014 | 0.088 |
| | CV % | 23.2 | 1-2 | 24.3 | 26.4 | 29.6 | 12.8 | 23.2 | 15.8 |

TA-Fc-ABDEG-Alb23 showed the best PK profile among the test items, similar to previous results. All OA-Fc-ABDEG constructs showed a PK profile intermediate to TA-Fc-ABDEG-Alb23 and efgartigimod. However, inclusion of an albumin-binding VHH (Alb23 and its variants) resulted in a better PK profile when compared to inclusion of an irrelevant VHH (3Rab which binds to rabies virus).

To evaluate a potential impact of the Fc-ABDEG molecules on albumin levels after the administration to AlbuMus Rag1KO mice, total serum albumin levels were measured throughout the study at baseline (pre-dose) and post-dose according to the scheme in Table S27. Measured albumin concentrations were plotted as percentage to pre-dose (day 0, −2 h) prior test item administration (FIG. 26D). No pronounced decrease in albumin levels was observed in control mice treated with PBS during the course of the study. Albumin decreases were observed in mice treated with TA-Fc-ABDEG-Alb23 as previously demonstrated. A transient decrease in albumin was also observed in mice treated with OA-Fc-ABDEG-Alb23. Surprisingly, OA-Fc-ABDEG-Alb23-F32A was shown to increase albumin levels in mice similar to the increase seen with efgartigimod treatment.

In conclusion, this experiment corroborates previous results showing that incorporation of only one albumin-binding VHH fragment can substantially improve PK of Fc-ABDEG, allow Fc-ABDEG to mediate an efficient IgG depletion, and ameliorate the effects on circulating albumin levels observed with two-armed TA-Fc-ABDEG-Alb23.

Example 11: Recycling of Alb23 F32A VHH Variant

The goal of this study was to determine whether the Alb23-F32A variant, which binds to HSA with approximately 300× lower affinity than parental Alb23 VHH fragment, is recycled via Fc-dependent and/or albumin-dependent means.

To test whether the Alb23-F32A VHH fragment is recycled independent of Fc, Alb23-F32A was fused to the C-terminus of an irrelevant Fab fragment (Mota-Fab) via a 20GS linker (Mota-Fab-Alb23-SM). Alb23 VHH fragment (recycled by albumin) and 3Rab VHH fragment (not recycled by albumin) were also fused to the C-terminus of Mota-Fab via a 20GS linker as positive and negative controls, respectively.

AlbuMus Rag1KO (hFcRn+/+, hSA+/+, Rag1−/−) mice were randomly assigned to one of three groups (4-5 mice per group). The mice were single-dosed intraperitoneally (IP) according to the designated group and doses in Table S29.

Tracer IgG was administered to all groups prior to administration of test items. 25 mg/kg doses of Mota-Fab-VHH molecules were selected based on MW of the test items (~65 kDa) which is similar to the MW of OA-Fc-ABDEG-VHH molecules (such as OA-Fc-ABDEG-Alb23 and variants thereof). All animals were pre-weighed before dosing and dosed according to their body weights. Blood samples were collected before dosing of the test article (pre-dose, d0, −2 h) and after treatment for PK readouts (Table S29).

Blood samples were processed to serum and added to a 96-well plate (polypropylene) and stored at −80° C.

TABLE S29

Groups and dosing regimen

| Group | N | Test Article | Dose, mg/kg | Administration route | Blood sampling times |
|---|---|---|---|---|---|
| A | 4-5 | Mota-Fab-20GS-3Rab | 25 | IP, single dose | 0 d+1 h, 1 d, 2 d, 3 d, 4 d, 7 d, 8 d |
| B | 4-5 | Mota-Fab-20GS-Alb23 | | | |
| C | 4-5 | Mota-Fab-20GS-Alb23-SM | | | |

Results are shown in FIG. 27A. Alb23 F23A rescues PK of Mota-Fab via albumin recycling of Mota-Fab as compared to 3Rab (non-albumin binding VHH), but to a much lower extent than parental Alb23. In comparison, PK results from Example 10, a selection of which are represented in FIG. 27B, illustrates that both OA-Fc-ABDEG-20GS-Alb23 (ABDEG-20GS-Alb23) and OA-Fc-ABDEG-20GS-Alb23-F32A (ABDEG-20GS-Alb23-SM) have similar PK profiles. PK of both OA-Fc-ABDEG-20GS-Alb23 and OA-Fc-ABDEG-20GS-Alb23-SM are significantly improved when compared to efgartigimod despite the difference in albumin-dependent recycling between Alb23 and Alb23-F32A. These results suggest there is synergism between albumin-dependent recycling and Fc-dependent recycling for these molecules.

Example 12: PD/PK of ABDEG-30GS-Alb23-SM in Cynomolgus Monkeys

Based on previous in vitro and in vivo data showing reduced FcRn degradation and improved PK for OA-Fc-ABDEG-30GS-Alb23-F32A (ABDEG-30GS-Alb23-SM) without compromising PD, this study sought to measure PD/PK of OA-Fc-ABDEG-30GS-Alb23-F32A in cynomolgus monkeys.

Briefly, cynomolgus monkeys were randomly assigned to one of three groups and dosed according to the schedule described in Table S30.

TABLE S30

Groups and dosing regimen

| Group | N | Test Article | Dose, mg/kg | Administration route | Blood sampling times |
|---|---|---|---|---|---|
| 1 | 3 | ABDEG-30GS-Alb23-SM | 10 | IV, single dose | 0 d–2 h, 0 d+30 m, 1 d, 2 d, 3 d, 5 d, 7 d, 11 d, 15 d |
| 2, 3 | 5 | ABDEG-30GS-Alb23-SM | 60 | | 0 d–2 h, 0 d+30 m, 1 d, 2 d, 3 d, 5 d, 7 d, 11 d, 15 d, 21 d |

To evaluate pharmacodynamic effects of OA-Fc-ABDEG-30GS-Alb23-SM after a single IV administration at 10 and 60 mg/kg doses, the levels of total circulating IgG in serum samples were determined at baseline (pre-dose) and post-dose according to the bleeding scheme in Table S30. The obtained IgG concentrations were plotted as percentage to pre-dose (day 0, −2 h) prior to of OA-Fc-ABDEG-30GS-Alb23-SM administration (FIGS. 28A-28B). OA-Fc-ABDEG-30GS-Alb23-F32A demonstrated a pronounced PD effect on the clearance of total circulating IgG with an average observed maximum total IgG reduction of 38% and 64%, defined as IgG $C_{min}$, in individual monkeys in the dose groups of 10 and 60 mg/kg, respectively (FIGS. 28A-28B, Table S31).

TABLE S31

Pharmacodynamic properties of OA-Fc-ABDEG-30GS-Alb23-F32A in cynomolgus monkeys

| Test Article | Dose, µmol/kg | Dose, mg/kg | $C_{min}$ (% d0) | HED (mg/kg) |
|---|---|---|---|---|
| OA-HEL-ABDEG | 0.1 | 10 | 36 | 1.7 |
| ABDEG-30GS-Alb23-SM | 0.15 | 10 | 38 | 2.6 |
| SIM efgartigimod | 0.15 | 8.1 | 30 | 2.6 |
| OA-HEL-ABDEG | 0.2 | 20 | 50 | 3.5 |
| OA-HEL-ABDEG | 0.8 | 85 | 61 | 14 |
| ABDEG-30GS-Alb23-SM | 0.9 | 60 | 64 | 16 |
| SIM efgartigimod | 0.9 | 48.5 | 58 | 16 |

HED: human equivalent dose. Efgartigimod values are model simulated. Simulation of equimolar OA-HEL-ABDEG was not possible due to non-linear PK/PD, thus two values are shown which bracket the target dose of 0.15 µmol/kg.

The potential role of ADA developed in the monkeys after OA-Fc-ABDEG-30GS-Alb23-F32A administration cannot be excluded and should be taken into account when interpreting PD effects on total circulating IgG. Time points when presence of ADA was detected coupled with a steep concentration decline in PK curves are excluded from results.

Overall, the low dose OA-Fc-ABDEG-30GS-Alb23-F32A (10 mg/kg) reduced IgG better than equimolar dosed efgartigimod, and comparably to near-equimolar dosed OA-HEL-ABDEG (HEL (anti-hen egg lysozyme) Fab fragment fused to N-terminus of Fc-ABDEG). At a higher dose of OA-Fc-ABDEG-30GS-Alb23-F32A (60 mg/kg), the IgG reduction was comparable to efgartigimod and to OA-HEL-ABDEG.

To evaluate the PK profile of OA-Fc-ABDEG-30GS-Alb23-F32A after a single IV administration at 10 and 60 mg/kg doses, OA-Fc-ABDEG-Alb23 levels were determined in serum post-dose samples according to the bleeding scheme in Table S30. The obtained OA-Fc-ABDEG-30GS-Alb23-F32A concentrations were plotted over time during the course of the study (FIGS. 29A-29B). Sampling times with steep concentration decline of OA-Fc-ABDEG-30GS-Alb23-F32A levels and when ADA presence was detected were excluded from data. PK profiles in cynomolgus monkeys treated with equimolar doses of efgartigimod (model simulation) and nearly equimolar doses of OA-HEL-ABDEG (experimental data) and TA-Fc-ABDEG-Alb23 (experimental data) are plotted for comparison. Values for $C_{max}$ and $AUC_{(0-7)}$ are summarized in Table S32.

TABLE S32

Pharmacokinetic properties of OA-Fc-ABDEG-30GS-Alb23-F32A in cynomolgus monkeys

| Test Article | Dose, µmol/kg | Dose, mg/kg | $C_{max}$ (µmol/L) | $AUC_{0-7}$, day*µmol/L |
|---|---|---|---|---|
| ABDEG-30GS-Alb23-SM | 0.15 | 10 | 4.4 | 12 |
|  | 0.9 | 60 | 34 | 101 |
| OA-HEL-ABDEG | 0.2 | 20 | 4.8 | 6.9 |
|  | 0.8 | 85 | 20 | 16 |
| SIM efgartigimod | 0.15 | 8.1 | 2.5 | 1.4 |
|  | 0.9 | 48.5 | 18 | 8.8 |
| TA-ABDEG-Alb23 | DN to 0.15 | DN to 12 | 5 | 21 |
|  | 1 | 75 | 31 | 135 |

PK properties of OA-ABDEG-30GS-Alb23-SM were improved over equimolar doses of both efgartigimod and OA-HEL-ABDEG, and were similar, although slightly lower than PK of equimolar TA-Fc-ABDEG-Alb23. These results are similar to those previously presented in mice treated with OA-Fc-ABDEG-Alb23 compared to TA-Fc-ABDEG-Alb23 (Examples 6 & 7).

Safety of OA-ABDEG-30GS-Alb23-SM was evaluated by measuring serum albumin levels in response to single or repeated administration to cynomolgus monkeys. On day 1, group 1 (n=3) received a 10 mg/kg dose of ABDEG-30GS-Alb23-SM; group 2 (n=2) and group 3 (n=3) received a 60 mg/kg dose of ABDEG-30GS-Alb23-SM. After 4-week follow-up period, the monkeys in groups 1 and 2 were additionally dosed four times, once every week on day 29, day 36, day 43, and day 50 with 60 mg/kg of ABDEG-30GS-Alb23-SM. Serum albumin was analyzed with a BCG albumin assay. Results are shown in FIG. 30. Albumin levels were not significantly affected by single or repeated administration of OA-ABDEG-Alb23-SM, staying within the minimum and maximum albumin serum levels seen in these monkeys prior to administration of OA-ABDEG-Alb23-SM (predose). The serum albumin levels obtained during the study are also generally within the normal range of serum albumin in cynomolgus monkeys according to Park et al. (Lab Anim Res. 2016 June; 32(2):79-86).

Example 13: Impact of Repeated Administration of OA-Fc-ABDEG-30GS-Alb23-F32A on Albumin in AlbuMus Rag1KO Mouse Model The impact of OA-Fc-ABDEG-30GS-Alb23-F32A on serum albumin levels was further explored by measuring serum albumin levels following repeated weekly injections to AlbuMus Rag1KO mice.

Briefly, AlbuMus Rag1KO mice were randomly assigned into 5 groups (3-5 mice per group). The mice were single-dosed intraperitoneally (IP) according to the designated group and doses in Table S33. Tracer IgG was administered to all groups prior to administration of test items. The doses were selected based on MW of the test items to have equimolar doses thereof. All animals were pre-weighed before dosing and dosed according to their body weights.

Blood samples were collected before dosing of the test article and after treatment for albumin read-outs (Table S33).

Blood samples were processed to serum and added to a 96-well plate (polypropylene) and stored at −80° C.

TABLE S33

Groups and dosing regimen

| Group | N | Test Article | Dose, mg/kg | Administration route | Blood sampling times |
|---|---|---|---|---|---|
| A | 3 | PBS | — | IP, 4 doses administered on 0 d, 7 d, 4 d, 21 d | −19 d, −13 d, −6 d, 0 d, 0 d+1 h, 3 d, 7 d, 7 d+1 h, 10 d, 14 d, 14 d+1 h, 17 d, 21 d, 21 d+1 h, 24 d, 28 d, 35 d |
| B | 5 | OA-Fc-ABDEG-Alb23-F32A | 45 | | |
| C | 5 | TA-Fc-ABDEG-Alb23 | 50 | | |
| D | 5 | Anti-FcRn mAb1 | 100 | | |
| E | 5 | Anti-FcRn mAb2 | 100 | | |

PBS was included as a negative control and TA-Fc-ABDEG-Alb23, anti-FcRn mAb1 and anti-FcRn mAb2 were included as comparators since all three were previously shown to decrease serum albumin levels and cause FcRn degradation. Anti-FcRn mAb1 comprises the light chain sequence of SEQ ID NO: 134 and the heavy chain sequence of SEQ ID NO: 135. Anti-FcRn mAb2 comprises the light chain sequence of SEQ ID NO: 128 and the heavy chain sequence of SEQ ID NO: 129. Results are shown in FIG. 31A. Values are presented as a percentage of predose (−6 d) values averaged per group. As expected, administration of TA-Fc-ABDEG-Alb23, anti-FcRn mAb1, and anti-FcRn mAb2 resulted in significant decreases in serum albumin. Surprisingly, repeated administration of OA-Fc-ABDEG-30GS-Alb23-F32A not only failed to decrease serum albumin, but actually increased serum albumin levels over time.

To explore if the effect on albumin levels is consistent with the effect of these molecules on FcRn degradation, HEK FcRn WT GFP+ cells were incubated with each of the test articles listed in Table S33 in the presence (50000 nM) or absence of HSA and FcRn degradation was measured as previously described above. Results are shown in FIG. 31B. Incubation of HEK FcRn WT GFP+ cells with anti-FcRn mAbs (1 & 2) resulted in significant FcRn degradation in the presence and absence of HSA. As previously shown, FcRn degradation is seen upon incubation of HEK FcRn WT GFP+ cells with TA-Fc-ABDEG-Alb23 in the presence of HSA but not in the absence of HSA. In contrast, incubation of HEK FcRn WT GFP+ cells with OA-Fc-ABDEG-30GS-Alb23-F32A in the presence of HSA did not impact FcRn degradation to the same extent as seen with the other molecules.

Example 14: Optimization of OA-Fc-ABEDEG-30GS-Alb23-F32A to Reduce ADA Reaction

The C-terminus of VHH fragments is known to interact with pre-existing antibodies in human subjects. Since the C-terminus of the Alb23-F32A VHH fragment is exposed in the OA-Fc-ABDEG-30GS-Alb23-F32A (ABDEG-30GS-Alb23-SM) molecule, the goal of this study was to explore modifications to reduce ADA reactivity while maintaining functionality.

ABDEG-30GS-Alb23-SM was modified by adding an alanine to the C-terminus of the molecule (ABDEG-30GS-Alb23-SM-A). Binding of both ABDEG-30GS-Alb23-SM and ABDEG-30GS-Alb23-SM-A to pre-existing ADA was tested along with PBS as a negative control. Serum from 40 humans positive for pre-existing ADA to ABDEG was used. ABDEG-30GS-Alb23-SM, ABDEG-30GS-Alb23-SM-A, or PBS (blank, no coating) were coated on a 96-well plate, the plate was blocked with 1% PBS-casein, and the serum was applied. Binding of pre-existing ADA to the test articles was detected with HRP-conjugated anti-human Fab IgG. Results are presented in FIG. 32 showing that the alanine extension reduces binding to pre-existing ADA. Other C-terminal extensions (AG, GG, and PP) showed similar results (data not shown).

The additional C-terminal alanine did not significantly alter affinity of the molecule to HSA as shown in Table S34.

TABLE S34

Albumin binding affinity of OA-Fc-ABDEG-Alb23-F32A variant

| Samples | pH | ka (1/Ms) | kd (1/s) | KD (μM) |
|---|---|---|---|---|
| OA-Fc-ABDEG-Alb23 | 5.5 | 2.79E+04 | 1.86E−03 | 0.0665 |
| | 7.4 | 2.29E+04 | 3.36E−03 | 0.147 |
| ABDEG-30GS-Alb23-SM | 5.5 | 1.73E+04 | 3.51E−03 | 20.3 |
| | 7.4 | N/A | N/A | 49 |
| ABDEG-30GS-Alb23-SM-A | 5.5 | N/A | N/A | 19 |
| | 7.4 | N/A | N/A | 31.4 |

N/A: Not applicable

Effect of the additional C-terminal alanine on FcRn occupancy was measured using an FcRn occupancy assay as described in detail above. Briefly, U937 cells were incubated with a titration series of the test items in the presence of 2,500 nM HSA. Free FcRn was detected with a fluorescently labelled anti-FcRn Fab fragment recognizing IgG binding site on FcRn. Detected levels of free FcRn were normalized to the FcRn levels in cells treated with the assay buffer (placebo, 100%) and results are presented in FIG. 33A and in Table S35.

TABLE S35

FcRn occupancy after incubation of with ABDEG-Alb23-SM molecules in the presence of albumin in U937 cells

| Name | Mean IC$_{50}$, nM | SD |
|---|---|---|
| Efgartigimod (n = 7) | 2.9 | 1.4 |
| ABDEG-30GS-Alb23-SM (n = 3) | 2.1 | 0.1 |
| ABDEG-30GS-Alb23-SM-A (n = 2) | 2.3 | 0.5 |

Effect of the additional C-terminal alanine on FcRn degradation was measured using an FcRn occupancy assay as described in detail above. Briefly, HEK FcRn WT GFP+ cells were incubated with indicated concentrations of the test molecules (12.5 μM ABDEG-20GS-Alb23, 12.5 μM ABDEG-30GS-Alb23-SM, 12.5 μM ABDEG-30GS-Alb23-SM-A, and 5 nM anti-FcRn mAb1) in the absence of HSA or in the presence of 50,000 nM HSA and levels of FcRn were measured and presented as a percentage of untreated control values. Results are presented in FIG. 33B showing no difference in FcRn degradation between ABDEG-30GS-Alb23-SM and ABDEG-30GS-Alb23-SM-A.

Effect of the additional C-terminal alanine on PK/PD was measured in AlbuMus Rag1KO mice. Briefly, 20 AlbuMus Rag1KO mice were assigned to one of four groups as shown below in Table S36. Mice were preloaded intraperitoneally with IVIg (200 mg/kg) and hIgG1 (20 mg/kg) on day −3 (due to low levels on endogenous mIgG in mouse model). Test articles described in Table S36 were administered on day 0. Blood samples were drawn on Day 0, 2 hrs prior to administration of the test articles and again 1 hour after administration of the test articles, and on Days 1, 2, 4, 7, 9, 11, and 15 post-administration.

TABLE S36

Groups and dosing regimen

| Group | Test article | Dose (mg/kg) | # animals | Route, frequency | Readouts |
|---|---|---|---|---|---|
| 1 | efgartigimod | 20 | 5 | IP, single dose | PD tracer/total, PK |
| 2 | OA-Fc-ABDEG-20GS-Alb23 | 25 | 5 | | |
| 3 | ABDEG-30GS-Alb23-SM-A | 25 | 5 | | |
| 4 | PBS | — | 5 | | |

Results are shown in FIGS. 34A-34C. Administration of OA-Fc-ABDEG-20GS-Alb23 and ABDEG-30GS-Alb23-SM-A resulted in similar PD profiles (FIGS. 34A-34B). Both OA-Fc-ABDEG-20GS-Alb23 and ABDEG-30GS-Alb23-SM-A decreased tracer IgG1 and total IVIg to a greater extent than an equimolar dose of efgartigimod. The PK profile for ABDEG-30GS-Alb23-SM-A was slightly better than the PK profile for OA-Fc-ABDEG-20GS-Alb23, which is consistent with the results obtained from administration of ABDEG-30GS-Alb23-SM as shown in FIG. 25A.

Based upon the in vitro and in vivo data for ABDEG-30GS-Alb23-SM-A, this molecule has similar functional properties to ABDEG-30GS-Alb23-SM but has the advantage of reduced binding to ADA.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

The invention claimed is:

1. A heterodimeric protein comprising a first polypeptide and a second polypeptide, wherein:
   a) the first polypeptide comprises a first Fc domain comprising the amino acid sequence of SEQ ID NO: 5 and a VHH comprising the CDR1, CDR2, and CDR3 amino acid sequences of the VHH amino acid sequence set forth in SEQ ID NO: 44, and
   b) the second polypeptide comprises a second Fc domain comprising the amino acid sequence of SEQ ID NO: 8.

2. The heterodimeric protein of claim 1, wherein the CDR1, CDR2, and CDR3 amino acid sequences are set forth in SEQ ID NO: 14, SEQ ID NO: 11, and SEQ ID NO: 12, respectively.

3. The heterodimeric protein of claim 1, wherein the VHH comprises the amino acid sequence of SEQ ID NO: 44.

4. The heterodimeric protein of claim 1, wherein the VHH consists of the amino acid sequence of SEQ ID NO: 44.

5. The heterodimeric protein of claim 4, further comprising one or more additional amino acids at the C-terminal end of the VHH, wherein the one or more additional amino acids are selected from the group consisting of:
   a) A;
   b) AG;
   c) GG;
   d) PP; and
   e) AA.

6. The heterodimeric protein of claim 1, wherein the VHH is fused to the C-terminus of the first Fc domain via a peptide linker.

7. The heterodimeric protein of claim 6, wherein the peptide linker is a GS linker that is 20 or 30 amino acids in length.

8. The heterodimeric protein of claim 1, wherein the first Fc domain consists of the amino acid sequence of SEQ ID NO: 5.

9. The heterodimeric protein of claim 1, wherein the second Fc domain consists of the amino acid sequence of SEQ ID NO: 8.

10. A heterodimeric protein comprising a first polypeptide comprising the amino acid sequence of SEQ ID NO: 180 and a second polypeptide comprising the amino acid sequence of SEQ ID NO: 8.

11. The heterodimeric protein of claim 10, wherein the first polypeptide consists of the amino acid sequence of SEQ ID NO: 180 and the second polypeptide consists of the amino acid sequence of SEQ ID NO: 8.

12. The heterodimeric protein of claim 11, wherein the heterodimer protein consists of the first polypeptide and the second polypeptide.

13. A composition comprising the heterodimeric protein of claim 1 and at least one pharmaceutically acceptable carrier.

14. A composition comprising the heterodimeric protein of claim 10 and at least one pharmaceutically acceptable carrier.

\* \* \* \* \*